(12) United States Patent
Mori et al.

(10) Patent No.: US 8,927,536 B2
(45) Date of Patent: Jan. 6, 2015

(54) TETRAHYDROTHIAZEPINE DERIVATIVE

(71) Applicant: Daiichi Sankyo Company, Limited, Chuo-ku, Tokyo (JP)

(72) Inventors: Makoto Mori, Saitama (JP); Kunihiko Fujii, Tokyo (JP); Masaharu Inui, Tokyo (JP); Takayuki Baba, Chiba (JP); Yukari Onishi, Kanagawa (JP); Atsushi Aoyagi, Tokyo (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 0 days.

(21) Appl. No.: 14/057,004

(22) Filed: Oct. 18, 2013

(65) Prior Publication Data
US 2014/0080808 A1    Mar. 20, 2014

Related U.S. Application Data

(63) Continuation of application No. PCT/JP2012/060308, filed on Apr. 17, 2012.

(30) Foreign Application Priority Data

Apr. 19, 2011    (JP) ................. 2011-092650

(51) Int. Cl.
*A61K 31/553*    (2006.01)
*C07D 498/00*    (2006.01)

(52) U.S. Cl.
USPC ........................ 514/211.1; 540/552

(58) Field of Classification Search
USPC ........................ 514/211.1; 540/552
See application file for complete search history.

(56) References Cited

U.S. PATENT DOCUMENTS

| | | | |
|---|---|---|---|
| 7,799,782 B2 * | 9/2010 | Munson et al. | 514/234.5 |
| 2007/0259854 A1 | 11/2007 | Murakami | |
| 2010/0004221 A1 | 1/2010 | Hasegawa | |
| 2011/0288051 A1 | 11/2011 | Li | |

FOREIGN PATENT DOCUMENTS

| | | |
|---|---|---|
| JP | 2010-6707 A | 1/2010 |
| WO | 03/065983 A2 | 8/2003 |
| WO | 03/104207 A2 | 12/2003 |
| WO | 03/104208 A1 | 12/2003 |
| WO | 2006/030805 A1 | 3/2006 |
| WO | 2008/078725 A1 | 7/2008 |
| WO | 2009/045753 A1 | 4/2009 |

OTHER PUBLICATIONS

Buse, J., "Combining Insulin and Oral Agents," American Journal of Medicine 108(6A):23S-32S, Apr. 2000.
Carr, M.C., and J.D. Brunzell, "Abdominal Obesity and Dyslipidemia in the Metabolic Syndrome: Importance of Type 2 Diabetes and Familial Combined Hyperlipidemia in Coronary Artery Disease Risk," Journal of Clinical Endocrinology & Metabolism 89(6):2601-2607, Jun. 2004.
Cooper, M.S., et al., "Expression and Functional Consequences of 11β-Hydroxysteroid Dehydrogenase Activity in Human Bone," Bone 27(3):375-381, Sep. 2000.
Eckel, R.H., et al., "The Metabolic Syndrome," Lancet 365(9468):1415-1428, Apr. 2005.
Hermanowski-Vosatka, A., et al., "11β-HSD1 Inhibition Ameliorates Metabolic Syndrome and Prevents Progression of Atherosclerosis in Mice," Journal of Experimental Medicine 202(4):517-527, Aug. 2005.
Masuzaki, H., et al., "Transgenic Amplification of Glucocorticoid Action in Adipose Tissue Causes High Blood Pressure in Mice," Journal of Clinical Investigation 112(1):83-90, Jul. 2003.
Masuzaki, H., et al., "A Transgenic Model of Visceral Obesity and the Metabolic Syndrome," Science 294(5549):2166-2170, Dec. 2001.
Rauz, S., et al., "Expression and Putative Role of 11β-Hydroxysteroid Dehydrogenase Isozymes Within the Human Eye," Investigative Ophthalmology & Visual Science 42(9):2037-2042, Aug. 2001.
Sandeep, T.C., et al., "11β-Hydroxysteroid Dehydrogenase Inhibition Improves Cognitive Function in Healthy Elderly Men and Type 2 Diabetics," Proceedings of the National Academy of Sciences 101(17):6734-6739, Apr. 2004.

(Continued)

*Primary Examiner* — Rei-tsang Shiao
(74) *Attorney, Agent, or Firm* — Christensen O'Connor Johnson Kindness PLLC

(57) ABSTRACT

The present invention relates to a compound represented by the following general formula (I)

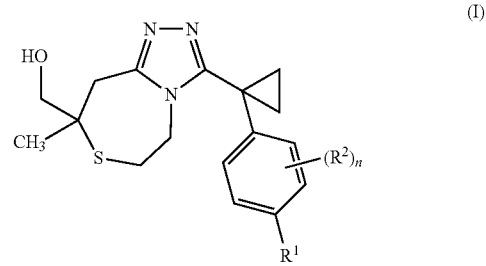

or a pharmacologically acceptable salt thereof having an excellent effect of inhibiting 11β-hydroxysteroid dehydrogenase type 1: General formula (I) wherein $R^1$ represents a phenyl group that may be substituted with 1 to 5 group(s) independently selected from substituent group A or a heterocyclic group that may be substituted with 1 to 4 group(s) independently selected from substituent group A; $R^2$ independently represents a halogen atom or a $C_1$-$C_6$ alkyl group; n represents an integer of 0 to 2; and substituent group A represents the group consisting of halogen atoms, $C_1$-$C_6$ alkyl groups, and so forth.

23 Claims, No Drawings

(56) References Cited

OTHER PUBLICATIONS

Seckl, J.R., and B.R. Walker, "Minireview: 11β-Hydroxysteroid Dehydrogenase Type 1—A Tissue-Specific Amplifier of Glucocorticoid Action," Endocrinology 142(4):1371-1376, Apr. 2001.

Zimmet, P., et al., "Global and Societal Implications of the Diabetes Epidemic," Nature 414(6865):782-787, Dec. 2001.

International Search Report mailed Jun. 5, 2012, issued in corresponding International Application No. PCT/JP2012/060308, filed Apr. 17, 2012, 13 pages.

International Preliminary Report on Patentability mailed Oct. 22, 2013, issued in corresponding International Application No. PCT/JP2012/060308, filed Apr. 17, 2012, 10 pages.

Extended European Search Report mailed Aug. 13, 2014, issued in corresponding European Application No. 12774851.5, filed Apr. 17, 2012, 6 pages.

\* cited by examiner

TETRAHYDROTHIAZEPINE DERIVATIVE

TECHNICAL FIELD

The present invention relates to a compound or a pharmacologically acceptable salt thereof that has the effect of inhibiting 11β-hydroxysteroid dehydrogenase type 1 (hereinafter, also referred to as 11β-HSD1) and is useful as a therapeutic agent for diabetes or the like, a method for producing the same, and production intermediates.

BACKGROUND ART

Along with changes in dietary habits, lifestyle, and living environment in recent years, patients with hyperglycemia, obesity, hyperlipidemia, and hypertension, as well as metabolic syndrome including two or more of these risk factors in combination, are increasing in number worldwide, which has become a social problem (Non Patent Literature 1). In any treatment, dietary therapy and exercise therapy are used, and if the effect is low, or the condition is severe, drug therapy is used in combination.

Diabetes is classified into insulin-dependent diabetes mellitus (type 1, IDDM) and non-insulin-dependent diabetes mellitus (type 2, NIDDM), which affects 90% or more of diabetic patients. Insulin injections are used for treatment of IDDM, and sulfonylurea agents, which promote secretion of insulin, thiazolidine dione drugs, which improve insulin resistance, glycosidase inhibitors, which inhibit sugar digestion and absorption, and biguanide drugs, which inhibit gluconeogenesis in the liver, and the like are used for treatment of NIDDM (Non Patent Literature 2). However, none of these drugs necessarily has adequate effects, and an increasing number of patients have serious complications, because efficacy attenuates after long term use.

In the treatment of patients with severe obesity conditions, centrally-acting anorectic agents are used. However, adequate effects have not been achieved due to the limited duration of use and rebound.

Examples of therapeutic agents for hypertension include calcium antagonists, which produce vasodilatation, diuretics, which promote excretion of salts, β blockers, which suppress the sympathetic nerves to reduce heart rate, α blockers, which suppress the sympathetic nerves to produce peripheral vasodilatation, angiotensin converting enzyme inhibitors and angiotensin receptor blockers, which inhibit vasoconstriction by angiotensin, and so forth. However, blood pressure control in early morning, the time of the day when stroke occurs most commonly, is difficult, and antihypertensive therapies are far from being adequate at present.

As therapeutic agents for hyperlipidemia, HMG-CoA reducing enzyme inhibitors, which inhibit cholesterol synthesis in the liver, fibrate drugs, which inhibit triglyceride synthesis in the liver, anion exchange resins, which promote excretion of bile acid, and the like are used. The ultimate aim of hyperlipidemia treatment is prevention of atherosclerotic diseases including coronary artery diseases and cerebral infarction. However, since the condition of atherosclerosis is caused not only by hyperlipidemia but also coexisting risk factors such as hypertension, diabetes, adiposity, and aging, it is critical to pay attention to such other risk factors all the time, and multidimensional approaches are required (Non Patent Literature 3).

Carbohydrate corticoid (cortisol in humans, corticosterone in rodents) is known to have various bioactivities for regulating blood sugar levels, blood pressure, and the like. For example, it is known that carbohydrate corticoid has a bioactivity of promoting the release of amino acids from muscles and the release of fatty acids and glycerol from adipose tissues into the blood via expression of various proteins to promote gluconeogenesis in the liver using these substrates, leading to the promotion of increased blood sugar levels. Furthermore, it is also known that carbohydrate corticoid has activities of maturing immature fat cells in adipose tissues, leading to adiposity, and acting on mineral corticoid receptors in the kidneys to elevate blood pressure. Mechanisms for regulating carbohydrate corticoid activity involve regulation of production and secretion of carbohydrate corticoid in the hypothalamus-pituitary gland-adrenal cortex route and recycling of carbohydrate corticoid by 11β-HSD1 (conversion from an inactive form to an active form) in target organs such as the liver, adipose tissues, and the lungs (Non Patent Literature 4). The 11β-HSD1 inhibitors are expected to prevent hyperglycemia, adiposity, hyperlipidemia, and/or hypertension by inhibiting carbohydrate corticoid actions in these tissues and to exhibit multidimensional effects on metabolic syndrome including these conditions in combination. These potentials are supported by reports of adiposity with visceral fat, aggravation of glucose tolerance impairment, insulin resistance, and elevated blood pressure in mice with highly expressed adipose tissue-specific 11β-HSD1 (Non Patent Literature 5 and Non Patent Literature 6). The term "metabolic syndrome" means a combination of symptoms associated with abnormal metabolic functions for carbohydrates and lipids in the organism. The diagnosis criteria for this syndrome vary with a number of international organizations, but are consistent in having two or more symptoms among glucose tolerance impairment (or insulin resistance), adiposity, hypertension, hypertriglyceridemia, and low HDL cholesterol levels in blood. These symptoms are described in detail in Non Patent Literature 7. Examples of other expected effects of the 11β-HSD1 inhibitors include effects on atherosclerosis (Non Patent Literature 8), dementia (Non Patent Literature 9), osteoporosis (Non Patent Literature 10), and glaucoma (Non Patent Literature 11).

As a compound having the effect of inhibiting 11β-HSD1, a compound in which a triazole ring bound with a biaryl group and a tetrahydrothiazepine ring are condensed is described in Patent Literature 1. Furthermore, a compound in which a triazole ring bound with a cycloalkyl group and a diazepine ring are condensed is described in Patent Literature 2. Furthermore, a compound in which a condensed ring of a triazole ring and a pyridine ring and a biaryl group each bind to the same carbon atom in a cycloalkyl group is described in Patent Literature 3.

CITATION LIST

Patent Literature

Patent Literature 1: WO08/078,725 (corresponding U.S. Patent Publication No. US2010/0004221)
Patent Literature 2: WO06/030805 (corresponding U.S. Patent Publication No. US 2007/0259854)
Patent Literature 3: WO09/045,753 (corresponding U.S. Patent Publication No. US 2011/0288051)

Non Patent Literature

Non Patent Literature 1: Nature, vol. 414, p. 782 (2001)
Non Patent Literature 2: The American Journal of Medicine, vol. 108, p. 23 (2000)
Non Patent Literature 3: The Journal of Clinical Endocrinology & Metabolism), vol. 89, p. 2601 (2004)
Non Patent Literature 4: Endocrinology, vol. 142, p. 1371 (2001)

Non Patent Literature 5: Science, vol. 294, p. 2166 (2001)
Non Patent Literature 6: The Journal of Clinical Investigation, vol. 112, p. 83 (2003)
Non Patent Literature 7: The Lancet, vol. 365, p. 1415 (2005)
Non Patent Literature 8: The Journal of Experimental Medicine, vol. 202, p. 517 (2005)
Non Patent Literature 9: Proceedings of the National Academy of Sciences, vol. 101, p. 6734 (2004)
Non Patent Literature 10: Bone, vol. 27, p. 375 (2000)
Non Patent Literature 11: Investigative Ophthalmology & Visual Sciences, vol. 42, p. 2037 (2001)

SUMMARY OF INVENTION

Technical Problem

The inventors of the present invention conducted various research into compounds having the effect of inhibiting 11β-HSD1. As a result, they found that tetrahydrothiazepine derivatives having a specific chemical structure had an excellent effect of inhibiting 11β-HSD1. Furthermore, the present inventors found that a medicament containing a tetrahydrothiazepine derivative or a pharmacologically acceptable salt thereof as an active ingredient was useful. Since a tetrahydrothiazepine derivative or a pharmacologically acceptable salt thereof has the inhibitory effect described above, the medicament is useful as an 11β-HSD1 inhibitor or a therapeutic and/or prophylactic agent for diabetes, insulin resistance, diabetic complications, adiposity, dyslipidemia, hyperlipidemia, hypertension, fatty liver, atherosclerosis, dementia, osteoporosis, Cushing's syndrome, glaucoma, and/or metabolic syndrome. Furthermore, they found that the present invention was useful as a method for inhibiting 11β-HSD1 in an organism by administration of this medicament or as a method for therapeutic and/or prophylactic treatment of diabetes, insulin resistance, diabetic complications, adiposity, dyslipidemia, hyperlipidemia, hypertension, fatty liver, atherosclerosis, dementia, osteoporosis, Cushing's syndrome, glaucoma, and/or metabolic syndrome (particularly, a method for therapeutic and/or prophylactic treatment of type 2 diabetes). The present invention was accomplished based on the above-mentioned findings.

Furthermore, they found that the compound of the present invention was also excellent in terms of high safety.

In addition, they found an excellent production method and production intermediates for the production of the compound of the present invention.

Solution to Problem

The present invention relates to
(1) a compound represented by the general formula (I):

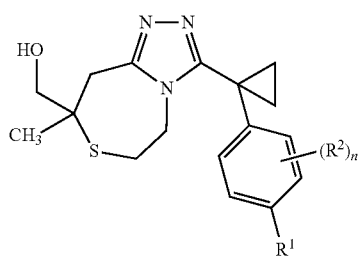

(I)

or a pharmacologically acceptable salt thereof
wherein $R^1$ represents a phenyl group that may be substituted with 1 to 5 group(s) independently selected from substituent group A or a heterocyclic group that may be substituted with 1 to 4 group(s) independently selected from substituent group A; $R^2$ independently represents a halogen atom or a $C_1$-$C_6$ alkyl group;
n represents 0, 1, or 2; and substituent group A represents the group consisting of halogen atoms, $C_1$-$C_6$ alkyl groups, $C_1$-$C_6$ halogenated alkyl groups, $C_1$-$C_6$ alkoxy groups, a carboxy group, $C_2$-$C_7$ carboxyalkyl groups, $C_2$-$C_7$ alkylcarbonyl groups, $C_2$-$C_7$ alkoxycarbonyl groups, a cyano group, $C_1$-$C_6$ alkylsulfonyl groups, groups represented by the formula —C(=O)—NR$^3$R$^4$ (R$^3$ and R$^4$ are identical to or different from each other and each independently represents a hydrogen atom, a $C_1$-$C_6$ alkyl group, or a $C_3$-$C_6$ cycloalkyl group, or R$^3$ and R$^4$ form a 4 to 6-membered saturated heterocyclic ring together with the nitrogen atom bound therewith, wherein the 4 to 6-membered saturated heterocyclic ring may further contain one oxygen atom), mono-$C_2$-$C_7$ alkoxycarbonylamino groups, and an oxo group, (2) a compound represented by the general formula (Ia):

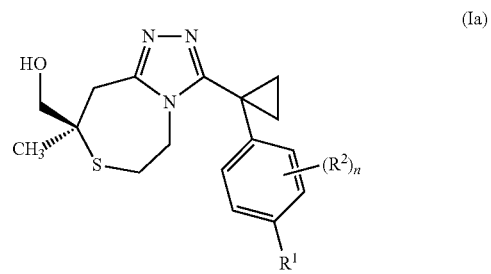

(Ia)

or a pharmacologically acceptable salt thereof
wherein $R^1$ represents a phenyl group that may be substituted with 1 to 5 group(s) independently selected from substituent group A or a heterocyclic group that may be substituted with 1 to 4 group(s) independently selected from substituent group A; $R^2$ independently represents a halogen atom or a $C_1$-$C_6$ alkyl group; n represents 0, 1, or 2; and
substituent group A represents the group consisting of halogen atoms, $C_1$-$C_6$ alkyl groups, $C_1$-$C_6$ halogenated alkyl groups, $C_1$-$C_6$ alkoxy groups, a carboxy group, $C_2$-$C_7$ carboxyalkyl groups, $C_2$-$C_7$ alkylcarbonyl groups, $C_2$-$C_7$ alkoxycarbonyl groups, a cyano group, $C_1$-$C_6$ alkylsulfonyl groups, groups represented by the formula —C(=O)—NR$^3$R$^4$ (R$^3$ and R$^4$ are identical to or different from each other and each independently represents a hydrogen atom, a $C_1$-$C_6$ alkyl group, or a $C_3$-$C_6$ cycloalkyl group, or R$^3$ and R$^4$ form a 4 to 6-membered saturated heterocyclic ring together with the nitrogen atom bound therewith, wherein the 4 to 6-membered saturated heterocyclic ring may further contain one oxygen atom), mono-$C_2$-$C_7$ alkoxycarbonylamino groups, and an oxo group, (3) the compound or a pharmacologically acceptable salt thereof according to (1) or (2) above, wherein $R^1$ represents a heterocyclic group that may be substituted with 1 to 4 group(s) independently selected from substituent group A, (4) the compound or a pharmacologically acceptable salt thereof according to any one of (1) to (3) above, wherein $R^1$ represents a pyridyl group, a pyrimidinyl group, or a pyrazolyl group that may be substituted with one group selected from substituent group A, (4-2) the compound or a pharmacologically acceptable salt thereof according to any one of (1) to (3) above, wherein $R^1$ represents a phenyl group, a 2-pyridyl group, a 3-pyridyl group, a 2-pyrimidinyl group, or a 4-pyrazolyl group that may be substituted with one group (the group is a methyl group, an ethyl group, or a dimethylaminocarbonyl group), (5) the compound or a pharmacologically acceptable salt thereof according to any one of (1) to (4) above, wherein substituent group A represents $C_1$-$C_6$ alkyl groups or groups represented by the formula —C(=O)—$NR^3R^4$ ($R^3$ and $R^4$ are identical to or different from each other and each independently represents a hydrogen atom, a $C_1$-$C_6$ alkyl group, or a $C_3$-$C_6$ cycloalkyl group, or $R^3$ and $R^4$ form a 4 to 6-membered saturated heterocyclic ring together with the nitrogen atom bound therewith, wherein the 4 to 6-membered saturated heterocyclic ring may further contain one oxygen atom), (5-2) the compound or a pharmacologically acceptable salt thereof according to any one of (1) to (3) above, wherein $R^1$ represents a 4-dimethylaminocarbonylphenyl group, a 3-dimethylaminocarbonylphenyl group, a 3-pyridyl group, a 4-dimethylaminocarbonyl-2-pyridyl group, a 2-pyrimidinyl group, a 5-methyl-2-pyrimidinyl group, a 2-oxazolyl group, a 4-pyrazolyl group, a 1-methyl-4-pyrazolyl group, or a 1-ethyl-4-pyrazolyl group, (5-3) the compound or a pharmacologically acceptable salt thereof according to any one of (1) to (3) above, wherein $R^1$ represents a 4-dimethylaminocarbonylphenyl group, a 3-pyridyl group, a 4-dimethylaminocarbonyl-2-pyridyl group, a 5-methyl-2-pyrimidinyl group, a 2-oxazolyl group, a 4-pyrazolyl group, or a 1-methyl-4-pyrazolyl group, (6) the compound or a pharmacologically acceptable salt thereof according to any one of (1) to (5) above, wherein n represents 0, (6-2) the compound or a pharmacologically acceptable salt thereof according to any one of (1) to (5) above, wherein n represents 1, and $R^2$ represents a fluorine atom, (7) {8-methyl-3-[1-(4-pyridin-3-ylphenyl)cyclopropyl]-5,6,8,9-tetrahydro[1,2,4]triazolo[4,3-d][1,4]thiazepin-8-yl}methanol, {(8R)-8-methyl-3-[1-(4-pyridin-3-ylphenyl)cyclopropyl]-5,6,8,9-tetrahydro[1,2,4]triazolo[4,3-d][1,4]thiazepin-8-yl}methanol, 4'-{1-[8-(hydroxymethyl)-8-methyl-5,6,8,9-tetrahydro[1,2,4]triazolo[4,3-d][1,4]thiazepin-3-yl]cyclopropyl}-N,N-dimethylbiphenyl-4-carboxamide, (8R)-4'-{1-[8-(hydroxymethyl)-8-methyl-5,6,8,9-tetrahydro[1,2,4]triazolo[4,3-d][1,4]thiazepin-3-yl]cyclopropyl}-N,N-dimethylbiphenyl-4-carboxamide, 4'-{1-[8-(hydroxymethyl)-8-methyl-5,6,8,9-tetrahydro[1,2,4]triazolo[4,3-d][1,4]thiazepin-3-yl]cyclopropyl}-N,N-dimethylbiphenyl-3-carboxamide, {3-[1-(3-fluoro-4-pyridin-3-ylphenyl)cyclopropyl]-8-methyl-5,6,8,9-tetrahydro[1,2,4]triazolo[4,3-d][1,4]thiazepin-8-yl}methanol, (8-methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl)methanol, {(8R)-8-methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl}methanol, {8-methyl-3-[1-(4-pyrimidin-2-ylphenyl)cyclopropyl]-5,6,8,9-tetrahydro[1,2,4]triazolo[4,3-d][1,4]thiazepin-8-yl}methanol, (8-methyl-3-{1-[4-(5-methylpyrimidin-2-yl)phenyl]cyclopropyl}-5,6,8,9-tetrahydro[1,2,4]triazolo[4,3-d][1,4]thiazepin-8-yl)methanol, {(8R)-8-methyl-3-{1-[4-(5-methylpyrimidin-2-yl)phenyl]cyclopropyl}-5,6,8,9-tetrahydro[1,2,4]triazolo[4,3-d][1,4]thiazepin-8-yl}methanol, 6-(4-{1-[8-(hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide, 6-(4-{1-[(8R)-8-(hydroxymethyl)-8-methyl-5,6,8,9-tetrahydro[1,2,4]thiazepin-3-yl]cyclopropyl}phenyl)-N,N-dimethylnicotinamide, {(8R)-8-methyl-3-{1-[4-(1H-pyrazol-4-yl)phenyl]cyclopropyl}-5,6,8,9-tetrahydro[1,2,4]triazolo[4,3-d][1,4]thiazepin-8-yl}methanol, (3-{1-[4-(1-ethyl-1H-pyrazol-4-yl)phenyl]cyclopropyl}-8-methyl-5,6,8,9-tetrahydro[1,2,4]triazolo[4,3-d][1,4]thiazepin-8-yl)methanol, (3-{1-[2-fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl)methanol, {(8R)-3-{1-[2-fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl}methanol, (8-methyl-3-{1-[4-(1,3-oxazol-2-yl)phenyl]cyclopropyl}-5,6,8,9-tetrahydro[1,2,4]triazolo[4,3-d][1,4]thiazepin-8-yl)methanol, or {(8R)-8-methyl-3-{1-[4-(1,3-oxazol-2-yl)phenyl]cyclopropyl}-5,6,8,9-tetrahydro[1,2,4]triazolo[4,3-d][1,4]thiazepin-8-yl}methanol, (7-2) {(8R)-8-methyl-3-[1-(4-pyridin-3-ylphenyl)cyclopropyl]-5,6,8,9-tetrahydro[1,2,4]triazolo[4,3-d][1,4]thiazepin-8-yl}methanol, (8R)-4'-{1-[8-(hydroxymethyl)-8-methyl-5,6,8,9-tetrahydro[1,2,4]triazolo[4,3-d][1,4]thiazepin-3-yl]cyclopropyl}-N,N-dimethylbiphenyl-4-carboxamide, {(8R)-8-methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl}methanol, {(8R)-8-methyl-3-{1-[4-(5-methylpyrimidin-2-yl)phenyl]cyclopropyl}-5,6,8,9-tetrahydro[1,2,4]triazolo[4,3-d][1,4]thiazepin-8-yl}methanol, 6-(4-{1-[(8R)-8-(hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide, {(8R)-8-methyl-3-{1-[4-(1H-pyrazol-4-yl)phenyl]cyclopropyl}-5,6,8,9-tetrahydro[1,2,4]triazolo[4,3-d][1,4]thiazepin-8-yl}methanol, {(8R)-3-{1-[2-fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl}methanol, or {(8R)-8-methyl-3-{1-[4-(1,3-oxazol-2-yl)phenyl]cyclopropyl}-5,6,8,9-tetrahydro[1,2,4]triazolo[4,3-d][1,4]thiazepin-8-yl}methanol, (7-3) [3-(1-biphenyl-4-ylcyclopropyl)-8-methyl-5,6,8,9-tetrahydro[1,2,4]triazolo[4,3-d][1,4]thiazepin-8-yl]methanol, {8-methyl-3-[1-(4-pyridin-3-ylphenyl)cyclopropyl]-5,6,8,9-tetrahydro[1,2,4]triazolo[4,3-d][1,4]thiazepin-8-yl}methanol, {(8S)-8-methyl-3-[1-(4-pyridin-3-ylphenyl)cyclopropyl]-5,6,8,9-tetrahydro[1,2,4]triazolo[4,3-d][1,4]thiazepin-8-yl}methanol, {(8R)-8-methyl-3-[1-(4-pyridin-3-ylphenyl)cyclopropyl]-5,6,8,9-tetrahydro[1,2,4]triazolo[4,3-d][1,4]thiazepin-8-yl}methanol, 4'-{1-[8-(hydroxymethyl)-8-methyl-5,6,8,9-tetrahydro[1,2,4]triazolo[4,3-d][1,4]thiazepin-3-yl]cyclopropyl}-N,N-dimethylbiphenyl-4-carboxamide, 4'-{1-[8-(hydroxymethyl)-8-methyl-5,6,8,9-tetrahydro[1,2,4]triazolo[4,3-d][1,4]thiazepin-3-yl]cyclopropyl}-N,N-dimethylbiphenyl-3-carboxamide, {3-[1-(3-fluoro-4-pyridin-3-ylphenyl)cyclopropyl]-8-methyl-5,6,8,9-tetrahydro[1,2,4]triazolo[4,3-d][1,4]thiazepin-8-yl}methanol, (8-methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl)methanol, {(8R)-8-methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl}methanol, 6-(4-{1-[8-(hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide, 6-(4-{1-[(8R)-8-(hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide, or {(8R)-3-{1-[2-fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl}methanol, (8) {(8R)-8-methyl-3-[1-(4-pyridin-3-ylphenyl)cyclopropyl]-5,6,8,9-tetrahydro[1,2,4]triazolo[4,3-d][1,4]thiazepin-8-yl}methanol represented by the following formula:

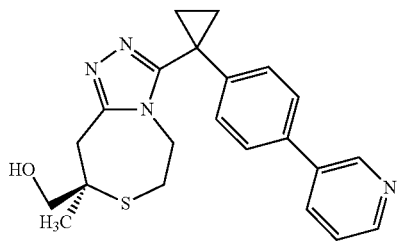 [SMILES: C[C@]1(CO)Cc2nnc(C3(c4ccc(-c5cccnc5)cc4)CC3)n2CCS1]

(8R)-(9){3-[1-(3-fluoro-4-pyridin-3-ylphenyl)cyclopropyl]-8-methyl-5,6,8,9-tetrahydro[1,2,4]triazolo[4,3-d][1,4]thiazepin-8-yl}methanol represented by the following formula:

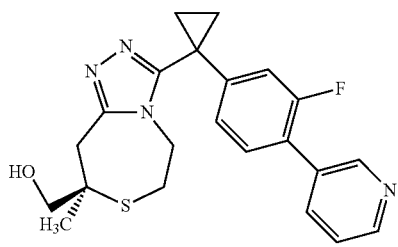 [SMILES: C[C@]1(CO)Cc2nnc(C3(c4ccc(-c5cccnc5)c(F)c4)CC3)n2CCS1]

(10) {(8R)-8-methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl}methanol represented by the following formula:

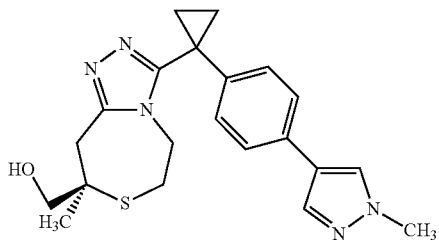 [SMILES: Cn1cc(-c2ccc(C3(c4nnc5n4CCS[C@@](C)(CO)C5)CC3)cc2)cn1]

(11) 6-(4-{1-[(8R)-8-(hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide represented by the following formula:

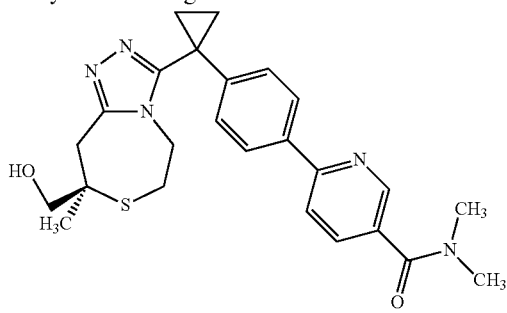

(12) {(8R)-3-{1-[2-fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl}methanol represented by the following formula:

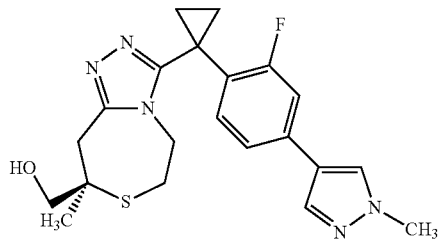 [SMILES: Cn1cc(-c2ccc(C3(c4nnc5n4CCS[C@@](C)(CO)C5)CC3)c(F)c2)cn1]

(13) [(8R)-8-methyl-3-{1-[4-(2-methylpyrimidin-5-yl)phenyl]cyclopropyl}-5,6,8,9-tetrahydro[1,2,4]triazolo[4,3-d][1,4]thiazepin-8-yl]methanol represented by the following formula:

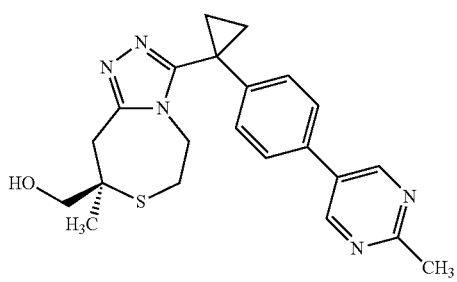 [SMILES: Cc1ncc(-c2ccc(C3(c4nnc5n4CCS[C@@](C)(CO)C5)CC3)cc2)cn1]

(14) [(8R)-3-{1-[2-fluoro-4-6-methylpyridazin-3-yl)phenyl]cyclopropyl}-8-methyl-5,6,8,9-tetrahydro[1,2,4]triazolo[4,3-d][1,4]thiazepine-8-yl]methanol represented by the following formula:

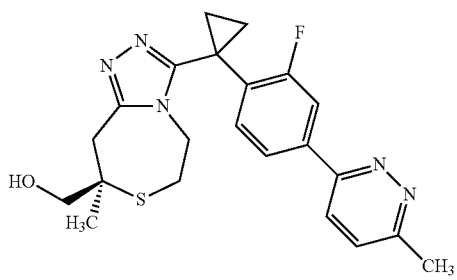 [SMILES: Cc1ccc(-c2ccc(C3(c4nnc5n4CCS[C@@](C)(CO)C5)CC3)c(F)c2)nn1]

(15) a pharmacologically acceptable salt of the compound according to any one of (7) to (14) above,

(16) an 11β-hydroxysteroid dehydrogenase type 1 inhibitor containing the compound or a pharmacologically acceptable salt thereof according to any one of (1) to (15) above as an active ingredient,

(17) a pharmaceutical composition containing the compound or a pharmacologically acceptable salt thereof according to any one of (1) to (15) above as an active ingredient, (17-2) the pharmaceutical composition, according to (17) above, which has the effect of inhibiting 11β-hydroxysteroid dehydrogenase type 1, (17-3) the pharmaceutical composition according to (17) above for therapeutic or prophylactic treatment of diabetes, insulin resistance, diabetic complications, adiposity, dyslipidemia, hyperlipidemia, hypertension, fatty liver, metabolic syndrome, atherosclerosis, dementia, osteoporosis, Cushing's syndrome, or glaucoma, (17-4) the pharmaceutical composition according to (17) above for therapeutic and/or prophylactic treatment of diabetes, (17-5) the pharmaceutical composition according to (17) above for therapeutic or prophylactic treatment of diabetic complications, dementia, or Cushing's syndrome,

(18) the pharmaceutical composition according to (17) above for therapeutic or prophylactic treatment of type 2 diabetes or improvement of insulin resistance,

(19) the pharmaceutical composition according to (17) above for therapeutic or prophylactic treatment of dyslipidemia or hyperlipidemia,

(20) the pharmaceutical composition according to (17) above, which is used for therapeutic or prophylactic treatment of hypertension,

(21) the pharmaceutical composition according to (17) above for therapeutic or prophylactic treatment of adiposity, fatty liver, atherosclerosis, osteoporosis, or glaucoma,

(22) use of the compound or a pharmacologically acceptable salt thereof according to any one of (1) to (15) above for production of a pharmaceutical composition, (22-2) the use according to (22) above, wherein the pharmaceutical composition is a pharmaceutical composition for therapeutic or prophylactic treatment of diabetes, insulin resistance, diabetic complications, adiposity, dyslipidemia, hyperlipidemia, hypertension, fatty liver, metabolic syndrome, atherosclerosis, dementia, osteoporosis, Cushing's syndrome, or glaucoma, (22-3) the use according to (22) above, wherein the pharmaceutical composition is a pharmaceutical composition for inhibiting 11β-hydroxysteroid dehydrogenase type 1, (22-4) the use according to (22) above, wherein the pharmaceutical composition is a pharmaceutical composition for therapeutic and/or prophylactic treatment of diabetes,

(23) a method for therapeutic or prophylactic treatment of a disease related to 11β-hydroxysteroid dehydrogenase type 1, comprising administering a pharmacologically effective amount of the compound or a pharmacologically acceptable salt thereof according to any one of (1) to (15) above to a homeotherm, (23-2) the method according to (23) above, wherein the disease is diabetes, insulin resistance, diabetic complications, adiposity, dyslipidemia, hyperlipidemia, hypertension, fatty liver, metabolic syndrome, atherosclerosis, dementia, osteoporosis, or glaucoma, (23-3) the method according to (23) above, wherein the disease is type 2 diabetes, (23-4) a method for inhibiting 11β-hydroxysteroid dehydrogenase type 1 comprising administering a pharmacologically effective amount of the compound or a pharmacologically acceptable salt thereof according to any one of (1) to (15) above to a homeotherm, (23-5) the method according to (23) above, wherein the homeotherm is a human,

(24) (7R)-7-({[t-butyl(dimethyl)silyl]oxy}methyl)-7-methyl-1,4-thiazepane-5-thione represented by the following formula:

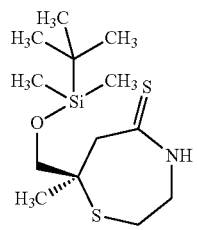 [SMILES: CC(C)(C)[Si](C)(C)OC[C@@]1(C)CC(=S)NCCS1]

(25) (7R)-7-({[t-butyl(dimethyl)silyl]oxy}methyl)-7-methyl-5-methylthio-2,3,6,7-tetrahydro-1,4-thiazepine represented by the following formula:

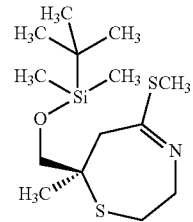

(25-2) a method for producing a compound represented by the general formula (Ia) or a pharmacologically acceptable salt thereof, comprising the following steps in which (7R)-7-({[t-butyl(dimethyl)silyl]oxy}methyl)-7-methyl-1,4-thiazepane-5-thione is a starting material and (7R)-7-({[t-butyl(dimethyl)silyl]oxy}methyl)-7-methyl-5-methylthio-2,3,6,7-tetrahydro-1,4-thiazepine is an intermediate:

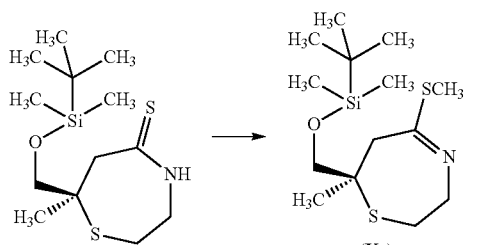

(Xa)

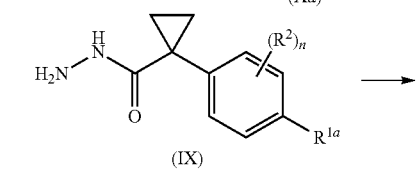

(IX)

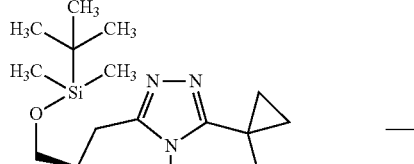

(XIa)

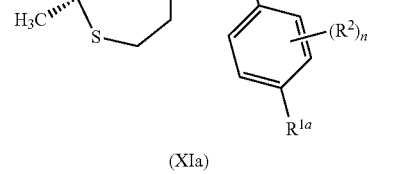

(Ia)

wherein $R^{1a}$ represents the same group as those defined for $R^1$, except that an amino group, a hydroxy group, and/or a carboxy group included in the $R^1$ group as a substituent is an amino group, a hydroxy group, and/or a carboxy group that may be protected, $R^2$ independently represents a halogen atom or a $C_1$-$C_6$ alkyl group, and n represents 0, 1, or 2, (25-3) a method for producing a compound represented by the general formula (Ia) or a pharmacologically acceptable salt thereof, comprising the following steps using (7R)-7-({[t-butyl(dimethyl)silyl]oxy}methyl)-7-methyl-5-methylthio-2,3,6,7-tetrahydro-1,4-thiazepine:

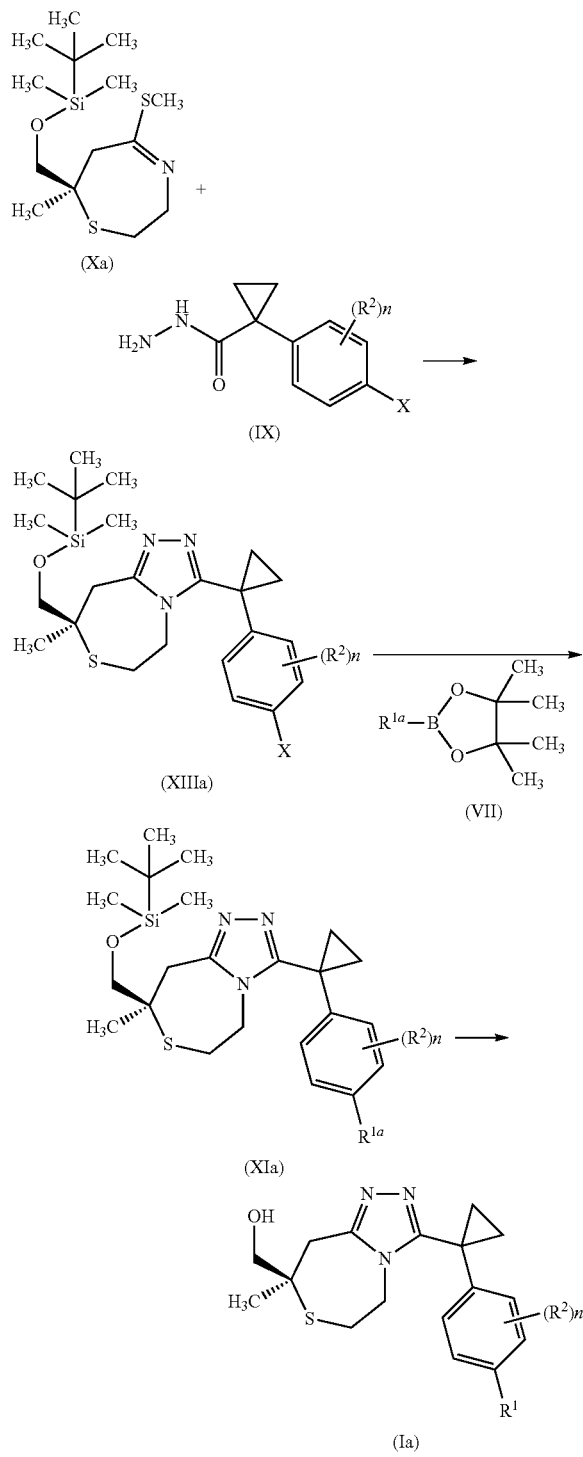

wherein $R^{1a}$ represents the same group as those defined for $R^1$, except that an amino group, a hydroxy group, and/or a carboxy group included in the $R^1$ group as a substituent is an amino group, a hydroxy group, and/or a carboxy group that may be protected, $R^2$ independently represents a halogen atom or a $C_1$-$C_6$ alkyl group, and n represents 0, 1, or 2, (25-4) the production method according to (25-2) above, wherein (7R)-7-({[t-butyl(dimethyl)silyl]oxy}methyl)-7-methyl-5-methylthio-2,3,6,7-tetrahydro-1,4-thiazepine produced with (7R)-7-({[t-butyl(dimethyl)silyl]oxy}methyl)-7-methyl-1,4-thiazepane-5-thione and an alkylating agent is used as a starting material, (25-5) (7R)-7-({[t-butyl(dimethyl)silyl]oxy}methyl)-7-methyl-1,4-thiazepane-5-thione which is an intermediate of the production method according to (25-2) or (25-4) above, and (25-6) (7R)-7-({[t-butyl(dimethyl)silyl]oxy}methyl)-7-methyl-5-methylthio-2,3,6,7-tetrahydro-1,4-thiazepine which is an intermediate of the production method according to (25-2), (25-3), or (25-4) above.

In the present invention, "halogen atom" means a fluorine atom, a chlorine atom, a bromine atom, or an iodine atom, preferably a fluorine atom or a chlorine atom, more preferably a fluorine atom.

In the present invention, "$C_1$-$C_6$ alkyl group" means a straight or branched alkyl group having 1 to 6 carbon atoms. Examples thereof include a methyl group, an ethyl group, a propyl group, an isopropyl group, a butyl group, an isobutyl group, an s-butyl group, a t-butyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, and a 1,2-dimethylbutyl group. Straight or branched alkyl groups having 1 to 4 carbons ($C_1$-$C_4$ alkyl group) are preferred, a methyl group and an ethyl group ($C_1$-$C_2$ alkyl groups) are more preferred, and a methyl group is yet more preferred.

In the present invention, "$C_1$-$C_6$ halogenated alkyl group" means a group in which 1 to 5 of the above-mentioned "halogen atoms" that are identical to or different from each other bind to the above-mentioned "$C_1$-$C_6$ alkyl group". Examples thereof include a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, a 2-bromoethyl group, a 2-chloroethyl group, and a 2-fluoroethyl group. Groups in which 1 to 5 of the above-mentioned "halogen atoms" that are identical to or different from each other bind to the above-mentioned "$C_1$-$C_4$ alkyl group" ($C_1$-$C_4$ halogenated alkyl groups) are preferred, groups in which 1 to 5 of the above-mentioned "halogen atoms" that are identical to or different from each other bind to the above-mentioned "$C_1$-$C_2$ alkyl group" ($C_1$-$C_2$ halogenated alkyl groups) are more preferred, and a trifluoromethyl group is yet more preferred.

In the present invention, "$C_1$-$C_6$ alkoxy group" means a group in which the above-mentioned "$C_1$-$C_6$ alkyl group" binds to an oxygen atom, specifically a straight or branched alkoxy group having 1 to 6 carbon atoms. Examples thereof include a methoxy group, an ethoxy group, a propoxy group, an isopropoxy group, a butoxy group, an isobutoxy group, an s-butoxy group, a t-butoxy group, a pentoxy group, a 2-methylbutoxy group, a 3-ethylpropoxy group, a neopentoxy group, a hexyloxy group and a 2,3-dimethylbutoxy group. Straight or branched alkoxy groups having 1 to 4 carbon atoms ($C_1$-$C_4$ alkoxy groups) are preferred, a methoxy group and an ethoxy group ($C_1$-$C_2$ alkoxy groups) are more preferred, and a methoxy group is yet more preferred.

In the present invention, "$C_2$-$C_7$ carboxyalkyl group" means a group in which one carboxy group binds to the above-mentioned "$C_1$-$C_6$ alkyl group". Examples thereof include a carboxymethyl group, a 2-carboxyethyl group, a 1-carboxyethyl group, and a 3-carboxypropyl group. Groups in which one carboxy group binds to the above-mentioned "$C_1$-$C_2$ carboxyalkyl group" ($C_2$-$C_3$ carboxyalkyl groups) are preferred, and a carboxymethyl group is more preferred.

In the present invention, "$C_2$-$C_7$ alkylcarbonyl group" means a group in which one of the above-mentioned "$C_1$-$C_6$ alkyl group" binds to a carbonyl group. Examples thereof include an acetyl group, a propionyl group, a butyryl group, an isobutyryl group, a pentanoyl group, a pivaloyl group, and a valeryl group. Groups in which one of the above-mentioned "$C_1$-$C_4$ alkyl group" binds to a carbonyl group ($C_2$-$C_5$ alkylcarbonyl groups) are preferred, an acetyl group and a propionyl group ($C_2$-$C_3$ alkylcarbonyl groups) are more preferred, and an acetyl group is yet more preferred.

In the present invention, "$C_2$-$C_7$ alkoxycarbonyl group" means a group in which one of the above-mentioned "$C_1$-$C_6$ alkoxy group" binds to a carbonyl group. Examples thereof include a methoxycarbonyl group, an ethoxycarbonyl, a propoxycarbonyl group, an isopropoxycarbonyl group, a butoxycarbonyl group, an isobutoxycarbonyl group, an s-butoxycarbonyl group, and a t-butoxycarbonyl group. Groups in which one of the above-mentioned "$C_1$-$C_4$ alkoxy group" binds to a carbonyl group ($C_2$-$C_5$ alkoxycarbonyl groups) are preferred, a methoxycarbonyl group and an ethoxycarbonyl group ($C_2$-$C_3$ alkoxycarbonyl groups) are more preferred, and a methoxycarbonyl group is yet more preferred.

In the present invention, "$C_1$-$C_6$ alkylsulfonyl group" means a group in which one of the above-mentioned "$C_1$-$C_6$ alkyl group" binds to a sulfonyl group, specifically a straight or branched alkylsulfonyl group having 1 to 6 carbon atoms. Examples thereof include a methylsulfonyl group, an ethylsulfonyl group, a propylsulfonyl group, an isopropylsulfonyl group, a butylsulfonyl group, an isobutylsulfonyl group, an s-butylsulfonyl, and a pentylsulfonyl group. Straight or branched alkylsulfonyl groups having 1 to 4 carbon atoms ($C_1$-$C_4$ alkylsulfonyl groups) are preferred, a methylsulfonyl group and an ethylsulfonyl group ($C_1$-$C_2$ alkylsulfonyl groups) are more preferred, and a methylsulfonyl group is yet more preferred.

In the present invention, "$C_3$-$C_6$ cycloalkyl group" means a cyclopropyl group, a cyclobutyl group, a cyclopentyl group, or a cyclohexyl group. A cyclopropyl group is preferred.

In the present invention, "group represented by the formula —C(=O)—NR$^3$R$^4$ (R$^3$ and R$^4$ are identical to or different from each other and each independently represents a hydrogen atom, a $C_1$-$C_6$ alkyl group, or a $C_3$-$C_6$ cycloalkyl group, or R$^3$ and R$^4$ form a 4 to 6-membered saturated heterocyclic ring together with the nitrogen atom bound therewith, wherein the 4 to 6-membered saturated heterocyclic ring may further contain one oxygen atom)" means a "group represented by the formula —C(=O)—NR$^3$R$^4$ (R$^3$ and R$^4$ are identical to or different from each other and each independently represents a hydrogen atom, a $C_1$-$C_6$ alkyl group, or a $C_3$-$C_6$ cycloalkyl group)" or a "group represented by the formula —C(=O)—NR$^3$R$^4$ (R$^3$ and R$^4$ form a 4 to 6-membered saturated heterocyclic ring together with the nitrogen atom bound therewith, wherein the 4 to 6-membered saturated heterocyclic ring may further contain one oxygen atom)".

The "group represented by the formula —C(=O)—NR$^3$R$^4$ (R$^3$ and R$^4$ are identical to or different from each other and each independently represents a hydrogen atom, a $C_1$-$C_6$ alkyl group, or a $C_3$-$C_6$ cycloalkyl group)" means a carbamoyl group, a "mono-$C_1$-$C_6$ alkylaminocarbonyl group (group in which an amino group bound with an above-mentioned "$C_1$-$C_6$ alkyl group" binds to a carbonyl group)", a "mono-$C_3$-$C_6$ cycloalkylaminocarbonyl group (group in which an amino group bound with an above-mentioned "$C_3$-$C_6$ cycloalkyl group" binds to a carbonyl group)", a "di-($C_1$-$C_6$ alkyl)aminocarbonyl group (group in which an amino group bound with two of the above-mentioned "$C_1$-$C_6$ alkyl groups" that are identical to or different from each other binds to a carbonyl group)", a "di-($C_3$-$C_6$ cycloalkyl)aminocarbonyl group (group in which an amino group bound with two of the above-mentioned "$C_3$-$C_6$ cycloalkyl groups" that are identical to or different from each other binds to a carbonyl group)", or a "N—($C_1$-$C_6$ alkyl)-N—($C_3$-$C_6$ cycloalkyl)aminocarbonyl group (group in which an amino group bound with the above-mentioned "$C_1$-$C_6$ alkyl group" and the above-mentioned "$C_3$-$C_6$ cycloalkyl group" binds to a carbonyl group)". Examples thereof include a carbamoyl group, a methylaminocarbonyl group, an ethylaminocarbonyl group, a propylaminocarbonyl group, a cyclopropylaminocarbonyl group, a cyclobutylaminocarbonyl group, a dimethylaminocarbonyl group, a diethylaminocarbonyl group, a dipropylaminocarbonyl group, an N-ethyl-N-methylaminocarbonyl group, an N-methyl-N-propylaminocarbonyl group, a dicyclopropylaminocarbonyl group, a dicyclobutylaminocarbonyl group, an N-cyclobutyl-N-cyclopropylaminocarbonyl group, an N-cyclopropyl-N-methylaminocarbonyl group, and an N-cyclopropyl-N-ethylaminocarbonyl group. A carbamoyl group, a methylaminocarbonyl group, an ethylaminocarbonyl group, a cyclopropylaminocarbonyl group, a dimethylaminocarbonyl group, and an N-ethyl-N-methylaminocarbonyl group are preferred, and a dimethylaminocarbonyl group is more preferred.

Examples of the "group represented by the formula —C(=O)—NR$^3$R$^4$ (R$^3$ and R$^4$ form a 4 to 6-membered saturated heterocyclic ring together with the nitrogen atom bound therewith, wherein the 4 to 6-membered saturated heterocyclic ring may further contain one oxygen atom)" include a (1-azetidinyl)carbonyl group, a (1-pyrrolidinyl)carbonyl group, a (1-piperidyl)carbonyl group, and a (4-morpholinyl)carbonyl group. A (1-pyrrolidinyl)carbonyl group, a (1-piperidyl)carbonyl group, and a (4-morpholinyl)carbonyl group are preferred.

In the present invention, "mono-$C_2$-$C_7$ alkoxycarbonylamino group" means a group in which a carbonyl group bound with an above-mentioned "$C_1$-$C_6$ alkoxy group" binds to an amino group. Examples thereof include a methoxycarbonylamino group, an ethoxycarbonylamino group, a propoxycarbonylamino group, an isopropoxycarbonylamino group, and a butoxycarbonylamino group. A methoxycarbonylamino group and an ethoxycarbonylamino group ($C_2$-$C_3$ alkoxycarbonylamino groups) are preferred, and a methoxycarbonylamino group is more preferred.

In the present invention, "heterocyclic ring" means a 4 to 7-membered heterocyclic ring that includes 1 to 3 sulfur atoms, oxygen atoms or/and nitrogen atoms and may further include 1 or 2 nitrogen atoms, in which the sulfur atom may bind to 2 oxygen atoms. Examples thereof include "aromatic heterocyclic rings" such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,3,4-oxadiazolyl group, a 1,3,4-thiadiazolyl group, a triazolyl group, a tetrazolyl group, a thiadiazolyl group, a pyranyl group, a pyridyl group, a pyridazinyl group, a pyrimidinyl group, and a pyrazinyl group and "partially or completely reduced saturated heterocyclic rings" such as a tetrahydropyranyl group, a tetrahydrothienyl group, a morpholinyl group, thiomorpholinyl group, a pyrrolidinyl group, a pyrrolinyl group, an imidazolidinyl group, a pyrazolidinyl group, a piperidinyl group, a piperazinyl group, an oxazolinyl group, an oxazolidinyl group, an isoxazolidinyl group, a thiazolinyl group, a thiazolidinyl group, a pyrazolidinyl group, a dioxolanyl group, dioxanyl group, and a 5,6-dihydro-4H-1,3-oxazine group. The above-mentioned heterocyclic ring may be condensed with another cyclic group such as a benzene ring ("condensed bicyclic heterocyclic ring"), and examples thereof include a benzothienyl group, a benzothiazolyl group, a benzoxazolyl group, an isobenzofuranyl group, a 1,3-dihydroisobenzofuranyl group, a quinolyl group, a 1,3-benzodioxolanyl group, a 1,4-benzodioxanyl group, an indolyl group, an isoindolyl group, and an indolinyl group. 5 or 6-Membered aromatic heterocyclic groups are preferred, a pyridyl group, a pyridazinyl group, a pyrimidinyl group, a pyrazinyl group, an oxazolyl group, an isoxazolyl group, a pyrazolyl group, an imidazolyl group, and a thiazolyl group are more preferred, a pyridyl group, a pyrimidinyl group, an oxazolyl group, and a pyrazolyl group are yet more preferred, and a 2-pyridyl group, a 3-pyridyl group, a 2-pyrimidinyl group, and a 4-pyrazolyl group are particularly preferred.

In the present invention, "phenyl group that may be substituted with 1 to 5 group(s) independently selected from substituent group A" means a phenyl group or a phenyl group substituted with 1 to 5 group(s) independently selected from substituent group A. A phenyl group that may be substituted with one group (the group is a methyl group, an ethyl group, or a dimethylaminocarbonyl group) is preferred, a 4-dimethylaminocarbonylphenyl group and a 3-dimethylaminocarbonylphenyl group are more preferred, and a 4-dimethylaminocarbonylphenyl group is yet more preferred.

In the present invention, "heterocyclic group that may be substituted with 1 to 4 group(s) independently selected from substituent group A" means a heterocyclic group or a heterocyclic group substituted with 1 to 4 group(s) independently selected from substituent group A. A 2-pyridyl group, a 3-pyridyl group, a 2-pyrimidinyl group, a 2-oxazolyl group, or a 4-pyrazolyl group that may be substituted with one group (the group is a methyl group, an ethyl group, or a dimethylaminocarbonyl group) is preferred, a 3-pyridyl group, a 4-dimethylaminocarbonyl-2-pyridyl group, a 2-pyrimidinyl group, a 5-methyl-2-pyrimidinyl group, a 2-oxazolyl group, a 4-pyrazolyl group, a 1-methyl-4-pyrazolyl group, and a 1-ethyl-4-pyrazolyl group are more preferred, and a 3-pyridyl group, a 4-dimethylaminocarbonyl-2-pyridyl group, a 5-methyl-2-pyrimidinyl group, a 2-oxazolyl group, a 4-pyrazolyl group, and a 1-methyl-4-pyrazolyl group are yet more preferred.

In the present invention, the general formula (I) is preferably the general formula (Ia).

In the present invention, $R^1$ preferably represents a phenyl group, a 2-pyridyl group, a 3-pyridyl group, a 2-pyrimidinyl group, or a 4-pyrazolyl group that may be substituted with one group (the group is a methyl group or a dimethylaminocarbonyl group), more preferably a 4-dimethylaminocarbonylphenyl group, a 3-dimethylaminocarbonylphenyl group, a 3-pyridyl group, a 4-dimethylaminocarbonyl-2-pyridyl group, a 2-pyrimidinyl group, a 5-methyl-2-pyrimidinyl group, a 4-pyrazolyl group, a 1-methyl-4-pyrazolyl group, or a 1-ethyl-4-pyrazolyl group, yet more preferably a 4-dimethylaminocarbonylphenyl group, a 3-pyridyl group, a 4-dimethylaminocarbonyl-2-pyridyl group, a 5-methyl-2-pyrimidinyl group, a 4-pyrazolyl group, or a 1-methyl-4-pyrazolyl group.

In the present invention, $R^2$ preferably represents a halogen atom, more preferably a fluorine atom.

In the present invention, n preferably represents 0 or 1.

In the present invention, substituent group A preferably represents the group consisting of halogen atoms, $C_1$-$C_6$ alkyl groups, $C_1$-$C_6$ halogenated alkyl groups, $C_1$-$C_6$ alkoxy groups, a carboxy group, a cyano group, groups represented by the formula —C(=O)—NR$^3$R$^4$ (R$^3$ and R$^4$ are identical to or different from each other and each independently represents a hydrogen atom, a $C_1$-$C_6$ alkyl group, or a $C_3$-$C_6$ cycloalkyl group, or $R^3$ and $R^4$ form a 4 to 6-membered saturated heterocyclic ring together with the nitrogen atom bound therewith, wherein the 4 to 6-membered saturated heterocyclic ring may further contain one oxygen atom), and an oxo group.

The compound represented by the general formula (I) of the present invention or a pharmacologically acceptable salt thereof includes all isomers (keto-enol isomer, diastereoisomer, optical isomer, rotational isomer, etc.).

The compound represented by the general formula (I) of the present invention or a pharmacologically acceptable salt thereof has various isomers because asymmetric carbon atoms exist in the molecule. In the compound of the present invention, these isomers and mixtures of these isomers are represented by a single formula, that is the general formula (I). Therefore, the present invention also includes all these isomers and mixtures of these isomers in arbitrary ratios.

The above-mentioned stereoisomers can be obtained by isolating the synthesized compound of the present invention by a usual optical resolution or isolation method as desired.

The compound represented by the general formula (Ia) of the present invention or a pharmacologically acceptable salt thereof is more preferred than a compound represented by the general formula (Ib) or a pharmacologically acceptable salt thereof.

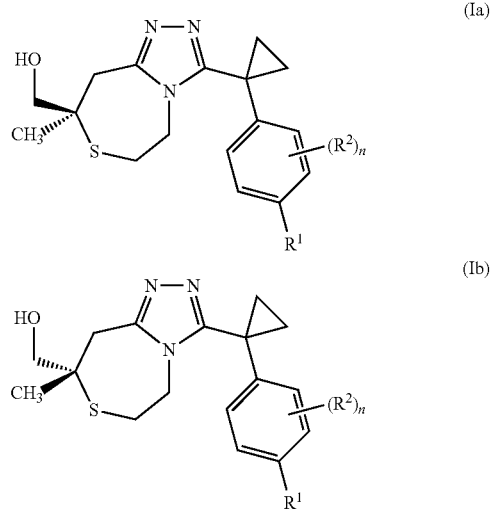

The compound represented by the general formula (I) of the present invention or a pharmacologically acceptable salt thereof may contain isotope(s) of one or more atom(s) constituting such a compound at a nonnatural ratio. Examples of the isotope include deuterium ($^2$H), tritium ($^3$H), iodine-125 ($^{125}$I), and carbon-14 ($^{14}$C). Furthermore, the compound may be radiolabeled with a radioisotope, for example, tritium ($^3$H), iodine-125 ($^{125}$I), or carbon-14 ($^{14}$C). Such a radiolabeled compound is useful as a therapeutic or prophylactic agent, a research reagent, for example an assay reagent, and a diagnostic agent, for example an in vivo diagnostic imaging agent. All isotopic variants of the compound of the present invention fall within the scope of the present invention, regardless of being radioactive or not.

"Pharmacologically acceptable salt thereof" refers to a salt that can be used as a medicament without significant toxicity. The compound represented by the general formula (I) of the present invention or the pharmacologically acceptable salt thereof can form a salt by reacting with an acid when it has a basic group or by reacting with a base when it has an acidic group.

Examples of salts of a basic group include inorganic acid salts including hydrohalides such as hydrofluorides, hydrochlorides, hydrobromides, and hydroiodides, nitrates, perchlorates, sulfates, and phosphates; organic acid salts including alkylsulfonic acid salts such as methanesulfonates, trifluoromethanesulfonates, and ethanesulfonates, arylsulfonic acid salts such as benzenesulfonates and p-toluenesulfonates, acetates, malates, fumarates, succinates, citrates, ascorbates, tartarates, oxalates, and maleates; and amino acid salts such as glycine salts, lysine salts, arginine salts, ornithine salts, glutamic acid salts, and aspartic acid salts.

Meanwhile, examples of salts of an acidic group include metal salts including alkali metal salts such as sodium salts, potassium salts, and lithium salts, alkaline earth metal salts such as calcium salts and magnesium salts, aluminium salts, and iron salts; and amine salts including inorganic salts such as ammonium salts and organic salts such as t-octylamine salts, dibenzylamine salts, morpholine salts, glucosamine salts, phenyl glycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanol amine salts, N-benzylphenethylamine salts, piperazine salts, tetramethyl ammonium salts, and tris(hydroxymethyl)aminomethane salts; and amino acid salts such as glycine salts, lysine salts, arginine salts, ornithine salts, glutamic acid salts, and aspartic acid salts.

When the compound represented by the general formula (I) of the present invention or a pharmacologically acceptable salt thereof is left in the atmosphere or recrystallized, a hydrate may be formed due to absorption of moisture or attachment of adsorbed water. Such hydrates also fall within the salts of the present invention.

The compound represented by the general formula (I) of the present invention or a pharmacologically acceptable salt thereof having the general formula (I) of the present invention may absorb other specific solvents to form solvates, and such solvates also fall within the salts of the present invention.

The compound represented by the general formula (I) of the present invention or the pharmacologically acceptable salt thereof is preferably the compound represented by the general formula (Ia) of the present invention.

In the present invention, "metabolic syndrome" means a condition in which the risk of coronary artery disease is significantly increased by a combination of a plurality of coronary risk factors based on insulin resistance (hyperlipidemia, diabetes, adiposity, hypertension, and so forth, which are lifestyle-related diseases) (Diabetes, Obesity and Metabolism, 9, 2007, 246-258, Journal of the American Medical Association, 285: 2486-2497 (2001), and Diabet. Med., 15: 539-553 (1998)).

Advantageous Effects of Invention

The novel tetrahydrothiazepine derivative represented by the general formula (I) of the present invention or a pharmacologically acceptable salt thereof has an excellent effect of inhibiting 11β-HSD1 and is useful as a medicament for prophylactic and/or therapeutic treatment of a disease in a homeotherm (preferably a mammal including a human) selected from the group consisting of the following diseases: diabetes, insulin resistance, diabetic complications, adiposity, dyslipidemia, hyperlipidemia, hypertension, fatty liver, metabolic syndrome, atherosclerosis, dementia, osteoporosis, Cushing's syndrome, and glaucoma. Preferably, the tetrahydrothiazepine derivative or a pharmacologically acceptable salt thereof can be used as a medicament for therapeutic treatment of the above-mentioned diseases.

DESCRIPTION OF EMBODIMENTS

The compound having the general formula (I) of the present invention can be produced by Methods A to C described below.

Solvents used for the reactions in each step of the following Methods A to C are not particularly limited so long as they do not inhibit the reaction and dissolve a starting material to a predetermined extent and are selected from the following solvent group, for example. The solvent group includes hydrocarbons such as pentane, hexane, octane, petroleum ether, ligroin, and cyclohexane; amides such as formamide, N,N-dimethylformamide, N,N-dimethylacetamide, N-methyl-2-pyrrolidone, N-methyl-2-pyrrolidinone, and hexamethylphosphoric acid triamide; ethers such as diethyl ether, diisopropyl ether, tetrahydrofuran, dioxane, dimethoxyethane, diethylene glycol dimethyl ether, cyclopentyl methyl ether; alcohols such as methanol, ethanol, n-propanol, i-propanol, n-butanol, 2-butanol, 2-methyl-1-propanol, t-butanol, isoamyl alcohols, diethylene glycol, glycerine, octanol, cyclohexanol, and methyl cellosolve; sulfoxides such as dimethyl sulfoxide; sulfones such as sulfolane; nitriles such as acetonitrile, propionitrile, butyronitrile, and isobutyronitrile; esters such as ethyl formate, ethyl acetate, propyl acetate, butyl acetate, and diethyl carbonate; ketones such as acetone, methyl ethyl ketone, 4-methyl-2-pentanone, methyl isobutyl ketone, isophorone, and cyclohexanone; nitrogen compounds such as nitroethane and nitrobenzene; halogenated hydrocarbons such as dichloromethane, 1,2-dichloroethane, chlorobenzene, dichlorobenzene, chloroform, and carbon tetrachloride; aromatic hydrocarbons such as benzene, toluene, and xylene; carboxylic acids such as acetic acid, formic acid, propionic acid, butyrylic acid, and trifluoroacetic acid; amines such as N-methylmorpholine, triethylamine, tripropylamine, tributylamine, diisopropylethylamine, dicyclohexylamine, N-methylpiperidine, pyridine, 2,6-lutidine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU), and piperidine; water; and mixed solvents thereof.

Examples of bases used for the reactions in each step of the following Methods A to C include alkali metal carbonates such as sodium carbonate, potassium carbonate, lithium carbonate, and cesium carbonate; alkali metal acetates such as sodium acetate, potassium acetate, lithium acetate, and cesium acetate; alkali metal hydrogen carbonates such as sodium hydrogencarbonate, potassium hydrogencarbonate, and lithium hydrogencarbonate; alkali metal hydrides such as lithium hydride, sodium hydride, and potassium hydride; alkali metal hydroxide such as sodium hydroxide, potassium hydroxide, and lithium hydroxide; alkali metal fluorides such as sodium fluoride and potassium fluoride; alkali metal alkoxides such as sodium methoxide, sodium ethoxide, sodium-t-butoxide, and potassium t-butoxide; alkali metal trialkyl siloxides such as sodium trimethyl siloxide, potassium trimethyl siloxide, and lithium trimethyl siloxide; organic bases such as N-methylmorpholine, triethylamine, tripropylamine, tributylamine, diisopropylethylamine, dicyclohexylamine, N-methylpiperidine, pyridine, 2,6-lutidine, collidine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), and 1,8-diazabicyclo[5.4.0]undec-7-ene (DBU); organic metal bases such as lithium diisopropyl amide, and lithium bis(trimethylsilyl)amide; and amino acids such as proline.

Examples of condensing agents used for the reactions in each step of the following Methods A to C include o-(7-azabenzotriazol-1-yl)-N,N,N',N'-tetramethyluronium hexafluorophosphate (HATU), 1-propanephosphonic acid cyclic anhydride (T3P), dicyclohexylcarbodiimide (DCCD), 1-ethyl-3-(3-dimethylaminopropyl)carbodiimide hydrochloride (WSC, WSCI.HCl, or EDCI), 1-ethyl-3-(3-dimethylaminopropyl)carbodiimide (EDAC), 4-(4,6-dimethoxy-1,3,5-triazin-2-yl)-4-methylmorpholinium chloride n-hydrate (DMT-MM), isobutyl chloroformate (IBCF), 1,1'-carbonyl bis-1H-imidazole (CDI), diethyl phosphorocyanidate (DEPC), diphenyl phosphorazidate (DPPA), N-hydroxysuccinimide, N-hydroxy-5-norbornene-2,3-dicarboxylmide, and dipyridyl disulfide. If necessary, 1-hydroxybenzotriazole (HOBt) or 1-hydroxybenzotriazole monohydrate (HOBt.H$_2$O) can be co-used.

Examples of the palladium catalysts used for the reactions in each step of the following Methods A to C include zerovalent or divalent palladium catalysts such as tetrakis(triphenylphosphine)palladium(0), palladium-active carbon, palladium(II) acetate, palladium(II) trifluoroacetate, palladium black, palladium(II) bromide, palladium(II) chloride, palladium(II) iodide, palladium(II) cyanide, palladium(II) nitrate, palladium(II) oxide, palladium(II) sulfate, dichlorobis(acetonitrile)palladium(II), dichlorobis(benzonitrile)palladium(II), dichloro(1,5-cyclooctadiene)palladium(II), acetyl acetone palladium(II), palladium(II) sulfide, [1,1'-bis(diphenylphosphino)ferrocene]palladium(II) dichloride, tris(dibenzylideneacetone)dipalladium(0), tetrakis(acetonitrile)palladium(II) tetrafluoroborate, and aryl chloride palladium dimer.

Examples of the acids used for the reactions in each step of the following Methods A to C include hydrogen halides such as hydrogen chloride gas and hydrogen bromide gas; mineral acids such as sulfuric acid, hydrobromic acid, and hydrochloric acid; organic sulfonic acids such as methanesulfonic acid, p-toluenesulfonic acid, pyridinium p-toluenesulfonate (PPTS), camphor sulfonic acid, and trifluoromethanesulfonic acid; carboxylic acids such as acetic acid, formic acid, and trifluoroacetic acid; Lewis acids such as aluminium chloride, zinc chloride, zinc iodide, tin tetrachloride, titanium trichloride, boron trifluoride, and boron tribromide; methyl sulfate; and acidic ion exchange resins.

In the reactions in each step of the following Methods A to C, the reaction temperature varies depending on solvents, starting materials, reagents, and the like, and the reaction time varies depending on solvents, starting materials, reagents, reaction temperature, and the like.

In the reactions in each step of the following Methods A to C, after completion of the reaction, each target compound is collected from the reaction mixture according to a usual method. For example, a target compound is obtained by suitably neutralizing the reaction mixture or removing insoluble matter, if any exists, by filtration, then adding organic solvents that do not mix with each other, such as water and ethyl acetate, to isolate an organic layer containing a target compound, washing the organic layer with water or the like, drying with anhydrous magnesium sulfate, anhydrous sodium sulfate, or the like, filtering, and then evaporating the solvents. If necessary, the resulting target compound can be isolated and purified by a usual method, for example, by suitably using common methods for isolation and purification of an organic compound, such as recrystallization and reprecipitation, in combination, applying chromatography, and eluting with an appropriate eluent. A target compound that is insoluble in the solvent can be purified by washing the crude product of a resulting solid with a solvent. Furthermore, the target compound in each step can be used as it is in the subsequent reaction without being purified.

In the reactions in each step of the following Methods A to C, $R^1$, $R^2$, and n have the same meaning as defined above. $R^{1a}$ represents the same group as those defined for $R^1$, except that an amino group, a hydroxy group, and/or a carboxy group included in the $R^1$ group as a substituent is an amino group, a hydroxy group, and/or a carboxy group that may be protected. X represents a halogen atom (preferably a chlorine atom, a bromine atom, or an iodine atom, more preferably a bromine atom). Y represents a halogen atom (preferably a chlorine atom, a bromine atom, or an iodine atom, more preferably a chlorine atom or an iodine atom). TBS represents a tertiary butyldimethylsilyl group, and Boc represents a tertiary butoxycarbonyl group.

Method A is a method for producing a compound represented by the general formula (I).

(Method A)

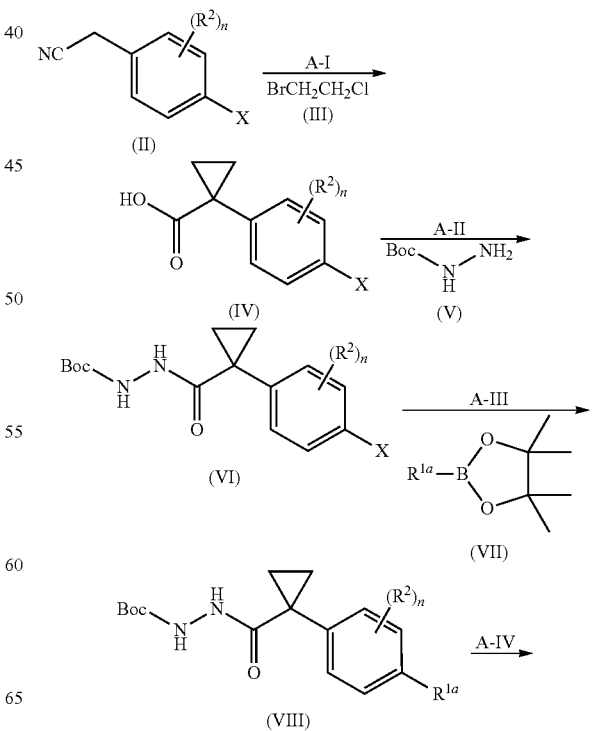

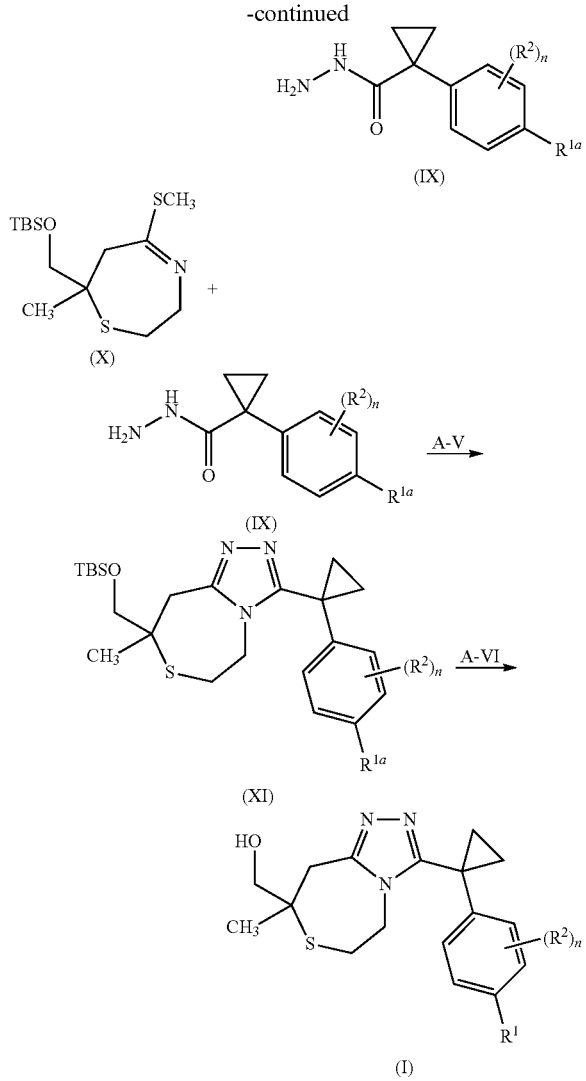

Step A-I

This step is a step for producing a compound represented by the general formula (IV) and consists of steps (i) and (ii).

(i) This step involves the reaction of a compound represented by the general formula (II) with compound (III) in the presence of a base and a phase transfer catalyst in a solvent.

The compound represented by the general formula (II) is a known compound or is easily produced by a known method using a known compound as a starting material or a similar method.

The solvent used in this step is preferably water.

The base used in this step is preferably an alkali metal hydroxide, more preferably sodium hydroxide or potassium hydroxide.

The phase transfer catalyst used in this step is preferably a tetrabutylammonium salt, a trioctylmethylammonium salt, a benzyltriethylammonium salt, or a benzyldimethyloctadecylammonium salt, more preferably benzyltriethylammonium chloride.

The reaction temperature in this step is usually 10° C. to 100° C., preferably 25° C. to 80° C.

The reaction time in this step is usually 0.1 h to 48 h, preferably 0.5 h to 24 h.

(ii) This step involves heating, in a solvent, the reaction mixture obtained in the above-mentioned step (i).

The solvent used in this step is preferably an alcohol, more preferably ethanol.

The reaction temperature in this step is usually 10° C. to 80° C., preferably 50° C. to 80° C.

The reaction time in this step is usually 1 h to 48 h, preferably 5 h to 24 h.

Step A-II

This step is a step for producing a compound represented by the general formula (VI).

This step involves the reaction of a compound represented by the general formula (IV) with compound (V) in the presence of a condensing agent and in the presence or absence of (preferably in the presence of) a base in a solvent.

The solvent used in this step is preferably an amide, more preferably N,N-dimethylformamide.

The condensing agent used in this step is preferably WSC. If necessary, HOBt or HOBt.H$_2$O can be co-used. Preferably, HOBt is co-used.

The base used in this step is preferably an organic base, more preferably triethylamine.

The reaction temperature in this step is usually −20° C. to 60° C., preferably 0° C. to 30° C.

The reaction time in this step is usually 0.5 h to 72 h, preferably 1 h to 24 h.

Step A-III

This step is a step for producing a compound represented by the general formula (VIII).

This step involves the reaction of a compound represented by the general formula (VI) with a compound represented by the general formula (VII) in the presence of a palladium catalyst and an inorganic base in a solvent.

The compound represented by the general formula (VII) used in this step is a known compound or is easily produced by a known method using a known compound as a starting material or a similar method.

The solvent used in this step is preferably an ether, more preferably dimethoxyethane.

The palladium catalyst used in this step is preferably a zerovalent palladium catalyst, more preferably tetrakis(triphenylphosphine)palladium.

The inorganic base used in this step is preferably an alkali metal carbonate, more preferably potassium carbonate.

The reaction temperature in this step is usually 25° C. to 130° C., preferably 60° C. to 100° C.

The reaction time in this step is usually 0.5 h to 72 h, preferably 1 h to 24 h.

Step A-IV

This step is a step for producing a compound represented by the general formula (IX).

This step involves the reaction of a compound represented by the general formula (VIII) with an acid in a solvent.

The solvent used in this step is preferably an alcohol, more preferably methanol.

The acid used in this step is preferably a mineral acid, more preferably hydrochloric acid, yet more preferably a solution of hydrochloric acid in dioxane.

The reaction temperature in this step is usually −20° C. to 60° C., preferably 0° C. to 40° C.

The reaction time in this step is usually 0.1 h to 48 h, preferably 0.5 h to 24 h.

Step A-V

This step is a step for producing a compound represented by the general formula (XI).

This step involves the reaction of compound (X) (WO2008/078725) with a compound represented by the general formula (IX) in a solvent.

The solvent used in this step is preferably an alcohol, more preferably n-butanol or t-butanol.

The reaction temperature in this step is usually 20° C. to 200° C., preferably 100° C. to 120° C.

The reaction time in this step is usually 0.5 h to 24 h, preferably 1 h to 12 h.

Step A-VI

This step is a step for producing a compound represented by the general formula (I).

This step involves the reaction of a compound represented by the general formula (XI) with an acid in a solvent and subsequent removal of a protective group of an amino group, a hydroxy group, and/or a carboxy group in $R^{1a}$ as desired.

The solvent used in this step is preferably an alcohol, more preferably methanol.

The acid used in this step is preferably a mineral acid, more preferably hydrochloric acid, yet more preferably a solution of hydrochloric acid in dioxane.

The reaction temperature in this step is usually −20° C. to 60° C., preferably 0° C. to 40° C.

The reaction time in this step is usually 1 h to 48 h, preferably 2 h to 24 h.

Method B is a method for producing a compound represented by the general formula (I).

(Method B)

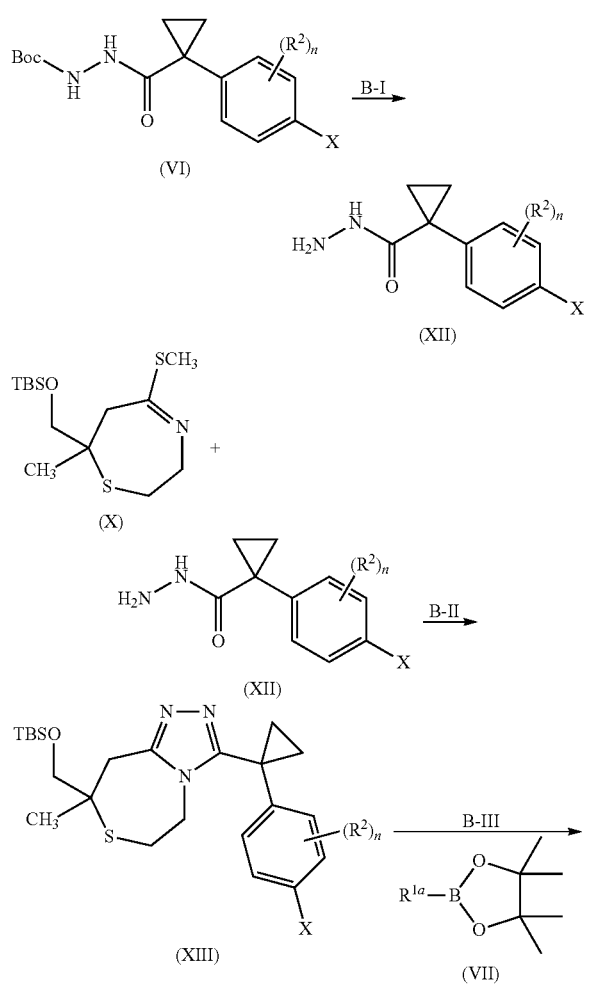

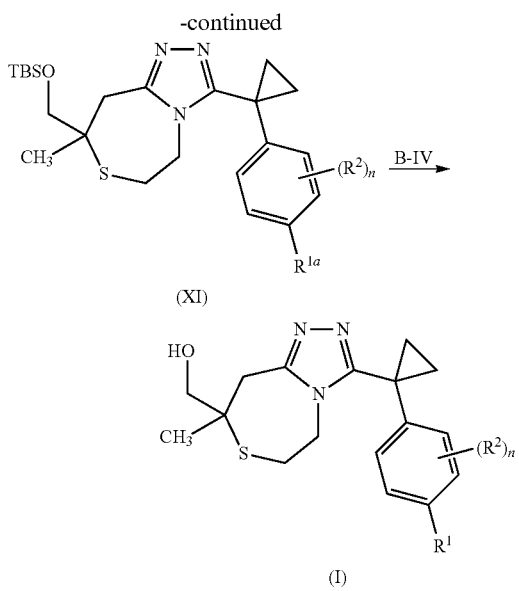

Step B-I

This step is a step for producing a compound represented by the general formula (XII).

This step involves the reaction of a compound represented by the general formula (VI) with an acid in a solvent in the same manner as in the step A-IV of the above-mentioned Method A.

Step B-II

This step is a step for producing a compound represented by the general formula (XIII).

This step involves the reaction of compound (X) with a compound represented by the general formula (XII) in a solvent in the same manner as in the step A-V of the above-mentioned Method A.

Step B-III

This step is a step for producing a compound represented by the general formula (XI).

This step involves the reaction of a compound represented by the general formula (XIII) with a compound represented by the general formula (VII) in the presence of a palladium catalyst and an inorganic base in a solvent in the same manner as in the step A-III of the above-mentioned Method A.

Step B-IV

This step is a step for producing a compound represented by the general formula (I).

This step involves the reaction of a compound represented by the general formula (XI) with an acid in a solvent in the same manner as in the step A-VI of the above-mentioned Method A and subsequent removal of a protective group of an amino group, a hydroxy group, and/or a carboxy group in $R^{1a}$ as desired.

Method C is a method for producing a compound represented by the general formula (I).

(Method C)

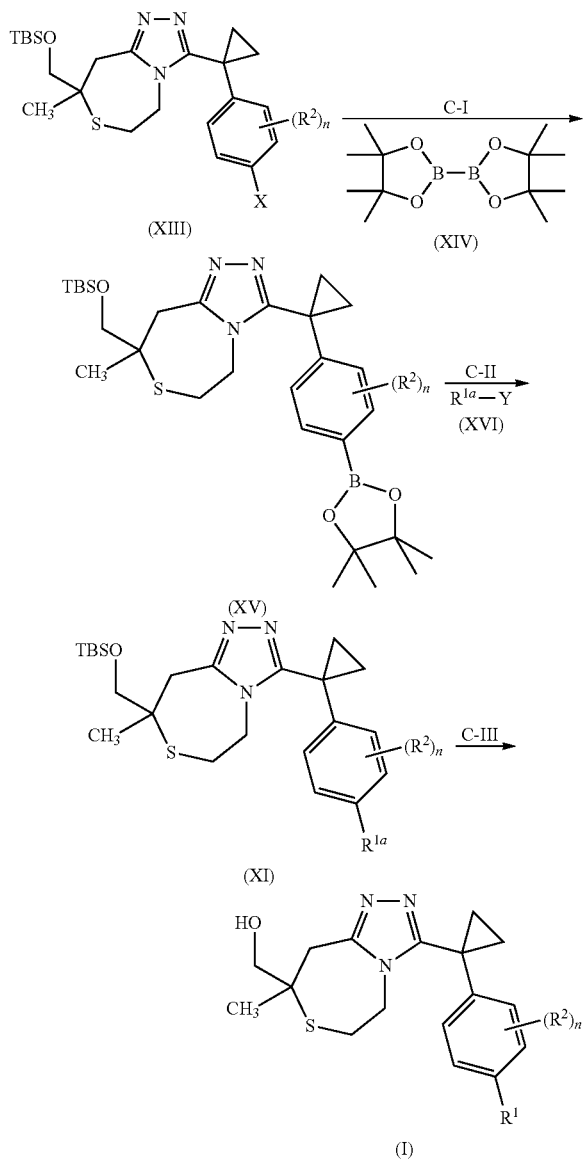

Step C-I

This step is a step for producing a compound represented by the general formula (XV).

This step involves the reaction of a compound represented by the general formula (XIII) with compound (XIV) in the presence of a palladium catalyst and an inorganic base in a solvent in the same manner as in the step A-III of the above-mentioned Method A.

Step C-II

This step is a step for producing a compound represented by the general formula (XI).

This step involves the reaction of a compound represented by the general formula (XV) with a compound represented by the general formula (XVI) in the presence of a palladium catalyst and an inorganic base in a solvent in the same manner as in the step A-III of the above-mentioned Method A.

The compound represented by the general formula (XVI) used in this step is a known compound or is easily produced by a known method using a known compound as a starting material or a similar method.

Step C-III

This step is a step for producing a compound represented by the general formula (I).

This step involves the reaction of a compound represented by the general formula (XI) with an acid in a solvent in the same manner as in the step A-VI of the above-mentioned Method A and subsequent removal of a protective group of an amino group, a hydroxy group, and/or a carboxy group in $R^{1a}$ as desired.

In the above description, protective groups of the "amino group that may be protected", the "hydroxy group that may be protected", and the "carboxyl group that may be protected" in the definitions of $R^{1a}$ are protective groups that can be cleaved by chemical methods such as hydrogenolysis, hydrolysis, electrolysis, and photodegradation, and represent protective groups commonly used in organic synthetic chemistry (for example, refer to T. W. Greene et al., Protective Groups in Organic Synthesis, 3rd Edition, John Wiley & Sons, Inc.

In the above description, "protective groups" of the "hydroxy group that may be protected" in the definitions of $R^{1a}$ are not particularly limited so long as they are protective groups of a hydroxy group used in the field of organic synthetic chemistry. Examples thereof include "alkylcarbonyl groups" including a formyl group, the above-mentioned "$C_2$-$C_7$ alkylcarbonyl group", $C_2$-$C_7$ halogenated alkylcarbonyl groups such as a 2,2,2-trichloroethylcarbonyl group, alkoxyalkylcarbonyl groups such as a methoxyacetyl group, unsaturated alkylcarbonyl groups such as an acryloyl group, a propioloyl group, a methacryloyl group, a crotonoyl group, an isocrotonoyl group, and an (E)-2-methyl-2-butenoyl group; "arylcarbonyl groups" including arylcarbonyl groups such as a benzoyl group, an α-naphthoyl group and a β-naphthoyl group, halogenated arylcarbonyl groups such as a 2-bromobenzoyl group and a 4-chlorobenzoyl group, $C_1$-$C_6$ alkylated arylcarbonyl groups such as a 2,4,6-trimethylbenzoyl group and a 4-toluoyl group, $C_1$-$C_6$ alkoxylated arylcarbonyl groups such as a 4-anisoyl group, nitrated arylcarbonyl groups such as a 4-nitrobenzoyl group and a 2-nitrobenzoyl group, $C_2$-$C_7$ alkoxycarbonylated arylcarbonyl groups such as a 2-(methoxycarbonyl)benzoyl group, and arylated arylcarbonyl groups such as a 4-phenylbenzoyl group; the above-mentioned "$C_2$-$C_7$ alkoxycarbonyl group", and "alkoxycarbonyl groups" such as $C_2$-$C_7$ alkoxycarbonyl groups substituted with a halogen or a tri-($C_1$-$C_6$ alkyl)silyl group such as a 2,2,2-trichloroethoxycarbonyl group and a 2-trimethylsilylethoxycarbonyl group; "tetrahydropyranyl or tetrahydrothiopyranyl groups" such as a tetrahydropyran-2-yl group, a 3-bromotetrahydropyran-2-yl group, a 4-methoxytetrahydropyran-4-yl group, a tetrahydrothiopyran-2-yl group, and a 4-methoxytetrahydrothiopyran-4-yl group; "tetrahydrofuranyl groups or tetrahydrothiofuranyl groups" such as a tetrahydrofuran-2-yl group and a tetrahydrothiofuran-2-yl group; "silyl groups" including a trimethylsilyl group, a triethylsilyl group, tri-($C_1$-$C_6$ alkyl)silyl groups such as an isopropyldimethylsilyl group, a t-butyldimethylsilyl group, a methyldiisopropylsilyl group, a methyldi-t-butylsilyl group, and a triisopropylsilyl group, ($C_1$-$C_6$ alkyl)diarylsilyl groups such as a diphenylmethylsilyl group, a diphenylbutylsilyl group, and a diphenylisopropylsilyl group, and di-($C_1$-$C_6$ alkyl)arylsilyl groups such as a phenyldiisopropylsilyl group; "alkoxymethyl groups" including ($C_1$-$C_6$ alkoxy)methyl groups such as a methoxymethyl group, a 1,1-dimethyl-1-methoxymethyl group, an ethoxymethyl group, a propoxymethyl group, an isopropoxymethyl group, a butoxymethyl group, and a t-butoxymethyl group, ($C_1$-$C_6$ alkoxy)-($C_1$-$C_6$ alkoxy)methyl groups such as a 2-methoxyethoxymethyl group, ($C_1$-$C_6$ halogenated alkoxy)methyl groups such as a 2,2,2-trichloroethoxymethyl group and a bis(2-chloroethoxy)methyl group; "substituted ethyl groups" including ($C_1$-$C_6$ alkoxy)ethyl groups such as a 1-ethoxyethyl group and a 1-(isopropoxy)ethyl group and halogenated ethyl groups such as a 2,2,2-trichloroethyl group; "aralkyl groups" including $C_1$-$C_6$ alkyl groups substituted with 1 to 3 aryl groups such as a benzyl group, an α-naphthylmethyl group, a β-naphthylmethyl group, a diphenylmethyl group, a triphenylmethyl group, an α-naphthyldiphenylmethyl group, and a 9-anthrylmethyl group and $C_1$-$C_6$ alkyl groups substituted with 1 to 3 aryl groups having an aryl ring substituted with a $C_1$-$C_6$ alkyl group such as a 4-methylbenzyl group, a 2,4,6-trimethylbenzyl group, a 3,4,5-trimethylbenzyl group, a 4-methoxybenzyl group, a 4-methoxyphenyldiphenylmethyl group, a 2-nitrobenzyl group, a 4-nitrobenzyl group, a 4-chlorobenzyl group, a 4-bromobenzyl group, or a 4-cyanobenzyl group, $C_1$-$C_6$ alkoxy groups, a nitro group, a halogen atom, or a cyano group; "alkenyloxycarbonyl groups" such as a vinyloxycarbonyl group and an allyloxycarbonyl group; and "aralkyloxycarbonyl groups" in which an aryl ring may be substituted with 1 or 2 $C_1$-$C_6$ alkoxy groups or a nitro group such as a benzyloxycarbonyl group, a 4-methoxybenzyloxycarbonyl group, a 3,4-dimethoxybenzyloxycarbonyl group, a 2-nitrobenzyloxycarbonyl group, and a 4-nitrobenzyloxycarbonyl group. Alkylcarbonyl groups, silyl groups, and aralkyl groups are more preferred.

In the above description, "protective groups" of the "carboxy group that may be protected" in the definition of $R^{1a}$ are not particularly limited so long as they are protective groups of a carboxy group used in the field of organic synthetic chemistry. Examples thereof include the above-mentioned "$C_1$-$C_6$ alkyl groups"; $C_2$-$C_6$ alkenyl groups such as a vinyl group and an allyl group; $C_2$-$C_6$ alkynyl groups such as an ethynyl group, a 1-propynyl group, a 2-propynyl group, a 1-methyl-2-propynyl group, and a 1-butynyl group; the above-mentioned "$C_1$-$C_6$ halogenated alkyl groups"; the above-mentioned "$C_1$-$C_6$ hydroxyalkyl groups"; ($C_2$-$C_7$ alkylcarbonyl)-($C_1$-$C_6$ alkyl) groups such as an acetylmethyl group; the above-mentioned "aralkyl groups"; and the above-mentioned "silyl groups". $C_1$-$C_6$ alkyl groups and aralkyl groups are preferred.

In the above description, "protective groups" of the "amino group that may be protected" in the definition of $R^{1a}$ are not particularly limited so long as they are protective groups of an amino group used in the field of organic synthetic chemistry, and examples thereof include groups similar to "alkylcarbonyl groups"; "arylcarbonyl groups"; "alkoxycarbonyl groups"; "silyl groups"; "aralkyl groups"; "alkenyloxycarbonyl groups"; and "aralkyloxycarbonyl groups" in the above-mentioned "protective groups of a hydroxy group" and "substituted methylene groups forming a Schiff's base" such as N,N-dimethylaminomethylene, benzylidene, 4-methoxybenzylidene, 4-nitrobenzylidene, salicylidene, 5-chlorosalicylidene, diphenylmethylene, and (5-chloro-2-hydroxyphenyl)phenyl methylene. Alkylcarbonyl groups, arylcarbonyl groups, and alkoxycarbonyl groups, more preferably alkoxycarbonyl groups are preferred.

The steps requiring protection/deprotection are performed according to known methods (for example, the methods described in Theodora W. Greene, Peter G. M. Wuts, "Protective Groups in Organic Synthesis", 1999, Wiley-Interscience Publication, etc.).

The effect of inhibiting 11β-HSD1, the effect of lowering blood sugar levels, the effect of improving insulin resistance, the effect of lowering lipids in blood, and so forth, of the compound or a pharmacologically acceptable salt thereof of the present invention can be confirmed using known methods (for example, methods described in the Examples).

The compound or a pharmacologically acceptable salt thereof of the present invention can be administered in various forms. Examples of the route of administration include oral administration using tablets, capsules, granules, emulsions, pills, powders, syrups (solutions), and the like and parenteral administration using injections (intravenous, intramuscular, subcutaneous, or intraperitoneal administration), drip infusions, suppositories (rectal administration), and the like. These various formulations can be prepared as drug products according to usual methods using aids usually used in the field of drug formulation such as excipients, binders, disintegrating agents, lubricants, flavoring agents, dissolving aids, suspensions, and coating agents in addition to an active ingredient.

In the use as a tablet, examples of carriers that can be used include excipients such as lactose, sucrose, sodium chloride, glucose, urea, starch, calcium carbonate, kaolin, crystalline cellulose, and silicic acid; binders such as water, ethanol, propanol, simple syrup, glucose solutions, starch solutions, gelatin solutions, carboxymethylcellulose, shellac, methylcellulose, potassium phosphate, and polyvinylpyrrolidone; disintegrating agents such as dry starch, sodium alginate, agar powder, laminaran powder, sodium hydrogencarbonate, calcium carbonate, polyoxylated ethylene sorbitan fatty acid esters, sodium lauryl sulfate, monoglyceride stearate, starch, and lactose; integration inhibitors such as sucrose, stearin, cocoa butter, and hydrogenated oil; absorption promoters such as quaternary ammonium salts and sodium lauryl sulfate; moisturizing agents such as glycerine and starch; adsorbents such as starch, lactose, kaolin, bentonite, and colloidal silicic acid; lubricants such as purified talc, stearate, fluoboric acid powder, and polyethylene glycol, and so forth. Furthermore, tablets coated in usual manners such as, for example, sugar-coated tablets, gelatin-coated tablets, enteric-coated tablets, film-coated tablets, double-layer tablets, and multi-layered tablets can be prepared as required.

In the use as a pill, examples of carriers that can be used include excipients such as glucose, lactose, cocoa butter, starch, hydrogenated vegetable oil, kaolin, and talc; binders such as powdered gum arabic, powdered tragacanth, gelatin, and ethanol; disintegrating agents such as laminaran agar, and so forth.

In the use as a suppository, a wide range of carriers known in this field can be used, and examples thereof include polyethylene glycol, cocoa butter, higher alcohols, higher alcohol esters, gelatin, semisynthesis glyceride, and so forth.

In the use as an injection, the formulation can be prepared as solutions, emulsions, or suspensions. Preferably, these solutions, emulsions, and suspensions are sterilized and are isotonic with blood. Solutions for producing these solutions, emulsions, and suspensions are not particularly limited so long as they can be used as diluents for medical use, and examples thereof include water, ethanol, propylene glycol, ethoxylated isostearyl alcohol, polyoxylated isostearyl alcohol, polyoxylated ethylene sorbitan fatty acid esters, and so forth. In this case, a sufficient amount for preparation of an isotonic solution of sodium chloride, glucose, or glycerine may be added to the formulation, and usual dissolving aids, buffers, soothing agents, and the like may also be added.

Furthermore, coloring materials, preservatives, flavors, flavoring agents, sweeteners, and the like can be added to the above-mentioned formulation, if necessary. Furthermore, other drugs can also be added.

The amount of an active ingredient compound contained in the above-mentioned formulation is not particularly limited, but is usually 0.5 to 70% by weight in the total composition, preferably 1 to 30% by weight.

The dose varies depending on symptoms, age, and the like of the patient (a homeotherm, in particular, a human). In the case of oral administration, the recommended adult daily dosage is from 0.1 mg as the lower limit (preferably 1 mg, more preferably 10 mg) to 2000 mg as the upper limit (preferably 100 mg), which is divided into 1 to 6 times depending on the symptoms.

EXAMPLES

Hereafter, the present invention will be more specifically explained with reference to the examples and the like. However, the scope of the present invention is not limited to these examples.

Elution for column chromatography in the examples was performed under observation by thin layer chromatography (TLC). In TLC observation, Silica Gel 60$F_{254}$ manufactured by Merck & Co., Inc. was used as a TLC plate, the solvent used as an elution solvent in column chromatography was used as a developing solvent, and a UV detector was used for detection. Silica Gel SK-85 (230 to 400 mesh) or Silica Gel SK-34 (70 to 230 mesh) manufactured by Merck & Co., Inc. or Chromatorex NH (200 to 350 mesh) manufactured by Fuji Silysia Chemical Ltd. was used as silica gel for columns. In addition to a conventional column chromatography device, an automated chromatography device (SP-1) manufactured by Biotage AB, an automated chromatography device (Parallel Frac FR-260) manufactured by Yamazen Corporation, or an automated chromatography device (CombiFlash Rf) manufactured by Teledyne Isco, Inc. was used as required. Abbreviations used in the examples have the following meanings: mg, milligram; g, gram; mL, milliliter; MHz, megahertz.

In the following examples, nuclear magnetic resonance (hereinafter, $^1$H NMR) spectra were expressed by using δ values (ppm) as chemical shift values and tetramethylsilane as a reference substance. Fragmentation patterns were represented by using s for a singlet, d for a doublet, t for a triplet, q for a quartet, and m for a multiplet.

Mass spectrometry (MS) was performed by the fast atom bombardment (FAB) method, the electron ionization (EI) method, or the electron spray ionization (ESI) method.

Example 1

[3-(1-Biphenyl-4-ylcyclopropyl)-8-methyl-5,6,8,9-tetrahydro[1,2,4]triazolo[4,3-d][1,4]thiazepin-8-yl]methanol

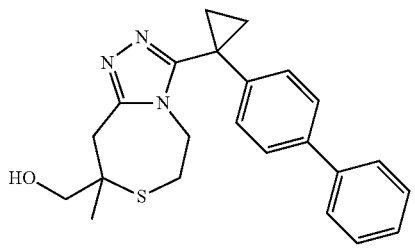

Example 1-1

1-(4-Chlorophenyl)cyclopropanecarbohydrazide

A solution of 1-(4-chlorophenyl)-1-cyclopropanecarboxylic acid (9.83 g, 50 mmol), tert-butyl carbazate (7.93 g, 60 mmol), 1-ethyl-3-(3-dimethylaminopropyl)carbodiimide hydrochloride (10.54 g, 55 mmol), 1-hydroxybenzotriazole monohydrate (7.43 g, 55 mmol), and triethylamine (12.65 mL, 125 mmol) in N,N-dimethylformamide (100 mL) was stirred overnight at room temperature. Water was added to the reaction mixture, the mixture was extracted with ethyl acetate, and the organic layer was washed with saturated aqueous sodium hydrogencarbonate and saturated sodium chloride solution and then dried with anhydrous sodium sulfate. After filtration, the filtrate was concentrated under reduced pressure. A 4 M solution (62.5 mL) of hydrochloric acid in 1,4-dioxane and methanol (200 mL) were added to the partially purified product, and the mixture was stirred overnight at room temperature. The reaction mixture was concentrated under reduced pressure, dichloromethane was added to the residue, and the organic layer was washed with saturated aqueous sodium hydrogencarbonate and saturated sodium chloride solution and then dried with anhydrous sodium sulfate. The filtrate was concentrated under reduced pressure, hexane was added to the obtained partially purified product, and the solid was collected by filtration to obtain the title compound (9.06 g, 86%) as a light brown solid.

$^1$H-NMR (400 MHz, CDCl$_3$) δ: 1.06 (2H, q, J=3.5 Hz), 1.63 (2H, q, J=3.5 Hz), 3.79 (2H, d, J=4.3 Hz), 6.42 (1H, m), 7.31-7.36 (4H, m).

Example 1-2

8-({[Tert-butyl(dimethyl)silyl]oxy}methyl)-3-[1-(4-chlorophenyl)cyclopropyl]-8-methyl-5,6,8,9-tetrahydro[1,2,4]triazolo[4,3-d][1,4]thiazepine A solution of the compound (2.03 g, 10 mmol) obtained in Example 1-1) and 7-({[tert-butyl(dimethyl)silyl]oxy}methyl)-7-methyl-5-(methylthio)-2,3,6,7-tetrahydro-1,4-thiazepine (WO2008078725) (3.2 g, 10 mmol) in n-butanol (50 mL) was stirred at 140° C. for 7 h. The reaction mixture was cooled to room temperature and concentrated under reduced pressure. The residue was purified by silica gel column chromatography (Isco Combiflash, 40 g, hexane:ethyl acetate=0:100 to 100:0, gradient) to obtain the title compound (2.27 g, 49%) as a light yellow oily substance.

$^1$H-NMR (400 MHz, CDCl$_3$) δ: 0.04 (3H, s), 0.06 (3H, s), 0.91 (9H, s), 1.17 (3H, s), 1.34-1.44 (2H, m), 1.52-1.64 (2H, m), 2.51 (1H, ddd, J=15.6, 7.8, 2.3 Hz), 2.67 (1H, ddd, J=15.6, 7.8, 2.0 Hz), 3.51 (2H, dd, J=16.2, 10.0 Hz), 3.65 (2H, q, J=6.1 Hz), 4.04 (1H, ddd, J=14.4, 7.9, 2.1 Hz), 4.27 (1H, ddd, J=14.5, 7.8, 2.3 Hz), 6.99-7.05 (2H, m), 7.23-7.27 (2H, m).

Example 1-3

3-(1-Biphenyl-4-ylcyclopropyl)-8-({[tert-butyl(dimethyl)silyl]oxy}methyl)-8-methyl-5,6,8,9-tetrahydro[1,2,4]triazolo[4,3-d][1,4]thiazepine A solution of the compound (232 mg, 0.5 mmol) obtained in Example 1-2), phenylboronic acid (61 mg, 0.5 mmol), tris(dibenzylideneacetone)dipalladium(0) (23 mg, 0.05 mmol), tricyclohexylphosphine (17 mg, 0.12 mmol), and tripotassium phosphate (186 mg, 0.85 mmol) in dioxane (2 mL) and water (1 mL) was stirred at 140° C. for 2 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, hexane:ethyl acetate=0:100 to 100:0, gradient) to obtain the title compound (197 mg, 78%) as a light yellow solid.

$^1$H-NMR (400 MHz, CDCl$_3$) δ: 0.05 (3H, s), 0.07 (3H, s), 0.91 (9H, s), 1.19 (3H, s), 1.41-1.69 (4H, m), 2.49-2.58 (1H, m), 2.63-2.73 (1H, m), 3.41 (2H, s), 3.53 (2H, dd, J=10.0, 16.2 Hz), 4.05-4.13 (1H, m), 4.35 (1H, ddd, J=14.6, 7.9, 2.2 Hz), 7.12-7.17 (2H, m), 7.31-7.37 (1H, m), 7.40-7.46 (2H, m), 7.50-7.57 (4H, m).

Example 1-4

[3-(1-Biphenyl-4-ylcyclopropyl)-8-methyl-5,6,8,9-tetrahydro[1,2,4]triazolo[4,3-d][1,4]thiazepin-8-yl]methanol A solution of the compound (197 mg, 0.39 mmol) obtained in Example 1-3) and 4 M hydrochloric acid (1,4-dioxane solution, 0.5 mL) in methanol (2 mL) was stirred at room temperature for 21 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 30:70, gradient) to obtain the title compound (138 mg, 91%) as a colorless solid.

$^1$H-NMR (500 MHz, CDCl$_3$) δ: 1.33 (3H, s), 1.41-1.45 (1H, m), 1.49-1.58 (2H, m), 1.62-1.66 (1H, m), 2.40 (1H, dd, J=15.4, 6.6 Hz), 2.60 (1H, dd, J=14.9, 9.5 Hz), 3.32 (1H, d, J=15.6 Hz), 3.39 (2H, dd, J=16.1, 11.7 Hz), 3.62 (1H, d, J=15.6 Hz), 4.08-4.15 (1H, m), 4.44 (1H, dd, J=14.4, 6.6 Hz), 7.14-7.18 (2H, m), 7.33-7.36 (1H, m), 7.41-7.45 (2H, m), 7.52-7.56 (4H, m).

MS (ESI) m/z: 392 [M+H]$^+$.

Example 2

{8-Methyl-3-[1-(4-pyridin-3-ylphenyl)cyclopropyl]-5,6,8,9-tetrahydro[1,2,4]triazolo[4,3-d][1,4]thiazepine-8-yl}methanol

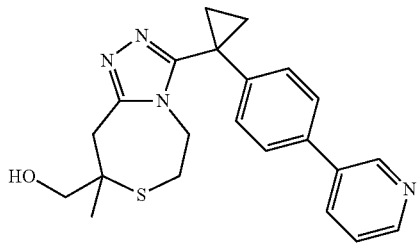 [SMILES: CC1(CO)Cc2nnc(C3(c4ccc(-c5cccnc5)cc4)CC3)n2CCS1]

Example 2-1

8-({[Tert-butyl(dimethyl)silyl]oxy}methyl)-8-methyl-3-[1-(4-pyridin-3-ylphenyl)cyclopropyl]-5,6,8,9-tetrahydro[1,2,4]triazolo[4,3-d][1,4]thiazepine A solution of the compound (232 mg, 0.5 mmol) obtained in Example 1-2), 3-pyridylboronic acid (61 mg, 0.5 mmol), tris(dibenzylideneacetone)dipalladium(0) (23 mg, 0.05 mmol), tricyclohexylphosphine (17 mg, 0.12 mmol), and tripotassium phosphate (186 mg, 0.85 mmol) in dioxane (2 mL) and water (1 mL) was stirred at 140° C. for 2 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, hexane:ethyl acetate=0:100 to 100:0, gradient) to obtain the title compound (207 mg, 82%) as a light yellow solid.

$^1$H-NMR (400 MHz, CDCl$_3$) δ: 0.05 (3H, s), 0.07 (3H, s), 0.91 (9H, s), 1.20 (3H, s), 1.45-1.54 (2H, m), 1.57-1.62 (1H, m), 1.65-1.70 (1H, m), 2.56 (1H, ddd, J=15.6, 7.8, 2.3 Hz), 2.71 (1H, ddd, J=15.5, 7.9, 2.1 Hz), 3.40 (2H, s), 3.53 (2H, dd, J=17.2, 10.2 Hz), 4.10 (1H, ddd, J=14.5, 8.0, 2.2 Hz), 4.34 (1H, ddd, J=14.5, 7.8, 2.3 Hz), 7.16-7.21 (2H, m), 7.35-7.38 (1H, m), 7.48-7.53 (2H, m), 7.83-7.86 (1H, m), 8.56-8.60 (1H, m), 8.80-8.82 (1H, m).

Example 2-2

{8-Methyl-3-[1-(4-pyridin-3-ylphenyl)cyclopropyl]-5,6,8,9-tetrahydro[1,2,4]triazolo[4,3-d][1,4]thiazepine-8-yl]methanol A solution of the compound (207 mg, 0.41 mmol) obtained in Example 2-1) and 4 M hydrochloric acid (1,4-dioxane solution, 0.5 mL) in methanol (2 mL) was stirred at room temperature for 21 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 30:70, gradient) to obtain the title compound (126 mg, 79%) as a colorless solid.

$^1$H-NMR (500 MHz, CDCl$_3$) δ: 1.33 (3H, s), 1.44-1.48 (1H, m), 1.50-1.54 (1H, m), 1.57-1.68 (2H, m), 2.44 (1H, dd, J=14.9, 5.6 Hz), 2.63 (1H, dd, J=15.6, 8.3 Hz), 3.32 (1H, d, J=15.1 Hz), 3.39 (2H, dd, J=18.1, 11.7 Hz), 3.62 (1H, d, J=15.1 Hz), 4.08-4.15 (1H, m), 4.44 (1H, dd, J=14.6, 5.4 Hz), 7.19-7.22 (2H, m), 7.35-7.39 (1H, m), 7.51-7.54 (2H, m), 7.84-7.88 (1H, m), 8.58-8.61 (1H, m), 8.80-8.83 (1H, m).

MS (ESI) m/z: 393 [M+H]$^+$.

Example 3

{(8S)-8-Methyl-3-[1-(4-pyridin-3-ylphenyl)cyclopropyl]-5,6,8,9-tetrahydro[1,2,4]triazolo[4,3-d][1,4]thiazepin-8-yl}methanol

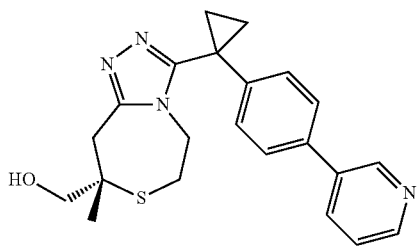 [SMILES: C[C@@]1(CO)Cc2nnc(C3(c4ccc(-c5cccnc5)cc4)CC3)n2CCS1]

Example 3-0

(7S)-7-({[t-Butyl(dimethyl)silyl]oxy}methyl)-7-methyl-1,4-thiazepane-5-thione

The second peak eluted by the application of 7-({[t-butyl(dimethyl)silyl]oxy}methyl)-7-1,4-thiazepane-5-thione (WO2008/078725) to a chiral column (CHIRALPAK AS-H, mobile phase: hexane/ethanol=70/30 (v/v)) was separated and concentrated to obtain the title compound as a colorless solid. The absolute configuration was determined as S configuration by X-ray structural analysis on monocrystals of a compound synthesized according to Example 3 with the title compound as a starting material.

Retention time: 6.0 min [column: CHIRALPAK AS-H (0.46 cm I.D.×25 mm), mobile phase: hexane/ethanol=70/30 (v/v), flow rate: 1.0 ml/min, temperature: 40° C., wavelength: 236 nm].

Example 3-1

(7S)-7-({[t-Butyl(dimethyl)silyl]oxy}methyl)-7-methyl-5-(methylthio)-2,3,6,7-tetrahydro-1,4-thiazepine The compound (2.00 g, 6.54 mmol) obtained in Example 3-0) was dissolved in tetrahydrofuran (11 mL). Potassium hydroxide (2.16 g, 39.72 mmol), water (7 mL), and methyl iodide (2.44 mL, 39.27 mmol) were added to the solution at room temperature, and the mixture was stirred for 1 h under a nitrogen atmosphere. The reaction mixture was extracted with ethyl acetate (50 mL), and the organic layer was washed with saturated sodium chloride solution and then dried with anhydrous magnesium sulfate. The solvent was distilled off under reduced pressure to obtain the title compound (2.17 g, 99%) in a yellow oily form.

$^1$H-NMR (400 MHz, CDCl$_3$) δ: 0.06 (3H, s), 0.07 (3H, s), 0.92 (9H, s), 1.30 (3H, s), 2.26 (3H, s), 2.63-2.78 (2H, m), 2.87 (1H, d, J=14.5 Hz), 3.06 (1H, d, J=14.5 Hz), 3.46 (1H, d, J=9.4 Hz), 3.59 (1H, d, J=9.4 Hz), 3.99 (1H, ddd, J=13.3, 7.8, 2.3 Hz), 4.09-4.16 (1H, m).

Example 3-2

(8S)-8-({[t-Butyl(dimethyl)silyl]oxy}methyl)-3-[1-(4-chlorophenyl)cyclopropyl]-8-methyl-5,6,8,9-tetrahydro[1,2,4]triazolo[4,3-d][1,4]thiazepine The compound (2.07 g, 6.54 mmol) obtained in Example 3-1) and the compound (1.38 g, 6.54 mmol) obtained in Example 1-1) were dissolved in 1-butanol (10 mL), and the mixture was stirred at 140° C. for 5 h under a nitrogen atmosphere. The reaction mixture was cooled to room temperature, then the solvent was distilled off, and the obtained residue was purified by silica gel column chromatography (elution solvent: ethyl acetate/hexane=30% to 80%) to obtain the title compound (1.27 g, 42%) in a white solid form.

$^1$H-NMR (400 MHz, CDCl$_3$) δ: 0.04 (3H, s), 0.07 (3H, s), 0.91 (9H, s), 1.18 (3H, s), 1.36-1.45 (2H, m), 1.53-1.58 (1H, m), 1.60-1.65 (1H, m), 2.51 (1H, ddd, J=15.6, 8.1, 2.2 Hz), 2.67 (1H, ddd, J=15.6, 8.1, 2.2 Hz), 3.38 (2H, s), 3.52 (2H, q, J=9.8 Hz), 4.05 (1H, ddd, J=14.4, 8.1, 2.0 Hz), 4.27 (1H, ddd, J=14.5, 7.9, 2.3 Hz), 7.02 (2H, d, J=8.8 Hz), 7.25 (2H, d, J=8.8 Hz).

Example 3-3

(8S)-8-({[t-Butyl(dimethyl)silyl]oxy}methyl)-8-methyl-3-[1-(4-pyridin-3-ylphenyl)cyclopropyl]-5,6,8,9-tetrahydro[1,2,4]triazolo[4,3-d][1,4]thiazepine The compound (105 mg, 0.23 mmol) obtained in Example 3-2), 3-pyridylboronic acid (31 mg, 0.25 mmol), tris(dibenzylideneacetone)dipalladium (11 mg, 0.01 mmol), tricyclohexylphosphine (8 mg, 0.03 mmol), and tripotassium phosphate (84 mg, 0.38 mmol) were dissolved in a mixed solvent of 1,4-dioxane (2 mL) and water (1 mL), and the mixture was stirred at 140° C. for 2 h under microwave irradiation. The reaction mixture was cooled to room temperature, then diluted with methylene chloride (20 mL), and separated into organic and aqueous layers by the addition of saturated aqueous sodium hydrogencarbonate (10 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=0% to 30%) to obtain a partially purified product (110 mg) of the title compound in a light yellow solid form.

$^1$H-NMR (400 MHz, CDCl$_3$) δ: 0.05 (3H, s), 0.07 (3H, s), 0.91 (9H, s), 1.20 (3H, s), 1.43-1.54 (2H, m), 1.56-1.62 (1H, m), 1.65-1.71 (1H, m), 2.56 (1H, ddd, J=15.6, 8.0, 2.5 Hz), 2.71 (1H, ddd, J=15.5, 7.9, 2.1 Hz), 3.40 (2H, s), 3.53 (2H, dd, J=18.0, 9.8 Hz), 4.09 (1H, ddd, J=14.1, 7.8, 2.3 Hz), 4.33 (1H, ddd, J=14.4, 7.9, 2.4 Hz), 7.19 (2H, d, J=8.2 Hz), 7.36 (1H, ddd, J=7.8, 4.7, 0.8 Hz), 7.51 (2H, d, J=8.2 Hz), 7.84 (1H, ddd, J=7.8, 2.3, 1.6 Hz), 8.59 (1H, dd, J=4.9, 1.8 Hz), 8.82 (1H, d, J=2.3 Hz).

Example 3-4

{(8S)-8-Methyl-3-[1-(4-pyridin-3-ylphenyl)cyclopropyl]-5,6,8,9-tetrahydro[1,2,4]triazolo[4,3-d][1,4]thiazepin-8-yl}methanol The compound (110 mg, 0.23 mmol) obtained in Example 3-3) was dissolved in methanol (3 mL). A 4 M solution (0.54 mL) of hydrochloric acid in dioxane was added to the solution, and the mixture was stirred at room temperature for 1 h. The solvent was distilled off, the residue was dissolved in a mixed solvent of methylene chloride (20 mL) and methanol (1 mL), and the mixture was separated into organic and aqueous layers by the addition of saturated aqueous sodium hydrogencarbonate (10 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=0% to 50%) to obtain the title compound (89 mg, 43%) in a white solid form.

$^1$H-NMR (400 MHz, CDCl$_3$) δ: 1.33 (3H, s), 1.42-1.48 (1H, m), 1.49-1.56 (1H, m), 1.56-1.66 (2H, m), 2.43 (1H, dd, J=15.4, 5.3 Hz), 2.44-2.49 (1H, brm), 2.63 (1H, dd, J=15.2, 10.2 Hz), 3.29-3.42 (3H, m), 3.62 (1H, d, J=15.6 Hz), 4.10-4.16 (1H, m), 4.44 (1H, ddd, J=14.9, 6.6, 1.6 Hz), 7.20 (2H, d, J=8.2 Hz), 7.36 (1H, dd, J=7.8, 5.1 Hz), 7.52 (2H, d, J=8.6 Hz), 7.84 (1H, d, J=7.8 Hz), 8.59 (1H, dd, J=5.1, 1.2 Hz), 8.82 (1H, s).

MS (ESI) m/z: 393.17483 (M+H)$^+$.

Example 4

{(8R)-8-Methyl-3-[1-(4-pyridin-3-ylphenyl)cyclopropyl]-5,6,8,9-tetrahydro[1,2,4]triazolo[4,3-d][1,4]thiazepin-8-yl}methanol

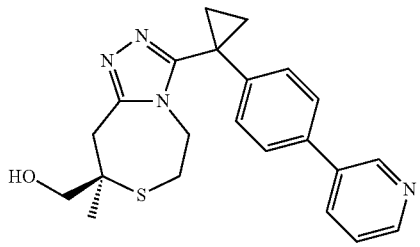 [SMILES: C[C@]1(CO)Cc2nnc(C3(c4ccc(-c5cccnc5)cc4)CC3)n2CCS1]

Example 4-0

(7R)-7-({[t-Butyl(dimethyl)silyl]oxy}methyl)-7-methyl-1,4-thiazepane-5-thione

The first peak eluted under the separation conditions of Example 3-0) was separated and concentrated to obtain the title compound as a colorless solid.

Retention time: 4.4 min [column: CHIRALPAK AS-H (0.46 cm I.D.×25 mm), mobile phase: hexane/ethanol=70/30 (v/v), flow rate: 1.0 ml/min, temperature: 40° C., wavelength: 236 nm].

Example 4-1

(7R)-7-({[t-Butyl(dimethyl)silyl]oxy}methyl)-7-methyl-5-(methylthio)-2,3,6,7-tetrahydro-1,4-thiazepine The compound (2.00 g, 6.54 mmol) obtained in Example 4-0) was dissolved in tetrahydrofuran (11 mL). Potassium hydroxide (2.16 g, 39.72 mmol), water (7 mL), and methyl iodide (2.44 mL, 39.27 mmol) were added to the solution at room temperature, and the mixture was stirred for 1 h under a nitrogen atmosphere. The reaction mixture was extracted with ethyl acetate (50 mL), and the organic layer was washed with saturated sodium chloride solution and then dried with anhydrous magnesium sulfate. The solvent was distilled off under reduced pressure to obtain the title compound (2.09 g, quant.) in a yellow oily form.

$^1$H-NMR (400 MHz, CDCl$_3$) δ: 0.06 (3H, s), 0.07 (3H, s), 0.92 (9H, s), 1.30 (3H, s), 2.26 (3H, s), 2.64-2.77 (2H, m), 2.87 (1H, d, J=14.6 Hz), 3.06 (1H, d, J=14.6 Hz), 3.46 (1H, d, J=9.8 Hz), 3.59 (1H, d, J=9.8 Hz), 3.99 (1H, ddd, J=13.3, 7.9, 1.8 Hz), 4.13 (1H, ddd, J=13.2, 7.8, 1.5 Hz).

Example 4-2

(8R)-8-({[t-Butyl(dimethyl)silyl]oxy}methyl)-3-[1-(4-chlorophenyl)cyclopropyl]-8-methyl-5,6,8,9-tetrahydro[1,2,4]triazolo[4,3-d][1,4]thiazepine The compound (2.09 g, 6.54 mmol) obtained in Example 4-1) and the compound (1.38 g, 6.54 mmol) obtained in Example 1-1) were dissolved in 1-butanol (10 mL), and the mixture was stirred at 140° C. for 6 h under a nitrogen atmosphere. The reaction mixture was cooled to room temperature, then the solvent was distilled off, and the obtained residue was purified by silica gel column chromatography (elution solvent: ethyl acetate/hexane=30% to 90%) to obtain the title compound (2.63 g, 87%) in a white solid form.

$^1$H-NMR (400 MHz, CDCl$_3$) δ: 0.04 (3H, s), 0.07 (3H, s), 0.91 (9H, s), 1.18 (3H, s), 1.35-1.45 (2H, m), 1.52-1.58 (1H, m), 1.59-1.65 (1H, m), 2.51 (1H, ddd, J=15.6, 7.8, 2.3 Hz), 2.67 (1H, ddd, J=15.5, 7.9, 2.2 Hz), 3.38 (2H, s), 3.52 (2H, dd, J=16.2, 10.0 Hz), 4.05 (1H, ddd, J=14.5, 7.8, 2.3 Hz), 4.27 (1H, ddd, J=14.5, 8.0, 2.5 Hz), 7.02 (2H, d, J=8.6 Hz), 7.25 (2H, d, J=8.6 Hz).

Example 4-3

(8R)-8-({[t-Butyl(dimethyl)silyl]oxy}methyl)-8-methyl-3-[1-(4-pyridin-3-ylphenyl)cyclopropyl]-5,6,8,9-tetrahydro[1,2,4]triazolo[4,3-d][1,4]thiazepine The compound (460 mg, 0.99 mmol) obtained in Example 4-2), 3-pyridylboronic acid (135 mg, 1.09 mmol), tris(dibenzylideneacetone)dipalladium (45 mg, 0.05 mmol), tricyclohexylphosphine (33 mg, 0.12 mmol), and tripotassium phosphate (370 mg, 1.68 mmol) were dissolved in a mixed solvent of 1,4-dioxane (2 mL) and water (1 mL), and the mixture was stirred at 140° C. for 2 h under microwave irradiation. The reaction mixture was cooled to room temperature, then diluted with methylene chloride (100 mL), and separated into organic and aqueous layers by the addition of saturated aqueous sodium hydrogencarbonate (30 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=0% to 30%) to obtain the title compound (455 mg, 91%) in a yellow solid form.

$^1$H-NMR (400 MHz, CDCl$_3$,) δ: 0.05 (3H, s), 0.07 (3H, s), 0.91 (9H, s), 1.20 (3H, s), 1.42-1.54 (2H, m), 1.56-1.71 (2H, m), 2.56 (1H, ddd, J=15.6, 7.8, 2.3 Hz), 2.71 (1H, ddd, J=15.5, 7.9, 2.1 Hz), 3.40 (2H, s), 3.53 (2H, dd, J=17.8, 10.0 Hz), 4.09 (1H, ddd, J=14.1, 7.4, 2.0 Hz), 4.33 (1H, ddd, J=14.5, 7.8, 2.3H), 7.19 (2H, d, J=8.6 Hz), 7.36 (1H, dd, J=7.8, 5.1 Hz), 7.51 (2H, d, J=8.6 Hz), 7.84 (1H, ddd, J=7.8, 2.3, 1.6 Hz), 8.59 (1H, dd, J=4.7, 1.6 Hz), 8.82 (1H, d, J=2.0 Hz).

Example 4-4

{(8R)-8-Methyl-3-[1-(4-pyridin-3-ylphenyl)cyclopropyl]-5,6,8,9-tetrahydro[1,2,4]triazolo[4,3-d][1,4]thiazepin-8-yl}methanol The compound (455 mg, 0.93 mmol) obtained in Example 4-3) was dissolved in methanol (4 mL). A 4 M solution (2.24 mL) of hydrochloric acid in dioxane was added to the solution, and the mixture was stirred at room temperature for 1 h. The solvent was distilled off, the residue was dissolved in a mixed solvent of methylene chloride (60 mL) and methanol (3 mL), and the mixture was separated into organic and aqueous layers by the addition of saturated aqueous sodium hydrogencarbonate (20 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=0% to 50%) to obtain the title compound (231 mg, 66%) in a white solid form.

$^1$H-NMR (400 MHz, CDCl$_3$) δ: 1.33 (3H, s), 1.43-1.48 (1H, m), 1.49-1.55 (1H, m), 1.57-1.68 (2H, m), 2.29-2.38 (1H, brm), 2.43 (1H, ddd, J=15.6, 6.6, 1.2 Hz), 2.63 (1H, ddd, J=15.6, 10.2, 1.2 Hz), 3.33 (1H, d, J=15.6 Hz), 3.38 (2H, s), 3.62 (1H, d, J=15.2 Hz), 4.12 (1H, dd, J=14.9, 9.4 Hz), 4.44 (1H, dd, J=14.5, 5.5 Hz), 7.20 (2H, d, J=8.2 Hz), 7.36 (1H, dd, J=7.8, 4.7 Hz), 7.52 (2H, d, J=8.2 Hz), 7.84 (1H, dt, J=8.0, 2.0 Hz), 8.59 (1H, d, J=3.5 Hz), 8.82 (1H, d, J=2.0 Hz).

HRMS (ESI) m/z: 393.1742 (M+H)$^+$.

Example 5

{8-Methyl-3-[1-(4-pyridin-4-ylphenyl)cyclopropyl]-5,6,8,9-tetrahydro[1,2,4]triazolo[4,3-d][1,4]thiazepine-8-yl}methanol

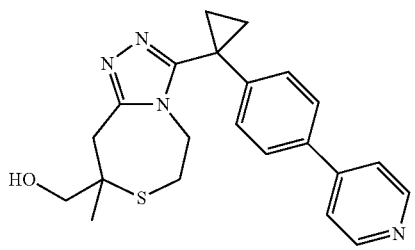 [SMILES: CC1(CO)Cc2nnc(C3(c4ccc(-c5ccncc5)cc4)CC3)n2CCS1]

Example 5-1

8-({[Tert-butyl(dimethyl)silyl]oxy}methyl)-8-methyl-3-[1-(4-pyridin-4-ylphenyl)cyclopropyl]-5,6,8,9-tetrahydro[1,2,4]triazolo[4,3-d][1,4]thiazepine A solution of the compound (232 mg, 0.5 mmol) obtained in Example 1-2), 4-pyridylboronic acid (61 mg, 0.5 mmol), tris(dibenzylideneacetone)dipalladium(0) (23 mg, 0.05 mmol), tricyclohexylphosphine (17 mg, 0.12 mmol), and tripotassium phosphate (186 mg, 0.85 mmol) in dioxane (2 mL) and water (1 mL) was stirred at 140° C. for 2 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 30:70, gradient) to obtain the title compound (174 mg, 69%) as a light yellow oily substance.

$^1$H-NMR (400 MHz, CDCl$_3$) δ: 0.05 (3H, s), 0.07 (3H, s), 0.91 (9H, s), 1.20 (3H, s), 1.44-1.54 (2H, m), 1.59-1.63 (1H, m), 1.66-1.71 (1H, m), 2.56 (1H, ddd, J=15.5, 7.9, 2.4 Hz), 2.71 (1H, ddd, J=15.5, 7.9, 2.1 Hz), 3.40 (2H, s), 3.53 (2H, dd, J=17.2, 9.8 Hz), 4.08 (1H, ddd, J=14.4, 7.9, 2.1 Hz), 4.32 (1H, ddd, J=14.4, 7.9, 2.4 Hz), 7.16-7.21 (2H, m), 7.46-7.49 (2H, m), 7.55-7.59 (2H, m), 8.64-8.67 (2H, m).

Example 5-2

{8-Methyl-3-[1-(4-pyridin-4-ylphenyl)cyclopropyl]-5,6,8,9-tetrahydro[1,2,4]triazolo[4,3-d][1,4]thiazepine-8-yl}methanol A solution of the compound (174 mg, 0.34 mmol) obtained in Example 5-1) and 4 M hydrochloric acid (1,4-dioxane solution, 0.43 mL) in methanol (2 mL) was stirred at room temperature for 21 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 30:70, gradient) to obtain the title compound (115 mg, 85%) as a colorless solid.

$^1$H-NMR (400 MHz, CDCl$_3$) δ: 1.33 (3H, s), 1.45-1.48 (1H, m), 1.51-1.56 (1H, m), 1.58-1.69 (2H, m), 2.39-2.48 (1H, m), 2.59-2.68 (1H, m), 3.33 (1H, d, J=15.2 Hz), 3.41 (2H, dd, J=14.7, 11.9 Hz), 3.62 (1H, d, J=15.2 Hz), 4.08-4.16 (1H, m), 4.42 (1H, dd, J=14.3, 6.1 Hz), 7.18-7.22 (2H, m), 7.45-7.49 (2H, m), 7.56-7.61 (2H, m), 8.63-8.68 (2H, m).

MS (ESI) m/z: 393 [M+H]$^+$.

Example 6

4'-{1-[8-(Hydroxymethyl)-8-methyl-5,6,8,9-tetrahydro[1,2,4]triazolo[4,3-d][1,4]thiazepin-3-yl]cyclopropyl}-N,N-dimethylbiphenyl-4-carboxamide

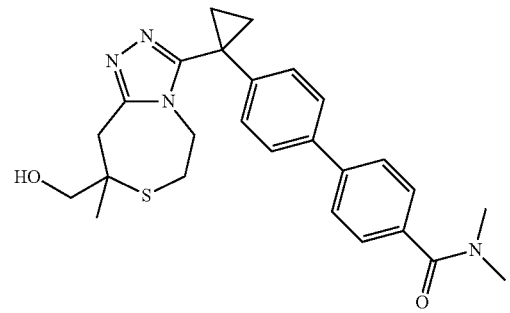 [SMILES: CN(C)C(=O)c1ccc(-c2ccc(C3(c4nnc5n4CCSC(C)(CO)C5)CC3)cc2)cc1]

Example 6-1

4'-{1-[8-({[Tert-butyl(dimethyl)silyl]oxy}methyl)-8-methyl-5,6,8,9-tetrahydro[1,2,4]triazolo[4,3-d][1,4]thiazepine-3-yl]cyclopropyl}-N,N-dimethylbiphenyl-4-carboxamide A solution of the compound (232 mg, 0.5 mmol) obtained in Example 1-2), 4-(N,N-dimethylaminocarbonyl)phenylboronic acid (96 mg, 0.5 mmol), tris(dibenzylideneacetone) dipalladium(0) (23 mg, 0.05 mmol), tricyclohexylphosphine (17 mg, 0.12 mmol), and tripotassium phosphate (186 mg, 0.85 mmol) in dioxane (2 mL) and water (1 mL) was stirred at 140° C. for 2 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 30:70, gradient) to obtain the title compound (318 mg, quant.) as a light yellow oily substance.

$^1$H-NMR (400 MHz, CDCl$_3$) δ: 0.05 (3H, s), 0.07 (3H, s), 0.91 (9H, s), 1.19 (3H, s), 1.42-1.52 (1H, m), 1.56-1.61 (1H, m), 1.63-1.69 (2H, m), 2.55 (1H, ddd, J=15.6, 7.8, 2.3 Hz), 2.69 (1H, ddd, J=15.6, 7.8, 2.0 Hz), 2.99-3.17 (6H, m), 3.40 (2H, s), 3.53 (2H, dd, J=17.4, 10.0 Hz), 4.05-4.13 (1H, m), 4.34 (1H, ddd, J=14.5, 7.8, 2.3 Hz), 7.15-7.17 (2H, m), 7.45-7.53 (4H, m), 7.56-7.61 (2H, m).

Example 6-2

4'-{1-[8-(Hydroxymethyl)-8-methyl-5,6,8,9-tetrahydro[1,2,4]triazolo[4,3-d][1,4]thiazepine-3-yl]cyclopropyl}-N,N-dimethylbiphenyl-4-carboxamide A solution of the compound (318 mg, 0.55 mmol) obtained in Example 6-1) and 4 M hydrochloric acid (1,4-dioxane solution, 0.69 mL) in methanol (2 mL) was stirred at room temperature for 21 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 30:70, gradient) to obtain the title compound (140 mg, 55%) as a colorless solid.

$^1$H-NMR (400 MHz, CDCl$_3$) δ: 1.33 (3H, s), 1.42-1.47 (1H, m), 1.50-1.60 (2H, m), 1.62-1.67 (1H, m), 2.39-2.46 (1H, m), 2.58-2.66 (1H, m), 3.03 (3H, s), 3.13 (3H, s), 3.33 (1H, d, J=15.2 Hz), 3.39 (2H, dd, J=14.9, 11.7 Hz), 3.62 (1H, d, J=15.2 Hz), 4.09-4.15 (1H, m), 4.44 (1H, dd, J=14.5, 5.9 Hz), 7.15-7.20 (2H, m), 7.47-7.51 (2H, m), 7.51-7.55 (2H, m), 7.57-7.59 (2H, m).

MS (ESI) m/z: 463 [M+H]$^+$.

Example 7

(8R)-4'-{1-[8-(Hydroxymethyl)-8-methyl-5,6,8,9-tetrahydro[1,2,4]triazolo[4,3-d][1,4]thiazepine-3-yl]cyclopropyl}-N,N-dimethylbiphenyl-4-carboxamide

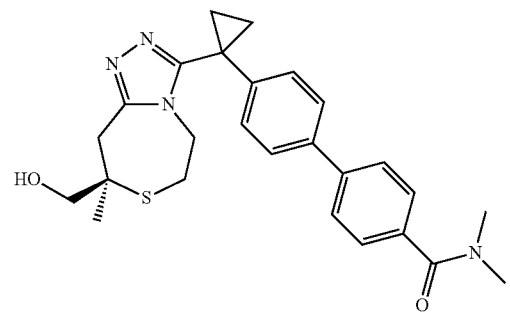 [SMILES: CN(C)C(=O)c1ccc(-c2ccc(C3(c4nnc5n4CCS[C@@](C)(CO)C5)CC3)cc2)cc1]

A mixed solution of the compound (100 mg, 0.197 mmol) obtained in Example 52-1), 4-(N,N-dimethylaminocarbonyl)phenylboronic acid (57 mg, 0.295 mmol), potassium carbonate (54 mg, 0.393 mmol), and tetrakis(triphenylphosphine)palladium (45 mg, 39 μmol) in 1,2-dimethoxyethane (2.00 mL) and water (0.50 mL) was stirred at 100° C. for 6 h. The reaction mixture was cooled to room temperature and then diluted with water. A mixed solvent of 2-propanol and dichloromethane (1:4) was added to the reaction mixture to separate an organic layer. The organic layer was dried with anhydrous sodium sulfate, then the solvent was distilled off under reduced pressure, and the residue was purified by silica gel column chromatography (ethyl acetate/methanol=9/1) to obtain a partially purified product (157 mg) of the title compound as a white solid. Tetrabutylammonium fluoride (1 M tetrahydrofuran solution, 286 μl 0.286 mmol) was added to a solution of the obtained partially purified product (theoretical amount: 113 mg, 0.197 mmol) in tetrahydrofuran (1.10 ml), and the mixture was stirred at room temperature for 5.5 h. Saturated aqueous sodium hydrogencarbonate was added to the reaction mixture, and a mixed solvent of dichloromethane and 2-propanol (4:1) was added to the reaction mixture to separate an organic layer. The organic layer was dried with anhydrous sodium sulfate, then the solvent was distilled off under reduced pressure, and the residue was purified by silica gel thin layer chromatography (ethyl acetate:methanol=9:1) to obtain the title compound (75 mg, 85%) as a yellow solid.

$^1$H-NMR (400 MHz, CD$_3$OD) δ: ppm: 1.16 (3H, s), 1.53-1.62 (4H, m), 2.62 (1H, ddd, J=15.7, 7.1, 2.6 Hz), 2.83 (1H, ddd, J=15.6, 8.0, 2.5 Hz), 3.03 (3H, s), 3.12 (3H, s), 3.35-3.49 (4H, m), 4.30-4.43 (2H, m), 7.19-7.22 (2H, m), 7.37-7.40 (1H, m), 7.52 (1H, t, J=8.0 Hz), 7.61-7.65 (3H, m), 7.70-7.73 (1H, m).

MS (FAB) m/z: 463 [M+H]$^+$.

Example 8

5-(4-{1-[8-(Hydroxymethyl)-8-methyl-5,6,8,9-tetrahydro[1,2,4]triazolo[4,3-d][1,4]thiazepine-3-yl]cyclopropyl}phenyl)-N,N-dimethylpyridine-2-carboxamide

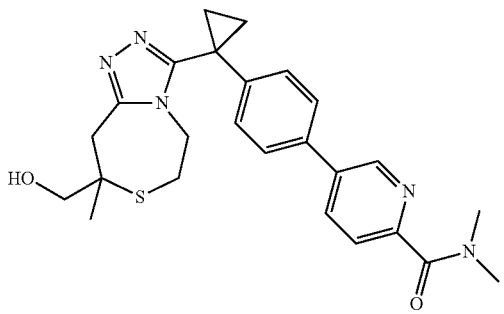 [SMILES: CN(C)C(=O)c1ccc(-c2ccc(C3(c4nnc5n4CCSC(C)(CO)C5)CC3)cc2)cn1]

Example 8-1

5-(4-{1-[8-({[Tert-butyl(dimethyl)silyl]oxy}methyl)-8-methyl-5,6,8,9-tetrahydro[1,2,4]triazolo[4,3-d][1,4]thiazepine-3-yl]cyclopropyl}phenyl)-N,N-dimethylpyridine-2-carboxamide A solution of the compound (232 mg, 0.5 mmol) obtained in Example 1-2), [6-(dimethylcarbamoyl)pyridin-3-yl]boronic acid (97 mg, 0.5 mmol), tris(dibenzylideneacetone)dipalladium(0) (23 mg, 0.05 mmol), tricyclohexylphosphine (17 mg, 0.12 mmol), and tripotassium phosphate (186 mg, 0.85 mmol) in dioxane (2 mL) and water (1 mL) was stirred at 140° C. for 2 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 20:80, gradient) to obtain the title compound (120 mg, 42%) as a light yellow oily substance.

$^1$H-NMR (400 MHz, CDCl$_3$) δ: 0.05 (3H, s), 0.07 (3H, s), 0.91 (9H, s), 1.20 (3H, s), 1.43-1.55 (2H, m), 1.58-1.71 (2H, m), 2.58 (1H, ddd, J=15.6, 7.8, 2.3 Hz), 2.68-2.77 (1H, m), 3.15 (3H, s), 3.16 (3H, s), 3.41 (2H, s), 3.54 (2H, dd, J=17.2, 10.2 Hz), 4.09 (1H, ddd, J=14.4, 7.9, 2.4 Hz), 4.33 (1H, ddd, J=14.4, 7.9, 2.4 Hz), 7.18-7.22 (2H, m), 7.51-7.55 (2H, m), 7.70-7.74 (1H, m), 7.92-7.96 (1H, m), 8.76-8.78 (1H, m).

Example 8-2

5-(4-{1-[8-(Hydroxymethyl)-8-methyl-5,6,8,9-tetrahydro[1,2,4]triazolo[4,3-d][1,4]thiazepin-3-yl]cyclopropyl}phenyl)-N,N-dimethylpyridine-2-carboxamide A solution of the compound (120 mg, 0.21 mmol) obtained in Example 8-1) and 4 M hydrochloric acid (1,4-dioxane solution, 0.26 mL) in methanol (2 mL) was stirred at room temperature for 21 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (63 mg, 65%) as a colorless solid.

$^1$H-NMR (400 MHz, CDCl$_3$) δ: 1.34 (3H, s), 1.45-1.49 (1H, m), 1.51-1.56 (1H, m), 1.59-1.68 (2H, m), 2.42-2.49 (1H, m), 2.62-2.70 (1H, m), 3.14 (3H, s), 3.16 (3H, s), 3.33 (1H, d, J=15.2 Hz), 3.40 (2H, dd, J=15.6, 11.7 Hz), 3.64 (1H, d, J=15.2 Hz), 4.09-4.16 (1H, m), 4.40-4.48 (1H, m), 7.19-7.24 (2H, m), 7.52-7.56 (2H, m), 7.71-7.73 (1H, m), 7.92-7.97 (1H, m), 8.76-8.79 (1H, m).

MS (ESI) m/z: 464 [M+H]$^+$.

Example 9

4'-{1-[8-(Hydroxymethyl)-8-methyl-5,6,8,9-tetrahydro[1,2,4]triazolo[4,3-d][1,4]thiazepin-3-yl]cyclopropyl}-N,N-dimethylbiphenyl-3-carboxamide

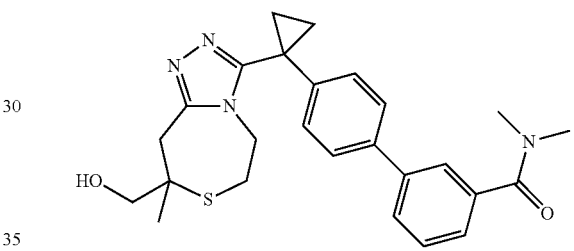

A solution of the compound (232 mg, 0.5 mmol) obtained in Example 1-2), 3-(N,N-dimethylaminocarbonyl)phenylboronic acid (97 mg, 0.5 mmol), tris(dibenzylideneacetone)dipalladium(0) (23 mg, 0.05 mmol), tricyclohexylphosphine (17 mg, 0.12 mmol), and tripotassium phosphate (186 mg, 0.85 mmol) in dioxane (2 mL) and water (1 mL) was stirred at 140° C. for 2 h under microwave irradiation. The reaction mixture was partially purified by silica gel chromatography (Isco Combiflash, 12 g, methanol:ethyl acetate=0:100 to 20:80, gradient). A solution of the obtained partially purified product (238 mg, 0.7 mmol) and 4 M hydrochloric acid (1,4-dioxane solution, 0.26 mL) in methanol (2 mL) was stirred at room temperature for 21 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (149 mg, 46%) as a colorless solid.

$^1$H-NMR (400 MHz, CDCl$_3$) δ: 1.33 (3H, s), 1.41-1.47 (1H, m), 1.50-1.60 (2H, m), 1.62-1.70 (1H, m), 2.42 (1H, dd, J=15.6, 5.9 Hz), 2.57-2.64 (1H, m), 3.01 (3H, s), 3.14 (3H, s), 3.32 (1H, d, J=15.2 Hz), 3.39 (2H, dd, J=16.4, 11.7 Hz), 3.64 (1H, d, J=16.4 Hz), 4.07-4.14 (1H, m), 4.45 (1H, dd, J=14.7, 6.1 Hz), 7.15-7.18 (2H, m), 7.36-7.39 (1H, m), 7.43-7.48 (1H, m), 7.51-7.54 (2H, m), 7.57-7.61 (2H, m).

MS (ESI) m/z: 463 [M+H]$^+$.

Example 10

{8-Methyl-3-[1-(3'-methylbiphenyl-4-yl)cyclopropyl]-5,6,8,9-tetrahydro[1,2,4]triazolo[4,3-d][1,4]thiazepin-8-yl}methanol

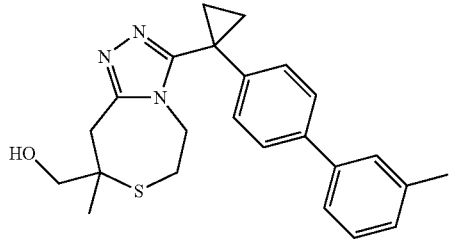

A solution of the compound (232 mg, 0.5 mmol) obtained in Example 1-2), 3-methylphenylboronic acid (105 mg, 0.77 mmol), tris(dibenzylideneacetone)dipalladium(0) (23 mg, 0.05 mmol), tricyclohexylphosphine (17 mg, 0.12 mmol), and tripotassium phosphate (186 mg, 0.85 mmol) in dioxane (2 mL) and water (1 mL) was stirred at 140° C. for 2 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was partially purified by silica gel chromatography (Isco Combiflash, 12 g, ethyl acetate:hexane=0:100 to 100:0, gradient). A solution of the obtained partially purified product (602 mg) and 4 M hydrochloric acid (1,4-dioxane solution, 0.69 mL) in methanol (2 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (331 mg, quant.) as a colorless solid.

$^1$H-NMR (400 MHz, CDCl$_3$) δ: 1.33 (3H, s), 1.40-1.73 (4H, m), 2.42 (3H, s), 2.36-2.43 (1H, m), 2.54-2.63 (1H, m), 3.28-3.42 (3H, m), 3.59-3.66 (1H, m), 4.05-4.14 (1H, m), 4.35-4.48 (1H, m), 7.02-7.06 (1H, m), 7.14-7.18 (3H, m), 7.27-7.37 (2H, m), 7.50-7.54 (2H, m).

MS (ESI) m/z: 406 [M+H]$^+$.

Example 11

{8-Methyl-3-[1-(2'-methylbiphenyl-4-yl)cyclopropyl]-5,6,8,9-tetrahydro[1,2,4]triazolo[4,3-d][1,4]thiazepin-8-yl}methanol

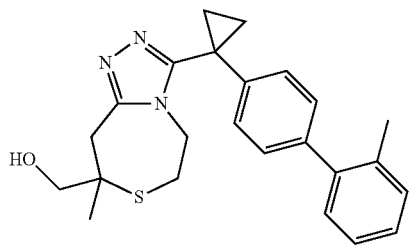 [SMILES: Cc1ccccc1-c1ccc(C2(c3nnc4n3CCSC(C)(CO)C4)CC2)cc1]

A solution of the compound (232 mg, 0.5 mmol) obtained in Example 1-2), 2-methylphenylboronic acid (105 mg, 0.77 mmol), tris(dibenzylideneacetone)dipalladium(0) (23 mg, 0.05 mmol), tricyclohexylphosphine (17 mg, 0.12 mmol), and tripotassium phosphate (186 mg, 0.85 mmol) in dioxane (2 mL) and water (1 mL) was stirred at 140° C. for 2 h under microwave irradiation. The reaction mixture was partially purified by silica gel chromatography (Isco Combiflash, 12 g, hexane:ethyl acetate=0:100 to 100:0, gradient). A solution of the obtained partially purified product and 4 M hydrochloric acid (1,4-dioxane solution, 1.7 mL) in methanol (2 mL) was stirred at room temperature for 21 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (251 mg, 88%) as a colorless solid.

$^1$H-NMR (400 MHz, CDCl$_3$) δ: 1.33 (3H, s), 1.43-1.49 (1H, m), 1.52-1.59 (2H, m), 1.61-1.68 (1H, m), 2.23 (3H, s), 2.36-2.44 (1H, m), 2.56-2.62 (1H, m), 3.30-3.42 (3H, m), 3.64 (1H, d, J=15.2 Hz), 4.08-4.17 (1H, m), 4.43-4.52 (1H, m), 7.12-7.27 (8H, m).

MS (ESI) m/z: 406 [M+H]$^+$.

Example 12

{8-Methyl-3-[1-(4'-methylbiphenyl-4-yl)cyclopropyl]-5,6,8,9-tetrahydro[1,2,4]triazolo[4,3-d][1,4]thiazepin-8-yl}methanol

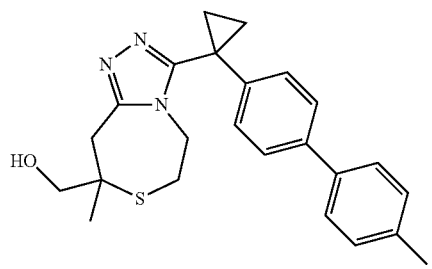

Example 12-1

8-({[Tert-butyl(dimethyl)silyl]oxy}methyl)-8-methyl-3-[1-(4'-methylbiphenyl-4-yl)cyclopropyl]-5,6,8,9-tetrahydro[1,2,4]triazolo[4,3-d][1,4]thiazepine A solution of the compound (324 mg, 0.7 mmol) obtained in Example 1-2), 4-methylphenylboronic acid (105 mg, 0.77 mmol), tris(dibenzylideneacetone)dipalladium(0) (32 mg, 0.04 mmol), tricyclohexylphosphine (24 mg, 0.08 mmol), and tripotassium phosphate (260 mg, 1.2 mmol) in dioxane (2 mL) and water (1 mL) was stirred at 140° C. for 2 h under microwave irradiation. The reaction mixture was purified by silica gel chromatography (Isco Combiflash, 12 g, hexane: ethyl acetate=0:100 to 100:0, gradient) to obtain the title compound (155 mg, 43%) as a brown oily substance.

$^1$H-NMR (400 Hz, CDCl$_3$) δ: 0.05 (3H, s), 0.07 (3H, s), 0.91 (9H, s), 1.19 (3H, s), 1.42-1.51 (2H, m), 1.54-1.59 (1H, m), 1.62-1.66 (1H, m), 2.40 (3H, s), 2.52 (1H, ddd, J=15.6, 8.0, 2.2 Hz), 2.67 (1H, ddd, J=15.6, 7.8, 2.0 Hz), 3.40 (2H, s), 3.52 (2H, dd, J=17.0, 10.0 Hz), 4.09 (1H, ddd, J=14.5, 8.2, 2.0 Hz), 4.34 (1H, ddd, J=14.5, 7.8, 2.3 Hz), 7.13 (2H, d, J=8.0 Hz), 7.24 (2H, d, J=8.0 Hz), 7.45 (2H, d, J=8.0 Hz), 7.50 (2H, d, J=8.0 Hz).

Example 12-2

{8-Methyl-3-[1-(4'-methylbiphenyl-4-yl)cyclopropyl]-5,6,8,9-tetrahydro[1,2,4]triazolo[4,3-d][1,4]thiazepin-8-yl}methanol A solution of the compound (155 mg, 0.3 mmol) obtained in Example 12-1) and 4 M hydrochloric acid (1,4-dioxane solution, 0.75 mL) in methanol (2 mL) was stirred at room temperature for 21 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (119 mg, 98%) as a colorless solid.

$^1$H-NMR (400 Hz, CDCl$_3$) δ: 1.33 (3H, s), 1.40-1.46 (1H, m), 1.49-1.59 (2H, m), 1.61-1.67 (1H, m), 2.37-2.45 (1H, m), 2.39 (3H, s) 2.60 (1H, dd, J=15.4, 8.0 Hz), 3.31 (1H, d, J=15.2 Hz), 3.38 (2H, dd, J=17.0, 11.9 Hz), 3.65 (1H, d, J=15.2 Hz), 4.07-4.14 (1H, m), 4.43-4.48 (1H, m), 7.15 (2H, d, J=8.0 Hz), 7.24 (2H, d, J=8.0 Hz), 7.46 (2H, d, J=8.0 Hz), 7.52 (2H, d, J=8.0 Hz).

MS (ESI) m/z: 406 [M+H]$^+$.

Example 13

(8-Methyl-3-{1-[4'-(pyrrolidin-1-ylcarbonyl)biphenyl-4-yl]cyclopropyl}-5,6,8,9-tetrahydro[1,2,4]triazolo[4,3-d][1,4]thiazepin-8-yl)methanol

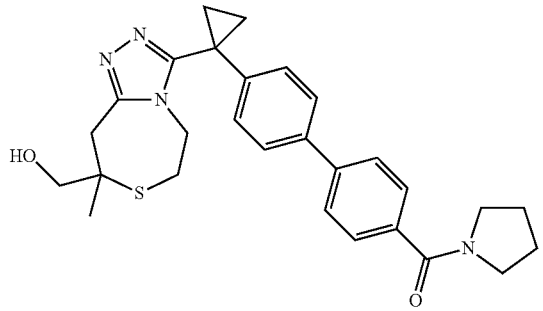

Example 13-1

8-({[Tert-butyl(dimethyl)silyl]oxy}methyl)-8-methyl-3-{1-[4'-(pyrrolidin-1-ylcarbonyl)biphenyl-4-yl]cyclopropyl}-5,6,8,9-tetrahydro[1,2,4]triazolo[4,3-d][1,4]thiazepine A solution of the compound (324 mg, 0.7 mmol) obtained in Example 1-2), 4-(pyrrolidin-1-ylcarbonyl)phenylboronic acid (32 mg, 0.77 mmol), tris(dibenzylideneacetone)dipalladium(0) (32 mg, 0.04 mmol), tricyclohexylphosphine (23 mg, 0.08 mmol), and tripotassium phosphate (260 mg, 1.19 mmol) in dioxane (2 mL) and water (1 mL) was stirred at 140° C. for 2 h under microwave irradiation. The reaction mixture was purified by silica gel chromatography (Isco Combiflash, 12 g, methanol:ethyl acetate=0:100 to 20:80, gradient) to obtain the title compound (385 mg, 91%) as a yellow oily substance.

$^1$H-NMR (500 Hz, CDCl$_3$) δ: 0.05 (3H, s), 0.07 (3H, s), 0.91 (9H, s), 1.19 (3H, s), 1.42-1.53 (2H, m), 1.56-1.61 (1H, m), 1.63-1.68 (1H, m), 1.84-2.00 (4H, m), 2.55 (1H, dd, J=15.5, 7.9 Hz), 2.69 (1H, dd, J=15.5, 7.9 Hz), 3.40 (2H, s), 3.46-3.57 (3H, m), 3.64-3.73 (2H, m), 4.06-4.15 (2H, m), 4.30-4.37 (1H, m), 7.16 (2H, d, J=8.0 Hz), 7.56 (2H, d, J=8.0 Hz), 7.59-7.65 (4H, m).

Example 13-2

(8-Methyl-3-{1-[4'-(pyrrolidin-1-ylcarbonyl)biphenyl-4-yl]cyclopropyl}-5,6,8,9-tetrahydro[1,2,4]triazolo[4,3-d][1,4]thiazepin-8-yl)methanol A solution of the compound (385 mg, 0.64 mmol) obtained in Example 13-1) and 4 M hydrochloric acid (1,4-dioxane solution, 2 mL) in methanol (3 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (241 mg, 77%) as a colorless solid.

¹H-NMR (400 Hz, CDCl₃) δ: 1.33 (3H, s), 1.42-1.47 (1H, m), 1.50-1.67 (3H, m), 1.86-1.92 (2H, m), 1.95-2.01 (2H, m), 2.35 (1H, t, J=6.7 Hz), 2.38-2.44 (1H, m), 2.56-2.64 (1H, m), 3.30-3.39 (2H, m), 3.48 (2H, t, J=6.5 Hz), 3.59-3.68 (4H, m), 4.07-4.15 (1H, m), 4.41-4.48 (1H, m), 7.15-7.18 (2H, m), 7.51-7.54 (2H, m), 7.56-7.61 (4H, m).

MS (ESI) m/z: 489 [M+H]⁺.

Example 14

{3-[1-(3-Fluorobiphenyl-4-yl)cyclopropyl]-8-methyl-5,6,8,9-tetrahydro[1,2,4]triazolo[4,3-d][1,4]thiazepin-8-yl}methanol

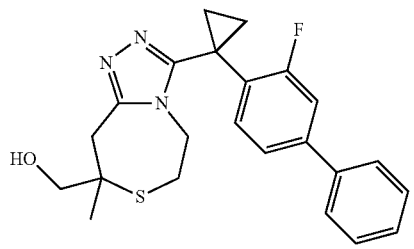 [SMILES: CC1(CO)Cc2nnc(C3(c4ccc(-c5ccccc5)cc4F)CC3)n2CCS1]

Example 14-1

(4-Bromo-2-fluorophenyl)acetonitrile

A solution of 4-bromo-2-fluorobenzyl bromide (26.8 g, 100 mmol) and sodium cyanide (5.4 g, 110 mmol) in ethanol (40 ml) and water (10 ml) was stirred at 100° C. for 8.5 h. The reaction mixture was cooled to room temperature, then concentrated under reduced pressure, and extracted with ethyl acetate, and the organic layer was washed with saturated sodium chloride solution and dried with anhydrous sodium sulfate. After filtration, the filtrate was concentrated under reduced pressure to obtain the title compound (22.6 g, quant.) as a black oily substance.

¹H-NMR (400 Hz, CDCl₃) δ: 3.73 (2H, s), 7.27-7.38 (3H, m).

Example 14-2

1-(4-bromo-2-fluorophenyl)cyclopropanecarbonitrile

A solution of the compound (22.6 g, 23.36 mmol) obtained in Example 14-1), 1-bromo-2-chloroethane (18.9 g, 132 mmol), benzyltriethylammonium chloride (0.48 g, 2.34 mmol), and potassium hydroxide (41.5 g, 739 mmol) in water (40 mL) was stirred at 40° C. for 9 h. The reaction mixture was cooled to room temperature and extracted with ethyl acetate, and the organic layer was washed with water, a 1 M aqueous hydrochloric acid solution, and saturated sodium chloride solution and dried with anhydrous sodium sulfate. After concentration under reduced pressure, the residue was purified by silica gel column chromatography (Isco Combiflash, 40 g, hexane:ethyl acetate=0:100 to 100:0, gradient) to obtain the title compound (24.6 g, 97%) as a black oily substance.

¹H-NMR (500 Hz, CDCl₃) δ: 1.38 (2H, m), 1.70 (2H, m), 7.20-7.32 (3H, m).

Example 14-3

1-(4-Bromo-2-fluorophenyl)cyclopropanecarboxylic acid

A solution of the compound (24.6 g, 102 mmol) obtained in Example 14-2) and potassium hydroxide (46 g, 820 mmol) in ethanol (200 ml) and water (40 ml) was heated to reflux for 7 h. The reaction mixture was cooled to room temperature, and then 5 N hydrochloric acid was added until the reaction mixture was rendered acidic. The deposited solid was collected by filtration, washed with water, and then dried to obtain the title compound (28.7 g, quant.) as a colorless solid.

¹H-NMR (400 Hz, CDCl₃) δ: 1.23 (2H, m), 1.72 (2H, m), 7.10-7.15 (1H, m), 7.22-7.25 (2H, m).

Example 14-4

1-(4-Bromo-2-fluorophenyl)cyclopropanecarbohydrazide

A solution of the compound (26.55 g, 102.5 mmol) obtained in Example 14-3), 1-ethyl-3-(3-dimethylaminopropyl)carbodiimide hydrochloride (21.6 g, 112.7 mmol), 1-hydroxybenzotriazole monohydrate (17.26 g, 112.7 mmol), triethylamine (42.9 mL, 307 mmol), and tert-butoxycarbonylhydrazide (16.3 g, 123 mmol) in N,N-dimethylformamide (400 mL) was stirred overnight at room temperature. Water was added to the reaction mixture, the mixture was extracted with ethyl acetate, and the organic layer was washed with saturated aqueous sodium hydrogencarbonate and saturated sodium chloride solution and then dried with anhydrous sodium sulfate. After filtration, the filtrate was concentrated under reduced pressure. A 4 M solution (60 mL) of hydrochloric acid in 1,4-dioxane and methanol (300 mL) were added to the obtained partially purified product, and the mixture was stirred at room temperature for 6.5 h. The reaction mixture was concentrated under reduced pressure, dichloromethane was added to the residue, and the organic layer was washed with saturated aqueous sodium hydrogencarbonate and saturated sodium chloride solution and then dried with anhydrous sodium sulfate. The filtrate was concentrated under reduced pressure, hexane was added to the obtained partially purified product, and the solid was collected by filtration to obtain the title compound (11.6 g, 42%) as a colorless solid.

¹H-NMR (400 Hz, CDCl₃) δ: 1.06 (2H, m), 1.68 (2H, m), 3.60-3.68 (2H, m), 6.53 (1H, m), 7.21-7.33 (3H, m).

Example 14-5

3-[1-(4-Bromo-2-fluorophenyl)cyclopropyl]-8-({[tert-butyl(dimethyl)silyl]oxy}methyl)-8-methyl-5,6,8,9-tetrahydro[1,2,4]triazolo[4,3-d][1,4]thiazepine A solution of the compound (2.73 g, 10 mmol) obtained in Example 14-4) and 7-({[tert-butyl(dimethyl)silyl]oxy}methyl)-7-methyl-5-(methylthio)-2,3,6,7-tetrahydro-1,4-thiazepine (3.2 g, 10 mmol) in n-butanol (50 mL) was stirred at 140° C. for 7 h. The reaction mixture was cooled to room temperature and concentrated under reduced pressure. The residue was purified by silica gel column chromatography (Isco Combiflash, 40 g, hexane:ethyl acetate=0:100 to 100:0, gradient) to obtain the title compound (2.09 g, 40%) as a colorless solid.

¹H-NMR (500 Hz, CDCl₃) δ: 0.01 (3H, s), 0.04 (3H, s), 0.89 (9H, s), 1.14 (3H, s), 1.42-1.51 (2H, m), 1.55-1.60 (1H, m), 1.63-1.70 (1H, m), 2.53-2.60 (1H, m), 2.72-2.78 (1H, m), 3.32-3.39 (2H, m), 3.46-3.52 (2H, m), 4.17-4.23 (1H, m), 4.43-4.49 (1H, m), 7.19-7.33 (3H, m).

Example 14-6

3-[1-(4-Bromo-2-fluorophenyl)cyclopropyl]-8-({[tert-butyl(dimethyl)silyl]oxy}methyl)-8-methyl-5,6,8,9-tetrahydro[1,2,4]triazolo[4,3-d][1,4]thiazepine A solution of the compound (421 mg, 0.8 mmol) obtained in Example 14-5), phenylboronic acid (195 mg, 1.6 mmol), tetrakis(triphenylphosphine)palladium(0) (184 mg, 0.16 mmol), and potassium carbonate (221 mg, 1.6 mmol) in dimethoxyethane (3.2 mL) and water (0.8 mL) was stirred at 100° C. for 7.5 h. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (191 mg, 46%) as a colorless solid.

$^1$H-NMR (500 Hz, CDCl$_3$) δ: 0.01 (3H, s), 0.04 (3H, s), 0.89 (9H, s), 1.15 (3H, s), 1.47-1.57 (2H, m), 1.57-1.63 (1H, m), 1.66-1.72 (1H, m), 2.53-2.60 (1H, m), 2.69-2.76 (1H, m), 3.36 (2H, m), 3.46-3.52 (2H, m), 4.21-4.27 (1H, m), 4.49-4.55 (1H, m), 7.23-7.25 (1H, m), 7.31-7.39 (2H, m), 7.41-7.48 (3H, m), 7.51-7.56 (2H, m).

Example 14-7

{3-[1-(3-Fluorobiphenyl-4-yl)cyclopropyl]-8-methyl-5,6,8,9-tetrahydro[1,2,4]triazolo[4,3-d][1,4]thiazepin-8-yl}methanol A solution of the compound (191 mg, 0.36 mmol) obtained in Example 14-6) and 4 M hydrochloric acid (1,4-dioxane solution, 2 mL) in methanol (3 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (161 mg, quant.) as a colorless solid.

$^1$H-NMR (400 Hz, CDCl$_3$) δ: 1.31 (3H, s), 1.45-1.50 (1H, m), 1.54-1.60 (2H, m), 1.68-1.74 (1H, m), 2.23 (1H, brs), 2.44-2.50 (1H, m), 2.55-2.62 (1H, m), 3.25-3.34 (3H, m), 3.58 (1H, d, J=15.3 Hz), 4.17-4.24 (1H, m), 4.66-4.73 (1H, m), 7.24-7.28 (1H, m), 7.34-7.40 (2H, m), 7.43-7.50 (3H, m), 7.52-7.56 (2H, m).

MS (ESI) m/z: 410 [M+H]$^+$.

Example 15

{3-[1-(2-Fluoro-4-pyridin-3-ylphenyl)cyclopropyl]-8-methyl-5,6,8,9-tetrahydro[1,2,4]triazolo[4,3-d][1,4]thiazepin-8-yl}methanol

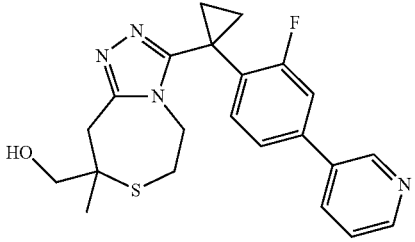 [SMILES: CC1(CO)Cc2nnc(C3(c4ccc(-c5cccnc5)cc4F)CC3)n2CCS1]

Example 15-1

8-({[Tert-butyl(dimethyl)silyl]oxy}methyl)-3-[1-(2-fluoro-4-pyridin-3-ylphenyl)cyclopropyl]-8-methyl-5,6,8,9-tetrahydro[1,2,4]triazolo[4,3-d][1,4]thiazepine A solution of the compound (421 mg, 0.8 mmol) obtained in Example 14-5), 3-pyridylboronic acid (197 mg, 1.6 mmol), tetrakis(triphenylphosphine)palladium(0) (185 mg, 0.16 mmol), and potassium carbonate (221 mg, 1.6 mmol) in dimethoxyethane (3.2 mL) and water (0.8 mL) was stirred at 100° C. for 6 h. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (344 mg, 82%) as a colorless solid.

$^1$H-NMR (400 Hz, CDCl$_3$) δ: 0.02 (3H, s), 0.04 (3H, s), 0.89 (9H, s), 1.16 (3H, s), 1.48-1.63 (2H, m), 1.67-1.74 (2H, m), 2.55-2.63 (1H, m), 2.72-2.80 (1H, m), 3.36 (2H, s), 3.50 (2H, dd, J=16.8, 10.2 Hz), 4.20-4.28 (1H, m), 4.50-4.57 (1H, m), 7.23-7.28 (1H, m), 7.31-7.35 (1H, m), 7.36-7.40 (1H, m), 7.50-7.54 (1H, m), 7.81-7.85 (1H, m), 8.60-8.64 (1H, m), 8.79-8.82 (1H, m).

Example 15-2

{3-[1-(2-Fluoro-4-pyridin-3-ylphenyl)cyclopropyl]-8-methyl-5,6,8,9-tetrahydro[1,2,4]triazolo[4,3-d][1,4]thiazepin-8-yl}methanol A solution of the compound (517 mg, 1.0 mmol) obtained in Example 15-1) and 4 M hydrochloric acid (1,4-dioxane solution, 2 mL) in methanol (2 mL) was stirred at room temperature for 15 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (226 mg, 84%) as a colorless solid.

¹H-NMR (400 Hz, CDCl₃) δ: 1.31 (3H, s), 1.46-1.54 (1H, m), 1.56-1.64 (2H, m), 1.69-1.75 (1H, m), 2.38-2.44 (1H, m), 2.48-2.55 (1H, m), 2.59-2.67 (1H, m), 3.26-3.36 (3H, m), 3.58 (1H, d, J=15.3 Hz), 4.19-4.26 (1H, m), 4.65-4.72 (1H, m), 7.24-7.28 (1H, m), 7.34-7.40 (2H, m), 7.54-7.56 (1H, m), 7.82-7.85 (1H, m), 8.61-8.63 (1H, m), 8.79-8.82 (1H, m).

MS (ESI) m/z: 411 [M+H]⁺.

Example 16

{8-Methyl-3-[1-(4-pyridin-2-ylphenyl)cyclopropyl]-5,6,8,9-tetrahydro[1,2,4]triazolo[4,3-d][1,4]thiazepin-8-yl}methanol

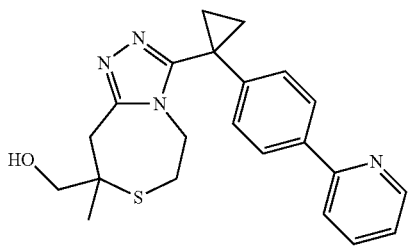 [SMILES: CC1(CO)Cc2nnc(C3(c4ccc(-c5ccccn5)cc4)CC3)n2CCS1]

Example 16-1

1-(4-Bromophenyl)cyclopropanecarboxylic acid

A solution of 4-bromophenylacetonitrile (50.0 g, 255 mmol), 1-bromo-2-chloroethane (26.5 mL, 319 mmol), benzyltriethylammonium chloride (1.16 g, 5.10 mol), and potassium hydroxide (100 g, 1.79 mol) in water (100 mL) was stirred at 50° C. for 3 h. Ethanol (400 mL) was added to the reaction mixture, and the mixture was stirred at 100° C. for 3 days. The reaction mixture was neutralized by pouring it into 5 N hydrochloric acid (360 mL) with ice cooling. The reaction mixture was extracted with dichloromethane, the organic layer was dried with anhydrous sodium sulfate, and then the solvent was distilled off under reduced pressure. Diisopropyl ether was added to the residue, and the precipitate was collected by filtration and dried under reduced pressure to obtain the title compound (50.4 g, 82%) as a white solid.

¹H-NMR (500 MHz, CDCl₃) δ: 1.23 (2H, q, J=3.7 Hz), 1.67 (2H, q, J=3.7 Hz), 7.22 (2H, dt, J=8.6, 2.2 Hz), 7.43 (2H, dt, J=8.6, 2.2 Hz).

Example 16-2

Tert-butyl 2-{[1-(4-bromophenyl)cyclopropyl]carbonyl}hydrazinecarboxylate

A solution of the compound (25.8 g, 107 mmol) obtained in Example 16-1), 1-hydroxybenzotriazole (15.9 g, 118 mmol), triethylamine (37.4 mL, 268 mol), 1-ethyl-3-(3-dimethylaminopropyl)carbodiimide hydrochloride (22.6 g, 118 mmol), and tert-butoxycarbonylhydrazide (17.0 g, 129 mmol) in N,N-dimethylformamide (500 mL) was stirred at room temperature for 15 h. Saturated aqueous sodium hydrogencarbonate was added to the reaction mixture, and the mixture was extracted with dichloromethane. The organic layer was washed with water and saturated sodium chloride solution in this order and dried with anhydrous sodium sulfate, and then the solvent was distilled off under reduced pressure. The residue was dried under reduced pressure to obtain the title compound (36.2 g, 95%) as a white solid.

¹H-NMR (400 MHz, CD₃OD) δ: 1.10 (2H, q, J=3.7 Hz), 1.45 (9H, s), 1.67 (2H, q, J=3.7 Hz), 6.31 (1H, brs), 6.82 (1H, brs), 7.33-7.37 (2H, brm), 7.52 (2H, dt, J=8.7, 2.2 Hz).

Example 16-3

1-(4-Bromophenyl)cyclopropanecarbohydrazide

A solution of the compound (855 g, 2.41 mol) obtained in Example 16-2) and 4 M hydrochloric acid (1,4-dioxane solution, 1.25 L) in methanol (6.0 L) was stirred overnight at room temperature. The reaction mixture was concentrated under reduced pressure, a 5 M aqueous sodium hydroxide solution (500 mL) was added to the residue at 0° C., the mixture was extracted with ethyl acetate, and the organic layer was washed with saturated sodium chloride solution and dried with anhydrous sodium sulfate. After concentration under reduced pressure, diisopropyl ether was added to the residue, and the white precipitate was collected by filtration and dried under reduced pressure to obtain the title compound (451 g, 73%) as a white solid.

¹H-NMR (400 MHz, CDCl₃) δ: 1.06 (2H, dd, J=6.8, 3.7 Hz), 1.62 (2H, dd, J=6.8, 3.7 Hz), 3.80 (2H, brs), 6.41 (1H, brs), 7.27 (2H, d, J=8.2 Hz), 7.50 (2H, d, J=8.2 Hz).

Example 16-4

3-[1-(4-Bromophenyl)cyclopropyl]-8-({[tert-butyl(dimethyl)silyl]oxy}methyl)-8-methyl-5,6,8,9-tetrahydro[1,2,4]triazolo[4,3-d][1,4]thiazepine A solution of 7-({[tert-butyl(dimethyl)silyl]oxy}methyl)-7-methyl-5-(methylthio)-2,3,6,7-tetrahydro-1,4-thiazepine (34.4 g, 108 mmol) and the compound (27.5 g, 108 mmol) obtained in Example 16-3) in 1-butanol (800 mL) was stirred at 140° C. for 6 h. The reaction mixture was cooled to room temperature, the solvent was distilled off under reduced pressure, and the residue was purified by silica gel column chromatography (ethyl acetate:hexane=1:1 to 1:0) to obtain the title compound (36.3 g, 66%) as a white solid.

¹H-NMR (500 MHz, CDCl₃) δ: 0.09 (3H, s), 0.11 (3H, s), 0.95 (9H, s), 1.20 (3H, s), 1.50-1.60 (4H, m), 2.67 (1H, dd, J=15.6, 7.3 Hz), 2.85 (1H, dd, J=15.6, 7.8 Hz), 3.41 (2H, dd, J=34.7, 15.1 Hz), 3.57 (2H, q, J=9.8 Hz), 4.29 (1H, dd, J=14.6, 7.3 Hz), 4.38 (1H, dd, J=14.6, 7.8 Hz), 7.07 (2H, dd, J=8.8, 2.2 Hz), 7.49 (2H, dd, J=8.8, 2.0 Hz).

Example 16-5

8-({[Tert-butyl(dimethyl)silyl]oxy}methyl)-8-methyl-3-{1-[4-(4,4,5,5-tetramethyl-1,3,2-dioxaborolan-2-yl)phenyl]cyclopropyl}-5,6,8,9-tetrahydro[1,2,4]triazolo[4,3-d][1,4]thiazepine A solution of the compound (14.18 g, 27.89 mmol) obtained in Example 16-4), bis(pinacolato)diboron (14.45 g, 55.78 mmol), 1,1'-bis(diphenylphosphino)ferrocene-palladium(II) dichloride-dichloromethane complex (2.28 g, 2.79 mmol), and potassium acetate (8.21 g, 83.66 mmol) in dioxane (140 mL) was heated to reflux for 4 h. The reaction mixture was cooled to room temperature, water (100 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate: methanol=70:30) to obtain the title compound (15.31 g, 99%) as a brown solid.

¹H-NMR (400 MHz, CDCl₃) δ: 0.05 (3H, s), 0.07 (3H, s), 0.91 (9H, s), 1.17 (3H, s), 1.24 (6H, s), 1.27 (6H, s), 1.43-1.47 (2H, m), 1.58-1.63 (2H, m), 2.46 (1H, ddd, J=15.6, 7.9, 2.2 Hz), 2.59 (1H, ddd, J=15.6, 7.7, 1.8 Hz), 3.39 (2H, s), 3.50 (1H, d, J=10.2 Hz), 3.53 (1H, d, J=10.2 Hz), 4.03 (1H, ddd, J=14.4, 7.9, 1.8 Hz), 4.26 (1H, ddd, J=14.4, 7.7, 2.2 Hz), 7.06 (2H, d, J=8.2 Hz), 7.72 (2H, d, J=8.2 Hz).

Example 16-6

8-({[Tert-butyl(dimethyl)silyl]oxy}methyl)-8-methyl-3-[1-(4-pyridin-2-ylphenyl)cyclopropyl]-5,6,8,9-tetrahydro[1,2,4]triazolo[4,3-d][1,4]thiazepine A solution of the compound (555 mg, 1.0 mmol) obtained in Example 16-5), 2-bromopyridine (243 mg, 2 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 100° C. for 30 min under microwave irradiation. The reaction mixture was cooled to room temperature and purified by silica gel chromatography (Isco Combiflash, 40 g, methanol:ethyl acetate=0:100 to 20:80, gradient) to obtain the title compound (346 mg, 68%) as a brown solid.

¹H-NMR (400 MHz, CDCl₃) δ: 0.05 (3H, s), 0.07 (3H, s), 0.91 (9H, s), 1.19 (3H, s), 1.46-1.52 (2H, m), 1.57-1.68 (2H, m), 2.47-2.56 (1H, m), 2.62-2.69 (1H, m), 3.36-3.41 (2H, m), 3.52 (2H, dd, J=15.8, 10.0 Hz), 4.03-4.10 (1H, m), 4.27-4.35 (1H, m), 7.15-7.20 (2H, m), 7.22-7.27 (1H, m), 7.68-7.71 (1H, m), 7.74-7.77 (1H, m), 7.90-7.94 (2H, m), 8.67-8.69 (1H, m).

Example 16-7

{8-Methyl-3-[1-(4-pyridin-2-ylphenyl)cyclopropyl]-5,6,8,9-tetrahydro[1,2,4]triazolo[4,3-d][1,4]thiazepin-8-yl}methanol A solution of the compound (346 mg, 0.68 mmol) obtained in Example 16-6) and 4 M hydrochloric acid (1,4-dioxane solution, 2 mL) in methanol (2 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (254 mg, 95%) as a colorless solid.

¹H-NMR (400 MHz, CDCl₃) δ: 1.31 (3H, s), 1.40-1.70 (4H, m), 2.33-2.41 (1H, m), 2.53-2.62 (1H, m), 3.27-3.40 (3H, m), 3.62 (1H, d, J=14.9 Hz), 4.03-4.11 (1H, m), 4.37-4.44 (1H, m), 7.16-7.26 (3H, m), 7.68-7.72 (1H, m), 7.74-7.80 (1H, m), 7.91-7.95 (2H, m), 8.66-8.70 (1H, m).

MS (ESI) m/z: 393 [M+H]⁺.

Example 17

{8-Methyl-3-{1-[4-(2-methylpyridin-3-yl)phenyl]cyclopropyl}-5,6,8,9-tetrahydro[1,2,4]triazolo[4,3-d][1,4]thiazepin-8-yl}methanol

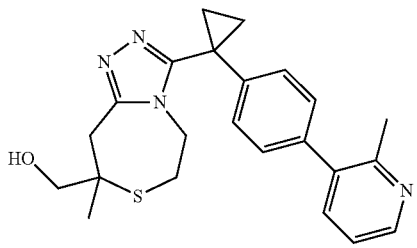 [SMILES: Cc1ncccc1-c1ccc(C2(c3nnc4n3CCSC(C)(CO)C4)CC2)cc1]

Example 17-1

8-({[Tert-butyl(dimethyl)silyl]oxy}methyl)-8-methyl-3-{1-[4-(2-methylpyridin-3-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-5), 3-bromo-2-methylpyridine (344 mg, 2 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 100° C. for 30 min under microwave irradiation. The reaction mixture was cooled to room temperature and purified by silica gel chromatography (Isco Combiflash, 40 g, methanol:ethyl acetate=0:100 to 20:80, gradient) to obtain the title compound (388 mg, 72%) as a brown solid.

¹H-NMR (400 MHz, CDCl₃) δ: 0.05 (3H, s), 0.07 (3H, s), 0.91 (9H, s), 1.19 (3H, s), 1.44-1.54 (2H, m), 1.57-1.62 (1H, m), 1.65-1.69 (1H, m), 2.47 (3H, s), 2.52-2.58 (1H, m), 2.65-2.73 (1H, m), 3.41 (2H, s), 3.53 (2H, dd, J=17.8, 10.0 Hz), 4.09-4.15 (1H, m), 4.32-4.40 (1H, m), 7.12-7.61 (6H, m), 8.48-8.51 (1H, m).

Example 17-2

{8-Methyl-3-{1-[4-(2-methylpyridin-3-yl)phenyl]cyclopropyl}-5,6,8,9-tetrahydro[1,2,4]triazolo[4,3-d][1,4]thiazepin-8-yl}methanol A solution of the compound (388 mg, 0.75 mmol) obtained in Example 17-1) and 4 M hydrochloric acid (1,4-dioxane solution, 2 mL) in methanol (2 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (204 mg, 67%) as a colorless solid.

¹H-NMR (400 MHz, CDCl₃) δ: 1.34 (3H, s), 1.44-1.68 (4H, m), 2.40-2.50 (4H, m), 2.57-2.65 (1H, m), 3.31-3.39 (3H, m), 3.62 (1H, d, J=15.2 Hz), 4.10-4.18 (1H, m), 4.43-

4.50 (1H, m), 7.15-7.20 (3H, m), 7.24-7.27 (2H, m), 7.47-7.50 (1H, m), 8.49-8.52 (1H, m).
MS (ESI) m/z: 407 [M+H]⁺.

Example 18

{8-Methyl-3-{1-[4-(6-methylpyridin-3-yl)phenyl]cyclopropyl}-5,6,8,9-tetrahydro[1,2,4]triazolo[4,3-d][1,4]thiazepin-8-yl}methanol

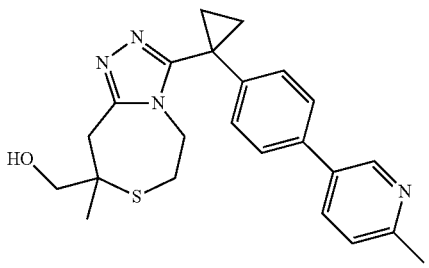 [SMILES: Cc1ccc(-c2ccc(C3(c4nnc5n4CCSC(C)(CO)C5)CC3)cc2)cn1]

Example 18-1

8-({[Tert-butyl(dimethyl)silyl]oxy}methyl)-8-methyl-3-{1-[4-(6-methylpyridin-3-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-5), 3-bromo-6-methylpyridine (344 mg, 2 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 100° C. for 30 min under microwave irradiation. The reaction mixture was cooled to room temperature and purified by silica gel chromatography (Isco Combiflash, 40 g, methanol:ethyl acetate=0:100 to 20:80, gradient) to obtain the title compound (342 mg, 66%) as a brown solid.
¹H-NMR (400 MHz, CDCl₃) δ: 0.05 (3H, s), 0.07 (3H, s), 0.91 (9H, s), 1.19 (3H, s), 1.42-1.52 (2H, m), 1.55-1.60 (1H, m), 1.62-1.70 (1H, m), 2.52-2.62 (4H, m), 2.66-2.74 (1H, m), 3.40 (2H, s), 3.53 (2H, dd, J=18.2, 10.0 Hz), 4.05-4.12 (1H, m), 4.29-4.36 (1H, m), 7.15-7.19 (2H, m), 7.20-7.23 (1H, m), 7.46-7.50 (2H, m), 7.71-7.76 (1H, m), 8.67-8.70 (1H, m).

Example 18-2

{8-Methyl-3-{1-[4-(6-methylpyridin-3-yl)phenyl]cyclopropyl}-5,6,8,9-tetrahydro[1,2,4]triazolo[4,3-d][1,4]thiazepin-8-yl}methanol A solution of the compound (342 mg, 0.66 mmol) obtained in Example 18-1) and 4 M hydrochloric acid (1,4-dioxane solution, 2 mL) in methanol (2 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (215 mg, 81%) as a colorless solid.

¹H-NMR (CDCl₃) δ: 1.31 (3H, s), 1.41-1.45 (1H, m), 1.47-1.52 (1H, m), 1.54-1.65 (2H, m), 2.37-2.44 (1H, m), 2.56-2.64 (4H, m), 3.27-3.38 (3H, m), 3.57-3.62 (1H, m), 4.05-4.13 (1H, m), 4.38-4.45 (1H, m, 7.16-7.18 (2H, m), 7.21-7.25 (1H, m), 7.46-7.50 (2H, m), 7.73-7.78 (1H, m), 8.66-8.69 (1H, m).
MS (ESI) m/z: 407 [M+H]⁺.

Example 19

{8-Methyl-3-{1-[4-(4-methylpyridin-3-yl)phenyl]cyclopropyl}-5,6,8,9-tetrahydro[1,2,4]triazolo[4,3-d][1,4]thiazepin-8-yl}methanol

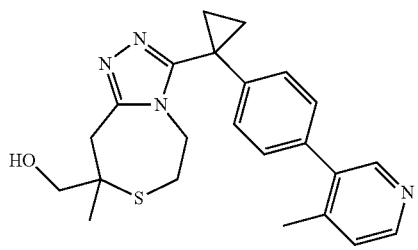 [SMILES: Cc1ccncc1-c1ccc(C2(c3nnc4n3CCSC(C)(CO)C4)CC2)cc1]

Example 19-1

8-({[Tert-butyl(dimethyl)silyl]oxy}methyl)-8-methyl-3-{1-[4-(4-methylpyridin-3-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-5), 3-bromo-4-methylpyridine (344 mg, 2 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 100° C. for 30 min under microwave irradiation. The reaction mixture was cooled to room temperature and purified by silica gel chromatography (Isco Combiflash, 40 g, methanol:ethyl acetate=0:100 to 20:80, gradient) to obtain the title compound (380 mg, 71%) as a brown solid.
¹H-NMR (400 MHz, CDCl₃) δ: 0.05 (3H, s), 0.07 (3H, s), 0.91 (9H, s), 1.20 (3H, s), 1.44-1.55 (2H, m), 1.57-1.62 (1H, m), 1.66-1.70 (1H, m), 2.26 (3H, s), 2.52-2.60 (1H, m), 2.67-2.75 (1H, m), 3.41 (2H, s), 3.53 (2H, dd, J=18.0, 10.2 Hz), 4.07-4.15 (1H, m), 4.32-4.40 (1H, m), 7.13-7.19 (3H, m), 7.22-7.27 (2H, m), 8.37-8.41 (1H, m), 8.42-8.46 (1H, m).

Example 19-2

{8-Methyl-3-{1-[4-(4-methylpyridin-3-yl)phenyl]cyclopropyl}-5,6,8,9-tetrahydro[1,2,4]triazolo[4,3-d][1,4]thiazepin-8-yl}methanol A solution of the compound (380 mg, 0.73 mmol) obtained in Example 19-1) and 4 M hydrochloric acid (1,4-dioxane solution, 2 mL) in methanol (2 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (230 mg, 78%) as a colorless solid.

$^1$H-NMR (400 MHz, CDCl$_3$) δ: 1.33 (3H, s), 1.45-1.50 (1H, m), 1.51-1.56 (1H, m), 1.58-1.67 (2H, m), 2.27 (3H, s), 2.41-2.48 (1H, m), 2.58-2.67 (1H, m), 3.30-3.43 (4H, m), 3.62 (1H, d, J=15.2 Hz, 4.10-4.18 (1H, m), 4.42-4.49 (1H, m), 7.15-7.21 (3H, m), 7.24-7.27 (2H, m), 8.39 (1H, s), 8.45 (1H, d, J=5.1 Hz).

MS (ESI) m/z: 407 [M+H]$^+$.

Example 20

{8-Methyl-3-=1-[4-(5-methylpyridin-3-yl)phenyl]cyclopropyl}-5,6,8,9-tetrahydro[1,2,4]triazolo[4,3-d][1,4]thiazepin-8-yl}methanol

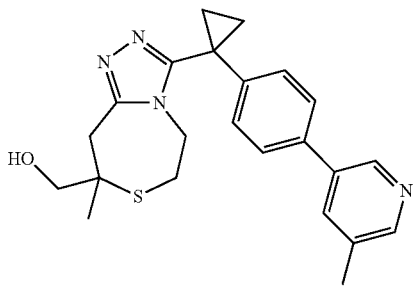 [SMILES: Cc1cncc(-c2ccc(C3(c4nnc5n4CCSC(C)(CO)C5)CC3)cc2)c1]

Example 20-1

3-{1-[4-(5-Bromopyridin-3-yl)phenyl]cyclopropyl}-8-({[tert-butyl(dimethyl)silyl]oxy}methyl)-8-methyl-5,6,8,9-tetrahydro[1,2,4]triazolo[4,3-d][1,4]thiazepine A solution of the compound (555 mg, 1.0 mmol) obtained in Example 16-5), 3,5-dibromopyridine (947 mg, 4 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 100° C. for 30 min under microwave irradiation. The reaction mixture was cooled to room temperature and purified by silica gel chromatography (Isco Combiflash, 40 g, methanol:ethyl acetate=0:100 to 20:80, gradient) to obtain the title compound (534 mg, 91%) as a brown solid.

$^1$H-NMR (400 MHz, CDCl$_3$) δ: 0.05 (3H, s), 0.07 (3H, s), 0.91 (9H, s), 1.20 (3H, s), 1.43-1.55 (2H, m), 1.58-1.63 (1H, m), 1.65-1.72 (1H, m), 2.52-2.60 (1H, m), 2.67-2.76 (1H, m), 3.40 (2H, s), 3.53 (2H, dd, J=17.2, 9.8 Hz), 4.03-4.13 (1H, m), 4.28-4.36 (1H, m), 7.16-7.20 (2H, m), 7.46-7.50 (2H, m), 7.97-7.99 (1H, m), 8.63-8.66 (1H, m), 8.70-8.73 (1H, m).

Example 20-2

{8-Methyl-3-{1-[4-(5-methylpyridin-3-yl)phenyl]cyclopropyl}-5,6,8,9-tetrahydro[1,2,4]triazolo[4,3-d][1,4]thiazepin-8-yl}methanol A solution of the compound (555 mg, 1.0 mmol) obtained in Example 20-1), a 50% solution (0.51 ml, 1.82 mmol) of trimethylboroxine in tetrahydrofuran, [1,1'-bis(diphenylphosphino)ferrocene]palladium(II) dichloride-dichloromethane complex (74 mg, 0.09 mmol), and cesium carbonate (594 mg, 1.82 mmol) in N,N-dimethylformamide (3 ml) was stirred at 130° C. for 2 h under microwave irradiation. The reaction mixture was cooled to room temperature and partially purified by silica gel chromatography (Isco Combiflash, 40 g, methanol:ethyl acetate=0:100 to 40:60, gradient). A solution of the obtained partially purified product and 4 M hydrochloric acid (1,4-dioxane solution, 2 mL) in methanol (2 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (108 mg, 29%) as a colorless solid.

$^1$H-NMR (CDCl$_3$) δ: 1.34 (3H, s), 1.44-1.70 (4H, m), 2.39-2.47 (1H, m), 2.45 (3H, s), 2.59-2.67 (1H, m), 3.30-3.42 (3H, m), 3.60-3.68 (1H, m), 4.12 (1H, dd, J=14.9, 8.5 Hz), 4.44 (1H, dd, J=14.9, 7.0 Hz), 7.19-7.23 (2H, m), 7.50-7.54 (2H, m), 7.75-7.81 (1H, m), 8.44 (1H, brs), 8.65 (1H, brs).

MS (ESI) m/z: 407 [M+H]$^+$.

Example 21

{8-Methyl-3-{1-[4-(6-methylpyridin-2-yl)phenyl]cyclopropyl}-5,6,8,9-tetrahydro[1,2,4]triazolo[4,3-d][1,4]thiazepin-8-yl}methanol

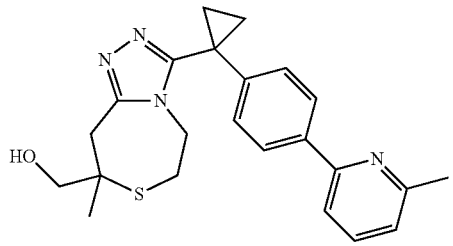 [SMILES: Cc1cccc(-c2ccc(C3(c4nnc5n4CCSC(C)(CO)C5)CC3)cc2)n1]

Example 21-1

8-({[Tert-butyl(dimethyl)silyl]oxy}methyl)-8-methyl-3-{1-[4-(6-methylpyridin-2-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-5), 6-bromo-2-picoline (344 mg, 2 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 100° C. for 1 h under microwave irradiation. The reaction mixture was cooled to room temperature and purified by silica gel chromatography (Isco Combiflash, 40 g, methanol:ethyl acetate=0:100 to 20:80, gradient) to obtain the title compound (425 mg, 82%) as a yellow oily substance.

$^1$H-NMR (400 MHz, CDCl$_3$) δ: 0.05 (2H, s), 0.07 (3H, s), 0.91 (9H, s), 1.19 (3H, s), 1.42-1.52 (2H, m), 1.56-1.68 (2H, m), 2.49-2.56 (1H, m), 2.62 (3H, s), 2.62-2.70 (1H, m), 3.39 (2H, s), 3.52 (2H, dd, J=16.8, 10.6 Hz), 4.03-4.09 (1H, m), 4.25-4.35 (1H, m), 7.07-7.11 (1H, m), 7.14-7.18 (2H, m), 7.46-7.50 (1H, m), 7.60-7.65 (1H, m), 7.88-7.92 (2H, m).

Example 21-2

{8-Methyl-3-{1-[4-(6-methylpyridin-2-yl)phenyl]cyclopropyl}-5,6,8,9-tetrahydro[1,2,4]triazolo[4,3-d][1,4]thiazepin-8-yl}methanol A solution of the compound (425 mg, 0.82 mmol) obtained in Example 21-1) and 4 M hydrochloric acid (1,4-dioxane solution, 2 mL) in methanol (2 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (286 mg, 86%) as a colorless solid.
$^1$H-NMR (400 MHz, CDCl$_3$) δ: 1.33 (3H, s), 1.40-1.46 (1H, m), 1.51-1.69 (3H, m), 2.34-2.42 (1H, m), 2.55-2.65 (4H, m), 3.29-3.40 (3H, m), 3.61 (1H, d, J=15.2 Hz), 4.03-4.12 (1H, m), 4.38-4.46 (1H, m), 7.09-7.13 (1H, m), 7.16-7.20 (2H, m), 7.47-7.51 (1H, m), 7.62-7.68 (1H, m), 7.90-7.95 (2H, m).
MS (ESI) m/z: 407 [M+H]$^+$.

Example 22

{8-Methyl-3-{1-[4-(5-methylpyridin-2-yl)phenyl]cyclopropyl}-5,6,8,9-tetrahydro[1,2,4]triazolo[4,3-d][1,4]thiazepin-8-yl}methanol

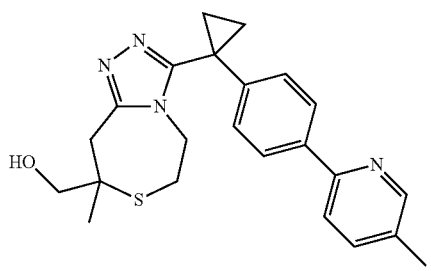 [SMILES: Cc1ccc(-c2ccc(C3(c4nnc5n4CCSC(C)(CO)C5)CC3)cc2)nc1]

Example 22-1

8-({[Tert-butyl(dimethyl)silyl]oxy}methyl)-8-methyl-3-{1-[4-(5-methylpyridin-2-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-5), 6-bromo-3-picoline (344 mg, 2 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 100° C. for 1 h under microwave irradiation. The reaction mixture was cooled to room temperature and purified by silica gel chromatography (Isco Combiflash, 40 g, methanol:ethyl acetate=0:100 to 20:80, gradient) to obtain the title compound (107 mg, 21%) as a yellow oily substance.

$^1$H-NMR (400 MHz, CDCl$_3$) δ: 0.05 (3H, s), 0.07 (3H, s), 0.91 (9H, s), 1.18 (3H, s), 1.43-1.68 (4H, m), 2.38 (3H, s), 2.48-2.56 (1H, m), 2.61-2.70 (1H, m), 3.39 (2H, s), 3.48-3.56 (2H, m), 4.02-4.10 (1H, m), 4.28-4.34 (1H, m), 7.15-7.19 (2H, m), 7.56-7.63 (2H, m), 7.87-7.92 (2H, m), 8.50-8.53 (1H, m).

Example 22-2

{8-Methyl-3-{1-[4-(5-methylpyridin-2-yl)phenyl]cyclopropyl}-5,6,8,9-tetrahydro[1,2,4]triazolo[4,3-d][1,4]thiazepin-8-yl}methanol A solution of the compound (107 mg, 0.21 mmol) obtained in Example 22-1) and 4 M hydrochloric acid (1,4-dioxane solution, 2 mL) in methanol (2 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (69 mg, 83%) as a colorless solid.
$^1$H-NMR (400 MHz, CDCl$_3$) δ: 1.33 (3H, s), 1.41-1.69 (4H, m), 2.35-2.43 (4H, m), 2.54-2.62 (1H, m), 3.27-3.38 (3H, m), 3.59-3.65 (1H, m), 4.04-4.13 (1H, m), 4.38-4.46 (1H, m), 7.17-7.22 (2H, m), 7.61-7.67 (2H, m), 7.90-7.96 (2H, m), 8.52-8.55 (1H, m).
MS (ESI) m/z: 407 [M+H]$^+$.

Example 23

{8-Methyl-3-{1-[4-(4-methylpyridin-2-yl)phenyl]cyclopropyl}-5,6,8,9-tetrahydro[1,2,4]triazolo[4,3-d][1,4]thiazepin-8-yl}methanol

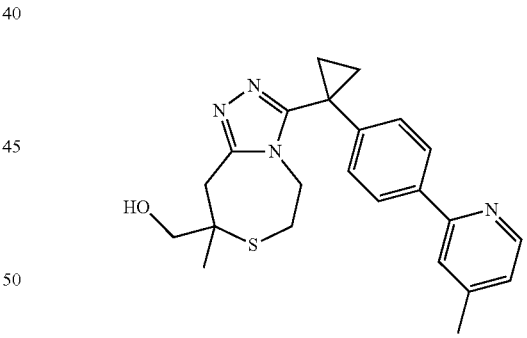

Example 23-1

8-({[Tert-butyl(dimethyl)silyl]oxy}methyl)-8-methyl-3-{1-[4-(4-methylpyridin-2-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-5), 2-bromo-4-picoline (344 mg, 2 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 100° C. for 1 h under microwave irradiation. The reaction mixture was cooled to room temperature and purified by silica gel chromatography (Isco Combiflash, 40 g, methanol:ethyl acetate=0:100 to 20:80, gradient) to obtain the title compound (104 mg, 20%) as a light yellow oily substance.

$^1$H-NMR (400 MHz, CDCl$_3$) δ: 0.05 (3H, s), 0.07 (3H, s), 0.91 (9H, s), 1.18 (3H, s), 1.41-1.69 (4H, m), 2.41 (3H, s), 2.45-2.56 (1H, m), 2.58-2.67 (1H, m), 3.35-3.40 (2H, m), 3.47-3.55 (2H, m), 3.99-4.10 (1H, m), 4.22-4.34 (1H, m), 7.03-7.08 (1H, m), 7.13-7.19 (2H, m), 7.50-7.52 (1H, m), 7.88-7.92 (2H, m), 8.51-8.54 (1H, m).

Example 23-2

{8-Methyl-3-{1-[4-(4-methylpyridin-2-yl)phenyl]cyclopropyl}-5,6,8,9-tetrahydro[1,2,4]triazolo[4,3-d][1,4]thiazepin-8-yl}methanol A solution of the compound (104 mg, 0.2 mmol) obtained in Example 23-1 and 4 M hydrochloric acid (1,4-dioxane solution, 2 mL) in methanol (2 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (47 mg, 58%) as a colorless solid.

$^1$H-NMR (400 MHz, CDCl$_3$) δ: 1.32 (3H, s), 1.40-1.47 (1H, m), 1.53-1.71 (3H, m), 2.33-2.40 (1H, m), 2.43 (3H, s), 2.52-2.60 (1H, m), 3.28-3.40 (3H, m), 3.61 (1H, d, J=15.2 Hz), 4.04-4.12 (1H, m), 4.38-4.45 (1H, m), 7.07-7.10 (1H, m), 7.17-7.21 (2H, m), 7.51-7.54 (1H, m), 7.91-7.94 (2H, m), 8.52-8.55 (1H, m).

MS (ESI) m/z: 407 [M+H]$^+$.

Example 24

{8-Methyl-3-{1-[4-(3-methylpyridin-2-yl)phenyl]cyclopropyl}-5,6,8,9-tetrahydro[1,2,4]triazolo[4,3-d][1,4]thiazepin-8-yl}methanol

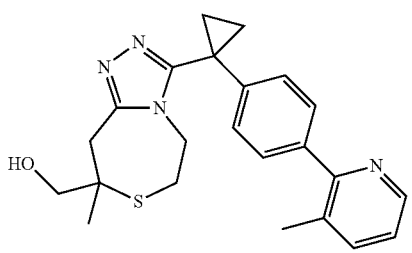 [SMILES: Cc1cccnc1-c1ccc(C2(c3nnc4n3CCSC(C)(CO)C4)CC2)cc1]

Example 24-1

8-({[Tert-butyl(dimethyl)silyl]oxy}methyl)-8-methyl-3-{1-[4-(3-methylpyridin-2-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-5), 2-bromo-3-picoline (344 mg, 2 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 100° C. for 1 h under microwave irradiation. The reaction mixture was cooled to room temperature and purified by silica gel chromatography (Isco Combiflash, 40 g, methanol:ethyl acetate=0:100 to 20:80, gradient) to obtain the title compound (430 mg, 83%) as a light yellow oily substance.

$^1$H-NMR (400 MHz, CDCl$_3$) δ: 0.05 (3H, s), 0.07 (3H, s), 0.91 (9H, s), 1.19 (3H, s), 1.44-1.53 (2H, m), 1.56-1.61 (1H, m), 1.64-1.69 (1H, m), 2.33 (3H, s), 2.51-2.60 (1H, m), 2.66-2.74 (1H, m), 3.39 (2H, s), 3.53 (2H, dd, J=16.4, 9.8 Hz), 4.02-4.11 (2H, m), 4.27-4.36 (1H, m), 7.13-7.19 (3H, m), 7.42-7.48 (2H, m), 7.54-7.59 (1H, m), 8.48-8.52 (1H, m).

Example 24-2

{8-Methyl-3-{1-[4-(3-methylpyridin-2-yl)phenyl]cyclopropyl}-5,6,8,9-tetrahydro[1,2,4]triazolo[4,3-d][1,4]thiazepin-8-yl}methanol A solution of the compound (430 mg, 0.83 mmol) obtained in Example 24-1) and 4 M hydrochloric acid (1,4-dioxane solution, 2 mL) in methanol (2 mL) was stirred at room temperature for 5 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (284 mg, 85%) as a colorless solid.

$^1$H-NMR (400 MHz, CDCl$_3$) δ: 1.33 (3H, s), 1.41-1.49 (1H, m), 1.51-1.67 (3H, m), 2.34 (3H, s), 2.38-2.46 (1H, m), 2.57-2.65 (1H, m), 3.28-3.40 (3H, m), 3.60 (1H, d, J=15.2 Hz), 4.05-4.13 (1H, m), 4.39-4.46 (1H, m), 7.15-7.19 (2H, m), 7.24-7.26 (1H, m), 7.46-7.50 (2H, m), 7.59-7.66 (1H, m), 8.51-8.54 (1H, m).

MS (ESI) m/z: 407 [M+H]$^+$.

Example 25

{3-[1-(2-Fluorobiphenyl-4-yl)cyclopropyl]-8-methyl-5,6,8,9-tetrahydro[1,2,4]triazolo[4,3-d][1,4]thiazepin-8-yl}methanol

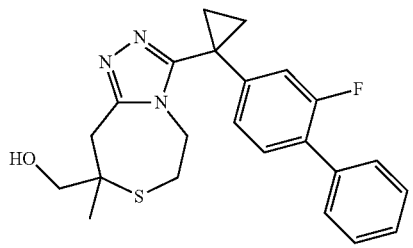 [SMILES: CC1(CO)Cc2nnc(C3(c4ccc(-c5ccccc5)c(F)c4)CC3)n2CCS1]

Example 25-1

1-Bromo-4-(bromomethyl)-2-fluorobenzene

A solution of 4-bromo-3-fluorotoluene (11.34 g, 60 mmol), azobisisobutyronitrile (0.99 g, 6 mmol), and N-bromosuccinimide (11.75 g, 66 mmol) in carbon tetrachloride (60 ml) was heated to reflux for 3.5 h. The reaction mixture was cooled to room temperature and then filtered through Celite, and the solvent in the filtrate was distilled off under reduced pressure. The residue was purified by silica gel column chromatography (Isco Combiflash, 40 g, ethyl acetate:hexane=0:100 to 100:0, gradient) to obtain the title compound (12.8 g, 80%) as a light yellow solid.

$^1$H-NMR (400 MHz, CDCl$_3$) δ: 4.41 (2H, s), 7.04-7.08 (1H, m), 7.15-7.19 (1H, m), 7.49-7.54 (1H, m).

Example 25-2

1-(4-Bromo-3-fluorophenyl)cyclopropanecarbohydrazide

A solution of the compound (12.8 g, 47.8 mmol) obtained in Example 25-1) and sodium cyanide (2.58 g, 52.6 mmol) in ethanol (20 ml) and water (5 ml) was heated to reflux for 3 h. The reaction mixture was cooled to room temperature, then concentrated under reduced pressure, and then extracted with ethyl acetate, and the organic layer was washed with saturated sodium chloride solution and dried with anhydrous sodium sulfate. After filtration, the filtrate was concentrated under reduced pressure. 1-Bromo-2-chloroethane (18.9 g, 132 mmol), benzyltriethylammonium chloride (0.48 g, 2.34 mmol), potassium hydroxide (41.5 g, 739 mmol), and water (40 mL) were added to the residue, and the mixture was stirred at 50° C. for 7.5 h. The reaction mixture was cooled to room temperature and extracted with dichloromethane, and the organic layer was washed with water, a 1 M aqueous hydrochloric acid solution, and saturated sodium chloride solution and dried with anhydrous sodium sulfate. After filtration, the filtrate was concentrated under reduced pressure. Potassium hydroxide (21.4 g, 382 mmol), ethanol (100 ml), and water (25 ml) were added to the obtained residue, and the mixture was heated to reflux for 9 h. The reaction mixture was cooled to room temperature, then 5 N hydrochloric acid was added until the reaction mixture was rendered acidic, and then the mixture was concentrated under reduced pressure. The residue was extracted with dichloromethane, dried with anhydrous sodium sulfate, and then filtered, and the solvent in the filtrate was distilled off under reduced pressure. 1-Ethyl-3-(3-dimethylaminopropyl)carbodiimide hydrochloride (7.36 g, 38.9 mmol), 1-hydroxybenzotriazole monohydrate (5.88 g, 112.7 mmol), triethylamine (14.6 mL, 105 mmol), tert-butoxycarbonylhydrazide (5.53 g, 41.9 mmol), and N,N-dimethylformamide (100 mL) were added to the obtained residue, and the mixture was stirred overnight at room temperature. Water was added to the reaction mixture, the mixture was extracted with ethyl acetate, and the organic layer was washed with saturated aqueous sodium hydrogencarbonate and saturated sodium chloride solution and then dried with anhydrous sodium sulfate. After filtration, the filtrate was concentrated under reduced pressure. A 4 M solution (20 mL) of hydrochloric acid in 1,4-dioxane and methanol (100 mL) were added to the obtained partially purified product, and the mixture was stirred at room temperature for 6 h. The reaction mixture was concentrated under reduced pressure, dichloromethane was added to the residue, and the organic layer was washed with saturated aqueous sodium hydrogencarbonate and saturated sodium chloride solution and then dried with anhydrous sodium sulfate. After filtration, the filtrate was concentrated under reduced pressure, and the residue was purified by silica gel column chromatography (Isco Combiflash, 40 g, ethyl acetate:dichloromethane=0:100 to 100:0, gradient) to obtain the title compound (4.17 g, 44%) as a brown solid.

$^1$H-NMR (400 MHz, CDCl$_3$) δ: 1.08 (2H, q, J=3.6 Hz), 1.64 (2H, q, J=3.6 Hz), 7.06-7.10 (1H, m), 7.14-7.18 (1H, m), 7.53-7.57 (1H, m).

Example 25-3

3-[1-(4-Bromo-3-fluorophenyl)cyclopropyl]-8-({[tert-butyl(dimethyl)silyl]oxy}methyl)-8-methyl-5,6,8,9-tetrahydro[1,2,4]triazolo[4,3-d][1,4]thiazepine A solution of the compound (4.1 g, 15 mmol) obtained in Example 25-2) and 7-({[tert-butyl(dimethyl)silyl]oxy}methyl)-7-methyl-5-(methylthio)-2,3,6,7-tetrahydro-1,4-thiazepine (4.79 g, 15 mmol) in n-butanol (30 mL) was stirred at 140° C. for 3.5 h. The reaction mixture was cooled to room temperature and concentrated under reduced pressure. The residue was purified by silica gel column chromatography (Isco Combiflash, 40 g, ethyl acetate:dichloromethane=0:100 to 100:0, gradient) to obtain the title compound (3.47 g, 44%) as a brown solid.

$^1$H-NMR (400 MHz, CDCl$_3$) δ: 0.05 (3H, s), 0.07 (3H, s), 0.91 (9H, s), 1.19 (3H, s), 1.36-1.48 (2H, m), 1.55-1.70 (2H, m), 2.53-2.60 (1H, m), 2.72-2.79 (1H, m), 3.39 (2H, s), 3.53 (2H, dd, J=14.7, 10.0 Hz), 4.02-4.10 (1H, m), 4.22-4.29 (1H, m), 6.74 (1H, dd, J=8.2, 2.3 Hz), 6.83 (1H, dd, J=9.8, 2.0 Hz), 7.44 (1H, dd, J=8.2, 7.0 Hz).

Example 25-4

{3-[1-(2-Fluorobiphenyl-4-yl)cyclopropyl]-8-methyl-5,6,8,9-tetrahydro[1,2,4]triazolo[4,3-d][1,4]thiazepin-8-yl}methanol A solution of the compound (526 mg, 1.0 mmol) obtained in Example 25-3), phenylboronic acid (244 mg, 2.0 mmol), tetrakis(triphenylphosphine)palladium(0) (231 mg, 0.2 mmol), and potassium carbonate (276 mg, 2.0 mmol) in dimethoxyethane (4 mL) and water (1 mL) was stirred at 100° C. for 3.5 h. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was partially purified by silica gel chromatography (Isco Combiflash, 40 g, methanol:ethyl acetate=0:100 to 40:60, gradient). A solution of this partially purified product and 4 M hydrochloric acid (1,4-dioxane solution, 2 mL) in methanol (2 mL) was stirred at room temperature for 14 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (138 mg, 34%) as a colorless solid.

$^1$H-NMR (500 MHz, CDCl$_3$) δ: 1.34 (3H, s), 1.39-1.52 (2H, m), 1.60-1.65 (2H, m), 2.47-2.53 (1H, m), 2.68-2.74 (1H, m), 3.34 (1H, d, J=29.8 Hz), 3.38-3.45 (2H, m), 3.66 (1H, d, J=15.1 Hz), 4.11-4.18 (1H, m), 4.41-4.47 (1H, m), 6.85-6.88 (1H, m), 6.90-6.93 (1H, m), 7.36-7.39 (2H, m), 7.41-7.46 (2H, m), 7.49-7.52 (2H, m).

MS (ESI) m/z: 410 [M+H]⁺.

Example 26

{3-[1-(3-Fluoro-4-pyridin-3-ylphenyl)cyclopropyl]-8-methyl-5,6,8,9-tetrahydro[1,2,4]triazolo[4,3-d][1,4]thiazepin-8-yl}methanol

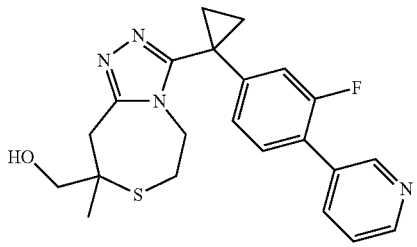 [SMILES: CC1(CO)Cc2nnc(C3(c4ccc(-c5cccnc5)c(F)c4)CC3)n2CCS1]

Example 26-1

8-({[Tert-butyl(dimethyl)silyl]oxy}methyl)-3-[1-(3-fluoro-4-pyridin-3-ylphenyl)cyclopropyl]-8-methyl-5,6,8,9-tetrahydro[1,2,4]triazolo[4,3-d][1,4]thiazepine A solution of the compound (526 mg, 1.0 mmol) obtained in Example 25-3), 3-pyridylboronic acid (244 mg, 2.0 mmol), tetrakis(triphenylphosphine)palladium(0) (231 mg, 0.2 mmol), and potassium carbonate (276 mg, 2.0 mmol) in dimethoxyethane (4 mL) and water (1 mL) was stirred at 100° C. for 3.5 h. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (517 mg, 99%) as a yellow oily substance.

¹H-NMR (500 MHz, CDCl₃) δ: 0.05 (3H, s), 0.07 (3H, s), 0.91 (9H, s), 1.21 (3H, s), 1.43-1.75 (4H, m), 2.60-2.66 (1H, m), 2.76-2.83 (1H, m), 3.41 (2H, s), 3.52-3.58 (2H, m), 4.09-4.14 (1H, m), 4.29-4.36 (1H, m), 6.87-6.97 (2H, m), 7.34-7.40 (2H, m), 7.84-7.88 (1H, m), 8.60-8.62 (1H, m), 8.75-8.77 (1H, m).

Example 26-2

{3-[1-(3-Fluoro-4-pyridin-3-ylphenyl)cyclopropyl]-8-methyl-5,6,8,9-tetrahydro[1,2,4]triazolo[4,3-d][1,4]thiazepine-8-yl}methanol A solution of the compound (517 mg, 1.0 mmol) obtained in Example 26-1), and 4 M hydrochloric acid (1,4-dioxane solution, 2 mL) in methanol (2 mL) was stirred at room temperature for 15 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (353 mg, 87%) as a colorless solid.

¹H-NMR (500 MHz, CDCl₃) δ: 1.34 (3H, s), 1.46-1.53 (2H, m), 1.61-1.69 (2H, m), 2.50-2.54 (1H, m), 2.71-2.76 (1H, m), 3.35 (1H, d, J=15.1 Hz), 3.42 (2H, dd, J=18.1, 11.7 Hz), 3.63 (1H, d, J=15.6 Hz), 4.12-4.18 (1H, m), 4.39-4.44 (1H, m), 6.88-6.97 (2H, m), 7.36-7.39 (2H, m), 7.83-7.86 (1H, m), 8.59-8.62 (1H, m), 8.75-8.77 (1H, m).

MS (ESI) m/z: 411 [M+H]⁺.

Example 27

(3-{1-[4-(3-Chloropyridin-2-yl)phenyl]cyclopropyl}-8-methyl-5,6,8,9-tetrahydro[1,2,4]triazolo[4,3-d][1,4]thiazepin-8-yl)methanol

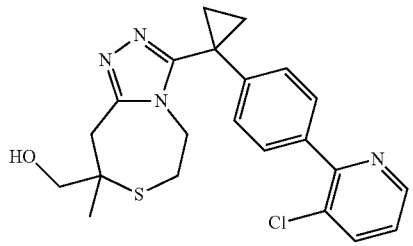 [SMILES: CC1(CO)Cc2nnc(C3(c4ccc(-c5ncccc5Cl)cc4)CC3)n2CCS1]

Example 27-1

8-({[Tert-butyl(dimethyl)silyl]oxy}methyl)-3-{1-[4-(3-chloropyridin-2-yl)phenyl]cyclopropyl}-8-methyl-5,6,8,9-tetrahydro[1,2,4]triazolo[4,3-d][1,4]thiazepine A solution of the compound (555 mg, 1.0 mmol) obtained in Example 16-5), 2-bromo-3-chloropyridine (294 mg, 2 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (193 mg, 36%) as a black oily substance.

¹H-NMR (400 MHz, CDCl₃) δ: 0.05 (3H, s), 0.07 (3H, s), 0.91 (9H, s), 1.19 (3H, s), 1.45-1.55 (2H, m), 1.57-1.62 (1H, m), 1.64-1.71 (1H, m), 2.51-2.59 (1H, m), 2.65-2.74 (1H, m), 3.39 (2H, s), 3.53 (2H, dd, J=16.6, 10.0 Hz), 4.03-4.11 (1H, m), 4.27-4.35 (1H, m), 7.14-7.19 (2H, m), 7.20-7.25 (1H, m), 7.66-7.69 (2H, m), 7.77-7.81 (1H, m), 8.56-8.59 (1H, m).

Example 27-2

(3-{1-[4-(3-Chloropyridin-2-yl)phenyl]cyclopropyl}-8-methyl-5,6,8,9-tetrahydro[1,2,4]triazolo[4,3-d][1,4]thiazepine-8-yl)methanol A solution of the compound (193 mg, 0.36 mmol) obtained in Example 27-1) and 4 M hydrochloric acid (1,4-dioxane solution, 1 mL) in methanol (2 mL) was stirred at room temperature for 5 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (120 mg, 79%) as a colorless solid.

$^1$H-NMR (500 MHz, CDCl$_3$) δ: 1.33 (3H, s), 1.46-1.51 (1H, m), 1.52-1.57 (1H, m), 1.58-1.63 (1H, m), 1.64-1.68 (1H, m), 2.40-2.46 (1H, m), 2.60-2.67 (1H, m), 3.32 (1H, d, J=15.1 Hz), 3.39 (2H, dd, J=18.6, 11.7 Hz), 3.65 (1H, d, J=15.1 Hz), 4.07-4.14 (1H, m), 4.40-4.47 (1H, m), 7.17-7.20 (2H, m), 7.21-7.24 (1H, m), 7.68-7.71 (2H, m), 7.78-7.81 (1H, m), 8.57-8.59 (1H, m).

Example 28

(3-{1-[4-(3-Fluoropyridin-2-yl)phenyl]cyclopropyl}-8-methyl-5,6,8,9-tetrahydro[1,2,4]triazolo[4,3-d][1,4]thiazepin-8-yl)methanol

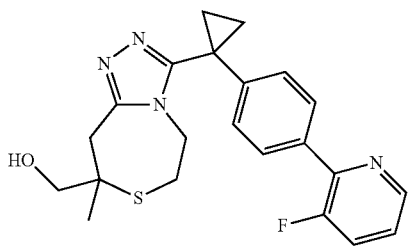

Example 28-1

8-({[Tert-butyl(dimethyl)silyl]oxy}methyl)-3-{1-[4-(3-fluoropyridin-2-yl)phenyl]cyclopropyl}-8-methyl-5,6,8,9-tetrahydro[1,2,4]triazolo[4,3-d][1,4]thiazepine A solution of the compound (555 mg, 1.0 mmol) obtained in Example 16-5), 2-chloro-3-fluoropyridine (201 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (359 mg, 68%) as a black oily substance.

$^1$H-NMR (400 MHz, CDCl$_3$) δ: 0.05 (3H, s), 0.07 (3H, s), 0.91 (9H, s), 1.19 (3H, s), 1.45-1.54 (2H, m), 1.58-1.63 (1H, m), 1.65-1.70 (1H, m), 2.50-2.58 (1H, m), 2.63-2.72 (1H, m), 3.40 (2H, s), 3.53 (2H, dd, J=16.4, 10.2 Hz), 4.03-4.11 (1H, m), 4.27-4.35 (1H, m), 7.16-7.20 (2H, m), 7.24-7.29 (1H, m), 7.45-7.51 (1H, m), 7.90-7.93 (2H, m), 8.48-8.52 (1H, m).

Example 28-2

(3-{1-[4-(3-Fluoropyridin-2-yl)phenyl]cyclopropyl}-8-methyl-5,6,8,9-tetrahydro[1,2,4]triazolo[4,3-d][1,4]thiazepin-8-yl)methanol A solution of the compound (359 mg, 0.68 mmol) obtained in Example 28-1) and 4 M hydrochloric acid (1,4-dioxane solution, 1 mL) in methanol (3 mL) was stirred at room temperature for 5 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (260 mg, 93%) as a colorless solid.

$^1$H-NMR (500 MHz, CDCl$_3$) δ: 1.33 (3H, s), 1.46-1.50 (1H, m), 1.52-1.57 (1H, m), 1.59-1.63 (1H, m), 1.64-1.68 (1H, m), 2.40-2.45 (1H, m), 2.60-2.68 (1H, m), 3.32 (1H, d, J=15.6 Hz), 3.35-3.43 (2H, m), 3.65 (1H, d, J=15.1 Hz), 4.07-4.14 (1H, m), 4.40-4.46 (1H, m), 7.17-7.20 (2H, m), 7.21-7.25 (1H, m), 7.68-7.70 (2H, m), 7.78-7.81 (1H, m), 8.57-8.59 (1H, m).

MS (ESI) m/z: 411 [M+H]$^+$.

Example 29

[8-Methyl-3-(1-{4-[3-(trifluoromethyl)pyridin-2-yl]phenyl}cyclopropyl)-5,6,8,9-tetrahydro[1,2,4]triazolo[4,3-d][1,4]thiazepin-8-yl]methanol

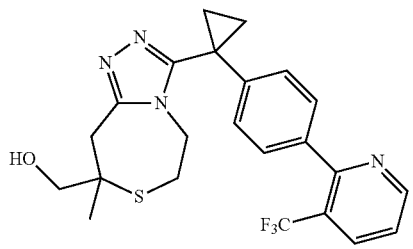 [SMILES: CC1(CO)Cc2nnc(C3(c4ccc(-c5ncccc5C(F)(F)F)cc4)CC3)n2CCS1]

Example 29-1

8-({[Tert-butyl(dimethyl)silyl]oxy}methyl)-8-methyl-3-(1-{4-[3-(trifluoromethyl)pyridin-2-yl]phenyl}cyclopropyl)-5,6,8,9-tetrahydro[1,2,4]triazolo[4,3-d][1,4]thiazepine A solution of the compound (555 mg, 1.0 mmol) obtained in Example 16-5), 2-bromo-3-trifluoromethyl pyridine (338 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (535 mg, 93%) as a black oily substance.

$^{1}$H-NMR (400 MHz, CDCl$_{3}$) δ: 0.05 (3H, s), 0.07 (3H, s), 0.91 (9H, s), 1.19 (3H, s), 1.46-1.54 (2H, m), 1.59-1.63 (1H, m), 1.64-1.70 (1H, m), 2.46-2.54 (1H, m), 2.60-2.68 (1H, m), 3.38-3.40 (2H, m), 3.39 (2H, s), 4.03-4.12 (1H, m), 4.27-4.34 (1H, m), 7.14-7.19 (2H, m), 7.40-7.47 (3H, m), 8.05-8.09 (1H, m), 8.81-8.85 (1H, m).

Example 29-2

[8-Methyl-3-(1-{4-[3-(trifluoromethyl)pyridin-2-yl]phenyl}cyclopropyl)-5,6,8,9-tetrahydro[1,2,4]triazolo[4,3-d][1,4]thiazepin-8-yl]methanol A solution of the compound (535 mg, 0.93 mmol) obtained in Example 29-1) and 4 M hydrochloric acid (1,4-dioxane solution, 1 mL) in methanol (4 mL) was stirred at room temperature for 5 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (280 mg, 65%) as a colorless solid.

$^{1}$H-NMR (500 MHz, CDCl$_{3}$) δ: 1.33 (3H, s), 1.43-1.48 (1H, m), 1.53-1.61 (2H, m), 1.67-1.73 (1H, m), 2.35-2.41 (1H, m), 2.54-2.61 (1H, m), 3.29-3.42 (3H, m), 3.65 (1H, d, J=14.6 Hz), 4.06-4.14 (1H, m), 4.39-4.46 (1H, m), 7.17-7.21 (2H, m), 7.41-7.47 (3H, m), 8.06-8.10 (1H, m), 8.81-8.84 (1H, m).

MS (ESI) m/z: 461 [M+H]$^{+}$.

Example 30

(3-{1-[4-(3-Methoxypyridin-2-yl)phenyl]cyclopropyl}-8-methyl-5,6,8,9-tetrahydro[1,2,4]triazolo[4,3-d][1,4]thiazepin-8-yl)methanol

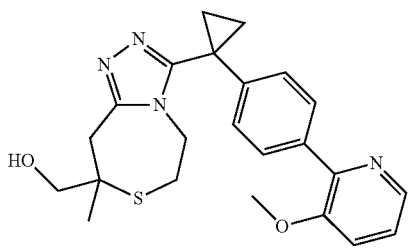 [SMILES: COc1cccnc1-c1ccc(C2(c3nnc4n3CCSC(C)(CO)C4)CC2)cc1]

A solution of the compound (555 mg, 1.0 mmol) obtained in Example 16-5), 2-bromo-3-methoxypyridine (290 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 40:60, gradient) to obtain a partially purified product (589 mg, quant.) as a brown oily substance. This partially purified product was dissolved in a solution of 4 M hydrochloric acid (1,4-dioxane solution, 1 mL) in methanol (4 mL), and the mixture was stirred at room temperature for 5 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (280 mg, 65%) as a colorless solid.

$^{1}$H-NMR (400 MHz, CDCl$_{3}$) δ: 1.36 (3H, s), 1.45-1.52 (1H, m), 1.54-1.63 (2H, m), 1.64-1.70 (1H, m), 2.40-2.48 (1H, m), 2.51 (1H, t, J=6.7 Hz), 2.60-2.68 (1H, m), 3.35 (1H, d, J=15.3 Hz), 3.38-3.43 (2H, m), 3.64 (1H, d, J=15.3 Hz), 3.90 (3H, s), 4.09-4.17 (1H, m), 4.43-4.49 (1H, m), 7.18-7.21 (2H, m), 7.26-7.34 (2H, m), 7.91-7.93 (2H, m), 8.32-8.35 (1H, m).

MS (ESI) m/z: 423 [M+H]$^{+}$.

Example 31

2-(4-{1-[8-(Hydroxymethyl)-8-methyl-5,6,8,9-tetrahydro[1,2,4]triazolo[4,3-d][1,4]thiazepin-3-yl]cyclopropyl}phenyl)nicotinonitrile

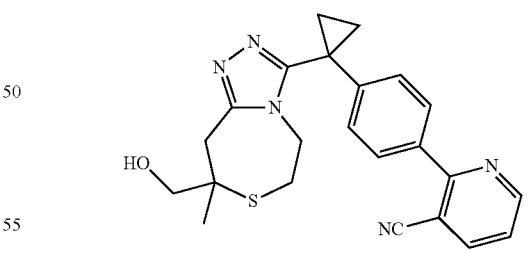

A solution of the compound (555 mg, 1.0 mmol) obtained in Example 16-5), 2-chloronicotinonitrile (290 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was partially purified by silica gel chromatography (Isco Combiflash, 40 g, methanol:ethyl acetate=0:100 to 20:80, gradient). A solution of this partially purified product (444 mg, 0.83 mmol) and 4 M hydrochloric acid (1,4-dioxane solution, 1 mL) in methanol (4 mL) was stirred at room temperature for 5 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (286 mg, 82%) as a colorless solid.

$^1$H-NMR (400 MHz, CDCl$_3$) δ: 1.33 (3H, s), 1.45-1.52 (1H, m), 1.55-1.64 (2H, m), 1.67-1.73 (1H, m), 2.37 (1H, brs), 2.41 (1H, ddd, J=15.5, 6.5, 1.4 Hz), 2.57 (1H, ddd, J=15.4, 9.8, 1.4 Hz), 3.33 (1H, d, J=15.2 Hz), 3.37 (2H, s), 3.61 (1H, d, J=15.2 Hz), 4.10 (1H, ddd, J=14.8, 9.8, 1.4 Hz), 4.42 (1H, ddd, J=14.8, 6.5, 1.4 Hz), 7.25 (2H, d, J=8.6 Hz), 7.40 (1H, dd, J=7.8, 4.7 Hz), 7.87 (2H, d, J=8.6 Hz), 8.08 (1H, dd, J=7.8, 2.0 Hz), 8.87 (1H, dd, J=4.7, 2.0 Hz).

MS (ESI) m/z: 418 [M+H]$^+$.

Example 32

(8-Methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl)methanol

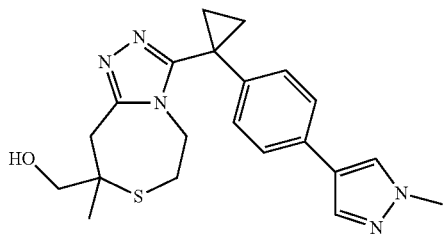 [SMILES: Cn1cc(-c2ccc(C3(c4nnc5n4CCSC(C)(CO)C5)CC3)cc2)cn1]

Example 32-1

8-({[Tert-butyl(dimethyl)silyl]oxy}methyl)-8-methyl-3-{1-[4-(1-methyl-1H-pyrazol-4-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-4), 1-methyl-4-(4,4,5,5-tetramethyl-1,3,2-dioxaborolan-2-yl)-1H-pyrazole (312 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (373 mg, 73%) as a colorless foamy substance.

$^1$H-NMR (400 MHz, CDCl$_3$) δ: 0.04 (3H, s), 0.07 (3H, s), 0.91 (9H, s), 1.18 (3H, s), 1.38-1.47 (2H, m), 1.53-1.63 (2H, m), 2.46-2.54 (1H, m), 2.60-2.68 (1H, m), 3.38 (2H, s), 3.48-3.55 (2H, m), 3.94 (3H, s), 4.03-4.11 (1H, m), 4.28-4.35 (1H, m), 7.05-7.09 (2H, m), 7.34-7.40 (2H, m), 7.58 (1H, s), 7.71 (1H, s).

Example 32-2

(8-Methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl)methanol A solution of the compound (373 mg, 0.73 mmol) obtained in Example 32-1) and 4 M hydrochloric acid (1,4-dioxane solution, 1 mL) in methanol (4 mL) was stirred at room temperature for 5 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (297 mg, quant.) as a colorless solid.

$^1$H-NMR (400 MHz, CDCl$_3$) δ: 1.32 (3H, s), 1.35-1.41 (1H, m), 1.45-1.54 (2H, m), 1.60-1.66 (9H, m), 1.69 (1H, brs), 2.34-2.40 (1H, m), 2.55 (1H, ddd, J=15.6, 9.8, 1.6 Hz), 3.29-3.49 (3H, m), 3.60 (1H, d, J=15.2 Hz), 3.94 (3H, s), 4.06-4.12 (1H, m), 4.41-4.46 (1H, m), 7.08-7.11 (2H, m), 7.37-7.40 (2H, m), 7.59 (1H, s), 7.73 (1H, s).

MS (ESI) m/z: 396 [M+H]$^+$.

Example 33

{(8S)-8-Methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl}methanol

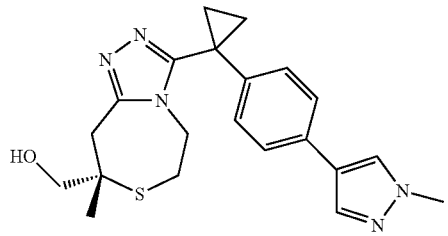 [SMILES: Cn1cc(-c2ccc(C3(c4nnc5n4CCS[C@](C)(CO)C5)CC3)cc2)cn1]

Example 33-1

(8S)-8-({[t-Butyl(dimethyl)silyl]oxy}methyl)-8-methyl-3-{1-[4-(1-methyl-1H-pyrazol-4-yl)phenyl]cyclopropyl}-5,6,8,9-tetrahydro[1,2,4]triazolo[4,3-d][1,4]thiazepine The compound (200 mg, 0.43 mmol) obtained in Example 3-2), 1-methyl-4-(4,4,5,5-tetramethyl-1,3,2-dioxaborolan-2- yl)-1H-pyrazole (100 mg, 0.47 mmol), tris(dibenzylideneacetone)dipalladium (20 mg, 0.02 mmol), tricyclohexylphosphine (15 mg, 0.05 mmol), and tripotassium phosphate (160 mg, 0.73 mmol) were dissolved in a mixed solvent of 1,4-dioxane (2 mL) and water (1 mL), and the mixture was stirred at 140° C. for 2 h under microwave irradiation. The reaction mixture was cooled to room temperature, then diluted with methylene chloride (50 mL), and separated into organic and aqueous layers by the addition of saturated aqueous sodium hydrogencarbonate (20 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=0% to 20%) to obtain the title compound (140 mg, 64%) in a light yellow solid form.

$^1$H-NMR (400 MHz, CDCl$_3$) δ: 0.05 (3H, s), 0.07 (3H, s), 0.91 (9H, s), 1.18 (3H, s), 1.37-1.47 (2H, m), 1.52-1.64 (2H, m), 2.51 (1H, ddd, J=15.6, 7.8, 2.3 Hz), 2.64 (1H, ddd, J=15.5, 7.9, 2.1 Hz), 3.38 (2H, s), 3.51 (2H, dd, J=17.6, 10.2 Hz), 3.94 (3H, s), 4.07 (1H, ddd, J=14.5, 7.8, 2.0 Hz), 4.32 (1H, ddd, J=14.6, 7.9, 2.2 Hz), 7.08 (2H, d, J=8.2 Hz), 7.38 (2H, d, J=8.2 Hz), 7.58 (1H, s), 7.72 (1H, s).

Example 33-2

{(8S)-8-Methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl}methanol The compound (280 mg, 0.55 mmol) obtained in Example 33-1) was dissolved in methanol (3 mL). A 4 N solution (1.37 mL) of hydrochloric acid in dioxane was added to the solution, and the mixture was stirred at room temperature for 1 h. The solvent was distilled off, the residue was dissolved in a mixed solvent of methylene chloride (50 mL) and methanol (2 mL), and the mixture was separated into organic and aqueous layers by the addition of saturated aqueous sodium hydrogencarbonate (10 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=0% to 50%) to obtain the title compound (175 mg, 81%) in a colorless solid form.

$^1$H-NMR (400 MHz, CDCl$_3$) δ: 1.32 (3H, s), 1.35-1.41 (1H, m), 1.45-1.55 (2H, m), 1.59-1.67 (1H, m), 2.37 (1H, ddd, J=15.6, 6.3, 1.6 Hz), 2.55 (1H, ddd, J=16.4, 10.2, 1.6 Hz), 3.31 (1H, d, J=15.2 Hz), 3.36 (2H, d, J=3.9 Hz), 3.60 (1H, d, J=15.2 Hz), 3.94 (3H, s), 4.09 (1H, ddd, J=14.9, 9.8, 1.6 Hz), 4.44 (1H, ddd, J=14.9, 6.3, 1.6 Hz), 7.09 (2H, d, J=8.6 Hz), 7.39 (2H, d, J=8.6 Hz), 7.59 (1H, s), 7.73 (1H, s).

MS (ESI) m/z: 396.18596 (M+H)$^+$.

Example 34

{(8R)-8-Methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl}methanol

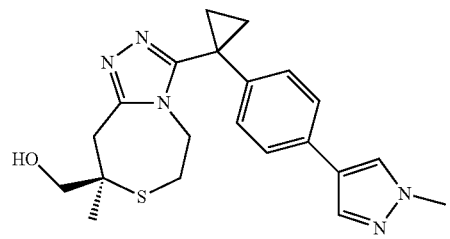 [SMILES: Cn1cc(-c2ccc(C3(c4nnc5n4CCS[C@@](C)(CO)C5)CC3)cc2)cn1]

Example 34-1

(8R)-8-({[t-Butyl(dimethyl)silyl]oxy}methyl)-8-methyl-3-{1-[4-(1-methyl-1H-pyrazol-4-yl)phenyl]cyclopropyl}-5,6,8,9-tetrahydro[1,2,4]triazolo[4,3-d][1,4]thiazepine The compound (255 mg, 0.55 mmol) obtained in Example 4-2), 1-methyl-4-(4,4,5,5-tetramethyl-1,3,2-dioxaborolan-2-yl)-1H-pyrazole (126 mg, 0.60 mmol), tris(dibenzylideneacetone)dipalladium (25 mg, 0.03 mmol), tricyclohexylphosphine (29 mg, 0.07 mmol), and tripotassium phosphate (205 mg, 0.93 mmol) were dissolved in a mixed solvent of 1,4-dioxane (2 mL) and water (1 mL), and the mixture was stirred at 140° C. for 2 h under microwave irradiation. The reaction mixture was cooled to room temperature, then diluted with methylene chloride (60 mL), and separated into organic and aqueous layers by the addition of saturated aqueous sodium hydrogencarbonate (20 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=0% to 20%) to obtain the title compound (283 mg, quant.) in a colorless solid form.

$^1$H-NMR (400 MHz, CDCl$_3$) δ: 0.04 (3H, s), 0.07 (3H, s), 0.91 (9H, s), 1.18 (3H, s), 1.38-1.47 (2H, m), 1.52-1.63 (2H, m), 2.51 (1H, ddd, J=15.6, 7.8, 2.3 Hz), 2.64 (1H, ddd, J=15.6, 7.8, 2.0 Hz), 3.38 (2H, s), 3.52 (2H, dd, J=17.2, 9.8 Hz), 3.94 (3H, s), 4.07 (1H, ddd, J=14.5, 8.2, 2.0 Hz), 4.32 (1H, ddd, J=14.4, 7.9, 2.1 Hz), 7.08 (2H, d, J=8.6 Hz), 7.38 (2H, d, J=8.2 Hz), 7.58 (1H, s), 7.72 (1H, s).

Example 34-2

{(8R)-8-Methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl}methanol The compound (403 mg, 0.79 mmol) obtained in Example 34-1) was dissolved in methanol (4 mL). A 4 N solution (1.98 mL) of hydrochloric acid in dioxane was added to the solution, and the mixture was stirred at room temperature for 1 h. The solvent was distilled off, the residue was dissolved in a mixed solvent of methylene chloride (50 mL) and methanol (2 mL), and the mixture was separated into organic and aqueous layers by the addition of saturated aqueous sodium hydrogencarbonate (20 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=0% to 50%) to obtain the title compound (228 mg, 73%) in a colorless solid form.

$^1$H-NMR (400 MHz, CDCl$_3$) δ: 1.32 (3H, s), 1.35-1.41 (1H, m), 1.45-1.55 (2H, m), 1.59-1.68 (1H, m), 2.37 (1H, ddd, J=15.2, 6.3, 1.2 Hz), 2.55 (1H, ddd, J=15.6, 9.8, 1.2 Hz), 3.31 (1H, d, J=15.2 Hz), 3.37 (2H, d, J=3.9 Hz), 3.60 (1H, d, J=15.2 Hz), 3.94 (3H, s), 4.09 (2H, ddd, J=14.5, 9.8, 1.2 Hz), 4.44 (1H, ddd, J=14.9, 6.3, 1.2 Hz), 7.09 (2H, d, J=8.6 Hz), 7.39 (2H, d, J=8.6 Hz), 7.59 (1H, s), 7.73 (1H, s).

MS (ESI) m/z: 396.18512 (M+H)$^+$.

Example 35

{8-Methyl-3-[1-(4-pyrimidin-5-ylphenyl)cyclopropyl]-5,6,8,9-tetrahydro[1,2,4]triazolo[4,3-d][1,4]thiazepin-8-yl}methanol

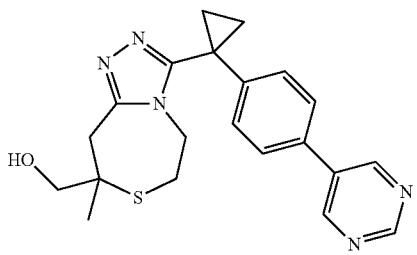 [SMILES: CC1(CO)Cc2nnc(C3(c4ccc(-c5cncnc5)cc4)CC3)n2CCS1]

A solution of the compound (555 mg, 1.0 mmol) obtained in Example 16-5), 5-bromopyrimidine (243 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was partially purified by silica gel chromatography (Isco Combiflash, 40 g, methanol:ethyl acetate=0:100 to 30:70, gradient) to obtain a colorless solid (313 mg). The obtained partially purified product was dissolved in 4 M hydrochloric acid (1,4-dioxane solution, 1 mL) and methanol (4 mL), and the mixture was stirred at room temperature for 15 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (241 mg, 61%) as a colorless solid.

$^1$H-NMR (400 MHz, CDCl$_3$) δ: 1.33 (3H, s), 1.45-1.49 (1H, m), 1.51-1.55 (1H, m), 1.60-1.69 (2H, m), 2.42-2.50 (1H, m), 2.64-2.70 (1H, m), 3.34 (1H, d, J=15.6 Hz), 3.41 (2H, dd, J=15.2, 12.1 Hz), 3.62 (1H, d, J=15.2 Hz), 4.09-4.16 (1H, m), 4.38-4.45 (1H, m), 7.22-7.25 (2H, m), 7.50-7.54 (2H, m), 8.92 (2H, s), 9.20 (1H, s).

MS (ESI) m/z: 394 [M+H]$^+$.

Example 36

{8-Methyl-3-[1-(4-pyrimidin-2-ylphenyl)cyclopropyl]-5,6,8,9-tetrahydro[1,2,4]triazolo[4,3-d][1,4]thiazepin-8-yl}methanol

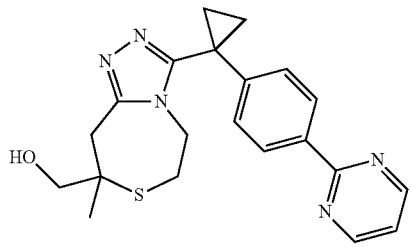 [SMILES: CC1(CO)Cc2nnc(C3(c4ccc(-c5ncccn5)cc4)CC3)n2CCS1]

Example 36-1

8-({[Tert-butyl(dimethyl)silyl]oxy}methyl)-8-methyl-3-[1-(4-pyrimidin-2-ylphenyl)cyclopropyl]-5,6,8,9-tetrahydro[1,2,4]triazolo[4,3-d][1,4]thiazepine A solution of the compound (555 mg, 1.0 mmol) obtained in Example 16-5), 2-chloropyrimidine (171 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (397 mg, 78%) as a light yellow solid.

$^1$H-NMR (400 MHz, CDCl$_3$) δ: 0.05 (3H, s), 0.07 (3H, s), 0.91 (9H, s), 1.19 (3H, s), 1.50-1.53 (2H, m), 1.60-1.68 (2H, m), 2.51 (1H, ddd, J=15.5, 7.8, 2.1 Hz), 2.64 (1H, ddd, J=15.5, 7.9, 2.1 Hz), 3.40 (2H, s), 3.50 (1H, d, J=10.0 Hz), 3.54 (1H, d, J=10.0 Hz), 4.07 (1H, ddd, J=14.4, 7.9, 2.1 Hz), 4.31 (1H, ddd, J=14.4, 7.8, 2.1 Hz), 7.18 (2H, d, J=8.6 Hz), 7.19 (1H, t, J=5.1 Hz), 8.36 (2H, d, J=8.6 Hz), 8.79 (2H, d, J=5.1 Hz).

Example 36-2

{8-Methyl-3-[1-(4-pyrimidin-2-ylphenyl)cyclopropyl]-5,6,8,9-tetrahydro[1,2,4]triazolo[4,3-d][1,4]thiazepin-8-yl}methanol A solution of the compound (397 mg, 0.78 mmol) obtained in Example 36-1) and 4 M hydrochloric acid (1,4-dioxane solution, 1 mL) in methanol (4 mL) was stirred at room temperature for 15 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (191 mg, 62%) as a colorless solid.

$^1$H-NMR (400 MHz, CDCl$_3$) δ: 1.32 (3H, s), 1.44-1.49 (1H, m), 1.54-1.62 (2H, m), 1.67-1.73 (1H, m), 2.37 (1H, ddd, J=15.6, 6.5, 1.4 Hz), 2.58 (1H, ddd, J=15.6, 9.8, 1.6 Hz), 3.33 (1H, d, J=15.2 Hz), 3.36 (1H, d, J=11.7 Hz), 3.40 (1H, d, J=11.7 Hz), 3.62 (1H, d, J=15.2 Hz), 4.10 (1H, ddd, J=14.7, 9.8, 1.6 Hz), 4.41 (1H, ddd, J=14.7, 6.5, 1.4 Hz), 7.20 (1H, t, J=4.8 Hz), 7.20 (2H, d, J=8.6 Hz), 8.37 (2H, d, J=8.6 Hz), 8.80 (2H, d, J=4.8 Hz).

MS (ESI) m/z: 394 [M+H]$^+$.

Example 37

(3-{1-[4-(6-Methoxypyridazin-3-yl)phenyl]cyclopropyl}-8-methyl-5,6,8,9-tetrahydro[1,2,4]triazolo[4,3-d][1,4]thiazepin-8-yl)methanol

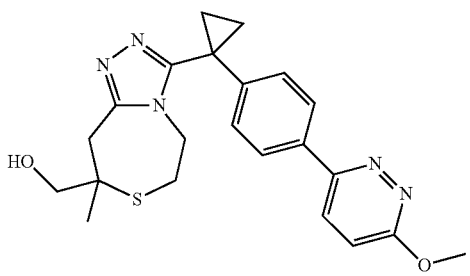 [SMILES: COc1ccc(-c2ccc(C3(c4nnc5n4CCSC(C)(CO)C5)CC3)cc2)nn1]

Example 37-1

8-({[Tert-butyl(dimethyl)silyl]oxy}methyl)-3-{1-[4-(6-chloropyridazin-3-yl)phenyl]cyclopropyl}-8-methyl-5,6,8,9-tetrahydro[1,2,4]triazolo[4,3-d][1,4]thiazepine A solution of the compound (1.39 mg, 2.5 mmol) obtained in Example 16-5), 3,6-dichloropyridazine (1.49 mg, 10 mmol), tetrakis(triphenylphosphine)palladium(0) (577 mg, 0.5 mmol), and potassium carbonate (691 mg, 5 mmol) in dimethoxyethane (10 mL) and water (2.5 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (647 mg, 48%) as a light yellow solid.

$^1$H-NMR (400 MHz, CDCl$_3$) δ: 0.05 (3H, s), 0.07 (2H, s), 0.91 (9H, s), 1.20 (3H, s), 1.49-1.56 (2H, m), 1.61-1.72 (2H, m), 2.51-2.58 (1H, m), 2.67-2.73 (1H, m), 3.41 (2H, s), 3.50-3.57 (2H, m), 4.03-4.10 (1H, m), 4.25-4.32 (1H, m), 7.18-7.22 (2H, m), 7.70-7.71 (1H, m), 7.98-8.02 (2H, m), 9.00-9.02 (1H, m).

Example 37-2

(3-{1-[4-(6-Methoxypyridazin-3-yl)phenyl]cyclopropyl}-8-methyl-5,6,8,9-tetrahydro[1,2,4]triazolo[4,3-d][1,4]thiazepin-8-yl)methanol A solution of the compound (1.35 mg, 2.5 mmol) obtained in Example 37-1) and 4 M hydrochloric acid (1,4-dioxane solution, 2.5 mL) in methanol (10 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (498 mg, 47%) as a colorless solid.

$^1$H-NMR (400 MHz, CDCl$_3$) δ: 1.32 (3H, s), 1.43-1.49 (1H, m), 1.52-1.57 (1H, m), 1.58-1.63 (1H, m), 1.65-1.70 (1H, m), 2.40 (1H, ddd, J=15.5, 6.5, 1.1 Hz), 2.53 (1H, brs), 2.61 (1H, ddd, J=15.5, 9.7, 1.6 Hz), 3.33 (1H, d, J=15.2 Hz), 3.38 (1H, d, J=11.7 Hz), 3.41 (1H, d, J=11.7 Hz), 3.61 (1H, d, J=15.2 Hz), 4.03 (3H, s), 4.10 (1H, ddd, J=14.7, 9.7, 1.1 Hz), 4.39 (1H, ddd, J=14.7, 6.5, 1.6 Hz), 7.07 (1H, d, J=0.8 Hz), 7.19 (2H, d, J=8.6 Hz), 7.96 (2H, d, J=8.6 Hz), 8.83 (1H, d, J=0.8 Hz).

MS (ESI) m/z: 424 [M+H]$^+$.

Example 38

{8-Methyl-3-[1-(4-pyrazin-2-ylphenyl)cyclopropyl]-5,6,8,9-tetrahydro[1,2,4]triazolo[4,3-d][1,4]thiazepin-8-yl}methanol

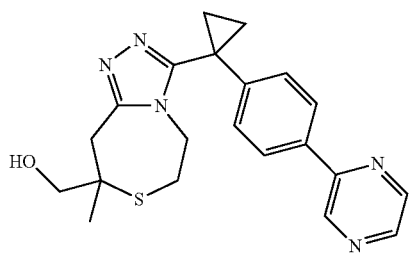 [SMILES: CC1(CO)Cc2nnc(C3(c4ccc(-c5cnccn5)cc4)CC3)n2CCS1]

Example 38-1

8-({[Tert-butyl(dimethyl)silyl]oxy}methyl)-8-methyl-3-[1-(4-pyrazin-2-ylphenyl)cyclopropyl]-5,6,8,9-tetrahydro[1,2,4]triazolo[4,3-d][1,4]thiazepine A solution of the compound (555 mg, 1.0 mmol) obtained in Example 16-5), chloropyrazin (231 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (217 mg, 43%) as a light yellow solid.

$^1$H-NMR (400 MHz, CDCl$_3$) δ: 0.05 (3H, s), 0.07 (3H, s), 0.91 (9H, s), 1.19 (3H, s), 1.47-1.55 (2H, m), 1.61-1.70 (2H, m), 2.50-2.58 (1H, m), 2.65-2.72 (1H, m), 3.40 (2H, s), 3.49-3.57 (2H, m), 4.04-4.13 (1H, m), 4.27-4.35 (1H, m), 7.19-7.23 (2H, m), 7.93-7.97 (2H, m), 8.50-8.51 (1H, m), 8.61-8.63 (1H, m), 8.99-9.01 (1H, m).

Example 38-2

{8-Methyl-3-[1-(4-pyrazin-2-ylphenyl)cyclopropyl]-5,6,8,9-tetrahydro[1,2,4]triazolo[4,3-d][1,4]thiazepin-8-yl}methanol A solution of the compound (217 mg, 0.43 mmol) obtained in Example 38-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (176 mg, quant.) as a colorless solid.

$^1$H-NMR (400 MHz, CDCl$_3$) δ: 1.33 (3H, s), 1.45-1.50 (1H, m), 1.53-1.58 (1H, m), 1.59-1.64 (1H, m), 1.66-1.71 (1H, m), 2.31 (1H, brs), 2.41 (1H, ddd, J=15.6, 6.5, 1.4 Hz), 2.62 (1H, ddd, J=15.6, 9.8, 1.4 Hz), 3.33 (1H, d, J=15.2 Hz), 3.36 (1H, d, J=11.7 Hz), 3.41 (1H, d, J=11.7 Hz), 3.62 (1H, d, J=15.2 Hz), 4.11 (1H, ddd, J=14.7, 9.8, 1.4 Hz), 4.42 (1H, ddd, J=14.7, 6.5, 1.4 Hz), 7.23 (2H, d, J=8.6 Hz), 7.97 (2H, d, J=8.6 Hz), 8.51 (1H, d, J=2.3 Hz), 8.62 (1H, dd, J=2.3, 1.4 Hz), 9.01 (1H, d, J=1.4 Hz).

MS (ESI) m/z: 394 [M+H]$^+$.

Example 39

(8-Methyl-3-{1-[4-(1,3-thiazol-2-yl)phenyl]cyclopropyl}-5,6,8,9-tetrahydro[1,2,4]triazolo[4,3-d][1,4]thiazepin-8-yl)methanol

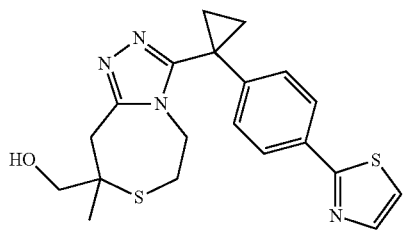 [SMILES: CC1(CO)Cc2nnc(C3(c4ccc(-c5nccs5)cc4)CC3)n2CCS1]

Example 39-1

8-({[Tert-butyl(dimethyl)silyl]oxy}methyl)-8-methyl-3-{1-[4-(1,3-thiazol-2-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-5), 2-bromothiazole (246 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (237 mg, 46%) as a light yellow solid.

$^1$H-NMR (400 MHz, CDCl$_3$) δ: 0.05 (3H, s), 0.07 (3H, s), 0.91 (9H, s), 1.19 (3H, s), 1.44-1.53 (2H, m), 1.59-1.69 (2H, m), 2.49-2.56 (1H, m), 2.63-2.71 (1H, m), 3.40 (2H, s), 3.48-3.56 (2H, m), 4.03-4.11 (1H, m), 4.25-4.34 (1H, m), 7.12-7.16 (2H, m), 7.32-7.34 (1H, m), 7.85-7.89 (3H, m).

Example 39-2

(8-Methyl-3-{1-[4-(1,3-thiazol-2-yl)phenyl]cyclopropyl}-5,6,8,9-tetrahydro[1,2,4]triazolo[4,3-d][1,4]thiazepin-8-yl)methanol A solution of the compound (237 mg, 0.46 mmol) obtained in Example 39-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (184 mg, quant.) as a colorless solid.

$^1$H-NMR (CDCl$_3$) δ: 1.32 (3H, s), 1.42-1.48 (1H, m), 1.51-1.61 (2H, m), 1.65-1.71 (1H, m), 2.40 (1H, ddd, J=15.6, 6.5, 1.2 Hz), 2.61 (1H, ddd, J=15.6, 9.7, 1.2 Hz), 3.33 (1H, d, J=15.2 Hz), 3.38 (1H, d, J=11.7 Hz), 3.42 (1H, d, J=11.7 Hz), 3.61 (1H, d, J=15.2 Hz), 4.11 (1H, ddd, J=14.8, 9.7, 1.2 Hz), 4.39 (1H, ddd, J=14.8, 6.5, 1.2 Hz), 7.16 (2H, d, J=8.6 Hz), 7.34 (1H, d, J=3.5 Hz), 7.86 (1H, d, J=3.5 Hz), 7.89 (2H, d, J=8.6 Hz).

MS (ESI) m/z: 399 [M+H]$^+$.

Example 40

(3-{1-[4-(6-Methoxypyridin-2-yl)phenyl]cyclopropyl}-8-methyl-5,6,8,9-tetrahydro[1,2,4]triazolo[4,3-d][1,4]thiazepin-8-yl)methanol

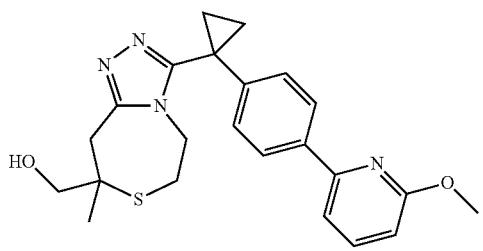 [SMILES: COc1cccc(-c2ccc(C3(c4nnc5n4CCSC(C)(CO)C5)CC3)cc2)n1]

Example 40-1

8-({[Tert-butyl(dimethyl)silyl]oxy}methyl)-3-{1-[4-(6-methoxypyridin-2-yl)phenyl]cyclopropyl}-8-methyl-5,6,8,9-tetrahydro[1,2,4]triazolo[4,3-d][1,4]thiazepine A solution of the compound (555 mg, 1.0 mmol) obtained in Example 16-5), 2-bromo-6-methoxypyridine (290 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (426 mg, 79%) as a light yellow oily substance.

$^1$H-NMR (500 MHz, CDCl$_3$) δ: 0.06 (3H, s), 0.08 (3H, s), 0.92 (9H, s), 1.20 (3H, s), 1.45-1.53 (2H, m), 1.58-1.62 (1H, m), 1.65-1.69 (1H, m), 2.51-2.57 (1H, m), 2.64-2.71 (1H, m), 3.40 (2H, s), 3.50-3.57 (2H, m), 4.03 (3H, s), 4.06-4.12 (1H, m), 4.29-4.36 (1H, m), 6.67-6.70 (1H, m), 7.14-7.18 (2H, m), 7.30-7.32 (1H, m), 7.60-7.64 (1H, m), 7.96-7.99 (2H, m).

Example 40-2

(3-{1-[4-(6-Methoxypyridin-2-yl)phenyl]cyclopropyl}-8-methyl-5,6,8,9-tetrahydro[1,2,4]triazolo[4,3-d][1,4]thiazepin-8-yl)methanol A solution of the compound (426 mg, 0.79 mmol) obtained in Example 40-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (320 mg, 95%) as a colorless solid.

$^1$H-NMR (400 MHz, CDCl$_3$) δ: 1.33 (3H, s), 1.40-1.47 (1H, m), 1.49-1.61 (2H, m), 1.63-1.70 (1H, m), 2.40 (1H, ddd, J=15.5, 6.5, 1.3 Hz), 2.46 (1H, brs), 2.60 (1H, ddd, J=15.5, 9.9, 1.3 Hz), 3.32 (1H, d, J=15.2 Hz), 3.37 (1H, d, J=11.7 Hz), 3.40 (1H, d, J=11.7 Hz), 3.61 (1H, d, J=15.2 Hz), 4.02 (3H, s), 4.10 (1H, ddd, J=14.7, 9.9, 1.3 Hz), 4.43 (1H, ddd, J=14.7, 6.5, 1.3 Hz), 6.69 (1H, d, J=7.8 Hz), 7.17 (2H, d, J=8.4 Hz), 7.31 (1H, d, J=7.8 Hz), 7.62 (1H, t, J=7.8 Hz), 7.99 (2H, d, J=8.4 Hz).

MS (ESI) m/z: 423 [M+H]$^+$.

Example 41

6-(4-{1-[8-(Hydroxymethyl)-8-methyl-5,6,8,9-tetrahydro[1,2,4]triazolo[4,3-d][1,4]thiazepin-3-yl]cyclopropyl}phenyl)pyridine-2-carbonitrile

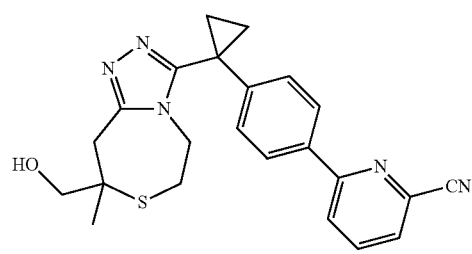 [SMILES: CC1(CO)Cc2nnc(C3(c4ccc(-c5cccc(C#N)n5)cc4)CC3)n2CCS1]

Example 41-1

6-(4-{1-[8-({[Tert-butyl(dimethyl)silyl]oxy}methyl)-8-methyl-5,6,8,9-tetrahydro[1,2,4]triazolo[4,3-d][1,4]thiazepin-3-yl]cyclopropyl}phenyl)pyridine-2-carbonitrile A solution of the compound (555 mg, 1.0 mmol) obtained in Example 16-5), 6-bromo-2-cyanopyridine (283 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (466 mg, 88%) as a light yellow oily substance.

$^1$H-NMR (400 MHz, CDCl$_3$) δ: 0.05 (3H, s), 0.07 (3H, s), 0.91 (9H, s), 1.19 (3H, s), 1.47-1.54 (2H, m), 1.61-1.70 (2H, m), 2.54 (1H, ddd, J=15.6, 7.8, 2.4 Hz), 2.69 (1H, ddd, J=15.6, 7.8, 2.0 Hz), 3.40 (2H, s), 3.51 (1H, d, J=9.8 Hz), 3.55 (1H, d, J=9.8 Hz), 4.07 (1H, ddd, J=14.4, 7.8, 2.0 Hz), 4.31 (1H, ddd, J=14.4, 7.8, 2.4 Hz), 7.20 (2H, d, J=8.5 Hz), 7.62 (1H, dd, J=7.3, 1.5 Hz), 7.86-7.92 (2H, m), 7.96 (2H, d, J=8.5 Hz).

Example 41-2

6-(4-{1-[8-(hydroxymethyl)-8-methyl-5,6,8,9-tetrahydro[1,2,4]triazolo[4,3-d][1,4]thiazepin-3-yl]cyclopropyl}phenyl)pyridine-2-carbonitrile A solution of the compound (466 mg, 0.88 mmol) obtained in Example 41-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (334 mg, 91%) as a colorless solid.

$^1$H-NMR (400 MHz, CDCl$_3$) δ: 1.34 (3H, s), 1.44-1.49 (1H, m), 1.54-1.63 (2H, m), 1.66-1.70 (1H, m), 2.22 (1H, brs), 2.42 (1H, ddd, J=15.5, 6.3, 1.8 Hz), 2.62 (1H, ddd, J=15.5, 9.9, 1.7 Hz), 3.33 (1H, d, J=15.2 Hz), 3.38 (2H, s), 3.63 (1H, d, J=15.2 Hz), 4.12 (1H, ddd, J=14.5, 9.9, 1.7 Hz), 4.44 (1H, ddd, J=14.5, 6.3, 1.8 Hz), 7.22 (2H, d, J=8.6 Hz), 7.85-7.98 (5H, m).

MS (ESI) m/z: 418 [M+H]$^+$.

Example 42

[8-Methyl-3-(1-{4-[5-(trifluoromethyl)pyridin-2-yl]phenyl}cyclopropyl)-5,6,8,9-tetrahydro[1,2,4]triazolo[4,3-d][1,4]thiazepin-8-yl]methanol

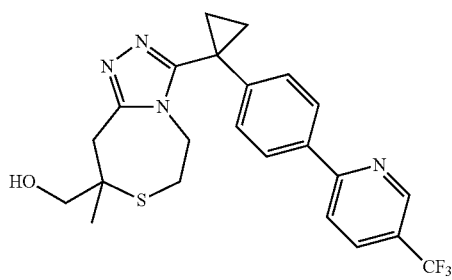 [SMILES: CC1(CO)Cc2nnc(C3(c4ccc(-c5ccc(C(F)(F)F)cn5)cc4)CC3)n2CCS1]

Example 42-1

8-({[Tert-butyl(dimethyl)silyl]oxy}methyl)-8-methyl-3-(1-{4-[5-(trifluoromethyl)pyridin-2-yl]phenyl}cyclopropyl)-5,6,8,9-tetrahydro[1,2,4]triazolo[4,3-d][1,4]thiazepine A solution of the compound (555 mg, 1.0 mmol) obtained in Example 16-5), 2-chloro-5-trifluoromethyl pyridine (272 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (574 mg, quant.) as a light yellow oily substance.

$^1$H-NMR (500 MHz, CDCl$_3$) δ: 0.05 (3H, s), 0.07 (3H, s), 0.91 (9H, s), 1.19 (3H, s), 1.47-1.54 (2H, m), 1.60-1.70 (2H, m), 2.51-2.58 (1H, m), 2.65-2.71 (1H, m), 3.40 (2H, s), 3.49-3.56 (2H, m), 4.04-4.10 (2H, m), 4.28-4.34 (1H, m), 7.18-7.22 (2H, m), 7.79-7.82 (1H, m), 7.95-7.99 (3H, m), 8.91-8.93 (1H, m).

Example 42-2

[8-Methyl-3-(1-{4-[5-(trifluoromethyl)pyridin-2-yl]phenyl}cyclopropyl)-5,6,8,9-tetrahydro[1,2,4]triazolo[4,3-d][1,4]thiazepin-8-yl]methanol A solution of the compound (574 mg, 1.0 mmol) obtained in Example 42-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (311 mg, 68%) as a colorless solid.

$^1$H-NMR (400 MHz, CDCl$_3$) δ: 1.33 (3H, s), 1.44-1.50 (1H, m), 1.53-1.58 (1H, m), 1.58-1.63 (1H, m), 1.67-1.71 (1H, m), 2.30 (1H, brs), 2.41 (1H, ddd, J=15.6, 6.5, 1.5 Hz), 2.61 (1H, ddd, J=15.6, 9.9, 1.5 Hz), 3.33 (1H, d, J=15.2 Hz), 3.36 (1H, d, J=12.1 Hz), 3.40 (1H, d, J=12.1 Hz), 3.62 (1H, d, J=15.2 Hz), 4.11 (1H, ddd, J=14.8, 9.9, 1.5 Hz), 4.42 (1H, ddd, J=14.8, 6.5, 1.5 Hz), 7.22 (2H, d, J=8.6 Hz), 7.82 (1H, d, J=8.2 Hz), 7.98 (1H, d, J=8.2 Hz), 7.98 (2H, d, J=8.6 Hz), 8.93 (1H, t, J=1.2 Hz).

MS (ESI) m/z: 461 [M+H]$^+$.

Example 43

(3-{1-[4-(2-Methoxypyridin-3-yl)phenyl]cyclopropyl}-8-methyl-5,6,8,9-tetrahydro[1,2,4]triazolo[4,3-d][1,4]thiazepin-8-yl)methanol

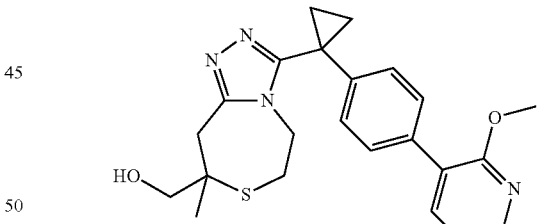

Example 43-1

8-({[Tert-butyl(dimethyl)silyl]oxy}methyl)-3-{1-[4-(2-methoxypyridin-3-yl)phenyl]cyclopropyl}-8-methyl-5,6,8,9-tetrahydro[1,2,4]triazolo[4,3-d][1,4]thiazepine A solution of the compound (555 mg, 1.0 mmol) obtained in Example 16-5), 3-bromo-2-methoxypyridine (293 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mix-

85 ture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (315 mg, 59%) as a light yellow oily substance.

$^1$H-NMR (400 MHz, CDCl$_3$) δ: 0.06 (3H, s), 0.08 (3H, s), 0.91 (9H, s), 1.19 (3H, s), 1.47-1.63 (4H, m), 2.54-2.63 (1H, m), 2.74-2.81 (1H, m), 3.24-3.60 (4H, m), 3.96 (3H, s), 4.08-4.17 (1H, m), 4.34-4.41 (1H, m), 6.97-7.01 (1H, m), 7.09-7.13 (2H, m), 7.47-7.51 (2H, m), 7.58-7.62 (1H, m), 8.12-8.15 (1H, m).

Example 43-2

(3-{1-[4-(2-Methoxypyridin-3-yl)phenyl]cyclopropyl}-8-methyl-5,6,8,9-tetrahydro[1,2,4]triazolo[4,3-d][1,4]thiazepin-8-yl)methanol A solution of the compound (315 mg, 0.59 mmol) obtained in Example 43-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (279 mg, quant.) as a colorless solid.

$^1$H-NMR (400 MHz, CDCl$_3$) δ: 1.33 (3H, s), 1.45-1.51 (2H, m), 1.56-1.63 (2H, m), 2.27 (1H, brs), 2.43 (1H, dd, J=15.3, 5.7 Hz), 2.62 (1H, dd, J=15.3, 9.8 Hz), 3.32 (1H, d, J=15.2 Hz), 3.35 (1H, d, J=11.3 Hz), 3.39 (1H, d, J=11.3 Hz), 3.62 (1H, d, J=15.2 Hz), 3.96 (3H, s), 4.12 (1H, dd, J=14.6, 9.8 Hz), 4.46 (1H, dd, J=14.6, 5.7 Hz), 6.97 (1H, dd, J=7.4, 5.1 Hz), 7.14 (2H, d, J=8.2 Hz), 7.50 (2H, d, J=8.2 Hz), 7.58 (1H, dt, J=7.4, 1.0 Hz), 8.15 (1H, dt, J=5.1, 1.0 Hz).

MS (ESI) m/z: 423 [M+H]$^+$.

Example 44

3-(4-{1-[8-(Hydroxymethyl)-8-methyl-5,6,8,9-tetrahydro[1,2,4]triazolo[4,3-d][1,4]thiazepin-3-yl]cyclopropyl}phenyl)pyridin-2-carbonitrile

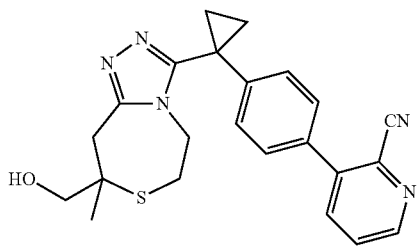 [SMILES: CC1(CO)Cc2nnc(C3(c4ccc(-c5cccnc5C#N)cc4)CC3)n2CCS1]

86

Example 44-1

3-(4-{1-[8-({[Tert-butyl(dimethyl)silyl]oxy}methyl)-8-methyl-5,6,8,9-tetrahydro[1,2,4]triazolo[4,3-d][1,4]thiazepin-3-yl]cyclopropyl}phenyl)pyridin-2-carbonitrile A solution of the compound (555 mg, 1.0 mmol) obtained in Example 16-5), 3-bromopyridine-2-carbonitrile (283 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (421 mg, 79%) as a light yellow oily substance.

$^1$H-NMR (400 MHz, CDCl$_3$) δ: 0.05 (3H, s), 0.07 (3H, s), 0.91 (9H, s), 1.19 (3H, s), 1.47-1.57 (2H, m), 1.61-1.66 (1H, m), 1.68-1.73 (1H, m), 2.53-2.62 (1H, m), 2.69-2.77 (1H, m), 3.40 (2H, s), 3.49-3.57 (2H, m), 4.06-4.13 (1H, m), 4.29-4.37 (1H, m), 7.20-7.24 (2H, m), 7.47-7.52 (2H, m), 7.56-7.60 (1H, m), 7.82-7.85 (1H, m), 8.69-8.71 (1H, m).

Example 44-2

3-(4-{1-[8-(Hydroxymethyl)-8-methyl-5,6,8,9-tetrahydro[1,2,4]triazolo[4,3-d][1,4]thiazepin-3-yl]cyclopropyl}phenyl)pyridine-2-carbonitrile A solution of the compound (421 mg, 0.79 mmol) obtained in Example 44-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (319 mg, 97%) as a colorless solid.

$^1$H-NMR (400 MHz, CDCl$_3$) δ: 1.33 (3H, s), 1.45-1.50 (1H, m), 1.56-1.63 (2H, m), 1.70-1.76 (1H, m), 2.29 (1H, brs), 2.42 (1H, ddd, J=15.4, 6.4, 1.5 Hz), 2.56 (1H, ddd, J=15.4, 9.8, 1.5 Hz), 3.34 (1H, d, J=15.2 Hz), 3.36 (2H, s), 3.61 (1H, d, J=15.2 Hz), 4.12 (1H, ddd, J=14.8, 9.8, 1.5 Hz), 4.43 (1H, ddd, J=14.8, 6.4, 1.5 Hz), 7.26 (2H, d, J=8.2 Hz), 7.51 (2H, d, J=8.2 Hz), 7.58 (1H, dd, J=8.2, 4.7 Hz), 7.84 (1H, dd, J=8.2, 1.6 Hz), 8.71 (1H, dd, J=4.7, 1.6 Hz).

MS (ESI) m/z: 418 [M+H]$^+$.

Example 45

5-(4-{1-[8-(Hydroxymethyl)-8-methyl-5,6,8,9-tetrahydro[1,2,4]triazolo[4,3-d][1,4]thiazepin-3-yl]cyclopropyl}phenyl)pyridine-2-carbonitrile

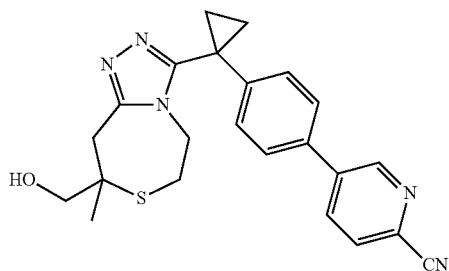 [SMILES: CC1(CO)Cc2nnc(C3(c4ccc(-c5ccc(C#N)nc5)cc4)CC3)n2CCS1]

Example 45-1

5-(4-{1-[8-({[Tert-butyl(dimethyl)silyl]oxy}methyl)-8-methyl-5,6,8,9-tetrahydro[1,2,4]triazolo[4,3-d][1,4]thiazepin-3-yl]cyclopropyl}phenyl)pyridine-2-carbonitrile A solution of the compound (555 mg, 1.0 mmol) obtained in Example 16-5), 5-bromo-2-pyridinecarbonitrile (283 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (372 mg, 70%) as a light yellow oily substance.

$^1$H-NMR (400 MHz, CDCl$_3$) δ: 0.05 (3H, s), 0.07 (3H, s), 0.91 (9H, s), 1.20 (3H, s), 1.45-1.55 (2H, m), 1.60-1.65 (1H, m), 1.68-1.73 (1H, m), 2.54-2.62 (1H, m), 2.70-2.78 (1H, m), 3.40 (2H, s), 3.51-3.59 (2H, m), 4.05-4.13 (1H, m), 4.28-4.35 (1H, m), 7.19-7.23 (2H, m), 7.51-7.55 (2H, m), 7.74-7.78 (1H, m), 7.95-7.99 (1H, m), 8.90-8.92 (1H, m).

Example 45-2

5-(4-{1-[8-(Hydroxymethyl)-8-methyl-5,6,8,9-tetrahydro[1,2,4]triazolo[4,3-d][1,4]thiazepin-3-yl]cyclopropyl}phenyl)pyridine-2-carbonitrile A solution of the compound (372 mg, 0.70 mmol) obtained in Example 45-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (248 mg, 85%) as a colorless solid.

$^1$H-NMR (400 MHz, CDCl$_3$) δ: 1.34 (3H, s), 1.45-1.50 (1H, m), 1.52-1.59 (2H, m), 1.62-1.67 (1H, m), 2.20 (1H, brs), 2.45 (1H, ddd, J=15.6, 6.1, 1.3 Hz), 2.64 (1H, ddd, J=15.6, 9.9, 1.3 Hz), 3.33 (1H, d, J=15.2 Hz), 3.39 (2H, s), 3.62 (1H, d, J=15.2 Hz), 4.13 (1H, ddd, J=14.7, 9.9, 1.3 Hz), 4.44 (1H, ddd, J=14.7, 6.1, 1.3 Hz), 7.23 (2H, d, J=8.6 Hz), 7.56 (2H, d, J=8.6 Hz), 8.01 (1H, dd, J=8.2, 2.3 Hz), 8.26 (1H, dd, J=8.2, 0.8 Hz), 8.76 (1H, dd, J=2.3, 0.8 Hz).

MS (ESI) m/z: 418 [M+H]$^+$.

Example 46

(3-{1-[4-(6-Methoxypyrimidin-4-yl)phenyl]cyclopropyl}-8-methyl-5,6,8,9-tetrahydro[1,2,4]triazolo[4,3-d][1,4]thiazepin-8-yl)methanol

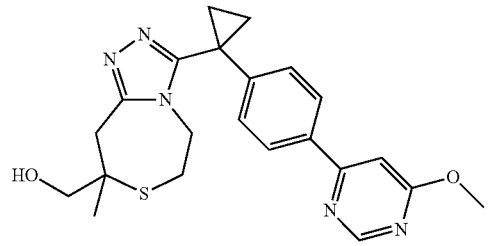 [SMILES: COc1cc(-c2ccc(C3(c4nnc5n4CCSC(C)(CO)C5)CC3)cc2)ncn1]

A solution of the compound (1.39 g, 2.5 mmol) obtained in Example 16-5), 4,6-dichloropyrimidine (1.49 g, 10 mmol), tetrakis(triphenylphosphine)palladium(0) (577 mg, 0.5 mmol), and potassium carbonate (691 mg, 5 mmol) in dimethoxyethane (10 mL) and water (2.5 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, a solution of 4 M hydrochloric acid (1,4-dioxane solution, 2.5 mL) in methanol (10 mL) was added to the residue, and the mixture was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (551 mg, 52%) as a colorless solid.

$^1$H-NMR (400 MHz, CDCl$_3$) δ: 1.32 (3H, s), 1.44-1.49 (1H, m), 1.52-1.57 (1H, m), 1.57-1.63 (1H, m), 1.65-1.70 (1H, m), 2.40 (1H, ddd, J=15.4, 6.5, 1.4 Hz), 2.61 (1H, ddd, J=15.4, 9.6, 1.6 Hz), 2.69 (1H, brs), 3.33 (1H, d, J=15.2 Hz), 3.40 (2H, s), 3.61 (1H, d, J=15.2 Hz), 4.03 (3H, s), 4.10 (1H, ddd, J=14.7, 9.6, 1.6 Hz), 4.38 (1H, ddd, J=14.7, 6.5, 1.4 Hz), 7.07 (1H, d, J=0.8 Hz), 7.19 (2H, d, J=8.6 Hz), 7.96 (2H, d, J=8.6 Hz), 8.83 (1H, d, J=0.8 Hz).

MS (ESI) m/z: 424 [M+H]$^+$.

Example 47

3-(4-{1-[8-(Hydroxymethyl)-8-methyl-5,6,8,9-tetrahydro[1,2,4]triazolo[4,3-d][1,4]thiazepin-3-yl]cyclopropyl}phenyl)isonicotinonitrile

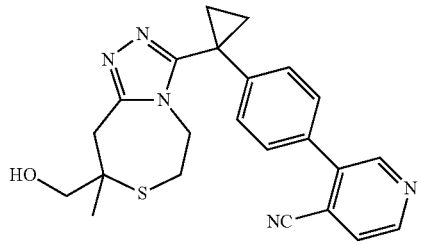 [SMILES: CC1(CO)Cc2nnc(C3(c4ccc(-c5cnccc5C#N)cc4)CC3)n2CCS1]

A solution of the compound (508 mg, 1.0 mmol) obtained in Example 16-4), 4-cyanopyridine-3-boronic acid pinacol ester (366 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was partially purified by silica gel chromatography (Isco Combiflash, 40 g, methanol:ethyl acetate=0:100 to 20:80, gradient). This partially purified product was dissolved in a solution of 4 M hydrochloric acid (1,4-dioxane solution, 1 mL) in methanol (4 mL), and the mixture was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (109 mg, 26%) as a colorless solid.

$^1$H-NMR (500 MHz, CDCl$_3$) δ: 1.33 (3H, s), 1.46-1.51 (1H, m), 1.55-1.59 (1H, m), 1.60-1.64 (1H, m), 1.69-1.74 (1H, m), 2.28 (1H, brs), 2.42 (1H, dd, J=15.4, 5.5 Hz), 2.57 (1H, dd, J=15.4, 9.2 Hz), 3.34 (1H, d, J=15.1 Hz), 3.37 (2H, s), 3.62 (1H, d, J=15.1 Hz), 4.12 (1H, dd, J=14.6, 9.2 Hz), 4.43 (1H, dd, J=14.6, 5.4 Hz), 7.27 (2H, d, J=8.8 Hz), 7.52 (2H, d, J=8.8 Hz), 7.61 (1H, d, J=4.9 Hz), 8.76 (1H, d, J=4.9 Hz), 8.83 (1H, s).

MS (ESI) m/z: 418 [M+H]$^+$.

Example 48

(3-{1-[4-(4-Chloropyridin-3-yl)phenyl]cyclopropyl}-8-methyl-5,6,8,9-tetrahydro[1,2,4]triazolo[4,3-d][1,4]thiazepin-8-yl)methanol

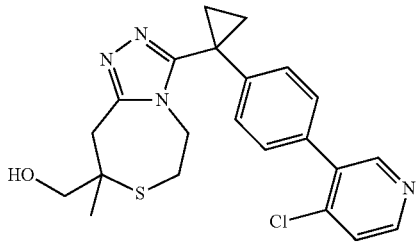 [SMILES: CC1(CO)Cc2nnc(C3(c4ccc(-c5cnccc5Cl)cc4)CC3)n2CCS1]

A solution of the compound (508 mg, 1.0 mmol) obtained in Example 16-4), 4-chloropyridine-3-boronic acid pinacol ester (366 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was partially purified by silica gel chromatography (Isco Combiflash, 40 g, methanol:ethyl acetate=0:100 to 20:80, gradient). This partially purified product was dissolved in a solution of 4 M hydrochloric acid (1,4-dioxane solution, 1 mL) in methanol (4 mL), and the mixture was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (135 mg, 32%) as a colorless solid.

$^1$H-NMR (500 MHz, CDCl$_3$) δ: 1.33 (3H, s), 1.46-1.51 (1H, m), 1.53-1.61 (2H, m), 1.62-1.69 (1H, m), 2.23 (1H, brs), 2.43 (1H, ddd, J=15.9, 6.6, 1.2 Hz), 2.61 (1H, ddd, J=15.9, 10.0, 1.2 Hz), 3.33 (1H, d, J=15.1 Hz), 3.35 (1H, d, J=11.7 Hz), 3.39 (1H, d, J=11.7 Hz), 3.62 (1H, d, J=15.1 Hz), 4.13 (1H, ddd, J=14.6, 10.0, 1.2 Hz), 4.45 (1H, ddd, J=14.6, 6.6, 1.2 Hz), 7.20 (2H, d, J=8.3 Hz), 7.40 (2H, d, J=8.3 Hz), 7.42 (1H, d, J=5.4 Hz), 8.47 (1H, d, J=5.4 Hz), 8.52 (1H, s).

MS (ESI) m/z: 427 [M+H]$^+$.

Example 49

[8-Methyl-3-(1-{4-[2-(trifluoromethyl)pyridin-3-yl]phenyl}cyclopropyl)-5,6,8,9-tetrahydro[1,2,4]triazolo[4,3-d][1,4]thiazepin-8-yl]methanol

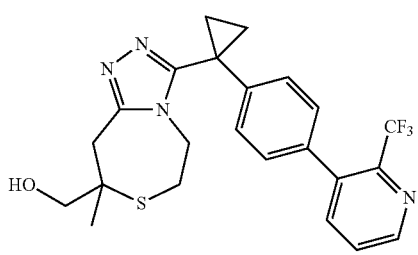

A solution of the compound (555 mg, 1.0 mmol) obtained in Example 16-5), 3-bromo-2-trifluoromethyl pyridine (339 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was partially purified by silica gel chromatography (Isco Combiflash, 40 g, methanol:ethyl acetate=0:100 to 40:60, gradient). This partially purified product was dissolved in a solution of 4 M hydrochloric acid (1,4-dioxane solution, 1 mL) in methanol (4 mL), and the mixture was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (135 mg, 32%) as a colorless solid.

$^1$H-NMR (500 MHz, CDCl$_3$) δ: 1.33 (3H, s), 1.42-1.47 (1H, m), 1.61-1.66 (2H, m), 1.71-1.75 (1H, m), 2.23 (1H, brs), 2.36 (1H, dd, J=15.6, 6.1 Hz), 2.52 (1H, dd, J=15.6, 10.0 Hz), 3.33 (1H, d, J=15.1 Hz), 3.34 (1H, d, J=11.7 Hz), 3.38 (1H, d, J=11.7 Hz), 3.62 (1H, d, J=15.1 Hz), 4.12 (1H, dd, J=14.4, 10.0 Hz), 4.43 (1H, dd, J=14.4, 6.1 Hz), 7.18 (2H, d, J=7.8 Hz), 7.27 (2H, d, J=7.8 Hz), 7.54 (1H, dd, J=7.8, 4.4 Hz), 7.70 (1H, d, J=7.8 Hz), 8.72 (1H, d, J=4.4 Hz).

MS (ESI) m/z: 461 [M+H]$^+$.

Example 50

{8-Methyl-3-[1-(4-pyridazin-3-ylphenyl)cyclopropyl]-5,6,8,9-tetrahydro[1,2,4]triazolo[4,3-d][1,4]thiazepin-8-yl}methanol

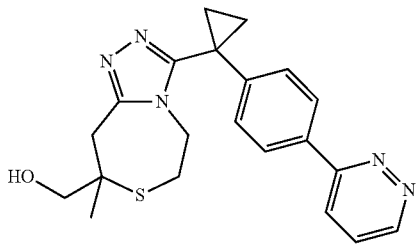 [SMILES: CC1(CO)Cc2nnc(C3(c4ccc(-c5cccnn5)cc4)CC3)n2CCS1]

Example 50-1

8-({[Tert-butyl(dimethyl)silyl]oxy}methyl)-8-methyl-3-[1-(4-pyridazin-3-ylphenyl)cyclopropyl]-5,6,8,9-tetrahydro[1,2,4]triazolo[4,3-d][1,4]thiazepine A solution of the compound (556 mg, 1.0 mmol) obtained in Example 16-5), 3-chloropyridazine (172 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (292 mg, 58%) as a light yellow oily substance.

$^1$H-NMR (400 MHz, CDCl$_3$) δ: 0.05 (3H, s), 0.07 (3H, s), 0.91 (9H, s), 1.19 (3H, s), 1.47-1.71 (4H, m), 2.51-2.58 (1H, m), 2.65-2.73 (1H, m), 3.40 (2H, s), 3.49-3.57 (2H, m), 4.04-4.11 (1H, m), 4.28-4.35 (1H, m), 7.20-7.25 (2H, m), 7.51-7.56 (1H, m), 7.81-7.85 (1H, m), 8.00-8.04 (2H, m), 9.14-9.17 (1H, m).

Example 50-2

{8-Methyl-3-[1-(4-pyridazin-3-ylphenyl)cyclopropyl]-5,6,8,9-tetrahydro[1,2,4]triazolo[4,3-d][1,4]thiazepin-8-yl}methanol A solution of the compound (292 mg, 0.58 mmol) obtained in Example 50-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (130 mg, 57%) as a colorless solid.

$^1$H-NMR (500 MHz, CDCl$_3$) δ: 1.33 (3H, s), 1.46-1.51 (1H, m), 1.54-1.59 (1H, m), 1.60-1.64 (1H, m), 1.67-1.71 (1H, m), 2.42 (1H, dd, J=15.3, 6.3 Hz), 2.62 (1H, dd, J=15.3, 9.0 Hz), 3.33 (1H, d, J=15.1 Hz), 3.38 (1H, d, J=12.2 Hz), 3.41 (1H, d, J=12.2 Hz), 3.62 (1H, d, J=15.1 Hz), 4.12 (1H, dd, J=14.6, 9.0 Hz), 4.42 (1H, dd, J=14.6, 6.3 Hz), 7.25 (2H, d, J=8.3 Hz), 7.54 (1H, dd, J=8.3, 4.6 Hz), 7.84 (1H, dd, J=8.8, 1.3 Hz), 8.03 (2H, d, J=8.3 Hz), 9.16 (1H, dd, J=4.6, 1.3 Hz).

MS (ESI) m/z: 394 [M+H]$^+$.

Example 51

(8-Methyl-3-{1-[4-(5-methylpyrimidin-2-yl)phenyl]cyclopropyl}-5,6,8,9-tetrahydro[1,2,4]triazolo[4,3-d][1,4]thiazepin-8-yl)methanol

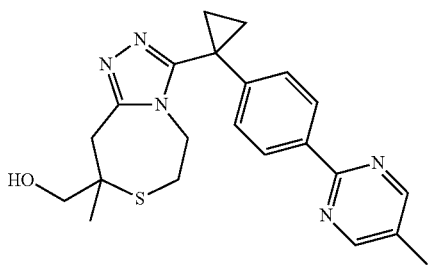 [SMILES: Cc1cnc(-c2ccc(C3(c4nnc5n4CCSC(C)(CO)C5)CC3)cc2)nc1]

Example 51-1

8-({[Tert-butyl(dimethyl)silyl]oxy}methyl)-8-methyl-3-{1-[4-(5-methylpyrimidin-2-yl)phenyl]cyclopropyl}-5,6,8,9-tetrahydro[1,2,4]triazolo[4,3-d][1,4]thiazepine A solution of the compound (556 mg, 1.0 mmol) obtained in Example 16-5), 2-chloro-5-methylpyrimidine (193 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (298 mg, 57%) as a brown oily substance.

$^1$H-NMR (400 MHz, CDCl$_3$) δ: 0.05 (3H, s), 0.07 (3H, s), 0.91 (9H, s), 1.19 (3H, s), 1.49-1.52 (2H, m), 1.58-1.67 (2H, m), 2.34 (3H, s), 2.50 (1H, ddd, J=15.6, 8.0, 2.2 Hz), 2.63 (1H, ddd, J=15.6, 7.7, 2.2 Hz), 3.40 (1H, d, J=10.2 Hz), 3.54 (1H, d, J=10.2 Hz), 4.06 (1H, ddd, J=14.6, 8.0, 2.2 Hz), 4.31 (1H, ddd, J=14.6, 7.7, 2.2 Hz), 7.17 (2H, dt, J=8.7, 2.0 Hz), 8.32 (2H, dt, J=8.7, 2.0 Hz), 8.62 (2H, s).

Example 51-2

(8-Methyl-3-{1-[4-(5-methylpyrimidin-2-yl)phenyl]cyclopropyl}-5,6,8,9-tetrahydro[1,2,4]triazolo[4,3-d][1,4]thiazepin-8-yl)methanol A solution of the compound (298 mg, 0.57 mmol) obtained in Example 51-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (114 mg, 49%) as a colorless solid.

$^1$H-NMR (500 MHz, CDCl$_3$) δ: 1.32 (3H, s), 1.43-1.47 (1H, m), 1.54-1.60 (2H, m), 1.67-1.71 (1H, m), 2.34-2.38 (4H, m), 2.56 (1H, dd, J=15.6, 9.6 Hz), 3.32 (1H, d, J=15.1 Hz), 3.35 (1H, d, J=12.2 Hz), 3.39 (1H, d, J=12.2 Hz), 3.61 (1H, d, J=15.1 Hz), 4.09 (1H, dd, J=14.5, 9.6 Hz), 4.41 (1H, dd, J=14.5, 6.3 Hz), 7.19 (2H, d, J=8.5 Hz), 8.33 (2H, d, J=8.5 Hz), 8.62 (2H, s).

MS (ESI) m/z: 408 [M+H]$^+$.

Example 52

{(8R)-8-Methyl-3-{1-[4-(5-methylpyrimidin-2-yl)phenyl]cyclopropyl}-5,6,8,9-tetrahydro[1,2,4]triazolo[4,3-d][1,4]thiazepin-8-yl}methanol

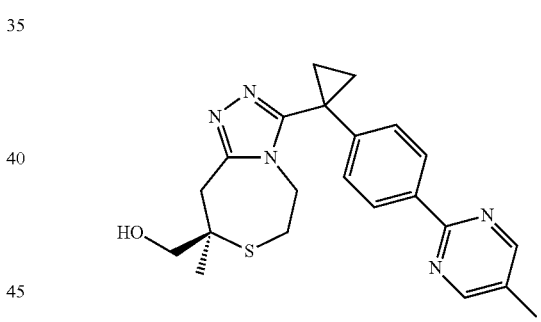

Example 52-1

(8R)-3-[1-(4-Bromophenyl)cyclopropyl]-8-({[t-butyl(dimethyl)silyl]oxy}methyl)-8-methyl-5,6,8,9-tetrahydro[1,2,4]triazolo[4,3-d][1,4]thiazepine The compound (1.02 g, 3.19 mmol) obtained in Example 4-1) and the compound (0.81 g, 3.19 mmol) obtained in Example 16-3) were dissolved in 1-butanol (5 mL), and the mixture was stirred at 140° C. for 6 h under a nitrogen atmosphere. The reaction mixture was cooled to room temperature, then the solvent was distilled off, and the obtained residue was purified by silica gel column chromatography (elution solvent: methanol/ethyl acetate=0% to 20%) to obtain the title compound (1.41 g, 85%) in a white solid form.

$^1$H-NMR (400 MHz, CDCl$_3$) δ: 0.04 (3H, s), 0.07 (3H, s), 0.91 (9H, s), 1.18 (3H, s), 1.36-1.45 (2H, m), 1.53-1.65 (2H, m), 2.52 (1H, ddd, J=15.5, 8.0, 2.5 Hz), 2.68 (1H, ddd, J=15.5, 7.9, 2.3 Hz), 3.38 (2H, s), 3.50 (1H, d, J=10.2 Hz), 3.54 (1H, d, J=10.2 Hz), 4.04 (1H, ddd, J=14.5, 7.9, 2.3 Hz), 4.27 (1H, ddd, J=14.5, 8.0, 2.5 Hz), 6.96 (2H, d, J=8.6 Hz), 7.40 (2H, d, J=8.6 Hz).

Example 52-2

(8R)-8-({[t-Butyl(dimethyl)silyl]oxy}methyl)-8-methyl-3-{1-[4-(4,4,5,5-tetramethyl-1,3,2-dioxaborolan-2-yl)phenyl]cyclopropyl}-5,6,8,9-tetrahydro[1,2,4]triazolo[4,3-d][1,4]thiazepine The compound (700 mg, 1.38 mmol) obtained in Example 52-1) was dissolved in 1,4-dioxane (15 mL). Bis(pinacolato) diboron (875 mg, 3.44 mmol), [1,1'-bis(diphenylphosphino) ferrocene]palladium(II) dichloride-dichloromethane complex (225 mg, 0.28 mmol), and potassium acetate (405 mg, 4.13 mmol) were added to the solution, and the mixture was heated to reflux for 8 h under a nitrogen atmosphere. The reaction mixture was cooled to room temperature, then the solvent was distilled off, and the obtained residue was purified by silica gel column chromatography (elution solvent: methanol/ethyl acetate=2% to 30%) to obtain the title compound (608 mg, 79%) in a brown solid form.

$^1$H-NMR (400 MHz, CDCl$_3$) δ: 0.05 (3H, s), 0.07 (3H, s), 0.91 (9H, s), 1.18 (3H, s), 1.33 (12H, s), 1.43-1.46 (2H, m), 1.58-1.61 (2H, m), 2.46 (1H, ddd, J=15.5, 8.1, 2.2 Hz), 2.59 (1H, ddd, J=15.6, 7.8, 2.3 Hz), 3.38 (2H, s), 3.49 (1H, d, J=9.8 Hz), 3.53 (1H, d, J=10.2 Hz), 4.02 (1H, ddd, J=14.6, 8.1, 2.1 Hz), 4.26 (1H, ddd, J=14.6, 7.7, 2.1 Hz), 7.06 (2H, d, J=8.2 Hz), 7.71 (2H, d, J=8.2 Hz).

Example 52-3

(8R)-8-({[t-Butyl(dimethyl)silyl]oxy}methyl)-8-methyl-3-{1-[4-(5-methylpyrimidin-2-yl)phenyl]cyclopropyl}-5,6,8,9-tetrahydro[1,2,4]triazolo[4,3-d][1,4]thiazepine The compound (600 mg, 1.08 mmol) obtained in Example 52-2), 2-chloro-5-methylpyrimidine (155 mg, 1.19 mmol), tris(dibenzylideneacetone)dipalladium (50 mg, 0.05 mmol), tricyclohexylphosphine (36 mg, 0.13 mmol), and tripotassium phosphate (400 mg, 1.84 mmol) were dissolved in a mixed solvent of 1,4-dioxane (3 mL) and water (1.5 mL), and the mixture was stirred at 140° C. for 2 h under microwave irradiation. The reaction mixture was cooled to room temperature, then diluted with methylene chloride (100 mL), and separated into organic and aqueous layers by the addition of saturated aqueous sodium hydrogencarbonate (30 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=0% to 20%) to obtain the title compound (348 mg, 62%) in a light yellow solid form.

$^1$H-NMR (400 MHz, CDCl$_3$) δ: 0.05 (3H, s), 0.07 (3H, s), 0.91 (9H, s), 1.19 (3H, s), 1.46-1.53 (2H, m), 1.61-1.68 (2H, m), 2.34 (3H, s), 2.50 (1H, ddd, J=15.6, 7.8, 2.3 Hz), 2.63 (1H, ddd, J=15.7, 7.7, 2.2 Hz), 3.40 (2H, s), 3.52 (2H, dd, J=15.8, 10.0 Hz), 4.06 (1H, ddd, J=14.5, 7.8, 2.3 Hz), 4.31 (1H, ddd, J=14.5, 7.8, 2.3 Hz), 7.17 (2H, d, J=8.6 Hz), 8.32 (2H, d, J=8.6 Hz), 8.62 (2H, d, J=0.8 Hz).

Example 52-4

{(8R)-8-Methyl-3-{1-[4-(5-methylpyrimidin-2-yl)phenyl]cyclopropyl}-5,6,8,9-tetrahydro[1,2,4]triazolo[4,3-d][1,4]thiazepin-8-yl}methanol The compound (348 mg, 0.67 mmol) obtained in Example 52-3) was dissolved in methanol (3 mL). A 4 N solution (1.67 mL) of hydrochloric acid in dioxane was added to the solution, and the mixture was stirred at room temperature for 1 h. The solvent was distilled off, the residue was dissolved in a mixed solvent of methylene chloride (50 mL) and methanol (2 mL), and the mixture was separated into organic and aqueous layers by the addition of saturated aqueous sodium hydrogencarbonate (20 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=10% to 60%) to obtain the title compound (216 mg, 79%) in a white solid form.

$^1$H-NMR (400 MHz, CDCl$_3$) δ: 1.32 (3H, s), 1.42-1.49 (1H, m), 1.54-1.60 (2H, m), 1.66-1.72 (1H, m), 2.23 (1H, t, J=7.0 Hz), 2.34 (3H, s), 2.36 (1H, ddd, J=16.0, 6.3, 1.2 Hz), 2.56 (1H, ddd, J=16.0, 9.8, 1.6 Hz), 3.30-3.41 (2H, m), 3.31 (1H, d, J=15.2 Hz), 3.61 (1H, d, J=15.2 Hz), 4.09 (1H, ddd, J=14.9, 9.8, 1.2 Hz), 4.42 (1H, ddd, J=14.5, 6.6, 1.2 Hz), 7.19 (2H, d, J=8.6 Hz), 8.33 (2H, d, J=8.6 Hz), 8.62 (2H, d, J=0.8 Hz).

MS (ESI) m/z: 408.18589 (M+H)$^+$.

Example 53

(3-{1-[4-(5-Chloropyridin-2-yl)phenyl]cyclopropyl}-8-methyl-5,6,8,9-tetrahydro[1,2,4]triazolo[4,3-d][1,4]thiazepin-8-yl)methanol

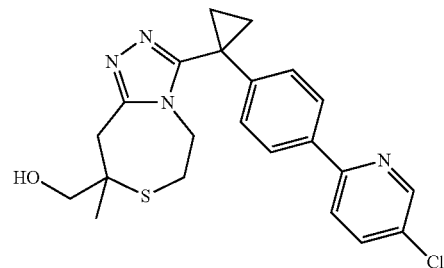 [SMILES: CC1(CO)Cc2nnc(C3(c4ccc(-c5ccc(Cl)cn5)cc4)CC3)n2CCS1]

Example 53-1

8-({[Tert-butyl(dimethyl)silyl]oxy}methyl)-3-{1-[4-(5-chloropyridin-2-yl)phenyl]cyclopropyl}-8-methyl-5,6,8,9-tetrahydro[1,2,4]triazolo[4,3-d][1,4]thiazepine A solution of the compound (555 mg, 1.0 mmol) obtained in Example 16-5), 2-bromo-5-chloropyridine (289 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (367 mg, 68%) as a light yellow oily substance.

$^1$H-NMR (500 MHz, CDCl$_3$) δ: 0.05 (3H, s), 0.07 (3H, s), 0.91 (9H, s), 1.19 (3H, s), 1.45-1.52 (2H, m), 1.59-1.68 (2H, m), 2.53 (1H, ddd, J=15.7, 8.0, 2.2 Hz), 2.67 (1H, ddd, J=15.7, 7.8, 2.0 Hz), 3.39 (2H, s), 3.51 (1H, d, J=10.1 Hz), 3.54 (1H, d, J=10.1 Hz), 4.06 (1H, ddd, J=14.4, 8.1, 2.0 Hz), 4.31 (1H, ddd, J=14.4, 7.8, 2.2 Hz), 7.17 (2H, d, J=8.6 Hz), 7.64 (1H, d, J=8.8 Hz), 7.72 (1H, dd, J=8.8, 2.4 Hz), 7.89 (2H, d, J=8.6 Hz), 8.61 (1H, d, J=2.4 Hz).

Example 53-2

(3-{1-[4-(5-Chloropyridin-2-yl)phenyl]cyclopropyl}-8-methyl-5,6,8,9-tetrahydro[1,2,4]triazolo[4,3-d][1,4]thiazepin-8-yl)methanol A solution of the compound (367 mg, 0.68 mmol) obtained in Example 53-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (318 mg, quant.) as a colorless solid.

$^1$H-NMR (400 MHz, CDCl$_3$) δ: 1.32 (3H, s), 1.42-1.48 (1H, m), 1.53-1.61 (2H, m), 1.64-1.70 (1H, m), 2.27 (1H, brs), 2.39 (1H, ddd, J=15.6, 6.5, 1.4 Hz), 2.59 (1H, ddd, J=15.6, 10.0, 1.4 Hz), 3.32 (1H, d, J=15.2 Hz), 3.35 (1H, d, J=11.7 Hz), 3.39 (1H, d, J=11.7 Hz), 3.61 (1H, d, J=15.2 Hz), 4.09 (1H, ddd, J=14.7, 10.0, 1.4 Hz), 4.42 (1H, ddd, J=14.7, 6.5, 1.4 Hz), 7.19 (2H, d, J=8.4 Hz), 7.65 (1H, d, J=8.4 Hz), 7.72 (1H, dd, J=8.4, 2.5 Hz), 7.90 (2H, d, J=8.4 Hz), 8.62 (1H, d, J=2.5 Hz).

MS (ESI) m/z: 427 [M+H]$^+$.

Example 54

(3-{1-[4-(5-Fluoropyridin-2-yl)phenyl]cyclopropyl}-8-methyl-5,6,8,9-tetrahydro[1,2,4]triazolo[4,3-d][1,4]thiazepin-8-yl)methanol

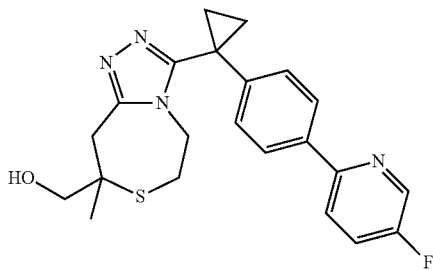 [SMILES: CC1(CO)Cc2nnc(C3(c4ccc(-c5ccc(F)cn5)cc4)CC3)n2CCS1]

Example 54-1

8-({[Tert-butyl(dimethyl)silyl]oxy}methyl)-3-{1-[4-(5-fluoropyridin-2-yl)phenyl]cyclopropyl}-8-methyl-5,6,8,9-tetrahydro[1,2,4]triazolo[4,3-d][1,4]thiazepine A solution of the compound (555 mg, 1.0 mmol) obtained in Example 16-5), 2-bromo-5-fluoropyridine (263 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (382 mg, 73%) as a light yellow oily substance.

$^1$H-NMR (500 MHz, CDCl$_3$) δ: 0.05 (3H, s), 0.07 (3H, s), 0.91 (9H, s), 1.19 (3H, s), 1.46-1.51 (2H, m), 1.58-1.63 (1H, m), 1.64-1.67 (1H, m), 2.53 (1H, ddd, J=15.7, 8.2, 2.3 Hz), 2.66 (1H, ddd, J=15.7, 7.8, 2.0 Hz), 3.39 (2H, s), 3.51 (1H, d, J=10.3 Hz), 3.54 (1H, d, J=10.3 Hz), 4.07 (1H, ddd, J=14.4, 7.8, 2.0 Hz), 4.31 (1H, ddd, J=14.4, 8.2, 2.3 Hz), 7.17 (2H, d, J=8.3 Hz), 7.46 (1H, td, J=8.3, 2.9 Hz), 7.69 (1H, dd, J=8.8, 4.4 Hz), 7.86 (2H, d, J=8.3 Hz), 8.52 (1H, d, J=2.9 Hz).

Example 54-2

(3-{1-[4-(5-Fluoropyridin-2-yl)phenyl]cyclopropyl}-8-methyl-5,6,8,9-tetrahydro[1,2,4]triazolo[4,3-d][1,4]thiazepin-8-yl)methanol A solution of the compound (367 mg, 0.68 mmol) obtained in Example 54-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 20:80, gradient) to obtain the title compound (304 mg, quant.) as a colorless solid.

$^1$H-NMR (400 MHz, CDCl$_3$) δ: 1.32 (3H, s), 1.41-1.47 (1H, m), 1.51-1.60 (2H, m), 1.65-1.70 (1H, m), 2.33 (1H, brs), 2.39 (1H, ddd, J=15.6, 6.4, 1.3 Hz), 2.58 (1H, ddd, J=15.6, 9.8, 1.3 Hz), 3.32 (1H, d, J=15.2 Hz), 3.35 (1H, d, J=11.7 Hz), 3.39 (1H, d, J=11.7 Hz), 3.61 (1H, d, J=15.2 Hz), 4.10 (1H, ddd, J=14.6, 9.9, 1.3 Hz), 4.42 (1H, ddd, J=14.6, 6.4, 1.3 Hz), 7.19 (2H, d, J=8.6 Hz), 7.47 (1H, td, J=8.6, 2.7 Hz), 7.69 (1H, dd, J=8.6, 4.3 Hz), 7.88 (2H, d, J=8.6 Hz), 8.52 (1H, d, J=2.7 Hz).

MS (ESI) m/z: 411 [M+H]$^+$.

Example 55

5-(4-{1-[8-(Hydroxymethyl)-8-methyl-5,6,8,9-tetrahydro[1,2,4]triazolo[4,3-d][1,4]thiazepin-3-yl]cyclopropyl}phenyl)-1-methylpyridine-2(1H)-one

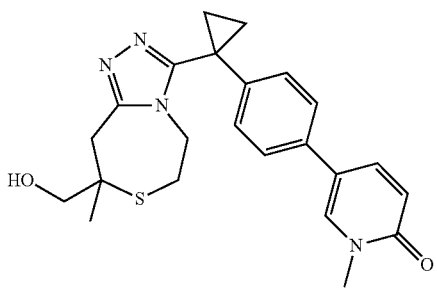 [SMILES: Cn1cc(-c2ccc(C3(c4nnc5n4CCSC(C)(CO)C5)CC3)cc2)ccc1=O]

Example 55-1

5-(4-{1-[8-({[Tert-butyl(dimethyl)silyl]oxy}methyl)-8-methyl-5,6,8,9-tetrahydro[1,2,4]triazolo[4,3-d][1,4]thiazepin-3-yl]cyclopropyl}phenyl)-1-methylpyridine-2(1H)-one A solution of the compound (555 mg, 1.0 mmol) obtained in Example 16-5), 5-bromo-1-methylpyridine-2(1H)-one (284 mg, 1.5 mmol), tetrakis(triphenylphosphine)palladium (0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (402 mg, 75%) as a light yellow oily substance.

$^1$H-NMR (400 MHz, CDCl$_3$) δ: 0.05 (3H, s), 0.07 (3H, s), 0.91 (9H, s), 1.19 (3H, s), 1.42-1.48 (2H, m), 1.56-1.67 (2H, m), 2.54 (1H, ddd, J=15.5, 8.0, 2.3 Hz), 2.69 (1H, ddd, J=15.5, 7.8, 2.2 Hz), 3.39 (2H, s), 3.51 (1H, d, J=10.2 Hz), 3.55 (1H, d, J=10.2 Hz), 3.62 (3H, s), 4.07 (1H, ddd, J=14.5, 8.0, 2.2 Hz), 4.32 (1H, ddd, J=14.5, 7.8, 2.3 Hz), 6.66 (1H, d, J=9.4 Hz), 7.12 (2H, d, J=8.4 Hz), 7.32 (2H, d, J=8.4 Hz), 7.48 (1H, d, J=2.5 Hz), 7.59 (1H, dd, J=9.4, 2.5 Hz).

Example 55-2

5-(4-{1-[8-(Hydroxymethyl)-8-methyl-5,6,8,9-tetrahydro[1,2,4]triazolo[4,3-d][1,4]thiazepin-3-yl]cyclopropyl}phenyl)-1-methylpyridine-2(1H)-one A solution of the compound (402 mg, 0.75 mmol) obtained in Example 55-1) and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (308 mg, 97%) as a colorless solid.

$^1$H-NMR (400 MHz, CDCl$_3$) δ: 1.33 (3H, s), 1.39-1.44 (1H, m), 1.48-1.54 (1H, m), 1.56-1.65 (2H, m), 2.22 (1H, brs), 2.41 (1H, ddd, J=15.4, 6.5, 1.5 Hz), 2.60 (1H, ddd, J=15.4, 9.9, 1.5 Hz), 3.32 (1H, d, J=15.2 Hz), 3.35 (1H, d, J=12.1 Hz), 3.39 (1H, d, J=12.1 Hz), 3.62 (3H, s), 3.62 (1H, d, J=15.2 Hz), 4.10 (1H, ddd, J=14.8, 9.9, 1.5 Hz), 4.43 (1H, ddd, J=14.8, 6.5, 1.5 Hz), 6.66 (1H, d, J=9.4 Hz), 7.14 (2H, d, J=8.6 Hz), 7.34 (2H, d, J=8.6 Hz), 7.48 (1H, d, J=2.7 Hz), 7.59 (1H, dd, J=9.4, 2.7 Hz).

MS (ESI) m/z: 423 [M+H]$^+$.

Example 56

(8-Methyl-3-{1-[4-(1-methyl-1H-pyrazol-5-yl)phenyl]cyclopropyl}-5,6,8,9-tetrahydro[1,2,4]triazolo[4,3-d][1,4]thiazepin-8-yl)methanol

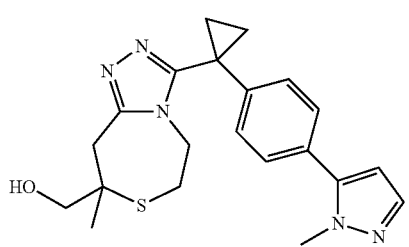 [SMILES: Cn1nccc1-c1ccc(C2(c3nnc4n3CCSC(C)(CO)C4)CC2)cc1]

Example 56-1

8-({[Tert-butyl(dimethyl)silyl]oxy}methyl)-8-methyl-3-{1-[4-(1-methyl-1H-pyrazol-5-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-4), 1-methyl-1H-pyrazole-5-boronic acid pinacol ester (321 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (159 mg, 31%) as a colorless solid.

$^1$H-NMR (400 MHz, CDCl$_3$) δ: 0.05 (3H, s), 0.07 (3H, s), 0.91 (9H, s), 1.20 (3H, s), 1.43-1.54 (2H, m), 1.57-1.62 (1H, m), 1.66-1.71 (1H, m), 2.57 (1H, ddd, J=15.5, 7.8, 2.3 Hz), 2.73 (1H, ddd, J=15.5, 7.9, 2.1 Hz), 3.40 (2H, s), 3.52 (1H, d, J=9.8 Hz), 3.56 (1H, d, J=9.8 Hz), 3.87 (3H, s), 4.10 (1H, ddd, J=14.4, 7.9, 2.1 Hz), 4.33 (1H, ddd, J=14.4, 7.8, 2.3 Hz), 6.28 (1H, d, J=2.0 Hz), 7.15 (2H, d, J=8.2 Hz), 7.34 (2H, d, J=8.2 Hz), 7.50 (1H, d, J=2.0 Hz).

Example 56-2

(8-Methyl-3-{1-[4-(1-methyl-1H-pyrazol-5-yl)phenyl]cyclopropyl}-5,6,8,9-tetrahydro[1,2,4]triazolo[4,3-d][1,4]thiazepin-8-yl)methanol A solution of the compound (159 mg, 0.31 mmol) obtained in Example 56-1) and 4 M hydrochloric acid (1,4-dioxane solution, 1 mL) in methanol (4 mL) was stirred at room temperature for 15 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (128 mg, quant.) as a colorless solid.

$^1$H-NMR (400 MHz, CDCl$_3$) δ: 1.33 (3H, s), 1.46-1.52 (2H, m), 1.61-1.66 (2H, m), 2.28 (1H, brs), 2.45 (1H, dd, J=15.1, 5.9 Hz), 2.65 (1H, dd, J=15.1, 9.6 Hz), 3.33 (1H, d, J=15.2 Hz), 3.37 (1H, d, J=12.5 Hz), 3.41 (1H, d, J=12.5 Hz), 3.62 (1H, d, J=15.2 Hz), 3.87 (3H, s), 4.13 (1H, dd, J=14.4, 9.6 Hz), 4.44 (1H, dd, J=14.4, 5.9 Hz), 6.28 (1H, s), 7.16 (2H, d, J=8.2 Hz), 7.36 (2H, d, J=8.2 Hz), 7.50 (1H, s).

MS (ESI) m/z: 396 [M+H]$^+$.

Example 57

(3-{1-[4-(4-Methoxypyridin-3-yl)phenyl]cyclopropyl}-8-methyl-5,6,8,9-tetrahydro[1,2,4]triazolo[4,3-d][1,4]thiazepin-8-yl)methanol

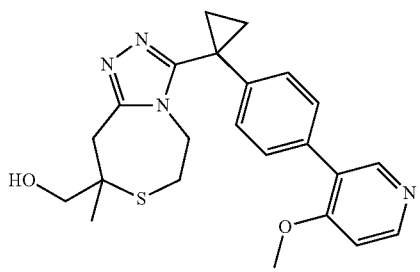 [SMILES: COc1ccncc1-c1ccc(C2(c3nnc4n3CCSC(C)(CO)C4)CC2)cc1]

Example 57-1

8-({[Tert-butyl(dimethyl)silyl]oxy}methyl)-3-{1-[4-(4-methoxypyridin-3-yl)phenyl]cyclopropyl}-8-methyl-5,6,8,9-tetrahydro[1,2,4]triazolo[4,3-d][1,4]thiazepine A solution of the compound (508 mg, 1.0 mmol) obtained in Example 16-4), 4-methoxypyridine-3-boronic acid pinacol ester (321 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (337 mg, 63%) as a colorless solid.

$^1$H-NMR (400 MHz, CDCl$_3$) δ: 0.05 (3H, s), 0.07 (3H, s), 0.91 (9H, s), 1.20 (3H, s), 1.44-1.60 (2H, m), 1.62-1.69 (2H, m), 2.57 (1H, ddd, J=15.5, 8.1, 2.2 Hz), 2.71 (1H, ddd, J=15.5, 7.9, 2.1 Hz), 3.40 (2H, s), 3.51 (1H, d, J=10.2 Hz), 3.55 (1H, d, J=10.2 Hz), 3.87 (3H, s), 4.10 (1H, ddd, J=14.5, 7.9, 2.1 Hz), 4.35 (1H, ddd, J=14.5, 8.1, 2.2 Hz), 6.90 (1H, dd, J=11.5, 5.9 Hz), 7.14 (2H, d, J=8.6 Hz), 7.44 (2H, d, J=8.6 Hz), 7.52 (1H, d, J=3.1 Hz), 8.48 (1H, dd, J=11.5, 5.9 Hz).

Example 57-2

(3-{1-[4-(4-Methoxypyridin-3-yl)phenyl]cyclopropyl}-8-methyl-5,6,8,9-tetrahydro[1,2,4]triazolo[4,3-d][1,4]thiazepin-8-yl)methanol A solution of the compound (337 mg, 0.63 mmol) obtained in Example 57-1) and 4 M hydrochloric acid (1,4-dioxane solution, 1 mL) in methanol (4 mL) was stirred at room temperature for 15 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (201 mg, 76%) as a colorless solid.

$^1$H-NMR (400 MHz, CDCl$_3$) δ: 1.33 (3H, s), 1.45-1.54 (2H, m), 1.57-1.64 (2H, m), 2.31 (1H, brs), 2.44 (1H, ddd, J=15.6, 6.5, 1.4 Hz), 2.62 (1H, ddd, J=15.6, 9.8, 1.6 Hz), 3.32 (1H, d, J=15.2 Hz), 3.37 (2H, s), 3.61 (1H, d, J=15.2 Hz), 3.87 (3H, s), 4.12 (1H, ddd, J=14.8, 9.8, 1.6 Hz), 4.45 (1H, ddd, J=14.8, 6.5, 1.4 Hz), 6.89 (1H, d, J=5.9 Hz), 7.16 (2H, d, J=8.6 Hz), 7.46 (2H, d, J=8.6 Hz), 8.40 (1H, s), 8.47 (1H, d, J=5.9 Hz).

MS (ESI) m/z: 423 [M+H]$^+$.

Example 58

(8-Methyl-3-{1-[4-(1-methyl-1H-imidazol-4-yl)phenyl]cyclopropyl}-5,6,8,9-tetrahydro[1,2,4]triazolo[4,3-d][1,4]thiazepin-8-yl)methanol

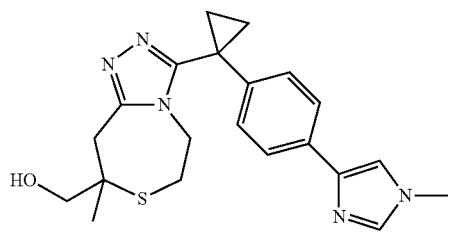 [SMILES: Cn1cnc(-c2ccc(C3(c4nnc5n4CCSC(C)(CO)C5)CC3)cc2)c1]

Example 58-1

8-({[Tert-butyl(dimethyl)silyl]oxy}methyl)-8-methyl-3-{1-[4-(1-methyl-1H-imidazol-4-yl)phenyl]cyclopropyl}-5,6,8,9-tetrahydro[1,2,4]triazolo[4,3-d][1,4]thiazepine A solution of the compound (555 mg, 1.0 mmol) obtained in Example 16-5), 4-iodo-1-methyl-1H-imidazole (312 mg, 1.5 mmol), tris(dibenzylideneacetone)dipalladium(0) (46 mg, 0.05 mmol), tricyclohexylphosphine (34 mg, 0.12 mmol), and tripotassium phosphate (372 mg, 1.7 mmol) in dioxane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 20:80, gradient) to obtain the title compound (148 mg, 29%) as a brown solid.

$^1$H-NMR (400 MHz, CDCl$_3$) δ: 0.04 (3H, s), 0.07 (3H, s), 0.91 (9H, s), 1.17 (3H, s), 1.41-1.46 (2H, m), 1.54-1.61 (2H, m), 2.46 (1H, ddd, J=15.6, 8.0, 2.2 Hz), 2.59 (1H, ddd, J=15.6, 7.8, 2.0 Hz), 3.38 (2H, s), 3.48 (1H, d, J=10.0 Hz), 3.52 (1H, d, J=10.0 Hz), 3.72 (3H, s), 4.06 (1H, ddd, J=14.4, 8.0, 2.0 Hz), 4.32 (1H, ddd, J=14.4, 7.8, 2.2 Hz), 7.09 (2H, d, J=8.4 Hz), 7.15 (1H, d, J=1.0 Hz), 7.46 (1H, d, J=1.0 Hz), 7.67 (2H, d, J=8.4 Hz).

Example 58-2

(8-Methyl-3-{1-[4-(1-methyl-1H-imidazol-4-yl)phenyl]cyclopropyl}-5,6,8,9-tetrahydro[1,2,4]triazolo[4,3-d][1,4]thiazepin-8-yl)methanol A solution of the compound (148 mg, 0.37 mmol) obtained in Example 58-1) and 4 M hydrochloric acid (1,4-dioxane solution, 1 mL) in methanol (4 mL) was stirred at room temperature for 15 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (90 mg, 61%) as a colorless solid.

$^1$H-NMR (400 MHz, CDCl$_3$) δ: 1.31 (3H, s), 1.35-1.40 (1H, m), 1.47-1.53 (2H, m), 1.62-1.66 (1H, m), 2.32 (1H, dd, J=15.1, 5.7 Hz), 2.50 (1H, dd, J=15.1, 8.4 Hz), 3.30 (1H, d, J=15.2 Hz), 3.32 (1H, d, J=11.3 Hz), 3.36 (1H, d, J=11.3 Hz), 3.59 (1H, d, J=15.2 Hz), 3.72 (3H, s), 4.08 (1H, dd, J=14.5, 8.4 Hz), 4.43 (1H, dd, J=14.5, 5.7 Hz), 7.11 (2H, d, J=8.2 Hz), 7.16 (1H, s), 7.46 (1H, s), 7.68 (2H, d, J=8.2 Hz).

MS (ESI) m/z: 396 [M+H]$^+$.

Example 59

(3-{1-[4-(6-Methoxypyridin-3-yl)phenyl]cyclopropyl}-8-methyl-5,6,8,9-tetrahydro[1,2,4]triazolo[4,3-d][1,4]thiazepin-8-yl)methanol

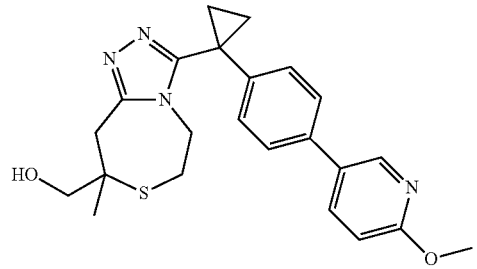 [SMILES: COc1ccc(-c2ccc(C3(c4nnc5n4CCSC(C)(CO)C5)CC3)cc2)cn1]

Example 59-1

8-({[Tert-butyl(dimethyl)silyl]oxy}methyl)-3-{1-[4-(6-methoxypyridin-3-yl)phenyl]cyclopropyl}-8-methyl-5,6,8,9-tetrahydro[1,2,4]triazolo[4,3-d][1,4]thiazepine A solution of the compound (508 mg, 1.0 mmol) obtained in Example 16-4), 2-methoxypyridine-5-boronic acid pinacol ester (352 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (200 mg, 37%) as a light yellow oily substance.

$^1$H-NMR (500 MHz, CDCl$_3$) δ: 0.05 (3H, s), 0.07 (3H, s), 0.91 (9H, s), 1.19 (3H, s), 1.42-1.46 (1H, m), 1.47-1.51 (1H, m), 1.55-1.59 (1H, m), 1.64-1.68 (1H, m), 2.55 (1H, ddd, J=15.6, 7.8, 2.4 Hz), 2.70 (1H, ddd, J=15.6, 8.1, 1.7 Hz), 3.40 (2H, s), 3.51 (1H, d, J=9.8 Hz), 3.55 (1H, d, J=9.8 Hz), 3.97 (3H, s), 4.09 (1H, ddd, J=14.4, 8.1, 1.7 Hz), 4.33 (1H, ddd, J=14.4, 7.8, 2.4 Hz), 6.81 (1H, d, J=8.3 Hz), 7.15 (2H, d, J=8.3 Hz), 7.44 (2H, d, J=8.3 Hz), 7.75 (1H, dd, J=8.3, 2.4 Hz), 8.35 (1H, d, J=2.4 Hz).

Example 59-2

(3-{1-[4-(6-Methoxypyridin-3-yl)phenyl]cyclopropyl}-8-methyl-5,6,8,9-tetrahydro[1,2,4]triazolo[4,3-d][1,4]thiazepin-8-yl)methanol A solution of the compound (200 mg, 0.37 mmol) obtained in Example 59-1) and 4 M hydrochloric acid (1,4-dioxane solution, 1 mL) in methanol (4 mL) was stirred at room temperature for 15 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (169 mg, quant.) as a colorless solid.

$^1$H-NMR (400 MHz, CDCl$_3$) δ: 1.33 (3H, s), 1.42-1.46 (1H, m), 1.48-1.53 (1H, m), 1.56-1.64 (2H, m), 2.29 (1H, brs), 2.42 (1H, dd, J=15.2, 5.5 Hz), 2.61 (1H, dd, J=15.2, 9.4 Hz), 3.32 (1H, d, J=15.2 Hz), 3.37 (2H, s), 3.62 (1H, d, J=15.2 Hz), 3.97 (3H, s), 4.11 (1H, dd, J=14.5, 9.4 Hz), 4.45 (1H, dd, J=14.5, 5.5 Hz), 6.81 (1H, d, J=8.6 Hz), 7.17 (2H, d, J=8.4 Hz), 7.46 (2H, d, J=8.4 Hz), 7.75 (1H, dd, J=8.6, 2.3 Hz), 8.35 (1H, d, J=2.3 Hz).

MS (ESI) m/z: 423 [M+H]$^+$.

Example 60

6-(4-{1-[8-(Hydroxymethyl)-8-methyl-5,6,8,9-tetrahydro[1,2,4]triazolo[4,3-d][1,4]thiazepin-3-yl]cyclopropyl}phenyl)nicotinonitrile

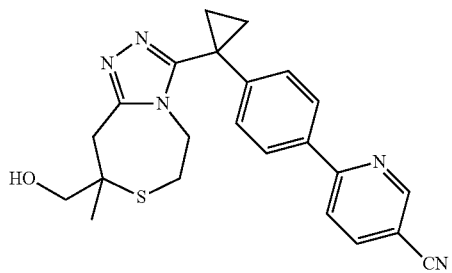 [SMILES: CC1(CO)Cc2nnc(C3(c4ccc(-c5ccc(C#N)cn5)cc4)CC3)n2CCS1]

Example 60-1

Tert-butyl 2-({1-[4-(4,4,5,5-tetramethyl-1,3,2-dioxaborolan-2-yl)phenyl]cyclopropyl}carbonyl)hydrazinecarboxylate A solution of the compound (654 mg, 1.84 mmol) obtained in Example 16-2), bis(pinacolato)diboron (935 mg, 3.68 mmol), potassium acetate (542 mg, 5.52 mmol), and dichloro-1,1-bis(diphenylphosphino)ferrocene palladium (II)-dichloromethane complex (150 mg, 0.184 mmol) in 1,4-dioxane (6.54 mL) was stirred at 110° C. for 3 h. The solvent was distilled off under reduced pressure, and water and ethyl acetate were added to the obtained residue to separate an organic layer. The organic layer was dried with anhydrous sodium sulfate, then the solvent was distilled off under reduced pressure, and the residue was purified by silica gel column chromatography (ethyl acetate:n-hexane=1:1) to obtain the title compound (741 mg, quant.) as a brown solid.

$^1$H-NMR (400 MHz, CDCl$_3$) δ: 1.13 (2H, q, J=3.6 Hz), 1.24 (6H, s), 1.27 (6H, s), 1.35 (9H, s), 1.66 (2H, q, J=3.6 Hz), 6.32 (1H, brs), 6.82 (1H, s), 7.47 (2H, d, J=7.8 Hz), 7.82 (2H, d, J=7.8 Hz).

Example 60-2

Tert-butyl 2-({1-[4-(5-cyanopyridin-2-yl)phenyl]cyclopropyl}carbonyl)hydrazinecarboxylate A mixed solution of the compound (100 g, 249 mmol) obtained in Example 60-1), 2-chloro-5-cyanopyridine (44.8 g, 323 mmol), potassium carbonate (68.7 g, 497 mmol), and tetrakis(triphenylphosphine)palladium (14.4 g, 12.4 mmol) in 1,2-dimethoxyethane (800 mL) and water (200 mL) was stirred at 100° C. for 8 h, then at 80° C. for 14 h, and further at 100° C. for 5 h. The reaction mixture was cooled to room temperature, insoluble substances were filtered off, dichloromethane was added to the filtrate, and the organic layer was washed with saturated aqueous sodium hydrogencarbonate and saturated sodium chloride solution in this order. The solvent was distilled off under reduced pressure, and the residue was washed with dichloromethane and hexane and then purified by silica gel column chromatography (ethyl acetate:methanol=1:1) to obtain the title compound (24.1 g, 26%) as a white solid.

$^1$H-NMR (400 MHz, CDCl$_3$) δ: 1.18 (2H, q, J=3.7 Hz), 1.45 (9H, s), 1.72 (2H, q, J=3.7 Hz), 7.62 (2H, d, J=8.2 Hz), 7.85 (1H, dd, J=8.2, 0.9 Hz), 8.04 (1H, dd, J=8.2, 2.1 Hz), 8.06 (2H, d, J=8.2 Hz), 8.95 (1H, dd, J=2.1, 0.9 Hz).

Example 60-3

1-[4-(5-Cyanopyridin-2-yl)phenyl]cyclopropanecarbohydrazide

A solution of the compound (72.7 g, 192 mmol) obtained in Example 60-2) in 2 N hydrochloric acid-dioxane (728 mL) was stirred at room temperature for 30 min and further at 50° C. for 30 min. The reaction mixture was cooled to room temperature, the solvent was distilled off under reduced pressure, dichloromethane was added to the residue, and the organic layer was washed with saturated sodium hydrogencarbonate and saturated sodium chloride solution in this order and then dried with anhydrous sodium sulfate. The solvent was distilled off under reduced pressure. The residue was solidified with a mixed solvent (600 mL) of ethyl acetate and hexane (1:5) and collected by filtration. The obtained solid was dried under reduced pressure to obtain the title compound (51.7 g, 97%) as a white solid.

$^1$H-NMR (400 MHz, CDCl$_3$) δ: 1.14 (2H, q, J=3.5 Hz), 1.68 (2H, q, J=3.5 Hz), 6.61 (1H, brs), 7.54 (2H, d, J=8.2 Hz), 7.85 (1H, d, J=8.2 Hz), 8.01-8.06 (3H, m), 8.95 (1H, d, J=1.6 Hz).

Example 60-4

6-(4-{1-[8-({[Tert-butyl(dimethyl)silyl]oxy}methyl)-8-methyl-5,6,8,9-tetrahydro[1,2,4]triazolo[4,3-d][1,4]thiazepin-3-yl]cyclopropyl}phenyl)nicotinonitrile A solution of 7-({[tert-butyl(dimethyl)silyl]oxy}methyl)-7-methyl-5-(methylthio)-2,3,6,7-tetrahydro-1,4-thiazepine (39.7 g, 124 mmol) and the compound (19.5 g, 70.1 mmol) obtained in Example 60-3) in 1-butanol (750 mL) was stirred at 140° C. for 13 h. The reaction mixture was cooled to room temperature, the solvent was distilled off under reduced pressure, and the residue was purified by silica gel column chromatography (ethyl acetate:methanol=9:1) to obtain the title compound (33.1 g, 89%) as a white solid.

$^1$H-NMR (400 MHz, CDCl$_3$) δ: 0.05 (3H, s), 0.07 (3H, s), 0.91 (9H, s), 1.19 (3H, s), 1.48-1.53 (1H, m), 1.62-1.70 (3H, m), 2.55 (1H, ddd, J=15.5, 7.7, 2.2 Hz), 2.70 (1H, ddd, J=15.5, 8.0, 2.2 Hz), 3.40 (2H, s), 3.51 (1H, d, J=10.2 Hz), 3.55 (1H, d, J=10.2 Hz), 4.07 (1H, ddd, J=14.4, 8.0, 2.2 Hz), 4.31 (1H, ddd, J=14.4, 7.7, 2.2 Hz), 7.20 (1H, d, J=8.6 Hz), 7.82 (1H, dd, J=8.6, 0.9 Hz), 7.98 (2H, d, J=8.6 Hz), 8.00 (1H, dd, J=8.6, 2.2 Hz), 8.92 (1H, dd, J=2.2, 0.9 Hz).

Example 60-5

6-(4-{1-[8-(Hydroxymethyl)-8-methyl-5,6,8,9-tetrahydro[1,2,4]triazolo[4,3-d][1,4]thiazepin-3-yl]cyclopropyl}phenyl)nicotinonitrile To a solution of the compound (33.1 g, 62.0 mmol) obtained in Example 60-4) in tetrahydrofuran (500 mL), tetrabutylammonium fluoride (74.4 mL, 1 M tetrahydrofuran solution) was added, and the mixture was stirred at room temperature for 1.5 h. Saturated aqueous sodium hydrogencarbonate was added to the reaction mixture, and the mixture was extracted with ethyl acetate. The organic layer was washed with saturated sodium chloride solution and then dried with anhydrous sodium sulfate, and the solvent was distilled off under reduced pressure. The concentrated residue was purified by silica gel column chromatography (ethyl acetate:methanol=4:1) to obtain the title compound (22.5 g, 87%) as a white solid.

$^1$H-NMR (500 MHz, CDCl$_3$) δ: 1.32 (3H, s), 1.44-1.49 (1H, m), 1.53-1.58 (1H, m), 1.59-1.63 (1H, m), 1.67-1.71 (1H, m), 2.43 (1H, dd, J=15.4, 6.1 Hz), 2.64 (1H, dd, J=15.4, 9.5 Hz), 2.82 (1H, brs), 3.33 (1H, d, J=15.6 Hz), 3.42 (2H, s), 3.61 (1H, d, J=15.6 Hz), 4.12 (1H, dd, J=14.4, 9.5 Hz), 4.39 (1H, dd, J=14.4, 6.1 Hz), 7.21 (2H, d, J=8.3 Hz), 7.82 (1H, d, J=8.3 Hz), 7.98-8.02 (3H, m), 8.91-8.93 (1H, m).

MS (FAB) m/z: 418 [M+H]$^+$.

Example 61

6-(4-{1-[(8R)-8-(Hydroxymethyl)-8-methyl-5,6,8,9-tetrahydro[1,2,4]triazolo[4,3-d][1,4]thiazepin-3-yl]cyclopropyl}phenyl)nicotinonitrile

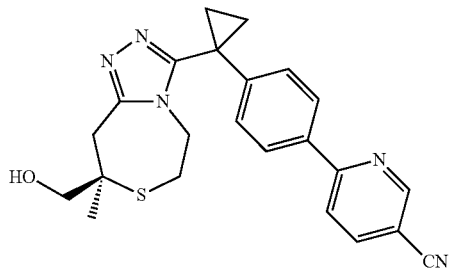 [SMILES: C[C@]1(CO)Cc2nnc(C3(c4ccc(-c5ccc(C#N)cn5)cc4)CC3)n2CCS1]

Example 61-1

6-(4-{1-[(8R)-8-({[t-Butyl(dimethyl)silyl]oxy}methyl)-8-methyl-5,6,8,9-tetrahydro[1,2,4]triazolo[4,3-d][1,4]thiazepin-3-yl]cyclopropyl}phenyl)nicotinonitrile The compound (418 mg, 1.31 mmol) obtained in Example 4-1) and the compound (364 mg, 1.31 mmol) obtained in Example 60-3) were dissolved in 1-butanol (5 mL), and the mixture was stirred at 140° C. for 5 h under a nitrogen atmosphere. The reaction mixture was cooled to room temperature, then the solvent was distilled off, and the obtained residue was purified by silica gel column chromatography (elution solvent: methanol/ethyl acetate=0% to 20%) to obtain the title compound (375 mg, 54%) in a white solid form.

$^1$H-NMR (400 MHz, CDCl$_3$) δ: 0.05 (3H, s), 0.07 (3H, s), 0.91 (9H, s), 1.19 (3H, s), 1.47-1.56 (2H, m), 1.62-1.71 (2H, m), 2.55 (1H, ddd, J=15.5, 7.9, 2.4 Hz), 2.70 (1H, ddd, J=15.6, 8.0, 2.2 Hz), 3.40 (2H, s), 3.51 (1H, d, J=10.2 Hz), 3.55 (1H, d, J=10.2 Hz), 4.07 (1H, ddd, J=14.5, 7.8, 2.0 Hz), 4.30 (1H, ddd, J=14.3, 8.0, 2.5 Hz), 7.20 (2H, d, J=8.6 Hz), 7.82 (1H, dd, J=8.2, 0.8 Hz), 7.98 (2H, d, J=8.6 Hz), 8.00 (1H, dd, J=8.6, 2.0 Hz), 8.92 (1H, dd, J=2.0, 0.8 Hz).

Example 61-2

6-(4-{1-[(8R)-8-(Hydroxymethyl)-8-methyl-5,6,8,9-tetrahydro[1,2,4]triazolo[4,3-d][1,4]thiazepin-3-yl]cyclopropyl}phenyl)nicotinonitrile The compound (375 mg, 0.70 mmol) obtained in Example 61-1) was dissolved in tetrahydrofuran (7 mL). Tetrabutylammonium fluoride (1.0 mol/L tetrahydrofuran solution, 0.84 mL, 0.84 mmol) was added to the solution at room temperature, and the mixture was stirred at room temperature for 1 h under a nitrogen atmosphere. Saturated aqueous sodium hydrogencarbonate (10 mL) was added to the reaction mixture, and the mixture was extracted with ethyl acetate (50 mL). The organic layer was washed with saturated sodium chloride solution and then dried with anhydrous magnesium sulfate. The solvent was distilled off under reduced pressure, and the obtained residue was purified by silica gel column chromatography (elution solvent: methanol/ethyl acetate=10% to 40%) to obtain the title compound (208 mg, 71%) in a white solid form.

$^1$H-NMR (400 MHz, CDCl$_3$) δ: 1.33 (3H, s), 1.44-1.51 (1H, m), 1.53-1.65 (2H, m), 1.66-1.73 (1H, m), 2.42 (1H, ddd, J=15.6, 6.6, 1.2 Hz), 2.63 (1H, ddd, J=15.6, 9.8, 1.6 Hz), 3.33 (1H, d, J=15.2 Hz), 3.40 (2H, dd, J=15.2, 11.7 Hz), 3.63 (1H, d, J=15.2 Hz), 4.11 (1H, ddd, J=14.9, 9.8, 1.2 Hz), 4.41 (1H, ddd, J=14.9, 6.3, 1.2 Hz), 7.22 (2H, d, J=8.2 Hz), 7.82 (1H, dd, J=8.2, 0.8 Hz), 7.99 (2H, d, J=8.6 Hz), 8.01 (1H, dd, J=8.2, 2.3 Hz), 8.93 (1H, dd, J=2.0, 0.8 Hz).

MS (ESI) m/z: 418.16926 (M+H)$^+$.

Example 62

5-(4-{1-[8-(Hydroxymethyl)-8-methyl-5,6,8,9-tetrahydro[1,2,4]triazolo[4,3-d][1,4]thiazepin-3-yl]cyclopropyl}phenyl)nicotinonitrile

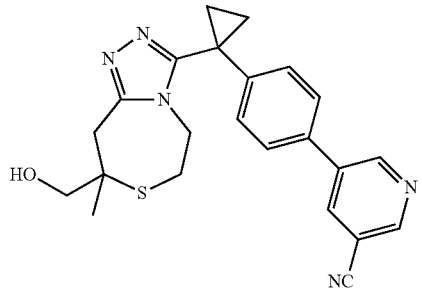 [SMILES: CC1(CO)Cc2nnc(C3(c4ccc(-c5cncc(C#N)c5)cc4)CC3)n2CCS1]

Example 62-1

5-(4-{1-[8-({[Tert-butyl(dimethyl)silyl]oxy}methyl)-8-methyl-5,6,8,9-tetrahydro[1,2,4]triazolo[4,3-d][1,4]thiazepin-3-yl]cyclopropyl}phenyl)nicotinonitrile A solution of the compound (508 mg, 1.0 mmol) obtained in Example 16-5), 3-bromo-5-cyanopyridine (274 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (238 mg, 45%) as a brown oily substance.

$^1$H-NMR (400 MHz, CDCl$_3$) δ: 0.05 (3H, s), 0.07 (3H, s), 0.91 (9H, s), 1.20 (3H, s), 1.45-1.55 (2H, m), 1.58-1.73 (2H, m), 2.58 (1H, ddd, J=15.5, 7.9, 2.4 Hz), 2.75 (1H, ddd, J=15.5, 8.0, 2.2 Hz), 3.41 (2H, s), 3.52 (1H, d, J=10.2 Hz), 3.56 (1H, d, J=10.2 Hz), 4.09 (1H, ddd, J=14.5, 8.0, 2.2 Hz), 4.32 (1H, ddd, J=14.5, 7.9, 2.4 Hz), 7.22 (2H, d, J=8.2 Hz), 7.50 (2H, d, J=8.2 Hz), 8.10 (1H, t, J=2.0 Hz), 8.85 (1H, d, J=2.0 Hz), 9.00 (1H, d, J=2.0 Hz).

Example 62-2

5-(4-{1-[8-(Hydroxymethyl)-8-methyl-5,6,8,9-tetrahydro[1,2,4]triazolo[4,3-d][1,4]thiazepin-3-yl] cyclopropyl}phenyl)nicotinonitrile A solution of the compound (238 mg, 0.45 mmol) obtained in Example 62-1) and 4 M hydrochloric acid (1,4-dioxane solution, 1 mL) in methanol (4 mL) was stirred at room temperature for 15 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (164 mg, 39%) as a colorless solid.

$^1$H-NMR (500 MHz, CDCl$_3$) δ: 1.33 (3H, s), 1.45-1.50 (1H, m), 1.51-1.55 (1H, m), 1.60-1.68 (2H, m), 2.45 (1H, dd, J=15.1, 6.8 Hz), 2.65 (1H, dd, J=15.1, 9.8 Hz), 3.33 (1H, d, J=15.1 Hz), 3.40 (2H, s), 3.62 (1H, d, J=15.1 Hz), 4.13 (1H, dd, J=14.6, 9.8 Hz), 4.43 (1H, dd, J=14.6, 6.8 Hz), 7.22 (2H, d, J=8.3 Hz), 7.56 (2H, d, J=8.3 Hz), 8.45 (1H, t, J=2.0 Hz), 8.97 (1H, d, J=2.0 Hz), 9.18 (1H, d, J=2.0 Hz).

MS (ESI) m/z: 418 [M+H]$^+$.

Example 63

{8-Methyl-3-[1-(4-pyrimidin-4-ylphenyl)cyclopropyl]-5,6,8,9-tetrahydro[1,2,4]triazolo[4,3-d][1,4] thiazepin-8-yl}methanol

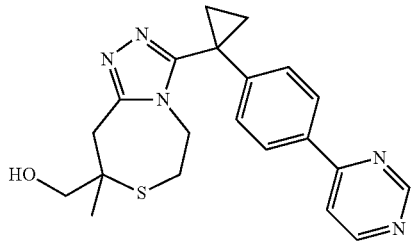 [SMILES: CC1(CO)Cc2nnc(C3(c4ccc(-c5ccncn5)cc4)CC3)n2CCS1]

A reaction mixture of the compound (555 mg, 1.0 mmol) obtained in Example 16-5), 4-bromopyrimidine hydrochloride (234 mg, 1.5 mmol), tetrakis(triphenylphosphine)palladium(0) (231 mg, 0.2 mmol), potassium carbonate (276 mg, 2 mmol), dimethoxyethane (4 mL), and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was partially purified by silica gel chromatography (Isco Combiflash, 40 g, methanol: ethyl acetate=0:100 to 20:80, gradient). This partially purified product was dissolved in a 4 M solution (1 mL) of hydrochloric acid in 1,4-dioxane and methanol (4 mL), and the mixture was stirred at room temperature for 15 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0: 100 to 40:60, gradient) to obtain the title compound (67 mg, 17%) as a colorless solid.

$^1$H-NMR (500 MHz, CDCl$_3$) δ: 1.33 (3H, s), 1.46-1.50 (1H, m), 1.55-1.64 (2H, m), 1.67-1.72 (1H, m), 2.21 (1H, brs), 2.41 (1H, dd, J=15.4, 6.1 Hz), 2.61 (1H, dd, J=15.4, 9.0 Hz), 3.33 (1H, d, J=15.1 Hz), 3.38 (2H, s), 3.62 (1H, d, J=15.1 Hz), 4.10 (1H, dd, J=14.6, 9.0 Hz), 4.40 (1H, dd, J=14.6, 6.1 Hz), 7.22 (2H, d, J=8.3 Hz), 7.69 (1H, d, J=5.4 Hz), 8.04 (2H, d, J=8.3 Hz), 8.77 (1H, d, J=5.4 Hz), 9.26 (1H, s).

MS (ESI) m/z: 394 [M+H]$^+$.

Example 64

(8-Methyl-3-{1-[4-(6-methylpyridazin-3-yl)phenyl] cyclopropyl}-5,6,8,9-tetrahydro[1,2,4]triazolo[4,3-d] [1,4]thiazepin-8-yl)methanol

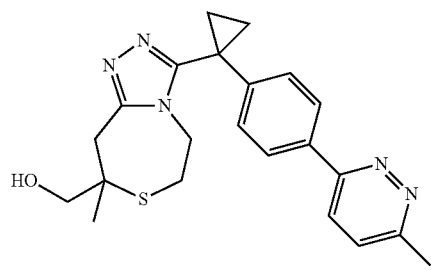 [SMILES: Cc1ccc(-c2ccc(C3(c4nnc5n4CCSC(C)(CO)C5)CC3)cc2)nn1]

Example 64-1

8-({[Tert-butyl(dimethyl)silyl]oxy}methyl)-8-methyl-3-{1-[4-(6-methylpyridazin-3-yl)phenyl]cyclopropyl}-5,6,8,9-tetrahydro[1,2,4]triazolo[4,3-d][1,4] thiazepine A solution of the compound (555 mg, 1.0 mmol) obtained in Example 16-5), 3-chloro-6-methylpyridazine (192 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 130° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (153 mg, 29%) as a brown solid.

$^1$H-NMR (400 MHz, CDCl$_3$) δ: 0.05 (3H, s), 0.07 (3H, s), 0.91 (9H, s), 1.19 (3H, s), 1.47-1.53 (1H, m), 1.59-1.64 (2H, m), 1.66-1.70 (1H, m), 2.55 (1H, ddd, J=15.5, 7.9, 2.2 Hz), 2.69 (1H, ddd, J=15.5, 7.9, 2.1 Hz), 2.76 (3H, s), 3.40 (2H, s), 3.51 (1H, d, J=9.8 Hz), 3.55 (1H, d, J=9.8 Hz), 4.08 (1H, ddd, J=14.3, 7.9, 2.1 Hz), 4.32 (1H, ddd, J=14.3, 7.9, 2.2 Hz), 7.21 (2H, d, J=8.6 Hz), 7.38 (1H, d, J=8.6 Hz), 7.72 (1H, d, J=8.6 Hz), 8.00 (2H, d, J=8.6 Hz).

Example 64-2

(8-Methyl-3-{1-[4-(6-methylpyridazin-3-yl)phenyl]cyclopropyl}-5,6,8,9-tetrahydro[1,2,4]triazolo[4,3-d][1,4]thiazepin-8-yl)methanol A solution of the compound (153 mg, 0.46 mmol) obtained in Example 64-1 and 4 M hydrochloric acid (1,4-dioxane solution, 1 mL) in methanol (4 mL) was stirred at room temperature for 16 h. The reaction mixture was concentrated under reduced pressure, saturated aqueous sodium hydrogencarbonate was added to the residue, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (103 mg, quant.) as a colorless solid.

$^1$H-NMR (400 MHz, CDCl$_3$) δ: 1.33 (3H, s), 1.44-1.49 (1H, m), 1.53-1.63 (2H, m), 1.65-1.70 (1H, m), 2.41 (1H, ddd, J=15.6, 6.3, 1.6 Hz), 2.61 (1H, ddd, J=15.6, 9.9, 1.7 Hz), 2.76 (3H, s), 3.33 (1H, d, J=15.3 Hz), 3.36 (1H, d, J=11.7 Hz), 3.40 (1H, d, J=11.7 Hz), 3.61 (1H, d, J=15.3 Hz), 4.11 (1H, ddd, J=14.7, 9.9, 1.7 Hz), 4.42 (1H, ddd, J=14.7, 6.3, 1.6 Hz), 7.23 (2H, d, J=8.6 Hz), 7.38 (1H, d, J=9.0 Hz), 7.72 (1H, d, J=9.0 Hz), 8.01 (2H, d, J=8.6 Hz).

MS (ESI) m/z: 408 [M+H]$^+$.

Example 65

6-(4-{1-[8-(Hydroxymethyl)-8-methyl-5,6,8,9-tetrahydro[1,2,4]triazolo[4,3-d][1,4]thiazepin-3-yl]cyclopropyl}phenyl)nicotinamide

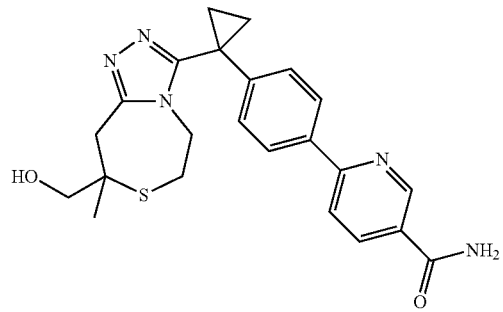 [SMILES: CC1(CO)Cc2nnc(C3(c4ccc(-c5ccc(C(N)=O)cn5)cc4)CC3)n2CCS1]

A solution of the compound (9.14 g, 17.2 mmol) obtained in Example 60-5) in 2 N hydrochloric acid-1,4-dioxane (200 mL) was stirred at 50° C. for 2 h. The reaction mixture was cooled to room temperature, methanol (40 mL) was added to the reaction mixture, and insoluble substances were dissolved by sonication. Saturated aqueous sodium hydrogencarbonate (400 mL) was added to the reaction mixture, and the mixture was extracted with dichloromethane and purified by silica gel column chromatography (ethyl acetate:methanol=3:2) to obtain the title compound (2.74 g, 38%) as a white solid.

$^1$H-NMR (400 MHz, CD$_3$OD) δ: 1.20 (3H, s), 1.60-1.62 (4H, m), 2.61 (1H, dq, J=15.7, 3.3 Hz), 2.83 (1H, ddd, J=15.6, 7.8, 2.7 Hz), 3.35-3.50 (4H, m), 4.29-4.43 (2H, m), 7.24 (2H, d, J=8.2 Hz), 7.95 (1H, d, J=8.2 Hz), 8.03 (2H, dt, J=8.7, 2.1 Hz), 8.30 (1H, dd, J=8.2, 2.3 Hz), 9.07 (1H, dd, J=2.8, 0.8 Hz).

MS (FAB) m/z: 436 [M+H]$^+$.

Example 66

6-(4-{1-[8-(Hydroxymethyl)-8-methyl-5,6,8,9-tetrahydro[1,2,4]triazolo[4,3-d][1,4]thiazepin-3-yl]cyclopropyl}phenyl)nicotinic acid

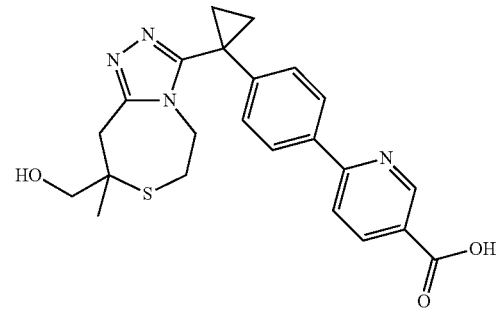 [SMILES: CC1(CO)Cc2nnc(C3(c4ccc(-c5ccc(C(=O)O)cn5)cc4)CC3)n2CCS1]

A mixed solution of the compound (200 mg, 0.458 mmol) obtained in Example 65 and potassium hydroxide (129 mg) in ethanol (5.00 mL) and water (1.50 mL) was stirred at 100° C. for 9 h. The reaction mixture was cooled to room temperature, poured into 0.05 N hydrochloric acid (50.0 mL) with ice cooling, extracted with dichloromethane/2-propanol (4/1), and dried with anhydrous sodium sulfate, and then the solvent was distilled off under reduced pressure. Diisopropyl ether was added to the residue, and the white precipitate was collected by filtration and dried under reduced pressure to obtain the title compound (166 mg, 83%) as a white solid.

$^1$H-NMR (400 MHz, CD$_3$OD) δ: 1.21 (3H, s), 1.62 (4H, dt, J=10.9, 4.3 Hz), 2.62 (1H, dq, J=15.8, 3.3 Hz), 2.84 (1H, ddd, J=15.8, 8.0, 2.7 Hz), 3.36-3.50 (4H, m), 4.29-4.43 (2H, m), 7.25 (2H, d, J=8.2 Hz), 7.97 (1H, d, J=8.6 Hz), 8.05 (2H, d, J=8.2 Hz), 8.40 (1H, dd, J=8.6, 2.1 Hz), 9.17 (1H, d, J=2.0 Hz).

MS (ESI) m/z: 437 [M+H]$^+$.

Example 67

6-(4-{1-[8-(Hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide

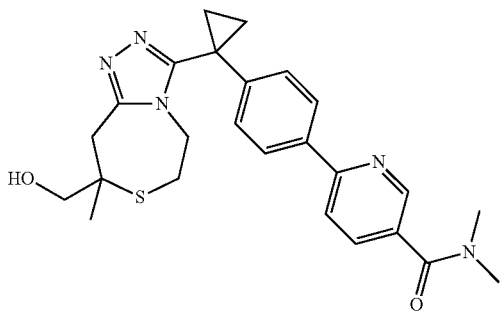

A solution of the compound (150 mg, 0.344 mmol) obtained in Example 66, dimethylamine hydrochloride (140 mg, 1.72 mmol), N,N-dimethylaminopyridine (4 mg, 34 µmol), and 1-ethyl-3-(3-dimethylaminopropyl)carbodiimide hydrochloride (198 mg, 1.03 mmol) in N,N-dimethylformamide (3.00 mL) was stirred at room temperature for 1.5 h. Saturated aqueous sodium hydrogencarbonate (100 mL) was added to the reaction mixture, the mixture was extracted with dichloromethane, and the organic layer was washed with water and dried with anhydrous sodium sulfate. Then the solvent was distilled off under reduced pressure. Diisopropyl ether was added to the residue, and the precipitate was collected by filtration and dried under reduced pressure to obtain the title compound (153 mg, 96%) as a white solid.

$^1$H-NMR (400 MHz, CD$_3$OD) δ: 1.20 (3H, s), 1.56-1.64 (4H, m), 2.61 (1H, ddd, J=15.6, 7.3, 2.4 Hz), 2.82 (1H, ddd, J=15.7, 7.9, 2.6 Hz), 3.07 (3H, s), 3.13 (3H, s), 3.35-3.49 (4H, m), 4.29-4.42 (2H, m), 7.24 (2H, d, J=8.8 Hz), 7.93 (2H, d, J=1.5 Hz), 8.01 (2H, d, J=8.8 Hz), 8.68 (1H, t, J=1.5 Hz).

MS (FAB) m/z: 464 [M+H]$^+$.

Example 68

6-(4-{1-[(8R)-8-(Hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide

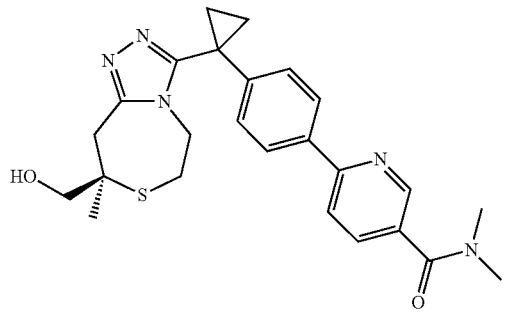

Example 68-1

6-(4-{1-[(8R)-8-(Hydroxymethyl)-8-methyl-5,6,8,9-tetrahydro[1,2,4]triazolo[4,3-d][1,4]thiazepin-3-yl]cyclopropyl}phenyl)nicotinic acid A mixed solution of the compound (500 mg, 1.20 mmol) obtained in Example 61 and potassium hydroxide (336 mg, 5.99 mmol) in ethanol (12.5 mL) and water (3.75 mL) was stirred at 100° C. for 7 h. The reaction mixture was cooled to room temperature, poured into 0.05 N hydrochloric acid (100 mL) with ice cooling, extracted with dichloromethane/2-propanol (4/1), and dried with anhydrous sodium sulfate, and then the solvent was distilled off under reduced pressure. Methanol was added to the residue, and the precipitate was collected by filtration. Dichloromethane/2-propanol (4/1) was added to the obtained precipitate, and the organic layer was washed with water, then dried with anhydrous sodium sulfate, and dried under reduced pressure to obtain the title compound (124 mg, 24%) as a white solid.

$^1$H-NMR (400 MHz, CD$_3$OD) δ: 1.19 (3H, s), 1.60 (4H, dt, J=10.9, 4.3 Hz), 2.60 (1H, dq, J=15.8, 3.3 Hz), 2.82 (1H, ddd, J=15.8, 8.0, 2.7 Hz), 3.34-3.48 (4H, m), 4.27-4.41 (2H, m), 7.23 (2H, d, J=8.2 Hz), 7.95 (1H, d, J=8.6 Hz), 8.03 (2H, d, J=8.2 Hz), 8.38 (1H, dd, J=8.6, 2.1 Hz), 9.15 (1H, d, J=2.0 Hz).

Example 68-2

6-(4-{1-[(8R)-8-(Hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide A solution of the compound (124 mg, 0.284 mmol) obtained in Example 68-1), dimethylamine hydrochloride (116 mg, 1.42 mmol), N,N-dimethylaminopyridine (3 mg, 28 µmol), and 1-ethyl-3-(3-dimethylaminopropyl)carbodiimide hydrochloride (163 mg, 0.852 mmol) in N,N-dimethylformamide (2.48 mL) was stirred at room temperature for 5.5 h. Saturated aqueous sodium hydrogencarbonate was added to the reaction mixture, the mixture was extracted with dichloromethane/2-propanol (4/1), and the organic layer was washed with water and dried with anhydrous sodium sulfate. Then the solvent was distilled off under reduced pressure. The residue was purified by silica gel thin layer chromatography (ethyl acetate:methanol=2:1) to obtain the title compound (85 mg, 65%) as a white solid.

$^1$H-NMR (500 MHz, CD$_3$OD) δ: 1.20 (3H, s), 1.56-1.64 (4H, m), 2.61 (1H, ddd, J=15.6, 7.3, 2.4 Hz), 2.82 (1H, ddd, J=15.7, 7.9, 2.6 Hz), 3.07 (3H, s), 3.13 (3H, s), 3.35-3.49 (4H, m), 4.29-4.42 (2H, m), 7.24 (2H, d, J=8.8 Hz), 7.93 (2H, d, J=1.5 Hz), 8.01 (2H, d, J=8.8 Hz), 8.68 (1H, t, J=1.5 Hz).

MS (FAB) m/z: 464 [M+H]$^+$.

Example 69

N-ethyl-6-(4-{1-[8-(Hydroxymethyl)-8-methyl-5,6,8,9-tetrahydro[1,2,4]triazolo[4,3-d][1,4]thiazepin-3-yl]cyclopropyl}phenyl)nicotinamide

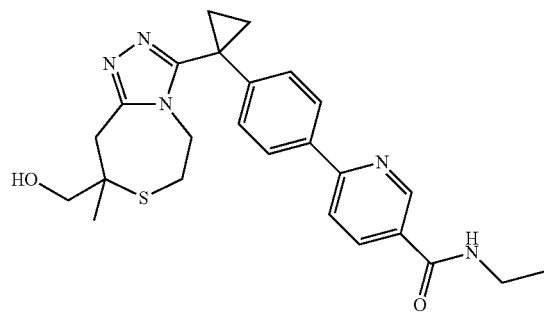 [SMILES: CCNC(=O)c1ccc(-c2ccc(C3(c4nnc5n4CCSC(C)(CO)C5)CC3)cc2)nc1]

A solution of the compound (150 mg, 0.344 mmol) obtained in Example 66, ethylamine hydrochloride (140 mg, 1.72 mmol), N,N-dimethylaminopyridine (4 mg, 34 μmol), and 1-ethyl-3-(3-dimethylaminopropyl)carbodiimide hydrochloride (198 mg, 1.03 mmol) in N,N-dimethylformamide (3.00 mL) was stirred at room temperature for 5 h. Saturated aqueous sodium hydrogencarbonate (100 mL) was added to the reaction mixture, the mixture was extracted with dichloromethane, and the organic layer was washed with water and dried with anhydrous sodium sulfate. Then the solvent was distilled off under reduced pressure. Diisopropyl ether was added to the residue, and the precipitate was collected by filtration and dried under reduced pressure to obtain the title compound (76 mg, 48%) as a white solid.

$^1$H-NMR (500 MHz, CD$_3$OD) δ: 1.20 (3H, s), 1.25 (3H, t, J=6.5 Hz), 1.57-1.64 (4H, m), 2.61 (1H, ddd, J=15.6, 7.3, 2.4 Hz), 2.82 (1H, ddd, J=15.6, 8.1, 2.7 Hz), 3.35-3.49 (6H, m), 4.30-4.41 (2H, m), 7.24 (2H, d, J=8.8 Hz), 7.94 (1H, d, J=8.8 Hz), 8.02 (2H, d, J=8.3 Hz), 8.25 (1H, dd, J=8.3, 1.9 Hz), 9.02 (1H, d, J=1.9 Hz).

MS (FAB) m/z: 464 [M+H]$^+$.

Example 70

N-Cyclopropyl-6-(4-{1-[8-(hydroxymethyl)-8-methyl-5,6,8,9-tetrahydro[1,2,4]triazolo[4,3-d][1,4]thiazepin-3-yl]cyclopropyl}phenyl)nicotinamide

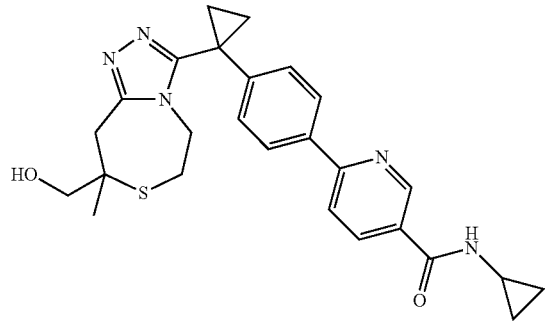 [SMILES: CC1(CO)Cc2nnc(C3(c4ccc(-c5ccc(C(=O)NC6CC6)cn5)cc4)CC3)n2CCS1]

A solution of the compound (150 mg, 0.344 mmol) obtained in Example 66, cyclopropylamine (119 μL, 1.72 mmol), N,N-dimethylaminopyridine (4 mg, 34 μmol), and 1-ethyl-3-(3-dimethylaminopropyl)carbodiimide hydrochloride (198 mg, 1.03 mmol) in N,N-dimethylformamide (3.00 mL) was stirred at room temperature for 5 h. Saturated aqueous sodium hydrogencarbonate (100 mL) was added to the reaction mixture, the mixture was extracted with dichloromethane, and the organic layer was washed with water and dried with anhydrous sodium sulfate. Then the solvent was distilled off under reduced pressure. Diisopropyl ether was added to the residue, and the precipitate was collected by filtration and purified by silica gel column chromatography (ethyl acetate:methanol=1:4) to obtain the title compound (29 mg, 18%) as a white solid.

$^1$H-NMR (500 MHz, CD$_3$OD) δ: 0.66 (2H, dt, J=7.8, 3.7 Hz), 0.81-0.85 (2H, m), 1.20 (3H, s), 1.57-1.63 (4H, m), 2.60 (1H, ddd, J=15.6, 7.3, 2.4 Hz), 2.82 (1H, ddd, J=15.9, 8.1, 2.4 Hz), 2.86-2.90 (1H, m), 3.35-3.49 (4H, m), 4.29-4.41 (2H, m), 7.23 (2H, d, J=8.8 Hz), 7.93 (1H, d, J=8.3 Hz), 8.01 (2H, d, J=8.3 Hz), 8.23 (1H, dd, J=8.3, 2.4 Hz), 8.99 (1H, d, J=2.4 Hz).

MS (ESI) m/z: 476 [M+H]$^+$.

Example 71

5-Fluoro-6-(4-{1-[8-(hydroxymethyl)-8-methyl-5,6,8,9-tetrahydro[1,2,4]triazolo[4,3-d][1,4]thiazepin-3-yl]cyclopropyl}phenyl)nicotinonitrile

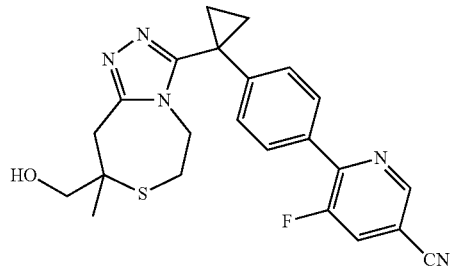 [SMILES: CC1(CO)Cc2nnc(C3(c4ccc(-c5ncc(C#N)cc5F)cc4)CC3)n2CCS1]

Example 71-1

6-(4-{1-[8-({[Tert-butyl(dimethyl)silyl]oxy}methyl)-8-methyl-5,6,8,9-tetrahydro[1,2,4]triazolo[4,3-d][1,4]thiazepin-3-yl]cyclopropyl}phenyl)-5-fluoronicotinonitrile A solution of the compound (555 mg, 1.0 mmol) obtained in Example 16-5), 6-chloro-5-fluoronicotinonitrile (187 mg, 1.5 mmol), tetrakis(triphenylphosphine)palladium(0) (231 mg, 0.2 mmol), and potassium carbonate (276 mg, 2 mmol) in dimethoxyethane (4 mL) and water (1 mL) was stirred at 120° C. for 1.5 h under microwave irradiation. The reaction mixture was cooled to room temperature, saturated aqueous sodium hydrogencarbonate was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 40 g, methanol:ethyl acetate=0:100 to 20:80, gradient) to obtain the title compound (451 mg, 82%) as a brown solid.

$^1$H-NMR (500 MHz, CDCl$_3$) δ: 0.05 (3H, s), 0.07 (3H, s), 0.91 (9H, s), 1.19 (3H, s), 1.48-1.56 (2H, m), 1.61-1.72 (2H, m), 2.57 (1H, ddd, J=15.6, 7.8, 2.0 Hz), 2.72 (1H, ddd, J=15.6, 7.8, 2.0 Hz), 3.40 (2H, s), 3.52 (1H, d, J=9.8 Hz), 3.55 (1H, d, J=9.8 Hz), 4.07 (1H, ddd, J=14.5, 7.8, 2.0 Hz), 4.31 (1H, ddd, J=14.5, 7.8, 2.0 Hz), 7.22 (2H, d, J=8.3 Hz), 7.79 (1H, dd, J=7.3, 2.4 Hz), 7.82 (2H, d, J=8.3 Hz), 8.73 (1H, d, J=2.4 Hz).

Example 71-2

5-Fluoro-6-(4-{1-[8-(hydroxymethyl)-8-methyl-5,6,8,9-tetrahydro[1,2,4]triazolo[4,3-d][1,4]thiazepin-3-yl]cyclopropyl}phenyl)nicotinonitrile A solution of the compound (451 mg, 0.82 mmol) obtained in Example 71-1) and tetrabutylammonium fluoride (1 M tetrahydrofuran solution, 0.98 mL) in tetrahydrofuran (4 mL) was stirred at room temperature for 18 h. Saturated aqueous ammonium chloride was added to the reaction mixture, the mixture was extracted with dichloromethane, and the organic layer was washed with saturated sodium chloride solution and dried with anhydrous sodium sulfate. After filtration, the filtrate was concentrated under reduced pressure, and the residue was purified by silica gel chromatography (Isco Combiflash, 12 g, methanol:ethyl acetate=0:100 to 40:60, gradient) to obtain the title compound (321 mg, 90%) as a colorless solid.

$^1$H-NMR (400 MHz, CDCl$_3$) δ: 1.33 (3H, s), 1.47-1.51 (1H, m), 1.54-1.58 (1H, m), 1.59-1.65 (1H, m), 1.68-1.73 (1H, m), 1.91 (1H, brs), 2.42 (1H, ddd, J=15.4, 6.5, 1.4 Hz), 2.60 (1H, ddd, J=15.4, 9.8, 1.4 Hz), 3.33 (1H, d, J=15.2 Hz), 3.39 (2H, s), 3.62 (1H, d, J=15.2 Hz), 4.11 (1H, ddd, J=14.7, 9.8, 1.4 Hz), 4.41 (1H, ddd, J=14.7, 6.5, 1.4 Hz), 7.24 (2H, d, J=8.6 Hz), 7.79 (1H, dd, J=7.4, 2.7 Hz), 7.82 (2H, d, J=8.6 Hz), 8.74 (1H, d, J=2.7 Hz).

MS (ESI) m/z: 436 [M+H]$^+$.

Example 72

{(8R)-8-Methyl-3-{1-[4-(1H-pyrazol-4-yl)phenyl]cyclopropyl}-5,6,8,9-tetrahydro[1,2,4]triazolo[4,3-d][1,4]thiazepin-8-yl}methanol

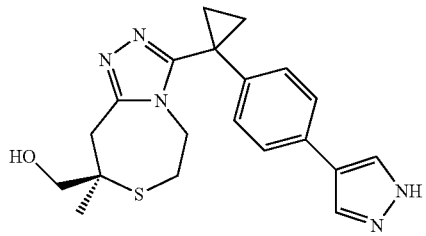 [SMILES: C[C@]1(CO)Cc2nnc(C3(c4ccc(-c5cn[nH]c5)cc4)CC3)n2CCS1]

A solution of the compound (500 mg, 0.98 mmol) obtained in Example 52-1), 4-(4,4,5,5-tetramethyl-1,3,2-dioxaborolan-2-yl)-1H-pyrazole (210 mg, 1.08 mmol), tetrakis(triphenylphosphine)palladium(0) (114 mg, 0.10 mmol), and potassium carbonate (272 mg, 1.97 mmol) in 1,2-dimethoxyethane (6 mL) and water (3 mL) was stirred at 120° C. for 1 h under microwave irradiation. The reaction mixture was cooled to room temperature, water (10 mL) was added to the reaction mixture, the mixture was extracted with ethyl acetate, and the organic layer was washed with saturated sodium chloride solution and dried with anhydrous sodium sulfate. After concentration under reduced pressure, the residue was partially purified by silica gel chromatography (ethyl acetate:methanol=40:60). A solution of the residue and 4 M hydrochloric acid (1,4-dioxane solution, 3 mL) in methanol (6 mL) was stirred overnight at room temperature. The reaction mixture was concentrated under reduced pressure, a 5 N aqueous sodium hydroxide solution (10 mL) was added to the residue, the mixture was extracted with dichloromethane, and the organic layer was washed with saturated sodium chloride solution and dried with anhydrous sodium sulfate. After concentration under reduced pressure, the residue was partially purified by silica gel chromatography (ethyl acetate/methanol=40:60). The residue was dissolved in a solution (8 mL) of ethyl acetate/methanol=3:1, and diisopropyl ether (20 mL) was gradually added to the mixture with stirring at room temperature to prepare a suspension. The suspension was stirred at 60° C. for 1 h and stirred for 1 h with cooling to room temperature. The colorless precipitate was collected by filtration and washed with diisopropyl ether. The solid was dried under reduced pressure to obtain the title compound (46 mg, 12%) as a colorless solid.

$^1$H-NMR (400 MHz, CDCl$_3$) δ: 1.33 (3H, s), 1.39-1.42 (1H, m), 1.47-1.53 (2H, m), 1.60-1.65 (1H, m), 2.38 (1H, ddd, J=15.7, 6.5, 1.5 Hz), 2.56 (1H, ddd, J=15.7, 9.8, 1.5 Hz), 3.31 (1H, d, J=15.3 Hz), 3.35 (2H, s), 3.61 (1H, d, J=15.3 Hz), 4.09 (1H, ddd, J=14.7, 9.8, 1.5 Hz), 4.45 (1H, ddd, J=14.8, 6.5, 1.5 Hz), 7.12 (2H, d, J=8.6 Hz), 7.44 (2H, d, J=8.6 Hz), 7.84 (2H, s).

MS (ESI) m/z: 382 [M+H]$^+$.

Example 73

(3-{1-[4-(1-Ethyl-1H-pyrazol-4-yl)phenyl]cyclopropyl}-8-methyl-5,6,8,9-tetrahydro[1,2,4]triazolo[4,3-d][1,4]thiazepin-8-yl)methanol

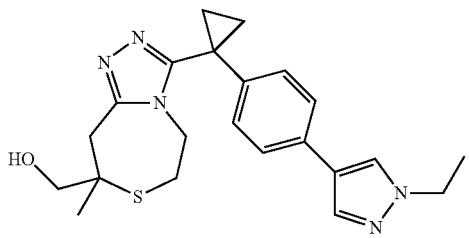 [SMILES: CCn1cc(-c2ccc(C3(c4nnc5n4CCSC(C)(CO)C5)CC3)cc2)cn1]

Example 73-1

8-({[Tert-butyl(dimethyl)silyl]oxy}methyl)-3-{1-[4-(1-ethyl-1H-pyrazol-4-yl)phenyl]cyclopropyl}-8-methyl-5,6,8,9-tetrahydro[1,2,4]triazolo[4,3-d][1,4]thiazepine A solution of the compound (300 mg, 0.59 mmol) obtained in Example 16-4), 1-ethyl-1H-pyrazole-4-boronic acid pinacol ester (144 mg, 0.65 mmol), tetrakis(triphenylphosphine)palladium(0) (68 mg, 0.06 mmol), and potassium carbonate (163 mg, 1.18 mmol) in 1,2-dimethoxyethane (3 mL) and water (1.5 mL) was stirred at 120° C. for 1 h under microwave irradiation. The reaction mixture was cooled to room temperature, water (3 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=70:30) to obtain the title compound (297 mg, 97%) in an orange oily form.

$^1$H-NMR (400 MHz, CDCl$_3$) δ: 0.04 (3H, s), 0.07 (3H, s), 0.91 (9H, s), 1.18 (3H, s), 1.37-1.46 (2H, m), 1.52 (3H, t, J=7.4 Hz), 1.58-1.61 (2H, m), 2.50 (1H, ddd, J=15.7, 7.9, 2.2 Hz), 2.64 (1H, dd, J=15.7, 7.0 Hz), 3.39 (2H, s), 3.50 (1H, d, J=10.2 Hz), 3.54 (1H, d, J=10.2 Hz), 4.07 (1H, ddd, J=14.4, 8.0, 1.9 Hz), 4.20 (2H, q, J=7.3 Hz), 4.32 (1H, ddd, J=14.4, 7.9, 2.3 Hz), 7.08 (2H, d, J=8.6 Hz), 7.39 (1H, d, J=8.2 Hz), 7.47 (1H, d, J=8.2 Hz), 7.61 (1H, s), 7.73 (1H, s).

Example 73-2

(3-{1-[4-(1-Ethyl-1H-pyrazol-4-yl)phenyl]cyclopropyl}-8-methyl-5,6,8,9-tetrahydro[1,2,4]triazolo[4,3-d][1,4]thiazepin-8-yl)methanol A solution of the compound (297 mg, 0.57 mmol) obtained in Example 73-1) and 4 M hydrochloric acid (1,4-dioxane solution, 2 mL) in methanol (10 mL) was stirred at room temperature for 2 h. The reaction mixture was concentrated under reduced pressure, saturated aqueous sodium hydrogencarbonate (10 mL) was added to the residue, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=20:80) to obtain the title compound (224 mg, 96%) as a colorless solid.

$^1$H-NMR (400 MHz, CDCl$_3$) δ: 1.31 (3H, s), 1.35-1.40 (1H, m), 1.46-1.52 (2H, m), 1.52 (3H, t, J=7.4 Hz), 1.58-1.66 (1H, m), 2.38 (1H, ddd, J=15.7, 6.7, 1.3 Hz), 2.57 (1H, dd, J=15.7, 9.5 Hz), 3.31 (1H, d, J=15.3 Hz), 3.39 (2H, s), 3.59 (1H, d, J=15.3 Hz), 4.10 (1H, ddd, J=14.6, 9.5, 1.4 Hz), 4.20 (2H, q, J=7.3 Hz), 4.42 (1H, dd, J=14.6, 6.7 Hz), 7.08 (2H, d, J=8.2 Hz), 7.40 (2H, d, J=8.2 Hz), 7.62 (1H, d, J=0.8 Hz), 7.74 (1H, d, J=0.8 Hz).

MS (ESI) m/z: 410 [M+H]$^+$.

Example 73B

[(8R)-(3-{1-[4-(1-Ethyl-1H-pyrazol-4-yl)phenyl]cyclopropyl}-8-methyl-5,6,8,9-tetrahydro[1,2,4]triazolo[4,3-d][1,4]thiazepin-8-yl)]methanol

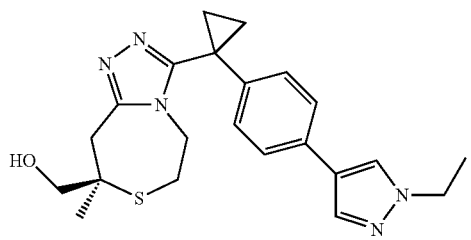 [SMILES: CCn1cc(-c2ccc(C3(c4nnc5n4CCS[C@@](C)(CO)C5)CC3)cc2)cn1]

Example 73B-1

(8R)-8-({[Tert-butyl(dimethyl)silyl]oxy}methyl)-3-{1-[4-(1-ethyl-1H-pyrazol-4-yl)phenyl]cyclopropyl}-8-methyl-5,6,8,9-tetrahydro[1,2,4]triazolo[4,3-d][1,4]thiazepine The compound (600 mg, 1.18 mmol) obtained in Example 52-1), 1-ethyl-1H-pyrazole-4-boronic acid pinacol ester (314 mg, 1.42 mmol), 1,1'-bis(diphenylphosphino)ferrocene-palladium(II) dichloride-dichloromethane complex (93 mg, 0.12 mmol), and potassium carbonate (489 mg, 3.54 mmol) were dissolved in a mixed solvent of 1,4-dioxane (4 mL) and water (2 mL), and the mixture was stirred at 90° C. for 5 h. The reaction mixture was cooled to room temperature and then diluted with ethyl acetate (200 mL). The organic layer was washed with saturated aqueous sodium hydrogencarbonate and saturated sodium chloride solution and then dried with anhydrous magnesium sulfate. The solvent was distilled off under reduced pressure, and the obtained residue was purified by silica gel column chromatography (ethyl acetate:hexane=40:60 to 100:0) to obtain the title compound (551 mg, 89%) as a white solid.

$^1$H-NMR (CDCl$_3$) δ: 0.04 (3H, s), 0.07 (3H, s), 0.91 (9H, s), 1.18 (3H, s), 1.39-1.45 (2H, m), 1.52 (3H, t, J=7.2 Hz), 1.54-1.63 (2H, m), 2.50 (1H, ddd, J=15.6, 8.2, 2.0 Hz), 2.63 (1H, ddd, J=15.2, 7.8, 2.0 Hz), 3.38 (2H, s), 3.51 (1H, dd, J=17.2, 10.2 Hz), 4.07 (1H, dd, J=14.9, 7.8 Hz), 4.20 (3H, q, J=7.3 Hz), 4.32 (1H, ddd, J=14.5, 7.4, 1.6 Hz), 7.08 (2H, d, J=7.8 Hz), 7.39 (2H, d, J=7.8 Hz), 7.62 (1H, s), 7.74 (1H, s).

Example (73B-2)

(8R)-3-{1-[4-(1-Ethyl-1H-pyrazol-4-yl)phenyl]cyclopropyl}-8-methyl-5,6,8,9-tetrahydro[1,2,4]triazolo[4,3-d][1,4]thiazepin-8-yl]methanol The compound (551 mg, 1.05 mmol) obtained in Example 73B-1) was dissolved in methanol (5 mL). 4 N hydrochloric acid-dioxane (2.60 mL) was added to the solution, and the mixture was stirred at room temperature for 2 h. The solvent was distilled off under reduced pressure, and the residue was separated into organic and aqueous layers with methylene chloride (150 mL) and saturated aqueous sodium hydrogencarbonate (50 mL). The organic layer was washed with saturated sodium chloride solution and then dried with anhydrous magnesium sulfate. The solvent was distilled off under reduced pressure, and the obtained residue was purified by silica gel column chromatography (methanol:ethyl acetate=0:100 to 30:70) to obtain the title compound (315 mg, 73%) as a white solid.

$^1$H-NMR (CDCl$_3$) δ: 1.32 (3H, s), 1.35-1.41 (2H, m), 1.46-1.53 (2H, m), 1.52 (3H, t, J=7.0 Hz), 2.33-2.42 (1H, m), 2.54 (1H, ddd, J=15.6, 9.8, 1.6 Hz), 3.30 (1H, d, J=15.2 Hz), 3.33-3.37 (2H, m), 3.60 (1H, d, J=15.2 Hz), 4.09 (1H, ddd, J=14.9, 10.2, 1.2 Hz), 4.20 (2H, q, J=7.3 Hz), 4.44 (1H, ddd, J=14.9, 6.3, 1.2 Hz), 7.10 (2H, d, J=7.8 Hz), 7.40 (2H, d, J=7.8 Hz), 7.63 (1H, s), 7.74 (1H, s).

MS (ESI) m/z: 410 [M+H]$^+$.

Example 74

{3-[1-(4-Isoxazol-4-ylphenyl)cyclopropyl]-8-methyl-5,6,8,9-tetrahydro[1,2,4]triazolo[4,3-d][1,4]thiazepin-8-yl}methanol

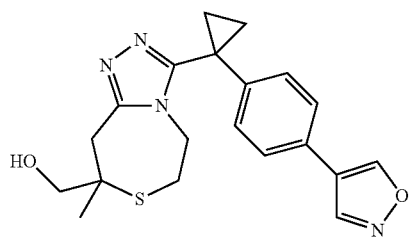 [SMILES: CC1(CO)Cc2nnc(C3(c4ccc(-c5cnoc5)cc4)CC3)n2CCS1]

Example 74-1

8-({[Tert-butyl(dimethyl)silyl]oxy}methyl)-3-[1-(4-isoxazol-4-ylphenyl)cyclopropyl]-8-methyl-5,6,8,9-tetrahydro[1,2,4]triazolo[4,3-d][1,4]thiazepine A solution of the compound (300 mg, 0.59 mmol) obtained in Example 16-4), isoxazol-4-boronic acid (73 mg, 0.65 mmol), tetrakis(triphenylphosphine)palladium(0) (68 mg, 0.06 mmol), and potassium carbonate (163 mg, 1.18 mmol) in 1,2-dimethoxyethane (3 mL) and water (1.5 mL) was stirred at 120° C. for 1 h under microwave irradiation. The reaction mixture was cooled to room temperature, water (3 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=70:30) to obtain the title compound (127 mg, 44%) as an orange solid.

$^1$H-NMR (400 MHz, CDCl$_3$) δ: 0.04 (3H, s), 0.06 (3H, s), 0.91 (9H, s), 1.18 (3H, s), 1.38-1.47 (2H, m), 1.49-1.61 (2H, m), 2.52 (1H, ddd, J=15.7, 8.0, 1.8 Hz), 2.69 (1H, ddd, J=15.7, 7.8, 2.3 Hz), 3.38 (2H, s), 3.50 (1H, d, J=10.2 Hz), 3.54 (1H, d, J=10.2 Hz), 4.01-4.13 (1H, m), 4.22-4.35 (1H, m), 6.96 (2H, d, J=8.6 Hz), 7.40 (2H, d, J=8.6 Hz), 7.46 (1H, s), 7.57 (1H, s).

Example 74-2

{3-[1-(4-Isoxazol-4-ylphenyl)cyclopropyl]-8-methyl-5,6,8,9-tetrahydro[1,2,4]triazolo[4,3-d][1,4]thiazepin-8-yl}methanol A solution of the compound (127 mg, 0.26 mmol) obtained in Example 74-1) and 4 M hydrochloric acid (1,4-dioxane solution, 2 mL) in methanol (10 mL) was stirred at room temperature for 2 h. The reaction mixture was concentrated under reduced pressure, saturated aqueous sodium hydrogencarbonate (10 mL) was added to the residue, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=20:80) to obtain the title compound (20 mg, 20%) as a yellow solid.

$^1$H-NMR (400 MHz, CDCl$_3$) δ: 1.25 (3H, s), 1.36-1.57 (2H, m), 1.59-1.72 (2H, m), 2.43 (1H, ddd, J=17.1, 8.7, 5.4 Hz), 2.59 (1H, ddd, J=15.7, 9.3, 3.6 Hz), 3.30 (1H, d, J=15.3 Hz), 3.37 (2H, s), 3.59 (1H, d, J=15.3 Hz), 4.03-4.13 (1H, m), 4.37 (1H, ddd, J=15.4, 6.4, 1.5 Hz), 7.09 (2H, d, J=8.6 Hz), 7.44 (2H, d, J=8.6 Hz), 7.56 (1H, s), 7.61 (1H, s).

MS (ESI) m/z: 383 [M+H]$^+$.

Example 75

(3-{1-[4-(1-Isopropyl-1H-pyrazol-4-yl)phenyl]cyclopropyl}-8-methyl-5,6,8,9-tetrahydro[1,2,4]triazolo[4,3-d][1,4]thiazepin-8-yl)methanol

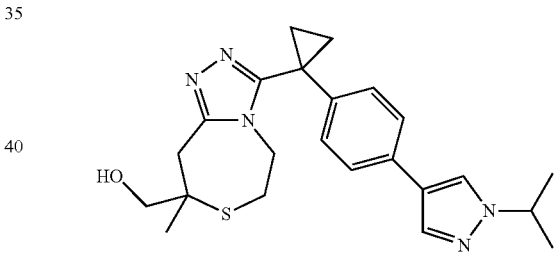

Example 75-1

8-({[Tert-butyl(dimethyl)silyl]oxy}methyl)-3-{1-[4-(1-isopropyl-1H-pyrazol-4-yl)phenyl]cyclopropyl}-8-methyl-5,6,8,9-tetrahydro[1,2,4]triazolo[4,3-d][1,4]thiazepine A solution of the compound (300 mg, 0.59 mmol) obtained in Example 16-4), 1-isopropylpyrazole-4-boronic acid pinacol ester (153 mg, 0.65 mmol), tetrakis(triphenylphosphine)palladium(0) (68 mg, 0.06 mmol), and potassium carbonate (163 mg, 1.18 mmol) in 1,2-dimethoxyethane (3 mL) and water (1.5 mL) was stirred at 120° C. for 1 h under microwave irradiation. The reaction mixture was cooled to room temperature, water (3 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=70:30) to obtain the title compound (217 mg, 68%) in an orange oily form.

¹H-NMR (400 MHz, CDCl₃) δ: 0.04 (3H, s), 0.07 (3H, s), 0.91 (9H, s), 1.24 (3H, s), 1.39-1.46 (2H, m), 1.54 (6H, d, J=6.7 Hz), 1.56-1.61 (2H, m), 2.49 (1H, ddd, J=15.7, 7.9, 2.3 Hz), 2.63 (1H, ddd, J=15.7, 7.6, 2.0 Hz), 3.38 (2H, s), 3.49 (1H, d, J=10.0 Hz), 3.53 (1H, d, J=10.0 Hz), 4.07 (1H, ddd, J=14.3, 7.6, 1.8 Hz), 4.32 (1H, ddd, J=14.3, 7.9, 2.1 Hz), 4.47-4.57 (1H, m), 7.08 (2H, d, J=8.5 Hz), 7.39 (2H, d, J=8.5 Hz), 7.64 (1H, s), 7.74 (1H, s).

Example 75-2

(3-{1-[4-(1-Isopropyl-1H-pyrazol-4-yl)phenyl]cyclopropyl}-8-methyl-5,6,8,9-tetrahydro[1,2,4]triazolo[4,3-d][1,4]thiazepin-8-yl)methanol A solution of the compound (217 mg, 0.40 mmol) obtained in Example 75-1 and 4 M hydrochloric acid (1,4-dioxane solution, 2 mL) in methanol (8 mL) was stirred at room temperature for 2 h. The reaction mixture was concentrated under reduced pressure, saturated aqueous sodium hydrogencarbonate (10 mL) was added to the residue, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=20:80) to obtain the title compound (203 mg, quant.) as a colorless solid.

¹H-NMR (400 MHz, CDCl₃) δ: 1.32 (3H, s), 1.35-1.42 (1H, m), 1.48-1.52 (2H, m), 1.54 (6H, d, J=6.7 Hz), 1.60-1.68 (1H, m), 2.36 (1H, ddd, J=15.6, 6.4, 1.3 Hz), 2.54 (1H, ddd, J=15.6, 9.8, 1.3 Hz), 3.30 (1H, d, J=15.3 Hz), 3.36 (2H, s), 3.60 (1H, d, J=15.3 Hz), 4.09 (1H, ddd, J=14.5, 9.8, 1.3 Hz), 4.43 (1H, dd, J=14.5, 6.4 Hz), 4.48-4.57 (2H, m), 7.09 (1H, d, J=8.2 Hz), 7.41 (1H, d, J=8.2 Hz), 7.65 (2H, s), 7.75 (2H, s). MS (ESI) m/z: 424 [M+H]⁺.

Example 76

(8-Methyl-3-{1-[4-(3-methyl-1H-pyrazol-4-yl)phenyl]cyclopropyl}-5,6,8,9-tetrahydro[1,2,4]triazolo[4,3-d][1,4]thiazepin-8-yl)methanol

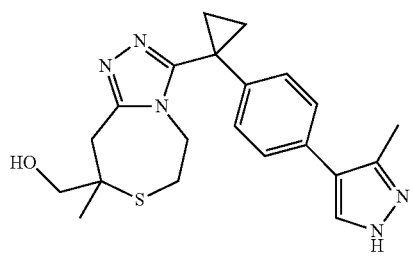 [SMILES: Cc1n[nH]cc1-c1ccc(C2(c3nnc4n3CCSC(C)(CO)C4)CC2)cc1]

Example 76-1

8-({[Tert-butyl(dimethyl)silyl]oxy}methyl)-8-methyl-3-{1-[4-(3-methyl-1H-pyrazol-4-yl)phenyl]cyclopropyl}-5,6,8,9-tetrahydro[1,2,4]triazolo[4,3-d][1,4]thiazepine A solution of the compound (300 mg, 0.59 mmol) obtained in Example 16-4), 3-methyl-1H-pyrazole-4-boronic acid pinacol ester (135 mg, 0.65 mmol), tetrakis(triphenylphosphine)palladium(0) (68 mg, 0.06 mmol), and potassium carbonate (163 mg, 1.18 mmol) in 1,2-dimethoxyethane (3 mL) and water (1.5 mL) was stirred at 120° C. for 1 h under microwave irradiation. The reaction mixture was cooled to room temperature, water (3 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=30:70) to obtain the title compound (213 mg, 71%) in an orange oily form.

¹H-NMR (400 MHz, CDCl₃) δ: 0.04 (3H, s), 0.07 (3H, s), 0.91 (9H, s), 1.19 (3H, s), 1.41-1.50 (2H, m), 1.56-1.63 (2H, m), 2.43 (3H, s), 2.54 (1H, dd, J=14.5, 7.0 Hz), 2.69 (1H, dd, J=16.4, 7.4 Hz), 3.39 (2H, s), 3.51 (1H, d, J=10.0 Hz), 3.55 (1H, d, J=10.0 Hz), 4.06-4.15 (1H, m), 4.34 (1H, dd, J=14.5, 7.4 Hz), 7.11 (2H, d, J=8.2 Hz), 7.32 (2H, d, J=8.2 Hz), 7.65 (1H, s).

Example 76-2

(8-Methyl-3-{1-[4-(3-methyl-1H-pyrazol-4-yl)phenyl]cyclopropyl}-5,6,8,9-tetrahydro[1,2,4]triazolo[4,3-d][1,4]thiazepin-8-yl)methanol A solution of the compound (213 mg, 0.42 mmol) obtained in Example 76-1) and 4 M hydrochloric acid (1,4-dioxane solution, 3 mL) in methanol (6 mL) was stirred at room temperature for 2 h. The reaction mixture was concentrated under reduced pressure, a 5 M aqueous sodium hydroxide solution (10 mL) was added to the residue, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=20:80) to obtain the title compound (113 mg, 68%) as a colorless solid.

¹H-NMR (400 MHz, CDCl₃) δ: 1.34 (3H, s), 1.36-1.46 (1H, m), 1.46-1.58 (2H, m), 1.61-1.66 (1H, m), 2.39-2.46 (4H, m), 2.63 (1H, dd, J=15.7, 9.6 Hz), 2.77 (1H, brs), 3.31 (1H, d, J=15.3 Hz), 3.49 (2H, s), 3.65 (1H, d, J=15.3 Hz), 4.11 (1H, dd, J=14.7, 9.6 Hz), 4.47 (1H, dd, J=14.7, 6.1 Hz), 7.11 (2H, d, J=7.4 Hz), 7.33 (2H, d, J=7.4 Hz), 7.66 (1H, s). MS (ESI) m/z: 396 [M+H]⁺.

Example 77

N-ethyl-6-(4-{1-[8-(hydroxymethyl)-8-methyl-5,6,8,9-tetrahydro[1,2,4]triazolo[4,3-d][1,4]thiazepin-3-yl]cyclopropyl}phenyl)-N-methyl nicotinamide

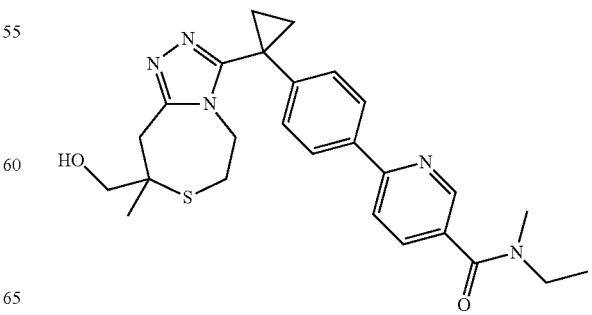

A solution of the compound (200 mg, 0.458 mmol) obtained in Example 66, ethylmethylamine (197 μL, 2.29 mmol), N,N-dimethylaminopyridine (6 mg, 46 mmol), and 1-ethyl-3-(3-dimethylaminopropyl)carbodiimide hydrochloride (264 mg, 1.37 mmol) in N,N-dimethylformamide (4.00 mL) was stirred at room temperature for 14 h. Saturated aqueous sodium hydrogencarbonate (100 mL) was added to the reaction mixture, the mixture was extracted with dichloromethane, and the organic layer was washed with water and dried with anhydrous sodium sulfate. Then the solvent was distilled off under reduced pressure. The residue was purified by preparative TLC (dichloromethane:methanol=9:1) to obtain the title compound (18 mg, 8%) as a brown solid.

$^1$H-NMR (400 MHz, CD$_3$OD) δ: 1.20 (3H, s), 1.29 (3H, t, J=9.2 Hz), 1.56-1.64 (4H, m), 2.61 (1H, ddd, J=15.7, 7.0, 2.7 Hz), 2.79-2.85 (1H, m), 3.04 (3/2H, s), 3.10 (3/2H, s), 3.35-3.49 (6H, m), 4.27-4.44 (2H, m), 7.23 (2H, d, J=8.7 Hz), 7.93 (1H, d, J=1.2 Hz), 8.01 (3H, d, J=8.7 Hz), 8.66 (1H, d, J=8.6 Hz).

MS (ESI) m/z: 478 [M+H]$^+$.

Example 78

8-Methyl-3-(1-{4-[5-(pyrrolidin-1-ylcarbonyl)pyridin-2-yl]phenyl}cyclopropyl)-5,6,8,9-tetrahydro[1,2,4]triazolo[4,3-d][1,4]thiazepin-8-yl]methanol

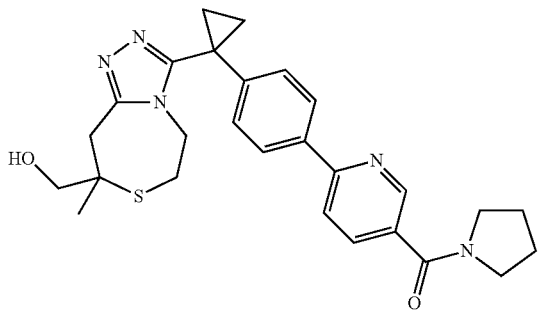 [SMILES: CC1(CO)Cc2nnc(C3(c4ccc(-c5ccc(C(=O)N6CCCC6)cn5)cc4)CC3)n2CCS1]

A solution of the compound (200 mg, 0.458 mmol) obtained in Example 66), pyrrolidine (188 μL, 2.29 mmol), N,N-dimethylaminopyridine (6 mg, 46 μmol), and 1-ethyl-3-(3-dimethylaminopropyl)carbodiimide hydrochloride (264 mg, 1.37 mmol) in N,N-dimethylformamide (4.00 mL) was stirred at room temperature for 14 h. Saturated aqueous sodium hydrogencarbonate (100 mL) was added to the reaction mixture, the mixture was extracted with dichloromethane, and the organic layer was washed with water and dried with anhydrous sodium sulfate. Then the solvent was distilled off under reduced pressure. The residue was purified by preparative TLC (dichloromethane:methanol=9:1) to obtain the title compound (24 mg, 11%) as a white solid.

$^1$H-NMR (400 MHz, CD$_3$OD) δ: 1.20 (3H, s), 1.57-1.64 (4H, m), 1.91-2.05 (4H, m), 2.61 (1H, ddd, J=15.7, 7.0, 2.7 Hz), 2.82 (1H, ddd, J=15.7, 8.0, 2.5 Hz), 3.35-3.50 (4H, m), 3.55 (2H, t, J=6.5 Hz), 3.63 (2H, t, J=6.8 Hz), 4.27-4.43 (2H, m), 7.24 (2H, d, J=8.2 Hz), 7.94 (1H, dd, J=8.2, 0.8 Hz), 7.99-8.04 (3H, m), 8.78 (1H, dd, J=2.3, 0.8 Hz).

MS (ESI) m/z: 490 [M+H]$^+$.

Example 79

[8-Methyl-3-(1-{4-[5-(morpholin-4-ylcarbonyl)pyridin-2-yl]phenyl}cyclopropyl)-5,6,8,9-tetrahydro[1,2,4]triazolo[4,3-d][1,4]thiazepin-8-yl]methanol

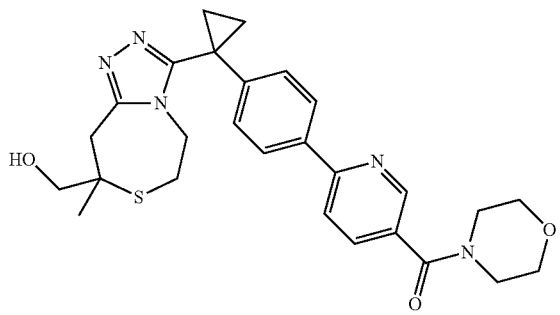 [SMILES: CC1(CO)Cc2nnc(C3(c4ccc(-c5ccc(C(=O)N6CCOCC6)cn5)cc4)CC3)n2CCS1]

A solution of the compound (200 mg, 0.458 mmol) obtained in Example 66, morpholine (200 μL, 2.29 mmol), N,N-dimethylaminopyridine (6 mg, 46 μmol), and 1-ethyl-3-(3-dimethylaminopropyl)carbodiimide hydrochloride (264 mg, 1.37 mmol) in N,N-dimethylformamide (4.00 mL) was stirred at room temperature for 14 h. Saturated aqueous sodium hydrogencarbonate (100 mL) was added to the reaction mixture, the mixture was extracted with dichloromethane, and the organic layer was washed with water and dried with anhydrous sodium sulfate. Then the solvent was distilled off under reduced pressure. The residue was purified by preparative TLC (dichloromethane:methanol=9:1) to obtain the title compound (69 mg, 11%) as a white solid.

$^1$H-NMR (400 MHz, CD$_3$OD) δ: 1.20 (3H, s), 1.60 (4H, ddd, J=14.2, 7.1, 3.8 Hz), 2.60 (1H, ddd, J=15.8, 7.2, 2.7 Hz), 2.82 (1H, ddd, J=15.8, 7.9, 2.6 Hz), 3.35-3.77 (13H, m), 4.32 (1H, ddd, J=14.8, 7.2, 2.6 Hz), 4.39 (1H, ddd, J=14.8, 7.9, 2.7 Hz), 7.23 (2H, dt, J=8.7, 2.1 Hz), 7.94 (1H, t, J=1.9 Hz), 8.02 (2H, dt, J=8.9, 2.1 Hz), 8.68 (1H, dd, J=1.9, 1.2 Hz).

MS (FAB) m/z: 506 [M+H]$^+$.

Example 80

(3-{1-[2-Fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl)methanol

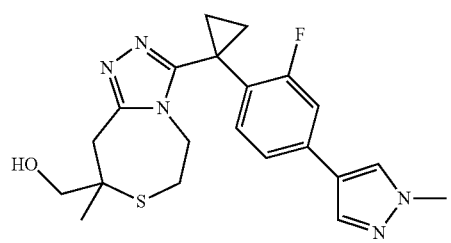 [SMILES: Cn1cc(-c2ccc(C3(c4nnc5n4CCSC(C)(CO)C5)CC3)c(F)c2)cn1]

Example 80-1

8-({[Tert-butyl(dimethyl)silyl]oxy}methyl)-3-{1-[2-fluoro-4-(1-methyl-1H-pyrazol-4-yl)phenyl]cyclopropyl}-8-methyl-5,6,8,9-tetrahydro[1,2,4]triazolo[4,3-d][1,4]thiazepine A solution of the compound (300 mg, 0.59 mmol) obtained in Example 14-5), 1-methyl-1H-pyrazole-4-boronic acid pinacol ester (130 mg, 0.65 mmol), tetrakis(triphenylphosphine)palladium(0) (66 mg, 0.06 mmol), and potassium carbonate (157 mg, 1.18 mmol) in 1,2-dimethoxyethane (3 mL) and water (1.5 mL) was stirred at 120° C. for 1 h under microwave irradiation. The reaction mixture was cooled to room temperature, water (3 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=70:30) to obtain the title compound (368 mg, quant.) in an orange oily form.

$^1$H-NMR (400 MHz, CDCl$_3$) δ: 0.04 (3H, s), 0.04 (3H, s), 0.88 (9H, s), 1.15 (3H, s), 1.50-1.72 (4H, m), 2.56 (1H, dd, J=14.1, 6.8 Hz), 2.76 (1H, dd, J=14.1, 5.1 Hz), 3.39-3.41 (1H, m), 3.50-3.52 (3H, m), 3.95 (3H, s), 4.25 (1H, dd, J=14.5, 6.5 Hz), 4.53 (1H, dd, J=14.5, 7.6 Hz), 7.11 (1H, d, J=12.5 Hz), 7.20 (1H, d, J=7.8 Hz), 7.40 (1H, t, J=7.8 Hz), 7.60 (1H, s), 7.72 (1H, s).

Example 80-2

(3-{1-[2-Fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl)methanol A solution of the compound (368 mg, 0.70 mmol) obtained in Example 80-1) and 4 M hydrochloric acid (1,4-dioxane solution, 3 mL) in methanol (6 mL) was stirred overnight at room temperature. The reaction mixture was concentrated under reduced pressure, a 5 M aqueous sodium hydroxide solution (10 mL) was added to the residue, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=20:80) to obtain the title compound (200 mg, 69%) as a colorless solid.

$^1$H-NMR (500 MHz, CDCl$_3$) δ: 1.30 (3H, s), 1.40-1.44 (1H, m), 1.50-1.55 (2H, m), 1.65-1.72 (1H, m), 2.46 (1H, dd, J=15.6, 6.3 Hz), 2.57 (1H, dd, J=15.6, 9.8 Hz), 3.23-3.36 (3H, m), 3.58 (1H, d, J=15.6 Hz), 3.94 (3H, s), 4.20 (1H, dd, J=14.0, 9.8 Hz), 4.67 (1H, dd, J=14.0, 4.9 Hz), 7.11 (1H, d, J=12.2 Hz), 7.20 (1H, d, J=8.2 Hz), 7.39 (1H, t, J=8.2 Hz), 7.60 (1H, s), 7.72 (1H, s).

MS (ESI) m/z: 414 [M+H]$^+$.

Example 81

{(8R)-3-{1-[2-Fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl}methanol

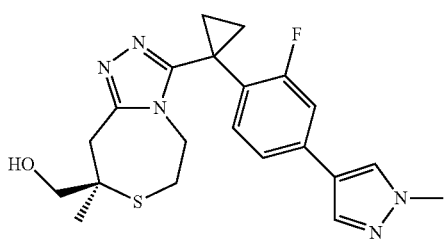 [SMILES: Cn1cc(-c2ccc(C3(c4nnc5n4CCS[C@@](C)(CO)C5)CC3)c(F)c2)cn1]

Example 81-1

(8R)-3-[1-(4-Bromo-2-fluorophenyl)cyclopropyl]-8-({[tert-butyl(dimethyl)silyl]oxy}methyl)-8-methyl-5,6,8,9-tetrahydro[1,2,4]triazolo[4,3-d][1,4]thiazepine A solution of the compound (2.00 g, 7.32 mmol) obtained in Example 14-4) and the compound (2.57 g, 8.06 mmol) obtained in Example 4-1) in n-butanol (40 mL) was stirred at 140° C. for 8 h. The reaction mixture was cooled to room temperature and concentrated under reduced pressure. The residue was purified by silica gel chromatography (ethyl acetate) to obtain the title compound (3.86 g, quant.) as a yellow solid.

$^1$H-NMR (400 MHz, CDCl$_3$) δ: 0.01 (3H, s), 0.04 (3H, s), 0.89 (9H, s), 1.14 (3H, s), 1.36-1.51 (2H, m), 1.53-1.70 (2H, m), 2.56 (1H, ddd, J=15.6, 7.8, 2.2 Hz), 2.74 (1H, ddd, J=15.6, 8.0, 2.0 Hz), 3.34 (2H, s), 3.46 (1H, d, J=10.2 Hz), 3.50 (1H, d, J=10.2 Hz), 4.19 (1H, ddd, J=14.5, 7.8, 2.0 Hz), 4.47 (1H, ddd, J=14.5, 8.0, 2.2 Hz), 7.21-7.33 (3H, m).

Example 81-2

(8R)-8-({[Tert-butyl(dimethyl)silyl]oxy}methyl)-3-{1-[2-fluoro-4-(1-methyl-1H-pyrazol-4-yl)phenyl]cyclopropyl}-8-methyl-5,6,8,9-tetrahydro[1,2,4]triazolo[4,3-d][1,4]thiazepine A solution of the compound (3.86 g, 7.32 mmol) obtained in Example 81-1), 1-methyl-1H-pyrazole-4-boronic acid pinacol ester (1.68 g, 8.06 mmol), tetrakis(triphenylphosphine)palladium(0) (850 mg, 0.73 mmol), and potassium carbonate (2.02 g, 14.65 mmol) in 1,2-dimethoxyethane (50 mL) and water (25 mL) was heated to reflux overnight with stirring. The reaction mixture was cooled to room temperature, water (20 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=100:0 to 70:30) to obtain the title compound (3.87 g, quant.) as a yellow solid.

$^1$H-NMR (500 MHz, CDCl$_3$) δ: 0.01 (3H, s), 0.04 (3H, s), 0.89 (9H, s), 1.14 (3H, s), 1.45-1.52 (2H, m), 1.57-1.60 (1H, m), 1.63-1.66 (1H, m), 2.54 (1H, dd, J=15.6, 7.8 Hz), 2.70 (1H, dd, J=15.6, 7.8 Hz), 3.35 (2H, s), 3.46 (1H, d, J=10.3 Hz), 3.50 (1H, d, J=10.3 Hz), 3.94 (3H, s), 4.21 (1H, dd, J=14.0, 7.8 Hz), 4.52 (1H, dd, J=14.0, 7.8 Hz), 7.10 (1H, d, J=12.2 Hz), 7.19 (1H, d, J=8.3 Hz), 7.38 (1H, t, J=8.3 Hz), 7.59 (1H, s), 7.72 (1H, s).

Example 81-3

{(8R)-3-{1-[2-Fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl}methanol A solution of the compound (3.87 g, 7.32 mmol) obtained in Example 81-2) and 4 M hydrochloric acid (1,4-dioxane solution, 15 mL) in methanol (30 mL) was stirred overnight at room temperature. The reaction mixture was concentrated under reduced pressure, a 5 M aqueous sodium hydroxide solution (20 mL) was added to the residue, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=30:70) to obtain the title compound (2.72 g, 90%) as a colorless solid.

$^1$H-NMR (400 MHz, CDCl$_3$) δ: 1.30 (3H, s), 1.40-1.45 (2H, m), 1.66-1.71 (2H, m), 2.46 (1H, dd, J=15.4, 6.3 Hz), 2.57 (1H, dd, J=15.4, 9.4 Hz), 2.66 (1H, brs), 3.27 (1H, d, J=15.2 Hz), 3.31 (2H, s), 3.56 (1H, d, J=15.2 Hz), 3.94 (3H, s), 4.20 (1H, dd, J=14.6, 9.4 Hz), 4.66 (1H, dd, J=14.6, 6.3 Hz), 7.11 (1H, dd, J=12.3, 1.8 Hz), 7.20 (1H, dd, J=8.1, 1.8 Hz), 7.39 (1H, t, J=8.1 Hz), 7.60 (1H, s), 7.72 (1H, s).

MS (ESI) m/z: 414 [M+H]$^+$.

Example 82

(3-{1-[3-Fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl)methanol

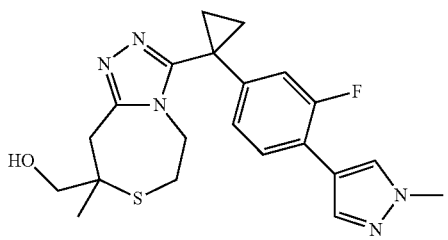 [SMILES: Cn1cc(-c2ccc(C3(c4nnc5n4CCSC(C)(CO)C5)CC3)cc2F)cn1]

Example 82-1

8-({[Tert-butyl(dimethyl)silyl]oxy}methyl)-3-{1-[3-fluoro-4-(1-methyl-1H-pyrazol-4-yl)phenyl]cyclopropyl}-8-methyl-5,6,8,9-tetrahydro[1,2,4]triazolo[4,3-d][1,4]thiazepine A solution of the compound (300 mg, 0.59 mmol) obtained in Example 25-3), 1-methyl-1H-pyrazole-4-boronic acid pinacol ester (130 mg, 0.65 mmol), tetrakis(triphenylphosphine)palladium(0) (66 mg, 0.06 mmol), and potassium carbonate (157 mg, 1.18 mmol) in 1,2-dimethoxyethane (3 mL) and water (1.5 mL) was stirred at 120° C. for 1 h under microwave irradiation. The reaction mixture was cooled to room temperature, water (3 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=70:30) to obtain the title compound (377 mg, quant.) in an orange oily form.

$^1$H-NMR (400 MHz, CDCl$_3$) δ: 0.05 (3H, s), 0.07 (3H, s), 0.91 (9H, s), 1.24 (3H, s), 1.40-1.48 (2H, m), 1.55-1.64 (2H, m), 2.57 (1H, ddd, J=15.5, 7.8, 2.2 Hz), 2.74 (1H, dd, J=15.5, 7.6, 1.7 Hz), 3.41 (2H, s), 3.52 (1H, d, J=10.2 Hz), 3.56 (1H, d, J=10.2 Hz), 3.95 (3H, s), 4.09 (1H, ddd, J=14.3, 7.6, 1.7 Hz), 4.31 (1H, dd, J=14.3, 7.8, 2.2 Hz), 6.81-6.86 (2H, m), 7.46 (1H, t, J=8.0 Hz), 7.74 (1H, s), 7.81 (1H, s).

Example 82-2

(3-{1-[3-Fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl)methanol A solution of the compound (377 mg, 0.71 mmol) obtained in Example 82-1) and 4 M hydrochloric acid (1,4-dioxane solution, 3 mL) in methanol (6 mL) was stirred overnight at room temperature. The reaction mixture was concentrated under reduced pressure, a 5 M aqueous sodium hydroxide solution (10 mL) was added to the residue, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=20:80) to obtain the title compound (219 mg, 75%) as a colorless solid.

$^1$H-NMR (400 MHz, CDCl$_3$) δ: 1.33 (3H, s), 1.39-1.50 (2H, m), 1.55-1.62 (2H, m), 2.45 (1H, dd, J=15.6, 6.4 Hz), 2.63 (1H, dd, J=15.6, 9.8 Hz), 3.27-3.42 (3H, m), 3.62 (1H, d, J=15.2 Hz), 3.95 (3H, s), 4.11 (1H, dd, J=14.6, 9.8 Hz), 4.42 (1H, dd, J=14.6, 6.4 Hz), 6.82-6.87 (2H, m), 7.46 (1H, t, J=8.2 Hz), 7.74 (1H, s), 7.81 (1H, s).

MS (ESI) m/z: 414 [M+H]$^+$.

Example 83

(8-Methyl-3-{1-[4-(1H-pyrazol-5-yl)phenyl]cyclopropyl}-5,6,8,9-tetrahydro[1,2,4]triazolo[4,3-d][1,4]thiazepin-8-yl)methanol

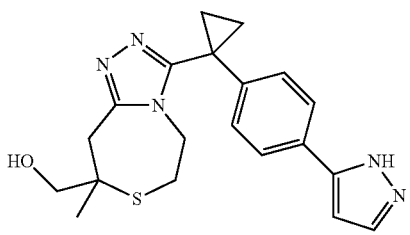 [SMILES: CC1(CO)Cc2nnc(C3(c4ccc(-c5ccn[nH]5)cc4)CC3)n2CCS1]

Example 83-1

8-({[Tert-butyl(dimethyl)silyl]oxy}methyl)-8-methyl-3-{1-[4-(1H-pyrazol-5-yl)phenyl]cyclopropyl}-5,6,8,9-tetrahydro[1,2,4]triazolo[4,3-d][1,4]thiazepine A solution of the compound (300 mg, 0.59 mmol) obtained in Example 16-4), 1H-pyrazole-3-boronic acid pinacol ester (126 mg, 0.65 mmol), tetrakis(triphenylphosphine)palladium (0) (68 mg, 0.06 mmol), and potassium carbonate (163 mg, 1.18 mmol) in 1,2-dimethoxyethane (3 mL) and water (1.5 mL) was stirred at 120° C. for 1 h under microwave irradiation. The reaction mixture was cooled to room temperature, water (3 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=70:30) to obtain the title compound (295 mg, quant.) in an orange oily form.

$^1$H-NMR (400 MHz, CDCl$_3$) δ: 0.04 (3H, s), 0.07 (3H, s), 0.91 (9H, s), 1.18 (3H, s), 1.36-1.50 (2H, m), 1.52-1.67 (2H, m), 2.44-2.57 (1H, m), 2.61-2.72 (1H, m), 3.38 (2H, s), 3.50 (1H, d, J=10.2 Hz), 3.54 (1H, d, J=10.2 Hz), 4.00-4.10 (1H, m), 4.23-4.35 (1H, m), 6.60 (1H, d, J=2.3 Hz), 6.96 (1H, d, J=8.8 Hz), 7.13 (1H, d, J=8.2 Hz), 7.40 (1H, d, J=8.8 Hz), 7.62 (1H, d, J=2.3 Hz), 7.70 (1H, d, J=8.2 Hz).

Example 83-2

(8-Methyl-3-{1-[4-(1H-pyrazol-5-yl)phenyl]cyclopropyl}-5,6,8,9-tetrahydro[1,2,4]triazolo[4,3-d][1,4]thiazepin-8-yl)methanol A solution of the compound (295 mg, 0.60 mmol) obtained in Example 83-1) and 4 M hydrochloric acid (1,4-dioxane solution, 3 mL) in methanol (6 mL) was stirred overnight at room temperature. The reaction mixture was concentrated under reduced pressure, a 5 M aqueous sodium hydroxide solution (10 mL) was added to the residue, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=20:80) to obtain the title compound (152 mg, 66%) as a colorless solid.

$^1$H-NMR (400 MHz, CDCl$_3$) δ: 1.32 (3H, s), 1.37-1.48 (1H, m), 1.50-1.57 (2H, m), 1.59-1.69 (1H, m), 2.35-2.46 (1H, m), 2.56-2.64 (1H, m), 3.30 (1H, dd, J=15.2, 1.2 Hz), 3.40 (2H, s), 3.62 (1H, d, J=15.2 Hz), 4.04-4.14 (1H, m), 4.35-4.47 (1H, m), 6.60 (1H, s), 6.97 (1H, d, J=7.0 Hz), 7.13 (1H, dd, J=8.2, 1.6 Hz), 7.42 (1H, d, J=7.8 Hz), 7.63 (1H, s), 7.71 (1H, d, J=8.2 Hz).
MS (ESI) m/z: 382 [M+H]$^+$.

Example 84

(8-Methyl-3-{1-[4-(1,3-oxazol-2-yl)phenyl]cyclopropyl}-5,6,8,9-tetrahydro[1,2,4]triazolo[4,3-d][1,4]thiazepin-8-yl)methanol

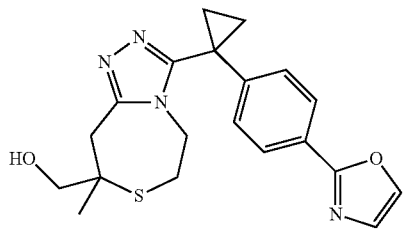 [SMILES: CC1(CO)Cc2nnc(C3(c4ccc(-c5ncco5)cc4)CC3)n2CCS1]

Example 84-1

8-({[Tert-butyl(dimethyl)silyl]oxy}methyl)-8-methyl-3-{1-[4-(1,3-oxazol-2-yl)phenyl]cyclopropyl}-5,6,8,9-tetrahydro[1,2,4]triazolo[4,3-d][1,4]thiazepine A solution of the compound (250 mg, 0.49 mmol) obtained in Example 16-4), oxazole (68 mg, 0.98 mmol), tetrakis(triphenylphosphine)palladium(0) (28 mg, 0.02 mmol), and lithium tert-butoxide (81 mg, 0.98 mmol) in dioxane (3 mL) was stirred for 2 h with heating to reflux. The reaction mixture was cooled to room temperature, saturated aqueous ammonium chloride (5 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=70:30) to obtain the title compound (260 mg, quant.) in a yellow oily form.

$^1$H-NMR (400 MHz, CDCl$_3$) δ: 0.05 (3H, s), 0.07 (3H, s), 0.91 (9H, s), 1.45-1.54 (2H, m), 1.58 (3H, s), 1.62-1.69 (2H, m), 2.51 (1H, ddd, J=15.7, 8.0, 2.3 Hz), 2.65 (1H, ddd, J=15.7, 8.1, 2.3 Hz), 3.40 (2H, s), 3.50 (1H, d, J=10.2 Hz), 3.54 (1H, d, J=10.2 Hz), 4.06 (1H, ddd, J=14.5, 8.1, 2.3 Hz), 4.29 (1H, ddd, J=14.5, 8.0, 2.3 Hz), 7.15 (1H, t, J=2.0 Hz), 7.17 (1H, t, J=2.0 Hz), 7.23 (1H, d, J=0.8 Hz), 7.70 (1H, d, J=0.8 Hz), 7.95 (1H, t, J=2.0 Hz), 7.98 (1H, t, J=2.0 Hz).

Example 84-2

(8-Methyl-3-{1-[4-(1,3-oxazol-2-yl)phenyl]cyclopropyl}-5,6,8,9-tetrahydro[1,2,4]triazolo[4,3-d][1,4]thiazepin-8-yl)methanol A solution of the compound (260 mg, 0.52 mmol) obtained in Example 84-1) and 4 M hydrochloric acid (1,4-dioxane solution, 3 mL) in methanol (6 mL) was stirred overnight at room temperature. The reaction mixture was concentrated under reduced pressure, a 5 M aqueous sodium hydroxide solution (10 mL) was added to the residue, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=20:80) to obtain the title compound (172 mg, 87%) as a colorless solid.

$^1$H-NMR (400 MHz, CDCl$_3$) δ: 1.33 (3H, s), 1.43-1.49 (2H, m), 1.66-1.70 (2H, m), 2.38 (1H, ddd, J=15.5, 6.4, 1.8 Hz), 2.56 (1H, ddd, J=15.5, 9.8, 1.5 Hz), 3.32 (1H, d, J=15.2 Hz), 3.50 (2H, s), 3.62 (1H, d, J=15.2 Hz), 4.09 (1H, ddd, J=14.7, 9.8, 1.4 Hz), 4.40 (1H, ddd, J=14.7, 6.4, 1.6 Hz), 7.17 (1H, t, J=2.0 Hz), 7.19 (1H, t, J=2.0 Hz), 7.23 (1H, d, J=0.8 Hz), 7.71 (1H, d, J=0.8 Hz), 7.97 (1H, t, J=2.0 Hz), 7.99 (1H, t, J=2.0 Hz).
MS (ESI) m/z: 383 [M+H]$^+$.

Example 85

{(8R)-8-Methyl-3-{1-[4-(1,3-oxazol-2-yl)phenyl]cyclopropyl}-5,6,8,9-tetrahydro[1,2,4]triazolo[4,3-d][1,4]thiazepin-8-yl}methanol

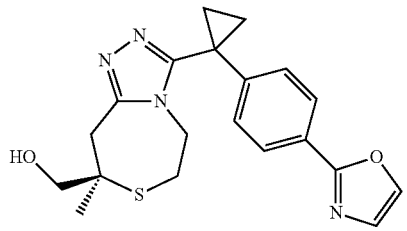 [SMILES: C[C@]1(CO)Cc2nnc(C3(c4ccc(-c5ncco5)cc4)CC3)n2CCS1]

Example 85-1

(8R)-8-({[Tert-butyl(dimethyl)silyl]oxy}methyl)-8-methyl-3-{1-[4-(1,3-oxazol-2-yl)phenyl]cyclopropyl}-5,6,8,9-tetrahydro[1,2,4]triazolo[4,3-d][1,4]thiazepine A solution of the compound (800 mg, 1.57 mmol) obtained in Example 52-1), oxazole (217 mg, 3.15 mmol), tetrakis(triphenylphosphine)palladium(0) (91 mg, 0.08 mmol), and lithium tert-butoxide (260 mg, 3.15 mmol) in dioxane (12 mL) was stirred for 2 h with heating to reflux. The reaction mixture was cooled to room temperature, saturated aqueous ammonium chloride (50 mL) was added to the reaction mixture, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=70:30) to obtain the title compound (674 mg, 86%) in a yellow oily form.

$^1$H-NMR (400 MHz, CDCl$_3$) δ: 0.05 (3H, s), 0.07 (3H, s), 0.91 (9H, s), 1.19 (3H, s), 1.45-1.54 (2H, m), 1.61-1.70 (2H, m), 2.51 (1H, ddd, J=15.7, 7.8, 2.3 Hz), 2.66 (1H, ddd, J=15.7, 8.0, 2.2 Hz), 3.40 (2H, s), 3.50 (1H, d, J=10.0 Hz), 3.54 (1H, d, J=10.0 Hz), 4.06 (1H, ddd, J=14.5, 8.0, 2.2 Hz), 4.29 (1H, ddd, J=14.5, 7.8, 2.3 Hz), 7.15 (1H, t, J=2.0 Hz), 7.17 (1H, t, J=2.0 Hz), 7.23 (1H, d, J=0.8 Hz), 7.70 (1H, d, J=0.8 Hz), 7.95 (1H, t, J=2.0 Hz), 7.98 (1H, t, J=2.0 Hz).

Example 85-2

{(8R)-8-Methyl-3-{1-[4-(1,3-oxazol-2-yl)phenyl]cyclopropyl}-5,6,8,9-tetrahydro[1,2,4]triazolo[4,3-d][1,4]thiazepin-8-yl}methanol A solution of the compound (674 mg, 1.36 mmol) obtained in Example 85-1) and 4 M hydrochloric acid (1,4-dioxane solution, 4 mL) in methanol (8 mL) was stirred overnight at room temperature. The reaction mixture was concentrated under reduced pressure, a 5 M aqueous sodium hydroxide solution (40 mL) was added to the residue, the mixture was extracted with ethyl acetate, and the organic layer was washed with saturated sodium chloride solution and dried with anhydrous sodium sulfate. After concentration under reduced pressure, the residue was purified by silica gel chromatography (ethyl acetate:methanol=20:80) to obtain the title compound (460 mg, 88%) as a yellow solid.

$^1$H-NMR (400 MHz, CDCl$_3$) δ: 1.32 (3H, s), 1.42-1.48 (1H, m), 1.51-1.62 (2H, m), 1.66-1.72 (1H, m), 2.39 (1H, ddd, J=15.6, 6.5, 1.4 Hz), 2.60 (1H, ddd, J=15.6, 9.8, 1.2 Hz), 2.92 (1H, brs), 3.33 (1H, d, J=15.2 Hz), 3.49 (2H, s), 3.61 (1H, d, J=15.2 Hz), 4.11 (1H, dd, J=14.8, 9.8 Hz), 4.38 (1H, dd, J=14.8, 6.5 Hz), 7.16 (1H, d, J=1.6 Hz), 7.18 (1H, d, J=1.6 Hz), 7.23 (1H, s), 7.71 (1H, s), 7.96 (1H, d, J=1.6 Hz), 7.98 (1H, d, J=1.6 Hz).

MS (ESI) m/z: 383 [M+H]$^+$.

Example 86

[8-Methyl-3-(1-{4-[5-(piperidin-1-ylcarbonyl)pyridin-2-yl]phenyl}cyclopropyl)-5,6,8,9-tetrahydro[1,2,4]triazolo[4,3-d][1,4]thiazepin-8-yl]methanol

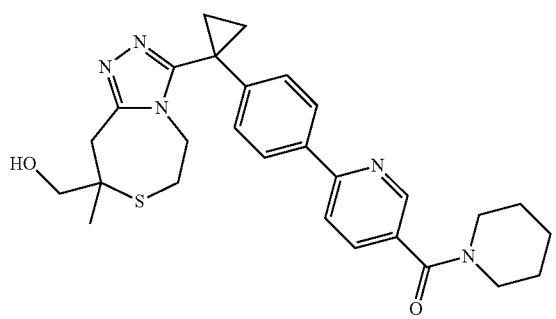 [SMILES: CC1(CO)Cc2nnc(C3(c4ccc(-c5ccc(C(=O)N6CCCCC6)cn5)cc4)CC3)n2CCS1]

A solution of the compound (200 mg, 0.458 mmol) obtained in Example 66, piperidine (210 μL, 2.29 mmol), N,N-dimethylaminopyridine (6 mg, 46 μmol), and 1-ethyl-3-(3-dimethylaminopropyl)carbodiimide hydrochloride (264 mg, 1.37 mmol) in N,N-dimethylformamide (4.00 mL) was stirred at room temperature for 6 h. Saturated aqueous sodium hydrogencarbonate (100 mL) was added to the reaction mixture, the mixture was extracted with dichloromethane/2-propanol (4/1), and the organic layer was washed with water and dried with anhydrous sodium sulfate. Then the solvent was distilled off under reduced pressure. The residue was purified by silica gel column chromatography (ethyl acetate:methanol=9:1 to 4:1) to obtain the title compound (26 mg, 11%) as a white solid.

$^1$H-NMR (500 MHz, CD$_3$OD) δ: 1.20 (3H, s), 1.59-1.74 (10H, m), 2.61 (1H, ddd, J=15.6, 7.3, 2.5 Hz), 2.82 (1H, ddd, J=15.6, 8.2, 2.3 Hz), 3.35-3.49 (6H, m), 3.74 (2H, brs), 4.32 (1H, ddd, J=14.7, 7.3, 2.3 Hz), 4.39 (1H, ddd, J=14.7, 8.2, 2.5 Hz), 7.23 (2H, d, J=8.3 Hz), 7.90 (1H, dd, J=8.0, 1.8 Hz), 7.94 (1H, d, J=8.0 Hz), 8.01 (2H, d, J=8.3 Hz), 8.64 (1H, d, J=1.8 Hz).

MS (FAB) m/z: 504 [M+H]$^+$.

Example 87

(8R)-8-Methyl-3-{1-[4-(5-methylpyrazin-2-yl)phenyl]cyclopropyl}-5,6,8,9-tetrahydro[1,2,4]triazolo[4,3-d][1,4]thiazepin-8-yl]methanol

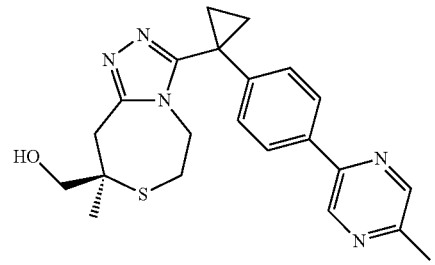 [SMILES: Cc1cnc(-c2ccc(C3(c4nnc5n4CCS[C@@](C)(CO)C5)CC3)cc2)cn1]

Example 87-1

(8R)-8-({[Tert-butyl(dimethyl)silyl]oxy}methyl)-8-methyl-3-{1-[4-(5-methylpyrazin-2-yl)phenyl]cyclopropyl}-5,6,8,9-tetrahydro[1,2,4]triazolo[4,3-d][1,4]thiazepine A solution of the compound (300 mg, 0.54 mmol) synthesized in Example 52-2), 2-bromo-5-methylpyrazine (234 mg, 1.35 mmol), tetrakis(triphenylphosphine)palladium(0) (125 mg, 0.11 mmol), and potassium carbonate (149 mg, 1.08 mmol) in water (2 mL) was heated to reflux for 3 h. The reaction mixture was cooled to room temperature and diluted with ethyl acetate (70 ml). The organic layer was washed with saturated aqueous sodium hydrogencarbonate and saturated sodium chloride solution and then dried with anhydrous magnesium sulfate. The solvent was distilled off under reduced pressure, and the obtained residue was purified by silica gel column chromatography (ethyl acetate:hexane=60:40 to 100:0) to obtain the title compound (139 mg, 49%) as a white solid.

$^1$H-NMR (CDCl$_3$) δ: 0.05 (3H, s), 0.07 (3H, s), 0.91 (9H, s), 1.19 (3H, s), 1.45-1.54 (2H, m), 1.61-1.71 (2H, m), 2.54 (1H, ddd, J=15.7, 8.2, 2.0 Hz), 2.60 (3H, s), 2.68 (1H, ddd, J=15.7, 7.8, 2.0 Hz), 3.40 (2H, s), 3.53 (2H, dd, J=16.2, 10.0 Hz), 4.07 (3H, ddd, J=14.5, 7.4, 2.3 Hz), 4.31 (1H, ddd, J=14.5, 7.8, 2.3 Hz), 7.19 (2H, d, J=7.8 Hz), 7.91 (2H, d, J=7.8 Hz), 8.49 (1H, s), 8.86 (1H, d, J=1.6 Hz).

Example 87-2

(8R)-8-Methyl-3-{1-[4-(5-methylpyrazin-2-yl)phenyl]cyclopropyl}-5,6,8,9-tetrahydro[1,2,4]triazolo[4,3-d][1,4]thiazepin-8-yl]methanol The compound (139 mg, 0.27 mmol) obtained in Example 87-1) was dissolved in methanol (4 mL). 4 N hydrochloric acid-dioxane (0.67 mL) was added to the solution, and the mixture was stirred at room temperature for 1 h. The solvent was distilled off under reduced pressure, and the residue was separated into organic and aqueous layers with methylene chloride (60 mL) and saturated aqueous sodium hydrogencarbonate (30 mL). The organic layer was washed with saturated sodium chloride solution and then dried with anhydrous magnesium sulfate. The solvent was distilled off under reduced pressure, and the obtained residue was purified by silica gel column chromatography (methanol:ethyl acetate=0:100 to 50:50) and further crystallized with a mixed solvent of diethyl ether and ethyl acetate to obtain the title compound (93 mg, 86%) as a white solid.

$^1$H-NMR (CDCl$_3$) δ: 1.33 (3H, s), 1.43-1.49 (1H, m), 1.51-1.63 (3H, m), 2.41 (1H, dd, J=14.9, 5.9 Hz), 2.56-2.65 (1H, m), 2.61 (3H, s), 3.32 (1H, d, J=15.2 Hz), 3.39 (2H, s), 3.62 (1H, d, J=15.2 Hz), 4.10 (1H, dd, J=14.5, 9.4 Hz), 4.42 (1H, dd, J=14.5, 5.1 Hz), 7.21 (2H, d, J=8.6 Hz), 7.93 (2H, d, J=8.6 Hz), 8.49 (1H, s), 8.87 (1H, d, J=1.6 Hz).
MS (ESI) m/z: 408 [M+H]$^+$.

Example 88

(8R)-8-Methyl-3-{1-[4-(2-methylpyrimidin-5-yl)phenyl]cyclopropyl}-5,6,8,9-tetrahydro[1,2,4]triazolo[4,3-d][1,4]thiazepin-8-yl]methanol

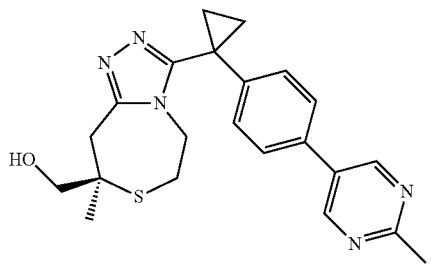 [SMILES: Cc1ncc(-c2ccc(C3(c4nnc5n4CCS[C@@](C)(CO)C5)CC3)cc2)cn1]

Example 88-1

1-[4-(2-Methylpyrimidin-5-yl)phenyl]cyclopropanecarbohydrazide

The compound (2.34 g, 6.59 mmol) obtained in Example 16-2), (2-methylpyrimidin-5-yl)boronic acid (1.00 g, 7.25 mmol), 1,1'-bis(diphenylphosphino)ferrocene-palladium(II) dichloride-dichloromethane complex (0.54 g, 0.66 mmol), and potassium carbonate (2.73 g, 19.76 mmol) were dissolved in a mixed solvent of 1,4-dioxane (20 mL) and water (10 mL), and the mixture was stirred at 90° C. for 3 h. The reaction mixture was cooled to room temperature and then diluted with ethyl acetate (150 mL). The organic layer was washed with saturated aqueous sodium hydrogencarbonate and saturated sodium chloride solution and then dried with anhydrous magnesium sulfate. The solvent was distilled off under reduced pressure, and the obtained residue was purified by silica gel column chromatography (ethyl acetate:hexane=50:50 to 100:0). The obtained partially purified product was dissolved in methanol (5 mL). 4 N hydrochloric acid-dioxane (2.39 mL) was added to the solution, and the mixture was stirred at room temperature for 2 h. The solvent was distilled off, and the residue was separated into organic and aqueous layers with methylene chloride (150 mL) and saturated aqueous sodium hydrogencarbonate (50 mL). The organic layer was washed with saturated sodium chloride solution and then dried with anhydrous magnesium sulfate. The solvent was distilled off under reduced pressure to obtain the title compound (591 mg, yield: 82%) as a white solid.

$^1$H-NMR (CDCl$_3$) δ: 1.13 (2H, dd, J=7.4, 3.5 Hz), 1.67 (2H, dd, J=7.8, 3.5 Hz), 2.80 (3H, s), 7.48-7.61 (4H, m), 8.84 (2H, s).

Example 88-2

(8R)-8-({[Tert-butyl(dimethyl)silyl]oxy}methyl)-8-methyl-3-{1-[4-(2-methylpyrimidin-5-yl)phenyl]cyclopropyl}-5,6,8,9-tetrahydro[1,2,4]triazolo[4,3-d][1,4]thiazepine A solution of the compound (591 mg, 2.23 mmol) obtained in Example 88-1) and the compound (750 mg, 2.35 mmol) obtained in Example 4-1) in t-butanol (10 mL) was stirred for 7 h under reflux conditions. The obtained reaction mixture was cooled to room temperature and concentrated under reduced pressure, and then the residue was purified by silica gel column chromatography (methanol:ethyl acetate=10:90 to 100:0) to obtain the title compound (861 mg, 70%) as a light yellow solid.

$^1$H-NMR (CDCl$_3$) δ: 0.05 (3H, s), 0.07 (3H, s), 0.91 (9H, s), 1.20 (3H, s), 1.43-1.55 (2H, m), 1.55-1.66 (2H, m), 2.58 (1H, ddd, J=15.6, 7.8, 2.3 Hz), 2.73 (1H, ddd, J=16.0, 8.2, 2.3 Hz), 2.79 (3H, s), 3.40 (2H, s), 3.54 (2H, dd, J=18.8, 9.8 Hz), 4.09 (1H, ddd, J=13.7, 7.8, 2.3 Hz), 4.32 (1H, ddd, J=14.5, 7.8, 2.3 Hz), 7.20 (2H, d, J=7.8 Hz), 7.49 (2H, d, J=7.8 Hz), 8.81 (2H, s).

Example 88-3

(8R)-8-Methyl-3-{1-[4-(2-methylpyrimidin-5-yl)phenyl]cyclopropyl}-5,6,8,9-tetrahydro[1,2,4]triazolo[4,3-d][1,4]thiazepin-8-yl]methanol The compound (861 mg, 1.65 mmol) obtained in Example 88-2) was dissolved in methanol (10 mL). 4 N hydrochloric acid-dioxane (4.12 mL) was added to the solution, and the mixture was stirred at room temperature for 1.5 h. The solvent was distilled off under reduced pressure, and the residue was separated into organic and aqueous layers with methylene chloride (150 mL) and saturated aqueous sodium hydrogencarbonate (50 mL). The organic layer was washed with saturated sodium chloride solution and then dried with anhydrous magnesium sulfate. The solvent was distilled off under reduced pressure, and the obtained residue was partially purified by silica gel column chromatography (elution solvent: methanol/ethyl acetate=0% to 30%). The obtained partially purified product was crystallized with a mixed solvent of diisopropyl ether and ethyl acetate to obtain the title compound (584 mg, 87%) in a white solid form.

$^1$H-NMR (CDCl$_3$) δ: 1.34 (3H, s), 1.43-1.55 (2H, m), 1.57-1.69 (2H, m), 2.46 (1H, ddd, J=15.6, 6.3, 1.2 Hz), 2.66 (1H, ddd, J=15.6, 10.2, 1.6 Hz), 2.79 (3H, s), 3.32 (1H, d, J=15.2 Hz), 3.41 (2H, s), 3.62 (1H, d, J=15.2 Hz), 4.12 (1H, dd, J=14.5, 10.6 Hz), 4.43 (1H, dd, J=14.5, 6.3 Hz), 7.22 (2H, d, J=8.6 Hz), 7.50 (2H, d, J=8.6 Hz), 8.82 (2H, s).
MS (ESI) m/z: 408 [M+H]$^+$.

Example 89

[(8R)-6-methylpyridazin-3-yl)phenyl]cyclopropyl}-8-methyl-5,6,8,9-tetrahydro[1,2,4]triazolo[4,3-d][1,4]thiazepine-8-yl]methanol

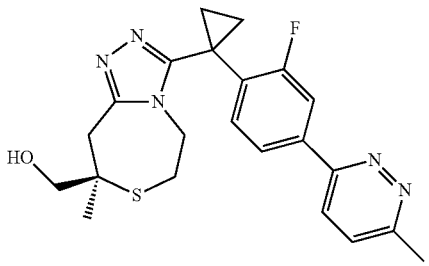 [SMILES: Cc1ccc(-c2ccc(C3(c4nnc5n4CCS[C@@](C)(CO)C5)CC3)c(F)c2)nn1]

Example 89-1

(8R)-8-({[Tert-butyl(dimethyl)silyl]oxy}methyl)-3-{1-[2-fluoro-4-(4,4,5,5-tetramethyl-1,3,2-dioxaborolan-2-yl)phenyl]cyclopropyl}-8-methyl-5,6,8,9-tetrahydro[1,2,4]triazolo[4,3-d][1,4]thiazepine The compound (1.34 g, 2.54 mmol) synthesized in Example 81-1 was dissolved in 1,4-dioxane (12 mL). Bis(pinacolato)diboron (1.61 mg, 6.35 mmol), [1,1'-bis(diphenylphosphino)ferrocene]palladium(II) dichloride-dichloromethane complex (0.41 g, 0.51 mmol), and potassium acetate (0.75 g, 7.62 mmol) were added to the solution, and the mixture was heated to reflux for 18 h under a nitrogen atmosphere. The reaction mixture was cooled to room temperature, then the solvent was distilled off, and the obtained residue was purified by silica gel column chromatography (methanol:ethyl acetate=0:100 to 20:80) to obtain the title compound (1.46 g, quant.) as a brown solid.
$^1$H-NMR (CDCl$_3$) δ: 0.01 (3H, s), 0.04 (3H, s), 0.89 (9H, s), 1.13 (3H, s), 1.27 (3H, s), 1.47-1.52 (2H, m), 1.60-1.67 (2H, m), 2.47 (1H, dd, J=16.0, 7.0 Hz), 2.62 (1H, dd, J=15.6, 7.0 Hz), 3.34 (2H, s), 3.47 (2H, dd, J=16.6, 10.0 Hz), 4.16 (1H, dd, J=14.5, 7.0 Hz), 4.45 (1H, dd, J=14.9, 7.0 Hz), 7.37 (1H, t, J=7.2 Hz), 7.43 (1H, d, J=11.3 Hz), 7.51 (1H, d, J=7.0 Hz).

Example 89-2

(8R)-8-({[Tert-butyl(dimethyl)silyl]oxy}methyl)-3-{1-[2-fluoro-4-(6-methylpyridazin-3-yl)phenyl]cyclopropyl}-8-methyl-5,6,8,9-tetrahydro[1,2,4]triazolo[4,3-d][1,4]thiazepine The compound (600 mg, 1.05 mmol) obtained in Example 89-1), 3-chloro-6-methylpyridazine (161 mg, 1.26 mmol), tris(dibenzylideneacetone)dipalladium (96 mg, 0.10 mmol), tricyclohexylphosphine (29 mg, 0.10 mmol), and tripotassium phosphate (458 mg, 2.09 mmol) were dissolved in a mixed solvent of 1,4-dioxane (2 mL) and water (1 mL), and the mixture was stirred at 140° C. for 2 h under microwave irradiation. The reaction mixture was cooled to room temperature, then diluted with methylene chloride (200 mL), and separated into organic and aqueous layers by the addition of saturated aqueous sodium hydrogencarbonate. The organic layer was washed with saturated sodium chloride solution and then dried with anhydrous magnesium sulfate. The solvent was distilled off under reduced pressure, and the obtained residue was purified by silica gel column chromatography (methanol:ethyl acetate=0:100 to 20:80) to obtain the title compound (366 mg, 65%) as a brown solid.
$^1$H-NMR (CDCl$_3$) δ: 0.02 (3H, s), 0.04 (3H, s), 0.89 (9H, s), 1.15 (3H, s), 1.49-1.75 (4H, m), 2.58 (1H, ddd, J=15.6, 8.0, 2.2 Hz), 2.71-2.80 (1H, m), 2.77 (3H, s), 3.36 (2H, s), 3.49 (3H, dd, J=15.1, 10.0 Hz), 4.22 (1H, ddd, J=14.5, 8.2, 1.6 Hz), 4.52 (1H, ddd, J=14.5, 7.8, 1.6 Hz), 7.41 (1H, d, J=9.0 Hz), 7.53 (1H, t, J=8.2 Hz), 7.72 (1H, d, J=8.6 Hz), 7.77 (1H, dd, J=8.2, 1.6 Hz), 7.82 (1H, dd, J=12.5, 1.6 Hz).

Example 89-3

[(8R)-3-{1-[2-Fluoro-4-(6-methylpyridazin-3-yl)phenyl]cyclopropyl}-8-methyl-5,6,8,9-tetrahydro[1,2,4]triazolo[4,3-d][1,4]thiazepin-8-yl]methanol The compound (366 mg, 0.68 mmol) obtained in Example 89-2) was dissolved in methanol (4 mL). 4 N hydrochloric acid-dioxane (1.69 mL) was added to the solution, and the mixture was stirred at room temperature for 2 h. The solvent was distilled off under reduced pressure, and the residue was separated into organic and aqueous layers with methylene chloride (150 mL) and saturated aqueous sodium hydrogencarbonate (50 mL). The organic layer was washed with saturated sodium chloride solution and then dried with anhydrous magnesium sulfate. The solvent was distilled off under reduced pressure, and the obtained residue was purified by silica gel column chromatography (methanol:ethyl acetate=0:100 to 20:80) to obtain the title compound (210 mg, 73%) as a white solid.
$^1$H-NMR (CDCl$_3$) δ: 1.30 (3H, s), 1.48-1.54 (1H, m), 1.56-1.64 (2H, m), 1.69-1.76 (1H, m), 2.50 (1H, ddd, J=15.6, 6.6, 1.2 Hz), 2.61 (1H, ddd, J=16.0, 9.4, 1.2 Hz), 2.77 (3H, s), 3.28 (1H, d, J=15.2 Hz), 3.33 (2H, t, J=5.9 Hz), 3.58 (1H, d, J=15.2 Hz), 4.23 (1H, dd, J=15.2, 9.0 Hz), 4.67 (1H, dd, J=14.9, 6.3 Hz), 7.41 (1H, d, J=8.6 Hz), 7.55 (1H, t, J=8.0 Hz), 7.72 (1H, d, J=8.6 Hz), 7.78 (1H, dd, J=8.0, 1.8 Hz), 7.83 (1H, dd, J=12.3, 1.8 Hz).
MS (ESI) m/z: 426 [M+H]$^+$.

Test Example 1

11β-HSD1 Enzyme Inhibition Experiment (1) Enzyme Source

A plasmid obtained by incorporating cDNA coding for a full-length of human 11β-HSD1 in a mammal cell expression vector pCIneo (Promega Corporation) was introduced into HEK293 cells using Lipofectamine Plus Reagent (Invitrogen Corporation) according to the package insert. 48 h later, the cells were collected and frozen at −80° C. Cells into which the pCIneo vector was introduced were prepared as a control. The cells were thawed and suspended in 20 mM HEPES, 1 mM ethylenediamine tetraacetic acid, 2 mM magnesium chloride (final concentrations), and a buffer containing a protease inhibitor cocktail (Roche), and the cells were disrupted using Polytron (KINEMATICA AG). The disrupted cell suspension was centrifuged at 1000×g at 4° C. for 10 min, and a supernatant thereof was recovered. The obtained supernatant was further ultracentrifuged at 105,000×g at 4° C. for 30 min, and the resulting precipitate was suspended in an assay buffer (50 mM tris buffer, 10% glycerol) as a microsome fraction and used as an enzyme source.

(2) Enzyme Inhibition Experiment

A reaction was performed on a 384-well plate (Greiner Bio One) using a reaction volume of 24 μL, and all the samples were diluted with an assay buffer (50 mM tris buffer, pH 7.4, 10% glycerol). 0.8 mM NADPH, 6 mM glucose 6-phosphate, 0.35 units/mL glucose 6-phosphate dehydrogenase (Sigma Chemical), and 3 mM magnesium chloride and a microsome fraction as an enzyme source were added to the plate, and a solution containing a test compound dissolved in a dimethyl sulfoxide/methanol solution was added at a final concentration of 0.1%. After the addition of the test compound, cortisone at a final concentration of 160 nM was added to start the reaction, and the reaction was performed at room temperature for 3 h. 25 μL of 100 mM carbenoxolone (Sigma Chemical) was added to terminate the reaction, and the amount of cortisol produced was measured with RUBYstar (BMG LABTECH JAPAN Ltd.) using a cortisol prototype kit (Cisbio International) according to the package insert. The $IC_{50}$ values of the compounds of Examples are shown below.

| Example No. | $IC_{50}$ nM |
|---|---|
| 1 | 3.3 |
| 2 | 2.6 |
| 3 | 6.3 |
| 4 | 1.3 |
| 6 | 2.6 |
| 9 | 1.8 |
| 26 | 0.3 |
| 32 | 2.0 |
| 34 | 1.0 |
| 67 | 5.4 |
| 68 | 6.7 |
| 81 | 2.2 |
| 88 | 1.7 |
| 89 | 1.3 |

Formulation Example 1

Capsule

| | |
|---|---|
| Compound of Example 1 or 2 | 50 mg |
| Lactose | 128 mg |
| Maize starch | 70 mg |
| Magnesium stearate | 2 mg |
| | 250 mg |

Powders of the above-mentioned prescription were mixed, the mixture was passed through a 60-mesh sieve, and this powder was encapsulated in a gelatin capsule (250 g) to produce a capsule.

Formulation Example 2

Tablet

| | |
|---|---|
| Compound of Example 1 or 2 | 50 mg |
| Lactose | 126 mg |
| Corn starch | 23 mg |
| Magnesium stearate | 1 mg |
| | 200 mg |

Powders of the above-mentioned prescription were mixed, the mixture was granulated using corn starch paste, and dried, and then compressed with a tableting machine to produce a tablet (200 mg per tablet). This tablet can be sugar-coated, if necessary.

INDUSTRIAL APPLICABILITY

The novel tetrahydrothiazepine derivative represented by the general formula (I) or (Ia) of the present invention or a pharmacologically acceptable salt thereof has an excellent 11β-HSD1 inhibitory effect and is useful as a medicament.

The invention claimed is:

1. A compound represented by the general formula (I):

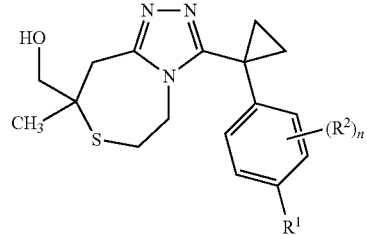

(I)

or a pharmacologically acceptable salt thereof
wherein
$R^1$ represents a phenyl group that may be substituted with 1 to 5 group(s) independently selected from substituent group A or a heterocyclic group that may be substituted with 1 to 4 group(s) independently selected from substituent group A;
$R^2$ independently represents a halogen atom or a $C_1$-$C_6$ alkyl group;
n represents 0, 1, or 2; and
substituent group A represents the group consisting of halogen atoms, $C_1$-$C_6$ alkyl groups, $C_1$-$C_6$ halogenated alkyl groups, $C_1$-$C_6$alkoxy groups, a carboxy group, $C_2$-$C_7$-carboxyalkyl groups, $C_2$-$C_7$alkylcarbonyl groups, $C_2$-$C_7$alkoxycarbonyl groups, a cyano group, $C_1$-$C_6$alkylsulfonyl groups, groups represented by the formula —C(=O)—$NR^3R^4$ ($R^3$ and $R^4$ are identical to or different from each other and each independently represents a hydrogen atom, a $C_1$-$C_6$ alkyl group, or a $C_3$-$C_6$cycloalkyl group, or $R^3$ and $R^4$ form a 4 to 6-membered saturated heterocyclic ring together with the nitrogen atom bound therewith, wherein the 4 to 6-membered saturated heterocyclic ring may further contain one oxygen atom), mono-$C_2$-$C_7$alkoxycarbonylamino groups, and an oxo group.

2. A compound represented by the general formula (Ia):

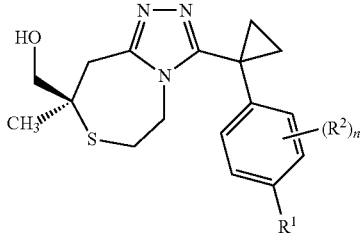

(Ia)

or a pharmacologically acceptable salt thereof wherein
R¹ represents a phenyl group that may be substituted with 1 to 5 group(s) independently selected from substituent group A or a heterocyclic group that may be substituted with 1 to 4 group(s) independently selected from substituent group A;
R² independently represents a halogen atom or a $C_1$-$C_6$ alkyl group;
n represents 0, 1, or 2; and
substituent group A represents the group consisting of halogen atoms, $C_1$-$C_6$ alkyl groups, $C_1$-$C_6$ halogenated alkyl groups, $C_1$-$C_6$alkoxy groups, a carboxy group, $C_2$-$C_7$-carboxyalkyl groups, $C_2$-$C_7$alkylcarbonyl groups, $C_2$-$C_7$alkoxycarbonyl groups, a cyano group, $C_1$-$C_6$alkylsulfonyl groups, groups represented by the formula —C(=O)—NR³R⁴ (R³ and R⁴ are identical to or different from each other and each independently represents a hydrogen atom, a $C_1$-$C_6$ alkyl group, or a $C_3$-$C_6$cycloalkyl group, or R³ and R⁴ form a 4 to 6-membered saturated heterocyclic ring together with the nitrogen atom bound therewith, wherein the 4 to 6-membered saturated heterocyclic ring may further contain one oxygen atom), mono-$C_2$-$C_7$alkoxycarbonylamino groups, and an oxo group.

3. The compound or a pharmacologically acceptable salt thereof according to claim 1, wherein R¹ represents a heterocyclic group that may be substituted with 1 to 4 group(s) independently selected from substituent group A.

4. The compound or a pharmacologically acceptable salt thereof according to claim 1, wherein R¹ represents a pyridyl group, a pyrimidinyl group, or a pyrazolyl group that may be substituted with one group selected from substituent group A.

5. The compound or a pharmacologically acceptable salt thereof according to claim 1, wherein substituent group A represents $C_1$-$C_6$ alkyl groups or groups represented by the formula —C(=O)—NR³R⁴ (R³ and R⁴ are identical to or different from each other and each independently represents a hydrogen atom, a $C_1$-$C_6$ alkyl group, or a $C_3$-$C_6$cycloalkyl group, or R³ and R⁴ form a 4 to 6-membered saturated heterocyclic ring together with the nitrogen atom bound therewith, wherein the 4 to 6-membered saturated heterocyclic ring may further contain one oxygen atom).

6. The compound or a pharmacologically acceptable salt thereof according to claim 1, wherein n represents 0.

7. A compound selected from the group consisting of:
[3-(1-biphenyl-4-ylcyclopropyl)-8-methyl-5,6,8,9-tetrahydro[1,2,4]triazolo[4,3-d][1,4]thiazepin-8-yl]methanol,
{8-methyl-3-[1-(4-pyridin-3-ylphenyl)cyclopropyl]-5,6,8,9-tetrahydro[1,2,4]triazolo[4,3-d][1,4]thiazepin-8-yl}methanol,
{(8S)-8-methyl-3-[1-(4-pyridin-3-ylphenyl)cyclopropyl]-5,6,8,9-tetrahydro[1,2,4]triazolo[4,3-d][1,4]thiazepin-8-yl}methanol,
{(8R)-8-methyl-3-[1-(4-pyridin-3-ylphenyl)cyclopropyl]-5,6,8,9-tetrahydro[1,2,4]triazolo[4,3-d][1,4]thiazepin-8-yl}methanol,
4'-{1-[8-(hydroxymethyl)-8-methyl-5,6,8,9-tetrahydro[1,2,4]triazolo[4,3-d][1,4]thiazepin-3-yl]cyclopropyl}-N,N-dimethylbiphenyl-4-carboxamide,
4'-{1-[8-(hydroxymethyl)-8-methyl-5,6,8,9-tetrahydro[1,2,4]triazolo[4,3-d][1,4]thiazepin-3-yl]cyclopropyl}-N,N-dimethylbiphenyl-3-carboxamide,
{3-[1-(3-fluoro-4-pyridin-3-ylphenyl)cyclopropyl]-8-methyl-5,6,8,9-tetrahydro[1,2,4]triazolo[4,3-d][1,4]thiazepin-8-yl}methanol,
(8-methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl)methanol,
{(8R)-8-methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl}methanol,
6-(4-{1-[8-(hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide,
6-(4-{1-[(8R)-8-(hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide, and
{(8R)-3-{1-[2-fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl}methanol.

8. 1 (8R)-8-methyl-3-[1-(4-pyridin-3-ylphenyl)cyclopropyl]-5,6,8,9-tetrahydro[1,2,4]triazolo[4,3-d][1,4]thiazepin-8-yl}methanol represented by the following formula:

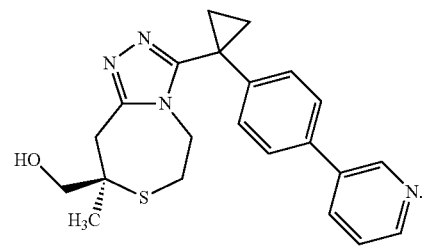 [SMILES: C[C@]1(CO)Cc2nnc(C3(c4ccc(-c5cccnc5)cc4)CC3)n2CCS1]

9. (8R-{3-[1-(3-fluoro-4-pyridin-3-ylphenyl)cyclopropyl]-8-methyl-5,6,8,9-tetrahydro[1,2,4]triazolo[4,3-d][1,4]thiazepin-8-yl}methanol represented by the following formula:

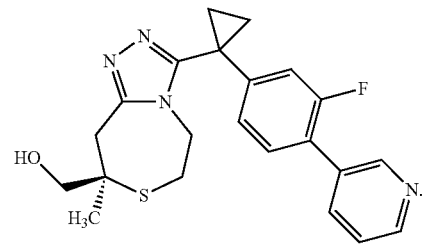 [SMILES: C[C@]1(CO)Cc2nnc(C3(c4ccc(-c5cccnc5)c(F)c4)CC3)n2CCS1]

10. {(8R)-8-methyl-3-{1-[4-(1-methyl-1H-pyrazol-4-yl)phenyl]cyclopropyl}-5,6,8,9-tetrahydro[1,2,4]triazolo[4,3-d][1,4]thiazepin-8-yl}methanol represented by the following formula:

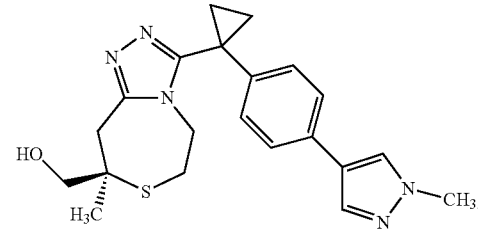 [SMILES: Cn1cc(-c2ccc(C3(c4nnc5n4CCS[C@@](C)(CO)C5)CC3)cc2)cn1]

11. 6-(4-{1-[(8R)-8-(hydroxymethyl)-8-methyl-5,6,8,9-tetrahydro[1,2,4]triazolo[4,3-d][1,4]thiazepin-3-yl]cyclopropyl}phenyl)-N,N-dimethylnicotinamide represented by the following formula:

14. [(8R)-3-{1-[2-fluoro-4-6-methylpyridazin-3-yl)phenyl]cyclopropyl}-8methyl-5,6,8,9-tetrahydro[1,2,4]triazolo[4,3-d][1,4]thiazepine-8-yl]methanol represented by the following formula:

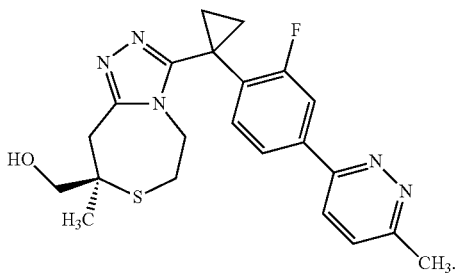

15. A compound according to any one of claims 7 to 14 further comprising a pharmacologically acceptable salt.

16. A pharmaceutical composition containing the compound or a pharmacologically acceptable salt thereof according to claim 1 as an active ingredient.

17. A method for therapeutic treatment of type 2 diabetes, comprising administering a pharmacologically effective amount of the compound or a pharmacologically acceptable salt thereof according to claim 1 to a homeotherm.

18. A method for therapeutic treatment of dyslipidemia or hyperlipidemia, comprising administering a pharmacologically effective amount of the compound or a pharmacologically acceptable salt thereof according to claim 1 to a homeotherm.

19. A method for therapeutic treatment of hypertension, comprising administering a pharmacologically effective amount of the compound or a pharmacologically acceptable salt thereof according to claim 1 to a homeotherm.

20. A method for therapeutic treatment of adiposity, fatty liver, atherosclerosis, osteoporosis, or glaucoma, comprising administering a pharmacologically effective amount of the compound or a pharmacologically acceptable salt thereof according to claim 1 to a homeotherm.

21. A method for inhibiting 11β-HSD1, comprising contacting 11β-HSD1 with a compound or a pharmacologically acceptable salt thereof according to claim 1.

22. A method for inhibiting 11β-HSD1 in a homeotherm, comprising administering to a homeotherm a compound or a pharmacologically acceptable salt thereof according to claim 1.

23. The method of claim 22, wherein the homeotherm is a human.

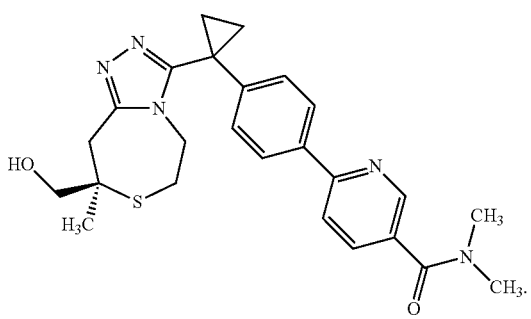 [SMILES: CN(C)C(=O)c1ccc(-c2ccc(C3(c4nnc5n4CCS[C@@](C)(CO)C5)CC3)cc2)nc1]

12. {(8R)-3-{1-[2-fluoro-4-(1-methyl-1H-pyrazol-4-yl)phenyl]cyclopropyl}-8-methyl-5,6,8,9-tetrahydro[1,2,4]triazolo[4,3-d][1,4]thiazepin-8-yl}methanol represented by the following formula:

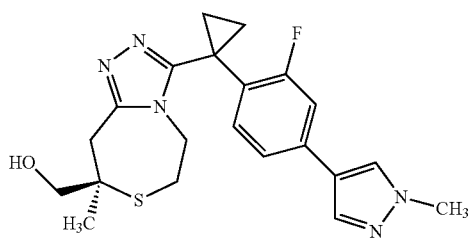 [SMILES: Cn1cc(-c2ccc(C3(c4nnc5n4CCS[C@@](C)(CO)C5)CC3)c(F)c2)cn1]

13. [(8R)-8-methyl-3-{1-[4-(2-methylpyrimidin-5-yl)phenyl]cyclopropyl}-5,6,8,9-tetrahydro[1,2,4]triazolo[4,3-d][1,4]thiazepin-8-yl]methanol represented by the following formula:

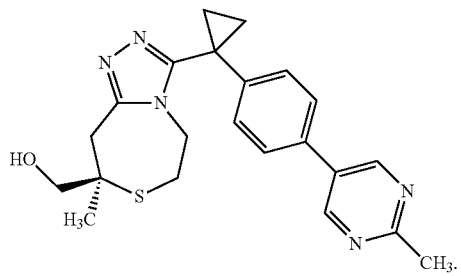 [SMILES: Cc1ncc(-c2ccc(C3(c4nnc5n4CCS[C@@](C)(CO)C5)CC3)cc2)cn1]

* * * * *

UNITED STATES PATENT AND TRADEMARK OFFICE
CERTIFICATE OF CORRECTION

PATENT NO. : 8,927,536 B2  
APPLICATION NO. : 14/057004  
DATED : January 6, 2015  
INVENTOR(S) : Mori et al.

Page 1 of 1

It is certified that error appears in the above-identified patent and that said Letters Patent is hereby corrected as shown below:

In the Specification

| COLUMN | LINE | ERROR |
|---|---|---|
| 57 | 15 | "{8-Methyl-3≡1-[4-(5-methylpyridin-3-yl)phenyl]" should read --{8-Methyl-3-{1-[4-(5-methylpyridin-3-yl)phenyl]-- |
| 125 | 3 | "(6 mg, 46 mmol)" should read --(6 mg, 46 µmol)-- |

Signed and Sealed this  
Twenty-third Day of August, 2016

Michelle K. Lee  
*Director of the United States Patent and Trademark Office*